(12) United States Patent
Felber et al.

(10) Patent No.: US 9,546,202 B2
(45) Date of Patent: Jan. 17, 2017

(54) EXPRESSION OF IL-12 FAMILY HETERODIMERS

(71) Applicant: The United States Of America, as represented by the Secretary, Department Of Health and Human Services, Washington, DC (US)

(72) Inventors: Barbara K. Felber, Rockville, MD (US); George N. Pavlakis, Rockville, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 168 days.

(21) Appl. No.: 14/244,768

(22) Filed: Apr. 3, 2014

(65) Prior Publication Data

US 2014/0206758 A1    Jul. 24, 2014

Related U.S. Application Data

(62) Division of application No. 12/992,077, filed as application No. PCT/US2009/043481 on May 11, 2009, now Pat. No. 8,715,964.

(60) Provisional application No. 61/052,916, filed on May 13, 2008, provisional application No. 61/052,239, filed on May 11, 2008.

(51) Int. Cl.
| | | |
|---|---|---|
| *C12N 15/00* | (2006.01) | |
| *C12P 21/04* | (2006.01) | |
| *C07K 14/54* | (2006.01) | |

(52) U.S. Cl.
CPC .......... *C07K 14/5434* (2013.01); *C07K 14/54* (2013.01)

(58) Field of Classification Search
None
See application file for complete search history.

(56) References Cited

U.S. PATENT DOCUMENTS

| | | |
|---|---|---|
| 5,830,451 A | 11/1998 | Devergne et al. |
| 5,965,726 A | 10/1999 | Pavlakis et al. |
| 5,972,596 A | 10/1999 | Pavlakis et al. |
| 6,174,666 B1 | 1/2001 | Pavlakis et al. |
| 6,291,664 B1 | 9/2001 | Pavlakis et al. |
| 6,414,132 B1 | 7/2002 | Pavlakis et al. |
| 6,794,498 B2 | 9/2004 | Pavlakis et al. |
| 2006/0160147 A1 | 7/2006 | Vandenbroeck et al. |
| 2014/0206758 A1* | 7/2014 | Felber .................. C07K 14/54 514/44 R |

FOREIGN PATENT DOCUMENTS

| | | |
|---|---|---|
| WO | WO 98/17814 A | 4/1998 |
| WO | WO 99/47679 A | 9/1999 |
| WO | WO 99/60135 A | 11/1999 |
| WO | WO 2007/084342 A | 7/2007 |
| WO | WO 2007/084364 A | 7/2007 |

OTHER PUBLICATIONS

Gascón, S., et al., "Dual-promoter lentiviral for constitutive and regulated gene expression in neurons," *J. Neurosci Methods*, vol. 168(1), pp. 104-112 (Feb. 15, 2008, Epub Sep. 29, 2007).
Jordan, M., et al., "Transient Expression of a Soluble and Secreted Form of Heterodimeric T-Cell Receptor in HEK-293," *New Developments and New Applications in Animal Cell Technology*, pp. 121-123 (1998).
Lee, Y-L., et al., "Construction of Vectors Expressing Bioactive Heterodimeric and Single-Chain Murine Interleukin-12 for Gene Therapy," *Human Gene Therapy*, vol. 9(4), pp. 457-465 (Mar. 1, 1998).
Li, J., et la., "A comparative study of different vector designs for the mammalian expression of recombinant IgG antibodies," *Journal of Immunological Methods*, vol. 318, pp. 113-124 (2007).
Li, J., et al., "Analysis of IgG heavy chain to light chain ration with mutant Encephalomyocarditis virus internal ribosome entry site," *Protein Engineering, Design & Selection*, vol. 20(10), pp. 491-496 (2007).
Liu, W., et al., "A balanced expression of two chains of heterodimer protein, the human interleukin-12, improves high-level expression of the protein in CHO cells," *Biochemical and Biophysical Research and Communications*, vol. 313(2), pp. 287-293 (Jan. 9, 2004).
Meier, T., et al., "Cloning, expression, purification, and characterization of the human Class la phosphoinositide 3-kinase isoforms," *Protein Expression and Purification*, vol. 35, pp. 218-224 (2004).
Schlatter, S., et al., "On the Optimal Ratio of Heavy to Light Chain Genes for Efficient Recombinant Antibody Production by CHO Cells," *Biotechnol. Prog.*, vol. 21, pp. 122-133 (2005).
Urano, J., et al., "Reconstitution of Yeast Farnesyltransferase from Individually Purified Subunits," *Methods in Molecular Biology: Protein Lipidation Protocols*, vol. 116, pp. 145-159 (1997).

* cited by examiner

*Primary Examiner* — Michael Burkhart
(74) *Attorney, Agent, or Firm* — Jean M. Lockyer; Kilpatrick Townsend & Stockton LLP

(57) ABSTRACT

The present invention provides methods of improving the levels and stability of expression of interleukin-12 family cytokine polypeptides by expressing the alpha and beta subunits of the polypeptides at their determined relative molar ratios that increase the levels and stability of expression of the heterodimer, e.g., in comparison to heterodimer expressed at an equimolar ratio.

16 Claims, 21 Drawing Sheets

EXPRESSION OF IL-12 FAMILY HETERODIMERS

CROSS-REFERENCE TO RELATED APPLICATIONS

This application is a divisional of U.S. application Ser. No. 12/992,077, filed Feb. 9, 2011 as the U.S. National Stage of PCT/US2009/043481, filed May 11, 2009, which claims the benefit of U.S. Provisional Application No. 61/052,239, filed on May 11, 2008 and U.S. Provisional Application No. 61/052,916, filed on May 13, 2008, the entire disclosures of each of which are hereby incorporated herein by reference.

REFERENCE TO SUBMISSION OF A SEQUENCE LISTING

The Sequence Listing written in file SEQTXT_77867-905068.txt, created on Apr. 2, 2014, 139,317 bytes, machine format IBM-PC, MS-Windows operating system, is hereby incorporated by reference.

FIELD OF THE INVENTION

The present invention provides methods for improved expression of IL-12 family cytokine heterodimeric proteins. The levels and efficiency of expression of heterodimeric proteins is improved by adjusting the relative ratios of transcription and translation of the polypeptides of a IL-12 family cytokine heterodimeric pair of polypeptides, e.g., alpha and beta subunits, e.g., in comparison to expression of the subunits at equimolar ratios.

BACKGROUND OF THE INVENTION

Many proteins are multimeric, composed of multiple and different subunits. Expression of the respective subunits provides a critical step in the production of a functional protein. To obtain maximal production of such proteins it is important to also optimize expression levels of individual subunits. The present invention is based, in part, on the discovery that production levels and secretion of several multimeric cytokines depends not only on the absolute levels of expression, but also on the relative levels of expression of individual subunits.

Optimized ratios of the subunits resulted in greatly increased extracellular levels of the heterodimeric proteins. We have identified the optimal ratios of subunits for several heterodimeric cytokines, including IL-12 family cytokines, e.g., IL-12 chains p35 and p40, IL-23 chains p19 and p40, IL-27 chains p28 and EBI3. The use of optimized expression strategies leads to improvement of cytokine expression. This strategy is of general application for the expression of any multimeric protein.

BRIEF SUMMARY OF THE INVENTION

The present invention provides methods for improving the expression of IL-12 family cytokine heterodimers by determining the relative ratio of expression of the alpha and beta subunits comprising the heterodimers that produces increased levels of expression, e.g., highest or desired levels of extracellular expression and stability of heterodimer.

Accordingly, in a first aspect, the invention provides methods of improving the level and stability of expression of an IL-12 family cytokine, wherein the IL-12 family cytokine comprises an alpha subunit and a beta subunit. In some embodiments, the methods comprise:
a) determining the ratio of the alpha subunit and the beta subunit that produces an increased level of expression of heterodimer; and
b) expressing the alpha subunit and the beta subunit from a cell at the determined ratio. The level of expression can be in comparison to expressing the alpha subunit and the beta subunit at a 1:1 ratio. Increased levels of expression of a IL-12 family cytokine are achieved when the alpha and beta subunits are expressed at a ratio other than 1:1, i.e., not at a 1:1 ratio.

In some embodiments, the IL-12 family cytokine is IL-12, and the alpha subunit (p35) and the beta subunit (p40) are expressed at a relative ratio in the range of about 1:3 to about 1:15, for example, about 1:8 to about 1:10, or at a ratio of about 1:5, 1:8, 1:10, 1:12, or 1:15.

In some embodiments, the IL-12 family cytokine is IL-23, and the alpha subunit (p19) and the beta subunit (p40) are expressed at a relative ratio in the range of about 1:3 to about 1:15, for example, about 1:8 to about 1:10, or at a ratio of about 1:5, 1:8, 1:10, 1:12, or 1:15.

In some embodiments, the IL-12 family cytokine is IL-27, and the alpha subunit (p28) and the beta subunit (EBI3) are expressed at a relative ratio in the range of about 3:1 to about 15:1, for example, about 8:1 to about 10:1, or at a ratio of about 5:1, 8:1, 10:1, 12:1, or 15:1.

In some embodiments, the highest level of extracellular expression of heterodimer is determined. In some embodiments, the expression of heterodimer is increased 3-fold, 4-fold, 5-fold, 10-fold, 15-fold, 20-fold, 30-fold, or more, as measured in vitro or in vivo, in comparison to heterodimers expressed at a relative molar ratio of 1:1.

In some embodiments, the alpha subunit and the beta subunit are expressed at the determined ratio by cotransfecting the cell with a first nucleic acid encoding the alpha subunit and a second nucleic acid encoding the beta subunit at the determined ratio for expression.

In some embodiments, the alpha subunit and the beta subunit are expressed at the determined ratio by transfecting the cell with a single plasmid comprising a first nucleic acid encoding the alpha subunit under the control of a first promoter and a second nucleic acid encoding the beta subunit under the control of a second promoter, wherein the first promoter and the second promoter are of different relative expression strengths to allow expression of the alpha subunit and the beta subunits at a determined ratio of expression. In some embodiments, the first promoter is relatively weaker in promoting expression and the second promoter is relatively stronger in promoter expression. In some embodiments, the first promoter is a simian CMV promoter and the second promoter is a human CMV promoter.

In some embodiments, the alpha subunit and the beta subunit are expressed at the determined ratio by transfecting the cell with a bicistronic nucleic acid encoding the alpha subunit and the beta subunit, wherein the nucleic acid encoding the alpha subunit and the nucleic acid encoding the beta subunit are separated by an internal ribosomal entry site.

In a related aspect, the invention provides methods of promoting the stability and secretion of an IL-12 heterodimer comprised of a p35 subunit and a p40 subunit, comprising expressing the p35 subunit and the p40 subunit in a cell at a ratio in the range of about 1:3 to about 1:15.

In some embodiments, the p35 subunit shares at least 95%, 96%, 97%, 98% or 99% nucleic acid sequence identity with SEQ ID NO:34 and the p40 subunit shares at least 95%, 96%, 97%, 98% or 99% nucleic acid sequence identity with SEQ ID NO:33. In some embodiments, the p35 subunit is SEQ ID NO:34 and the p40 subunit is SEQ ID NO:33.

In some embodiments, the p35 subunit and the p40 subunit are expressed at the ratio in the range of about 1:3 to about 1:15 by cotransfecting the cell with a first nucleic acid encoding the p35 subunit and a second nucleic acid encoding the p40 subunit at the ratio in the range of about 1:3 to about 1:15.

In some embodiments, the p35 subunit and the p40 subunit are expressed at the ratio in the range of about 1:3 to about 1:15 by transfecting the cell with a single plasmid comprising a first nucleic acid encoding the p35 subunit under the control of a first promoter and a second nucleic acid encoding the p40 subunit under the control of a second promoter, wherein the first promoter and the second promoter are of relative expression strengths to allow expression of the p35 subunit and the p40 subunits at the ratio in the range of about 1:3 to about 1:15. In some embodiments for expression of IL-12, the first promoter is a simian CMV promoter and the second promoter is a human CMV promoter.

In some embodiments, the p35 subunit and the p40 subunit are expressed at the ratio in the range of about 1:3 to about 1:15 by transfecting the cell with a bicistronic nucleic acid encoding the p35 subunit and the p40 subunit, wherein the nucleic acid encoding the p35 subunit and the nucleic acid encoding the p40 subunit are separated by an internal ribosomal entry site.

In another aspect, the invention provides methods of promoting the stability and secretion of an IL-23 heterodimer comprised of a p19 subunit and a p40 subunit, comprising expressing the p19 subunit and the p40 subunit in a cell at a ratio in the range of about 1:3 to about 1:15.

In some embodiments, the p19 subunit shares at least 95%, 96%, 97%, 98% or 99% nucleic acid sequence identity with SEQ ID NO:26 and the p40 subunit shares at least 95%, 96%, 97%, 98% or 99% nucleic acid sequence identity with SEQ ID NO:33. In some embodiments, the p19 subunit is SEQ ID NO:26 and the p40 subunit is SEQ ID NO:33.

In some embodiments, the p19 subunit and the p40 subunit are expressed at the ratio in the range of about 1:3 to about 1:15 by cotransfecting the cell with a first nucleic acid encoding the p19 subunit and a second nucleic acid encoding the p40 subunit at the ratio in the range of about 1:3 to about 1:15.

In some embodiments, the p19 subunit and the p40 subunit are expressed at the ratio in the range of about 1:3 to about 1:15 by transfecting the cell with a single plasmid comprising a first nucleic acid encoding the p19 subunit under the control of a first promoter and a second nucleic acid encoding the p40 subunit under the control of a second promoter, wherein the first promoter and the second promoter are of relative expression strengths to allow expression of the p19 subunit and the p40 subunits at the ratio in the range of about 1:3 to about 1:15. In some embodiments for expression of IL-23, the first promoter is a simian CMV promoter and the second promoter is a human CMV promoter.

In some embodiments, the p19 subunit and the p40 subunit are expressed at the ratio in the range of about 1:3 to about 1:15 by transfecting the cell with a bicistronic nucleic acid encoding the p19 subunit and the p40 subunit, wherein the nucleic acid encoding the p19 subunit and the nucleic acid encoding the p40 subunit are separated by an internal ribosomal entry site.

In a further aspect, the invention provides methods of promoting the stability and secretion of an IL-27 heterodimer comprised of a p28 subunit and an EBI3 subunit, comprising expressing the p28 subunit and the EBI3 subunit in a cell at a ratio in the range of about 3:1 to about 15:1.

In some embodiments, the p28 subunit shares at least 95%, 96%, 97%, 98% or 99% nucleic acid sequence identity with SEQ ID NO:29 and the EBI3 subunit shares at least 95%, 96%, 97%, 98% or 99% nucleic acid sequence identity with SEQ ID NO:30. In some embodiments, the p28 subunit is SEQ ID NO:29 and the EBI3 subunit is SEQ ID NO:30.

In some embodiments, the p28 subunit shares at least 95%, 96%, 97%, 98% or 99% nucleic acid sequence identity with SEQ ID NO:27 and the EBI3 subunit shares at least 95%, 96%, 97%, 98% or 99% nucleic acid sequence identity with SEQ ID NO:28. In some embodiments, the p28 subunit is SEQ ID NO:27 and the EBI3 subunit is SEQ ID NO:28.

In some embodiments, the p28 subunit and the EBI3 subunit are expressed at the ratio in the range of about 3:1 to about 15:1 by cotransfecting the cell with a first nucleic acid encoding the p28 subunit and a second nucleic acid encoding the EBI3 subunit at the ratio in the range of about 3:1 to about 15:1.

In some embodiments, the p28 subunit and the EBI3 subunit are expressed at the ratio in the range of about 3:1 to about 15:1 by transfecting the cell with a single plasmid comprising a first nucleic acid encoding the p28 subunit under the control of a first promoter and a second nucleic acid encoding the EBI3 subunit under the control of a second promoter, wherein the first promoter and the second promoter are of relative expression strengths to allow expression of the p28 subunit and the EBI3 subunits at the ratio in the range of about 3:1 to about 15:1. In some embodiments for expression of IL-27, the first promoter is a human CMV promoter and the second promoter is a simian CMV promoter.

In some embodiments, the p28 subunit and the EBI3 subunit are expressed at the ratio in the range of about 3:1 to about 15:1 by transfecting the cell with a bicistronic nucleic acid encoding the p28 subunit and the EBI3 subunit, wherein the nucleic acid encoding the p28 subunit and the nucleic acid encoding the EBI3 subunit are separated by an internal ribosomal entry site.

In a related aspect, the invention provides dual expression vectors for expressing a first subunit and a second subunit of a heterodimeric protein, comprising a first expression cassette for expressing the first subunit under the control of a relatively stronger promoter and a second expression cassette for expressing the second subunit under the control of a relatively weaker promoter.

With respect to the embodiments of the dual expression vectors some embodiments, the first subunit and the second subunit are expressed at a relative ratio in the range of about 3:1 to about 15:1.

In some embodiments, the relatively stronger promoter is a human CMV promoter and the relatively weaker promoter is a simian CMV promoter.

In some embodiments, the heterodimeric protein is an IL-12 family cytokine. In some embodiments, the IL-12 family cytokine is IL-12, and the first subunit is IL-12 p40 and the second subunit is IL-12 p35. In some embodiments, the dual expression vector comprises a first expression cassette that expresses IL-12 p40 under the control of a human CMV promoter and a second expression cassette that expresses IL-12 p35 under the control of the simian CMV promoter. In some embodiments, the p35 subunit shares at least 95%, 96%, 97%, 98% or 99% nucleic acid sequence identity with SEQ ID NO:34 and the p40 subunit shares at least 95%, 96%, 97%, 98% or 99% nucleic acid sequence identity with SEQ ID NO:33. In some embodiments, the p35 subunit is SEQ ID NO:34 and the p40 subunit is SEQ ID NO:33.

In some embodiments, the IL-12 family cytokine is IL-23, and the first subunit is IL-23 p40 and the second subunit is IL-23 p19. In some embodiments, the dual expression vector comprises a first expression cassette that expresses IL-23 p40 (i.e., IL-12 p40) under the control of a human CMV promoter and a second expression cassette that expresses IL-23 p19 under the control of the simian CMV promoter. In some embodiments, the p19 subunit shares at least 95%, 96%, 97%, 98% or 99% nucleic acid sequence identity with SEQ ID NO:26 and the p40 subunit shares at least 95%, 96%, 97%, 98% or 99% nucleic acid sequence identity with SEQ ID NO:33. In some embodiments, the p19 subunit is SEQ ID NO:26 and the p40 subunit is SEQ ID NO:33.

In some embodiments, the IL-12 family cytokine is IL-27, and the first subunit is IL-27 p28 and the second subunit is EBI3. In some embodiments, the dual expression vector comprises a first expression cassette that expresses IL-27 p28 under the control of a human CMV promoter and a second expression cassette that expresses IL-27 EBI3 under the control of the simian CMV promoter. In some embodiments, the p28 subunit shares at least 95%, 96%, 97%, 98% or 99% nucleic acid sequence identity with SEQ ID NO:29 and the EBI3 subunit shares at least 95%, 96%, 97%, 98% or 99% nucleic acid sequence identity with SEQ ID NO:30. In some embodiments, the p28 subunit is SEQ ID NO:29 and the EBI3 subunit is SEQ ID NO:30. In some embodiments, the p28 subunit shares at least 95%, 96%, 97%, 98% or 99% nucleic acid sequence identity with SEQ ID NO:27 and the EBI3 subunit shares at least 95%, 96%, 97%, 98% or 99% nucleic acid sequence identity with SEQ ID NO:28. In some embodiments, the p28 subunit is SEQ ID NO:27 and the EBI3 subunit is SEQ ID NO:28.

In some embodiments, the dual expression vector comprises a nucleic acid sequence of SEQ ID NO:1 (plasmid AG181). In some embodiments, the dual expression vector comprises a nucleic acid sequence of SEQ ID NO:3 (plasmid AG157). In some embodiments, the dual expression vector comprises a nucleic acid sequence of SEQ ID NO:7 (plasmid AG184). In some embodiments, the dual expression vector comprises a nucleic acid sequence of SEQ ID NO:10 (plasmid AG205). In some embodiments, the dual expression vector comprises a nucleic acid sequence of SEQ ID NO:14 (plasmid AG216). In some embodiments, the dual expression vector comprises a nucleic acid sequence of SEQ ID NO:32.

In a related aspect, the invention provides a nucleic acid sequence pair encoding an improved human interleukin-23 (IL-23) protein heterodimer comprised of a p19 subunit and a p40 subunit, wherein the nucleic acid sequence encoding the p19 subunit shares at least 95%, 96%, 97%, 98% or 99% nucleic acid sequence identity to SEQ ID NO:26 and the nucleic acid sequence encoding the p40 subunit shares at least 95%, 96%, 97%, 98% or 99% nucleic acid sequence identity to SEQ ID NO:33. In some embodiments, the nucleic acid sequence encoding the p19 subunit is SEQ ID NO:26 and the nucleic acid sequence encoding the p40 subunit is SEQ ID NO:33.

In another aspect, the invention provides a nucleic acid sequence pair encoding an improved human interleukin-27 (IL 27) protein heterodimer comprised of a p28 subunit and an EBI3 subunit, wherein the nucleic acid sequence encoding the p28 subunit shares at least 95%, 96%, 97%, 98% or 99% nucleic acid sequence identity to SEQ ID NO:29 and the nucleic acid sequence encoding the EBI3 subunit shares at least 95%, 96%, 97%, 98% or 99% nucleic acid sequence identity to SEQ ID NO:30. In some embodiments, the nucleic acid sequence encoding the p28 subunit is SEQ ID NO:29 and the nucleic acid sequence encoding the EBI3 subunit is SEQ ID NO:30.

In a related aspect, the invention provides a nucleic acid sequence pair encoding an improved murine interleukin-27 (IL 27) protein heterodimer comprised of a p28 subunit and an EBI3 subunit, wherein the nucleic acid sequence encoding the p28 subunit shares at least 95%, 96%, 97%, 98% or 99% nucleic acid sequence identity to SEQ ID NO:27 and the nucleic acid sequence encoding the EBI3 subunit shares at least 95%, 96%, 97%, 98% or 99% nucleic acid sequence identity to SEQ ID NO:28. In some embodiments, the nucleic acid sequence encoding the p28 subunit is SEQ ID NO:27 and the nucleic acid sequence encoding the EBI3 subunit is SEQ ID NO:28.

The invention further provides host cells, e.g., mammalian host cells, comprising the vectors and nucleic acids of the invention. The invention further provides expression cassettes and expression vectors comprising the improved IL-12 family nucleic acid pairs. The invention also provides compositions comprising the vectors and nucleic acids of the invention in a pharmaceutically acceptable carrier or excipient, e.g., for use as an adjuvant.

DEFINITIONS

A "IL-12 family cytokine" refers to a heterodimeric ligands comprised of an α subunit with helical structure (e.g., IL-12p35, IL-23p19, IL-27p28) and a β subunit (e.g., IL-12p40, IL-23p40 (which is identical to IL-12p40), EBI3). Exemplary members include IL-12, IL-23 and IL-27. Biologically active IL-12 is comprised of p35 and p40 subunits that together form the IL-12p70 heterodimer, which binds specifically to the IL-12Rβ1/IL-12Rβ2 receptor. IL-23 is comprised of the IL-12 p40 subunit paired with a p19 subunit protein. The IL-23 heterodimer binds to IL-12Rβ1 paired not with the IL-12Rβ2 subunit, but with the unique IL-23R. IL-27 is a heterodimeric cytokine containing the Epstein-Barr virus-induced gene 3 (EBI3) subunit (related to the IL-12 p40 subunit) paired with a p28 subunit with homology to the IL-12 p35 subunit. IL-27 binds to a receptor comprised of the IL-27Rα subunit and the gp130 subunit. IL-12 family cytokines are predominantly produced by activated monocytes, macrophages, and dendritic cells. The respective receptors are broadly expressed in many lymphocyte subsets and show some variation in expression levels on naïve- versus memory-phenotype CD4+ T cells. IL-12 family cytokine receptors are expressed on macrophages, dendritic cells, NK cells, and activated T cells. Functionally, IL-12 family cytokines regulate diverse functions of several lymphocyte subsets. They play a role in NK cell activation, as co-factors for T cell receptor (TCR)-induced T cell proliferation, as promoters of T cell cytokine production, and as regulators of B cell antibody production. IL-12 family cytokines are reviewed, for example, in Trinchieri, et al., *Immunity* (2003) 19:641-644; Brombacher, et al, *Trends in Immunol* (2003) 24(4):207-212; Hölscher, et al., *Med Microbiol Immunol* (2004) 193:1-17; Goriely, et al., *Nature Rev Immunol* (2008) 8(1):81-6; Kastelein, et al., *Annu Rev Immunol* (2007) 25:221-42; Beadling and Slifka, *Arch Immunol Ther Exp* (2006) 54(1):15-24; and Goriely and Goldman, *Am J Transplant* (2007) 7(2):278-84.

The terms "IL-12 protein heterodimer" or "IL-12 heterodimer" or "IL-12p70" refer to an IL-12 cytokine protein composed of its two monomeric polypeptide subunits, an IL-12p35 chain and an IL-12p40 chain. See, for example, Airoldi, et al., *Haematologica* (2002) 87:434-42.

The term "native mammalian IL-12" refers to any naturally occurring interleukin-12 nucleic acid and amino acid sequences of the IL-12 monomeric sequences, IL-12p35 and IL-12p40 from a mammalian species. Those of skill in the art will appreciate that interleukin-12 sequences are publicly available in gene databases, for example, GenBank through the National Center for Biotechnological Information on the worldwideweb at ncbi.nlm.nih.gov/entrez/query.fcgi?db=Nucleotide and ncbi.nlm.nih.gov/entrez/query.fcgi?db=Protein. Exemplified native mammalian IL-12 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-12 nucleic acid sequences include NM_002187 (human p40), NM_000882 (human p35), AY234218 (baboon p40), AY234219 (baboon p35); U19841 (rhesus monkey p40), U19842 (rhesus monkey p35); NM_022611 (rat p40), NM_053390 (rat p35), and NM_008352 (mouse p40), NM_008351 (mouse p35). Accession numbers for exemplified native mammalian IL-12 amino acid sequences include NP_002178 (human p40), NP_000873 (human p35), AAK84425 or AAD56385 (human p35); AAA86707 (rhesus monkey p35); P48095 (rhesus monkey p40); NP_072133 (rat p40), AAD51364 (rat p35), and NP_032378 (mouse p35), NP_032377 (mouse p40).

The term "interleukin-12" or "IL-12" refers to a polypeptide that has at least 90%, 91%, 92%, 93%, 94%, 95%, 96%, 97%, 98% or 99% sequence identity to a native mammalian IL-12 amino acid sequence (e.g., as described above and herein), or a nucleotide encoding such a polypeptide, is biologically active, meaning the mutated protein ("mutein") has functionality similar (75% or greater) to that of a native IL-12 protein in at least one functional assay. Exemplified functional assays of an IL-12 polypeptide include inducing the production of interferon-gamma (IFN-γ), for example, by T cells or natural killer (NK) cells, and promoting the differentiation of T helper-1 (Th1) cells. A T helper cell differentiated into a Th1 cell can be identified by secretion of IFN-γ. IFN-γ secreted by IL-12 stimulated T cells or NK cells can be conveniently detected, for example, in serum or cell culture supernatant using ELISA. ELISA methods and techniques are well known in the art, and kits for detecting IFN-γ are commercially available (e.g., R&D Systems, Minneapolis, Minn.; Peprotech, Rocky Hill, N.J.; and Biosource Intl., Camarillo, Calif.) See also, Coligan, et al., Current Methods in Immunology, 1991-2006, John Wiley & Sons; Harlow and Lane, *Using Antibodies: A Laboratory Manual*, 1998, Cold Spring Harbor Laboratory Press; and *The ELISA Guidebook*, Crowther, ed., 2000, Humana Press.

The terms "IL-23 protein heterodimer" or "IL-23 heterodimer" or "IL-23" refer to an IL-23 cytokine protein composed of its two monomeric polypeptide subunits, an IL-23p19 chain and an IL-23p40 chain (the same as an IL-12p40 chain). See, e.g., Kastelein, et al., *Annu Rev Immunol* (2007) 25:221-42; and Hunter, et al, *Nature Rev Immunol* (2005) 5:521-531.

The term "native mammalian IL-23" refers to any naturally occurring interleukin-23 nucleic acid and amino acid sequences of the IL-23 monomeric sequences, IL-23p19 and an IL-23p40 from a mammalian species (identical to the IL-12p40 described herein). Those of skill in the art will appreciate that interleukin-23 sequences are publicly available in gene databases, for example, GenBank. Exemplified native mammalian IL-23 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-23 p19 nucleic acid sequences include NM_016584 (human); AY359083 (human); AF301620 (human); XM_522436 (Pan troglodytes); and XM_001115026 (Macaca mulatta). Accession numbers for exemplified native mammalian IL-23 p19 amino acid sequences include NP_057668 (human); AAG37232 (human); AAH66267 (human); AAH66269 (human); XP_001115026 (*Macaca mulatta*); NP_001075991 (*Equus caballus*); ABB01676 (*Felis catus*); NP_569094 (*Rattus norvegicus*); ACC77208 (*Bos taurus*); and NP_112542 (*Mus musculus*). Additional sequences are described herein.

The term "interleukin-23" or "IL-23" refers to a polypeptide that has at least 90%, 91%, 92%, 93%, 94%, 95%, 96%, 97%, 98% or 99% sequence identity to a native mammalian IL-23 amino acid sequence (e.g., as described above and herein), or a nucleotide encoding such a polypeptide, is biologically active, meaning the mutated protein ("mutein") has functionality similar (75% or greater) to that of a native IL-23 protein in at least one functional assay. Both IL-23 and IL-12 can activate the transcription activator STAT4, and stimulate the production of interferon-gamma (IFNγ). In contrast to IL-12, which acts mainly on naive CD4(+) T cells, IL-23 preferentially acts on memory CD4(+) T cells. IL-23 promotes IL-17 production by several T-cell types including the T helper 17 (Th17)-cell subset. IL-17 is a potent pro-inflammatory cytokine that induces tissue damage at least in part through neutrophil recruitment. Exemplified functional assays of an IL-23 polypeptide include inducing the production of interferon-gamma (IFN-γ), for example, by T cells or natural killer (NK) cells, and promoting the differentiation of Th17 cells. See, e.g., Kastelein, et al., *Annu Rev Immunol* (2007) 25:221-42; Goriely, et al., *Nature Rev Immunol* (2008) 8(1):81-6; and Goriely and Goldman, *Am J Transplant* (2007) 7(2):278-84. IFN-γ secreted by IL-23 stimulated T cells or NK cells can be conveniently detected, for example, in serum or cell culture supernatant using ELISA, as described above.

The terms "IL-27 protein heterodimer" or "IL-27 heterodimer" or "IL-27" refer to an IL-27 cytokine protein composed of its two monomeric polypeptide subunits, an IL-27p28 chain and a Epstein-Barr virus-induced gene 3 (EBI3) subunit. The IL-27p28 subunit shares structural homology with the IL-12p35 subunit; the EBI3 subunit shares structural homology with the IL-12p40 subunit. See, e.g., Kastelein, et al., *Annu Rev Immunol* (2007) 25:221-42; and Hunter, et al, *Nature Rev Immunol* (2005) 5:521-531.

The term "native mammalian IL-27" refers to any naturally occurring interleukin-27 nucleic acid and amino acid sequences of the IL-27 monomeric sequences, IL-27p28 and an Epstein-Barr virus-induced gene 3 (EBI3) subunit from a mammalian species. Those of skill in the art will appreciate that interleukin-27 sequences are publicly available in gene databases, for example, GenBank. Exemplified native mammalian IL-23 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-27 p28 nucleic acid sequences include NM_145659 (human); BC062422 (human); AY099296 (human); EF064720 (human); XM_01169965 (*Pan troglodytes*); XM_001138224 (*Pan troglodytes*); XM_001097165

(Macaca mulatta); BC119402 (*Mus musculus*); NM_145636 (*Mus musculus*); and XM_344962 (*Rattus norvegicus*). Accession numbers for exemplified native mammalian IL-27 p28 amino acid sequences include NP_663634 (human); AAH62422 (human); AAM34498 (human); XP_001496678 (*Equus caballus*); XP_001138224 (Pan troglodytes); XP_849828 (*Canis familiaris*); NP_663611 (*Mus musculus*); EDL17402 (*Mus musculus*) and XP_344963 (*Rattus norvegicus*). Accession numbers for exemplified native mammalian EBI3 nucleic acid sequences include NM_005755 (human); BC015364 (human); BC046112 (human); L08187 (human); EF064740 (human). Accession numbers for exemplified native mammalian EBI3 amino acid sequences include NP_005746 (human); ABK41923; EAW69244 (human); AAA93193 (human); XP_001138182 (*Pan troglodytes*); NP_001093835 (*Bos taurus*); XP_542161 (*Canis familiaris*); XP_001118027 (*Macaca mulatta*); NP_056581 (*Mus musculus*); and NP_001102891 (*Rattus norvegicus*). Additional sequences are described herein.

The term "interleukin-27" or "IL-27" refers to a polypeptide that has at least 90%, 91%, 92%, 93%, 94%, 95%, 96%, 97%, 98% or 99% sequence identity to a native mammalian IL-27 amino acid sequence (e.g., as described above and herein), or a nucleotide encoding such a polypeptide, is biologically active, meaning the mutated protein ("mutein") has functionality similar (75% or greater) to that of a native IL-27 protein in at least one functional assay. IL-27 shares homology with IL-12p70 and IL-23 and signals through a receptor that shares the gp130 chain with the IL-6 receptor. IL-27 promotes Th1-cell differentiation, an effect that is most prominent in the absence of IL-12. However, IL-27 also has a major regulatory role by limiting Th17-cell differentiation. IL-27 also has a profound suppressive effect on the CD4+ T cell production of IL-2. IL-27 activates STAT1 and thereby upregulates suppressor of cytokine signaling 3 (SOCS3). See, e.g., Kastelein, et al., *Annu Rev Immunol* (2007) 25:221-42; Goriely, et al., *Nature Rev Immunol* (2008) 8(1):81-6; and Goriely and Goldman, *Am J Transplant* (2007) 7(2):278-84.

The term "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Degenerate codon substitutions can be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Degenerate codon substitutions for naturally occurring amino acids are in Table 1.

TABLE 1

| 1$^{st}$ position | 2$^{nd}$ position | | | | 3$^{rd}$ position |
|---|---|---|---|---|---|
| (5' end) | U(T) | C | A | G | (3' end) |
| U(T) | Phe | Ser | Tyr | Cys | U(T) |
| | Phe | Ser | Tyr | Cys | C |
| | Leu | Ser | STOP | STOP | A |
| | Leu | Ser | STOP | Trp | G |
| C | Leu | Pro | His | Arg | U(T) |
| | Leu | Pro | His | Arg | C |
| | Leu | Pro | Gln | Arg | A |
| | Leu | Pro | Gln | Arg | G |
| A | Ile | Thr | Asn | Ser | U(T) |
| | Ile | Thr | Asn | Ser | C |
| | Ile | Thr | Lys | Arg | A |
| | Met | Thr | Lys | Arg | G |
| G | Val | Ala | Asp | Gly | U(T) |
| | Val | Ala | Asp | Gly | C |
| | Val | Ala | Glu | Gly | A |
| | Val | Ala | Glu | Gly | G |

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region to a reference sequence (e.g., any one of the Accession Numbers or SEQ ID NOs disclosed herein) when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of am amino acid or nucleic acid sequences.

For sequence comparison, typically one sequence acts as a reference sequence, to which test sequences are compared (here, an entire "native mammalian" IL-12 p35 or IL-12 p40 amino acid or nucleic acid sequence). When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A preferred example of algorithm that is suitable for determining percent sequence identity and sequence similarity are the BLAST algorithms, which are described in Altschul et al., *Nuc. Acids Res.* 25:3389-3402 (1977) and Altschul et al., *J. Mol. Biol.* 215:403-410 (1990), respectively. BLAST software is publicly available through the National Center for Biotechnology Information on the worldwide web at ncbi.nlm.nih.gov/. Both default parameters or other non-default parameters can be used. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The term "GC content" refers to the percentage of a nucleic acid sequence comprised of deoxyguanosine (G) and/or deoxycytidine (C) deoxyribonucleosides, or guanosine (G) and/or cytidine (C) ribonucleoside residues.

The terms "mammal" or "mammalian" refer to any animal within the taxonomic classification mammalia. A mammal can refer to a human or a non-human primate. A mammal can refer to a domestic animal, including for example, canine, feline, rodentia, including lagomorpha, murine, rattus, Cricetinae (hamsters), etc. A mammal can refer to an agricultural animal, including for example, bovine, ovine, porcine, equine, etc.

DETAILED DESCRIPTION

1. Introduction

Figure 1:
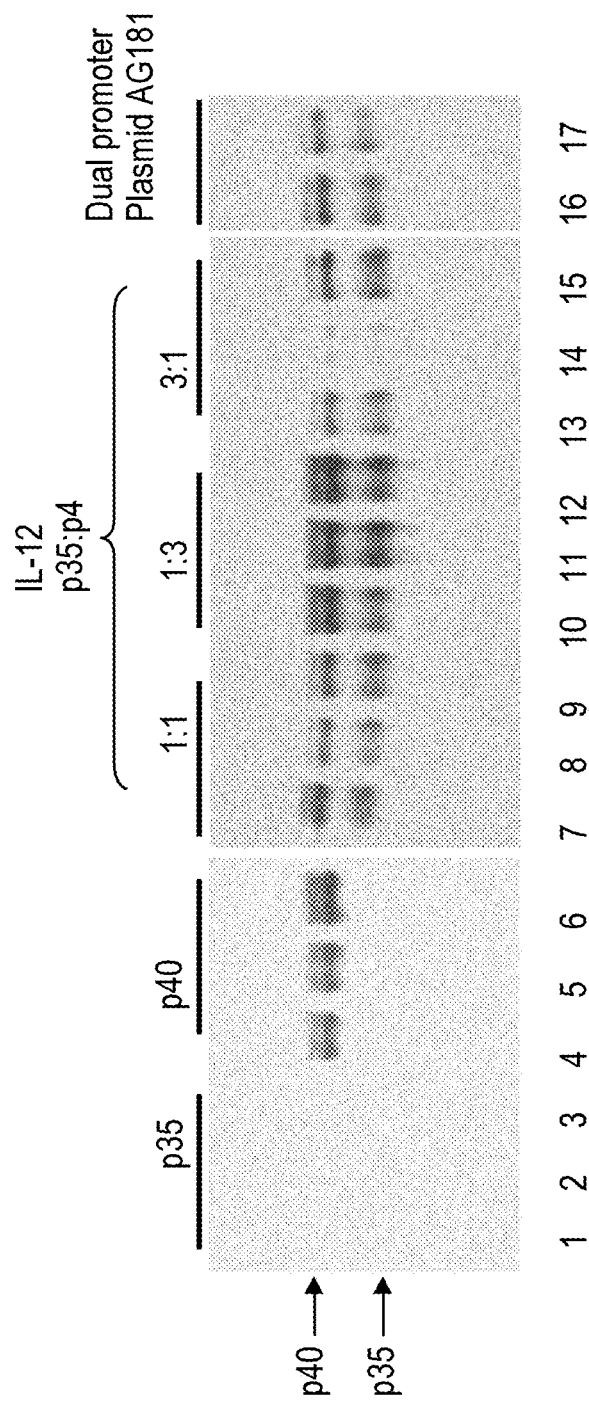
FIG. 1 demonstrates that the presence of excess of the IL-12 p40 subunit promotes stabilization and increased secretion of the IL-12 p35 subunit, resulting in increased production of human IL-12 heterodimer (p35+p40). Human 293 cells were transfected with 100 ng each of two plasmids expressing the individual subunits of human IL-12: p35 (lanes 1-3) and p40 (lanes 4-6), respectively. Three independent (identical) clones of each plasmid were purified and tested in the three lanes. Cotransfection of the p35+p40 subunits at a ratio of 1:1 (lanes 7-9), 1:3 (lanes 11-13) or 3:1 (lanes 13-15) were performed in triplicate. Transfection of IL-12 from the dual promoter plasmid AG181 (see, FIG. 2 below) was performed using two independent clones (lanes 16, 17). Supernatants were analyzed on Western immunoblots, and probed with an anti human IL-12 p70 antibody. In the presence of increased levels of the p40 subunit higher levels of the IL-12 heterodimer are produced and secreted. All coding sequence were improved, i.e., had inhibitory and/or instability sequences minimized, for expression.

The invention relates to increased expression levels of heterodimeric proteins, e.g., IL-12 family cytokines, and in general multimeric protein production by optimizing the relative expression ratios of the subunits in vitro and in vivo. Surprisingly, expressing the first and second subunits of a heterodimeric protein, e.g., an IL-12 family cytokine, at appropriate relative molar ratios results in increased expression levels, e.g., in the extracellular space, that are at least about 3-fold or 4-fold as measured in vitro (e.g., concentration in culture media) and at least about 20-fold or 30-fold as measured in vivo (e.g., concentration in serum) in comparison to expressing the first and second subunits at an equimolar ratio. Furthermore, achieving higher levels of extracellular expression of IL-12 family cytokines facilitates their efficacious concentrations when administered in vivo.

The invention finds use, for example, for the improved expression of heterodimeric and multimeric cytokines and other proteins of mammalian origin, e.g., murine, rhesus and human origin. Experimental testing is performed to identify which subunit is limiting and general methods are provided for increasing expression of heterodimeric polypeptides.

Once determined, relative expression ratios of the subunits can be achieved using any known methods. For example, optimized expression can be achieved upon coordinate production of optimal ratios of the respective subunits. Alternatively, the two or more subunits can be expressed from a single plasmid containing two or more promoters that differ in their expression strength (e.g., the human CMV promoter is stronger than the simian CMV promoter). Alternatively, the two subunits can be produced by bicistronic mRNAs (for example, ones that have internal ribosome entry sites, IRES) in the appropriate order so that expression ratios are optimal. The use of these optimized expression strategies leads to improvement of cytokine expression and prevents negative effects due to the excess production of single chains. This strategy is of general application to express multimeric proteins.

2. Nucleic Acid Sequences

As described herein, the nucleic acid and amino acid sequences of IL-12 family cytokine alpha and beta subunits, e.g., IL-12, IL-23, and IL-27 alpha and beta subunits, are known in the art. The sequences of native or naturally occurring IL-12 family cytokine subunits can be used. Alternatively, the coding sequences of one or more of the alpha and beta subunits can be improved to minimize or eliminate inhibitory or instability sequences according to known methods, e.g., described for example, in U.S. Pat. Nos. 5,965,726; 5,972,596; 6,174,666; 6,291,664; 6,414,132; and 6,794,498 and in PCT Publication Nos. WO 07/084,364 and WO 07/084,342, the disclosures of each of which are hereby incorporated herein by reference in their entirety for all purposes.

The improved high expressing IL-12 family cytokine nucleic acid sequences of the invention are generally based on a native mammalian interleukin-12 family cytokine coding sequence as a template. Nucleic acids sequences encoding native interleukin-12 family cytokines can be readily found in publicly available databases including, e.g., nucleotide, protein and scientific databases available on the worldwide web through the National Center for Biotechnology Information at ncbi.nlm.nih.gov. Native IL-12 family cytokine nucleic acid sequences can be conveniently cloned from mammalian dendritic cells and macrophages following appropriate stimulation (See, e.g., Goriely, et al., *Nature Rev Immunol* (2008) 8(1):81-6; Kastelein, et al., *Annu Rev Immunol* (2007) 25:221-42; Beadling and Slifka, *Arch Immunol Ther Exp* (2006) 54(1):15-24; and Goriely and Goldman, *Am J Transplant* (2007) 7(2):278-84). Protocols for isolation and stimulation of desired immune cell populations are well known in the art. See, for example, *Current Protocols in Immunology*, Coligan, et al., eds., 1991-2008, John Wiley & Sons.

The sequences are modified according to methods that simultaneously rectify several factors affecting mRNA traffic, stability and expression. Codons are altered to change the overall mRNA AT(AU)-content, to minimize or remove all potential splice sites, and to alter any other inhibitory sequences and signals affecting the stability and processing of mRNA such as runs of A or T/U nucleotides, AATAAA, ATTTA and closely related variant sequences, known to negatively affect mRNA stability. The methods applied to IL-12 coding nucleic acid sequences in the present application have been described in U.S. Pat. Nos. 6,794,498; 6,414,132; 6,291,664; 5,972,596; and 5,965,726 the disclosures of each of which are hereby incorporated herein by reference in their entirety for all purposes.

Generally, the changes to the nucleotide bases or codons of a coding IL-12 family cytokine sequences do not alter the amino acid sequence of the translated monomers comprising an IL-12 family cytokine heterodimer from the native alpha and beta subunit polypeptides. The changes are based upon the degeneracy of the genetic code, utilizing an alternative codon for an identical amino acid, as summarized in Table 1, above. In certain embodiments, it will be desirable to alter one or more codons to encode a similar amino acid residue rather than an identical amino acid residue. Applicable conservative substitutions of coded amino acid residues are described above.

Oftentimes, in carrying out the present methods for increasing the stability of an IL-12 family cytokine coding sequence, a relatively more A/T-rich codon of a particular amino acid is replaced with a relatively more G/C rich codon encoding the same amino acid. For example, amino acids encoded by relatively more A/T-rich and relatively more G/C rich codons are shown in Table 2.

TABLE 2

| Amino Acid | relatively more A/T-rich codon(s) | relatively more G/C-rich codon(s) |
|---|---|---|
| Ala | GCA, GCT | GCC, GCG |
| Asn | AAT | AAC |
| Asp | GAT | GAC |
| Arg | CGA, CGT, AGA | CGC, CGG, AGG |
| Cys | TGT | TGC |
| Gln | CAA | CAG |
| Glu | GAA | GAG |
| Gly | GGA, GGT | GGC, GGG |
| His | CAT | CAC |
| Ile | ATA, ATT | ATC |
| Leu | TTA, CTA, CTT | TTG, CTC, CTG |
| Lys | AAA | AAG |
| Phe | TTT | TTC |
| Pro | CCA, CCT | CCC, CCG |
| Ser | TCA, TCT, AGT | TCC, TCG, AGC |
| Thr | ACA, ACT | ACC, ACG |
| Tyr | TAT | TAC |
| Val | GTA, GTT | GTC, GTG |

Depending on the number of changes introduced, the improved IL-12 family cytokine nucleic acid sequences of the present invention can be conveniently made as completely synthetic sequences. Techniques for constructing synthetic nucleic acid sequences encoding a protein or synthetic gene sequences are well known in the art. Synthetic gene sequences can be commercially purchased through any of a number of service companies, including DNA 2.0 (Menlo Park, Calif.), Geneart (Toronto, Ontario, Canada), CODA Genomics (Irvine, Calif.), and GenScript, Corporation (Piscataway, N.J.). Alternatively, codon changes can be introduced using techniques well known in the art. The modifications also can be carried out, for example, by site-specific in vitro mutagenesis or by PCR or by any other genetic engineering methods known in art which are suitable for specifically changing a nucleic acid sequence. In vitro mutagenesis protocols are described, for example, in In Vitro *Mutagenesis Protocols*, Braman, ed., 2002, Humana Press, and in Sankaranarayanan, *Protocols in Mutagenesis*, 2001, Elsevier Science Ltd.

High level expressing improved IL-12 family cytokine sequences can be constructed by altering select codons throughout a native IL-12 family cytokine nucleic acid sequence, or by altering codons at the 5'-end, the 3'-end, or within a middle subsequence. It is not necessary that every codon be altered, but that a sufficient number of codons are altered so that the expression (i.e., transcription and/or translation) of the improved IL-12 family cytokine nucleic acid sequence is at least about 10%, 20%, 30%, 40%, 50%, 60%, 70%, 80%, 90%, 1-fold, 2-fold, 3-fold, 4-fold, 5-fold, 6-fold, or more abundant in comparison to expression from a native IL-12 family cytokine nucleic acid sequence under the same conditions. Expression can be detected over time or at a designated endpoint, using techniques known to those in the art, for example, using gel electrophoresis or anti-IL-12 antibodies in solution phase or solid phase binding reactions (e.g., ELISA, immunohistochemistry). ELISA kits for detecting either the alpha and beta subunits of IL-12 family cytokine family polypeptides and heterodimers are commercially available from, for example, R & D Systems (Minneapolis, Minn.), Invitrogen-Biosource (Carlsbad, Calif.), eBioscience (San Diego, Calif.), Santa Cruz Biotech (Santa Cruz, Calif.) and PeproTech, (Rocky Hill, N.J.).

The GC-content of an improved IL-12 family cytokine nucleic acid sequence is usually increased in comparison to a native IL-12 family cytokine nucleic acid sequence when applying the present methods. For example, the GC-content of an improved IL-12 p35, IL-12 p40 (IL-23 p40), IL-23 p19, IL-27 p28 or IL-27 EBI3 nucleic acid sequence can be at least about 50%, 51%, 52%, 53%, 54%, 55%, 56%, 57%, 58%, 59%, 60%, 61%, 62%, 63%, 64%, 65%, 70%, or more.

Exemplary improved IL-12 heterodimer sequences (i.e., p35 and p40 subunits) are described, for example, in PCT Publication No. WO 2007/084364. In some embodiments, the improved nucleic acid sequence encoding a human IL-23 p19 with reduced inhibitory/instability sequences is SEQ ID NO:26. In some embodiments, the improved nucleic acid sequence encoding a murine IL-27 p28 with reduced inhibitory/instability sequences is SEQ ID NO:27. In some embodiments, the improved nucleic acid sequence encoding a murine IL-27 EBI3 with reduced inhibitory/instability sequences is SEQ ID NO:28. In some embodiments, the improved nucleic acid sequence encoding a human IL-27 p28 with reduced inhibitory/instability sequences is SEQ ID NO:29. In some embodiments, the improved nucleic acid sequence encoding a human IL-27 EBI3 with reduced inhibitory/instability sequences is SEQ ID NO:30.

Once a high level expressing improved IL-12 nucleic acid sequence has been constructed, it can be cloned into a cloning vector, for example a TA-cloning® vector (Invitrogen, Carlsbad, Calif.) before subjecting to further manipulations for insertion into one or more expression vectors. Manipulations of improved IL-12 nucleic acid sequences, including recombinant modifications and purification, can be carried out using procedures well known in the art. Such procedures have been published, for example, in Sambrook and Russell, *Molecular Cloning: A Laboratory Manual*, 2001, Cold Spring Harbor Laboratory Press and *Current Protocols in Molecular Biology*, Ausubel, et al., eds., 1987-2008, John Wiley & Sons.

3. Expression Vectors

The alpha and beta subunit chains of the IL-12 family cytokines can be recombinantly expressed from a single plasmid or expression vector or from multiple plasmids or expression vectors. The alpha and beta subunit chains can be expressed from a single expression cassette or separate, independent expression cassettes. The expression vectors of the invention typically have at least two independent expression cassettes, one that will express an alpha subunit and one that will express a beta subunit of the heterodimer. Within each expression cassette, sequences encoding one or both IL-12 family cytokine subunit chains will be operably linked to expression regulating sequences. "Operably linked" sequences include both expression control sequences that are contiguous with the nucleic acid of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance protein stability; and when desired, sequences that enhance protein secretion. The regulating sequences independently can be the same or different between the two expression cassettes. Usually, the regulating sequences will be different. When expressing the alpha and beta subunit chains from a single expression cassette, an internal ribosome entry site (IRES) is included.

The expression vector can optionally also have a third independent expression vector for expressing a selectable marker. Selectable markers are well known in the art, and can include, for example, proteins that confer resistance to an antibiotics, fluorescent proteins, antibody epitopes, etc. Exemplified markers that confer antibiotic resistance include sequences encoding β-lactamases (against β-lactams including penicillin, ampicillin, carbenicillin), or sequences encoding resistance to tetracylines, aminoglycosides (e.g., kanamycin, neomycin), etc. Exemplified fluorescent proteins include green fluorescent protein, yellow fluorescent protein and red fluorescent protein.

The promoter(s) included in the expression cassette(s) should promote expression of one or both of the alpha and beta subunit chains in a mammalian cell. The promoter or promoters can be viral, oncoviral or native mammalian, constitutive or inducible, or can preferentially regulate transcription of one or both alpha and beta subunit chains in a particular tissue type or cell type (e.g., "tissue-specific").

A "constitutive" promoter is a promoter that is active under most environmental and developmental conditions. Exemplified constitutive promoters in mammalian cells include oncoviral promoters (e.g., simian cytomegalovirus (CMV), human CMV, simian virus 40 (SV40), rous sarcoma virus (RSV)), promoters for immunoglobulin elements (e.g., IgH), promoters for "housekeeping" genes (e.g., β-actin, dihydrofolate reductase).

As discussed below, the promoters controlling the expression of the alpha and beta subunits can be of relatively different (weaker or stronger) strengths to allow for expression of the alpha and beta subunits at the desired relative molar ratios. For example, the relatively stronger promoter can be a human CMV promoter and the relatively weaker promoter can be a simian CMV promoter. In another embodiment, the relatively stronger promoter can be a constitutive promoter and the relatively weaker promoter can be an inducible promoter.

In another embodiment, inducible promoters may be desired. An "inducible" promoter is a promoter that is active under environmental or developmental regulation. Inducible promoters are those which are regulated by exogenously supplied compounds, including without limitation, a zinc-inducible metallothionine (MT) promoter; an isopropyl thiogalactose (IPTG)-inducible promoter, a dexamethasone (Dex)-inducible mouse mammary tumor virus (MMTV) promoter; a tetracycline-repressible system (Gossen et al, *Proc. Natl. Acad. Sci. USA*, 89: 5547-5551 (1992)); the tetracycline-inducible system (Gossen et al., *Science*, 268: 1766-1769 (1995); see also Harvey et al., *Curr. Opin. Chem. Biol.*, 2: 512-518 (1998)); the RU486-inducible system (Wang et al., *Nat. Biotech.*, 15: 239-243 (1997) and Wang et al., *Gene Ther.*, 4: 432-441 (1997)); and the rapamycin-inducible system (Magari et al. *J. Clin. Invest.*, 100: 2865-2872 (1997)). Other types of inducible promoters which can be useful in this context are those which are regulated by a specific physiological state, e.g., temperature, acute phase, or in replicating cells only.

In another embodiment, the native promoter for a mammalian IL-12 family cytokine subunit can be used. The native promoter may be preferred when it is desired that expression of improved IL-12 family cytokine sequences should mimic the native expression. The native promoter can be used when expression of the improved IL-12 family cytokine must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic expression of a native IL-12 family cytokine polypeptide.

In another embodiment, the improved IL-12 family cytokine sequences can be operably linked to a tissue-specific promoter. For instance, if expression in lymphocytes or monocytes is desired, a promoter active in lymphocytes or monocytes, respectively, should be used. Examples of promoters that are tissue-specific are known for numerous tissues, including liver (albumin, Miyatake et al. *J. Virol.*, 71: 5124-32 (1997); hepatitis B virus core promoter, Sandig et al., *Gene Ther.*, 3: 1002-9 (1996); alpha-fetoprotein (AFP), Arbuthnot et al., *Hum. Gene Ther.* 7: 1503-14 (1996)), bone (osteocalcin, Stein et al., *Mol. Biol. Rep.*, 24: 185-96 (1997); bone sialoprotein, Chen et al., *J. Bone Miner. Res.*, 11: 654-64 (1996)), lymphocytes (CD2, Hansal et al., *J. Immunol.*, 161: 1063-8 (1998); immunoglobulin heavy chain; T cell receptor a chain), neuronal (neuron-specific enolase (NSE) promoter, Andersen et al. *Cell. Mol. Neurobiol.*, 13: 503-15 (1993); neurofilament light-chain gene, Piccioli et al., *Proc. Natl. Acad. Sci. USA*, 88: 5611-5 (1991); the neuron-specific vgf gene, Piccioli et al., *Neuron*, 15: 373-84 (1995)); among others.

Figure 2:
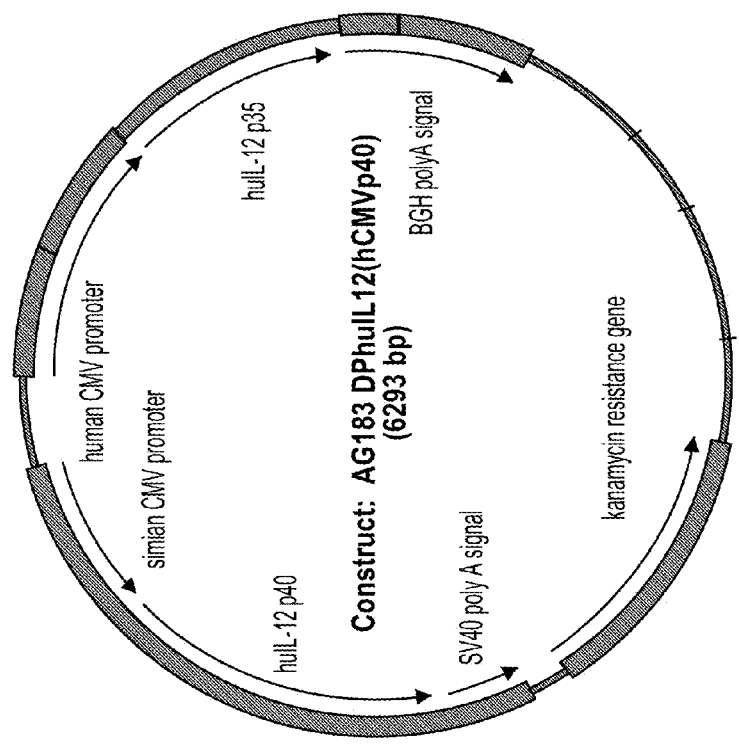
FIG. 2 provides a schematic of exemplary dual expression vectors for use in the present invention. The dual expression plasmids contain the human CMV promoter (stronger) and the bovine poly A signal, and the simian CMV promoter (weaker) and the SV40 polyA signal; the plasmid backbone contains the kanamycin resistance gene. In the plasmid AG181, the IL-12 p40 subunit is expressed from the stronger human CMV promoter and p35 is expressed from the weaker simian CMV promoter. In the plasmid AG183, the IL-12 p35 subunit is expressed from the stronger human CMV promoter and the IL-12 p40 subunit is expressed from the weaker simian CMV promoter.
Figure 2:
Figure 3:
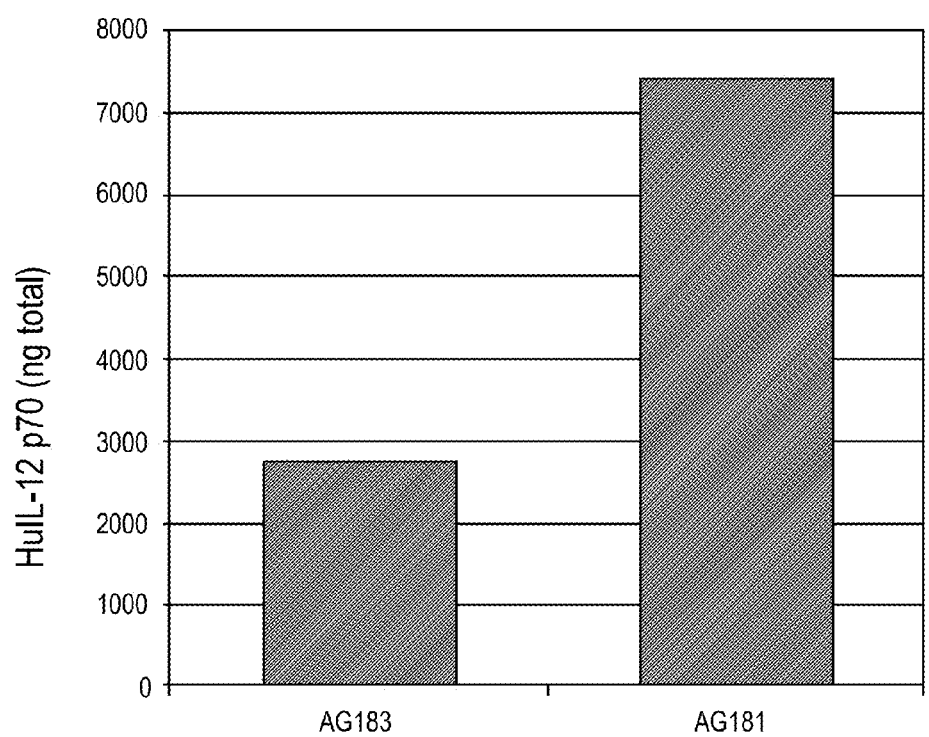
FIG. 3 illustrates expression of human IL-12 from dual expression plasmids AG181 and AG183 in transfected human 293 cells. Expressing the p40 subunit from the stronger human CMV promoter in plasmid AG181 produces about 3-fold higher levels of IL-12 (p70) in comparison to expressing the IL-12 p40 subunit from the weaker simian CMV promoter in plasmid AG183. Measurement of IL-12 was performed with a commercial ELISA (R&D or eBioscience) from the supernatant of the transfected cells.
Figure 4:
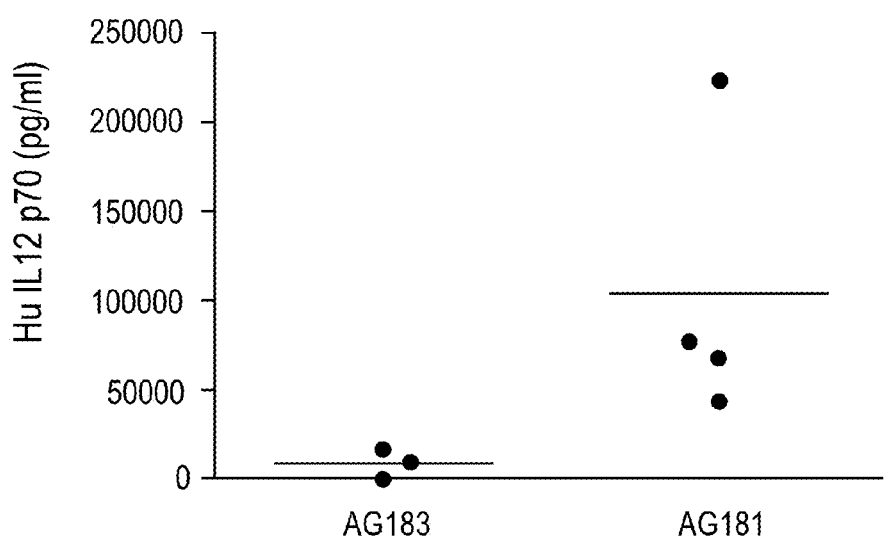
FIG. 4 illustrates expression of human IL-12 from the dual expression plasmids AG181 and AG183 upon DNA delivery in mice (hydrodynamic injection). 100 ng of plasmid DNA was injected in 1.6 ml of 0.9% NaCl solution over seven seconds in the tail vein of the mice. Expressing the p40 subunit from the stronger human CMV promoter in plasmid AG181 produces higher levels of IL-12 (p70) (103580 pg/ml+/−81554 average+/−SD) in comparison to expressing the IL-12 p40 subunit from the weaker simian CMV promoter in plasmid AG183 (9172 pg/ml+/−7935 average+/−SD). Measurement of IL-12 heterodimer was performed using a commercial ELISA (R&D) in the plasma of the injected mice at day 3 post injection.
Figure 5:
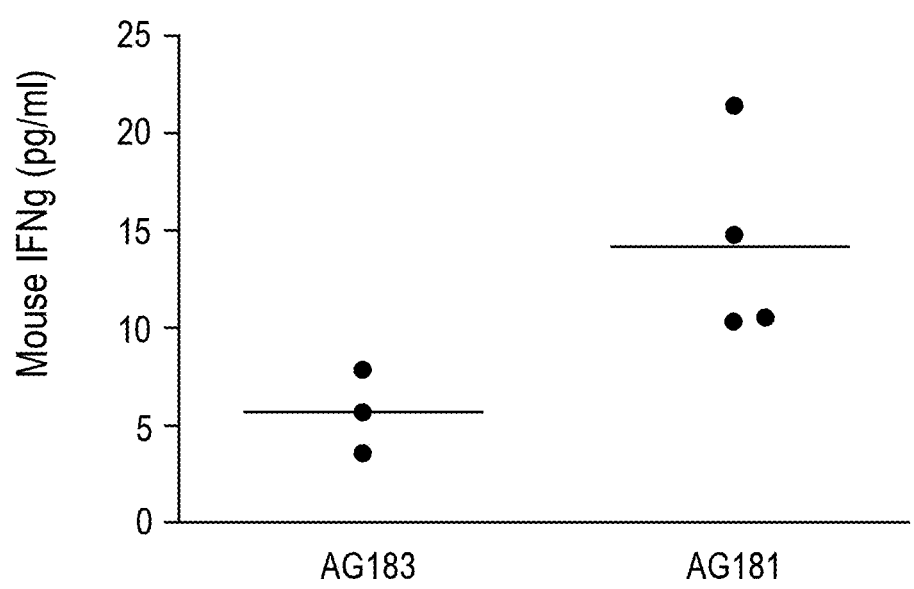
FIG. 5 illustrates that more efficient production of IL-12 promotes induction of higher levels of IFN-γ in the plasma of injected mice (hydrodynamic injection, as described in FIG. 4). At three days post-injection, the IFN-γ levels were measured in the plasma by ELISA (eBioscience). It should be noted that human IL-12 is minimally bioactive in mice, therefore the mouse IFN-γ levels produced were much lower that those produced after mouse IL-12 DNA injection.
Figure 6:
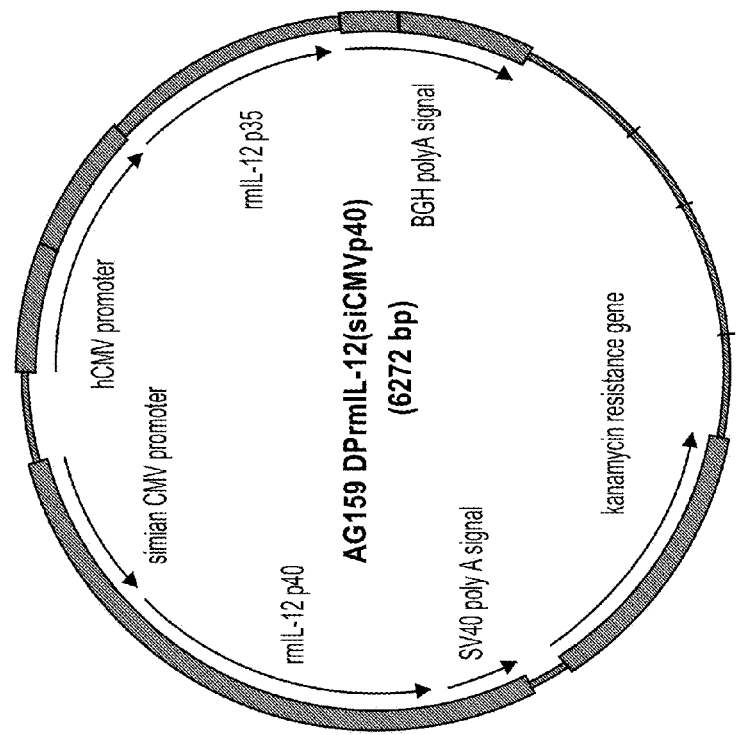
FIG. 6 illustrates rhesus macaque IL-12 dual expression plasmids. In plasmid AG157, the rhesus macaque IL-12 p40 subunit is expressed from the stronger human CMV promoter and p35 is expressed from the weaker simian CMV promoter. In plasmid AG159, the IL-12 p35 subunit is expressed from the stronger human CMV promoter and IL-12 p40 is expressed from the weaker simian CMV promoter.
Figure 6:
Figure 7:
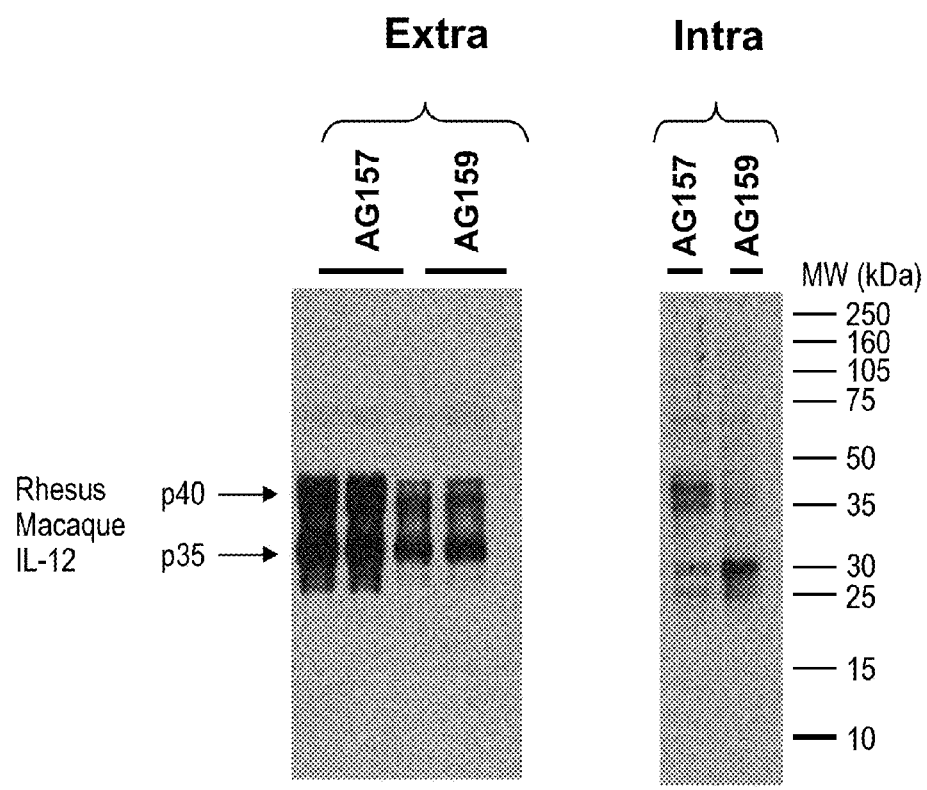
FIG. 7 illustrates expression of the rhesus macaque IL-12 from the dual expression plasmids in transfected human 293 cells. Supernatants and cell extracts were analyzed for the presence of IL-12 from transfected human 293 cells by Western immunoblot. AG157 expressing the IL-12 p40 subunit from the stronger human CMV promoter in plasmid AG157 produces more rhesus macaque IL-12 (p70) in comparison to expressing the IL-12 p40 subunit from the weaker simian CMV promoter in plasmid AG159. The presence of higher levels of p40 leads to more efficient export and stabilization of p35.
Figure 8:
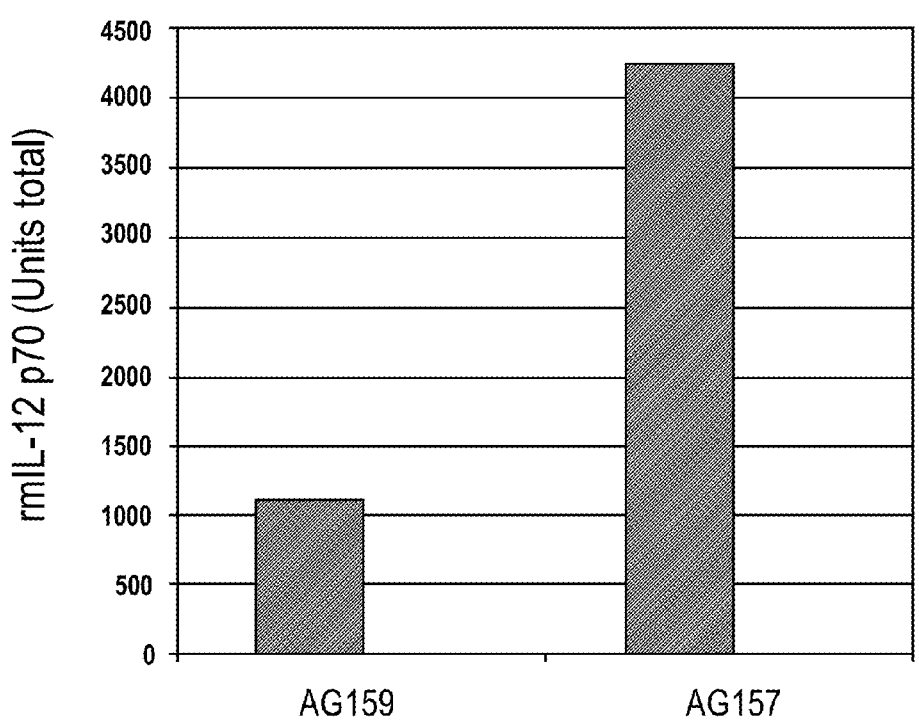
FIG. 8 illustrates quantification of the levels of rhesus macaque IL-12 expression (p70 heterodimer) upon transfection of human 293 cells using commercial ELISA. Expressing the p40 subunit from the stronger human CMV promoter in plasmid AG157 produces about 4-fold higher levels of IL-12 (p70) in comparison to expressing the IL-12 p40 subunit from the weaker simian CMV promoter in plasmid AG159 (analogous to the data presented for human IL-12 p70 heterodimer in FIG. 3).
Figure 9:
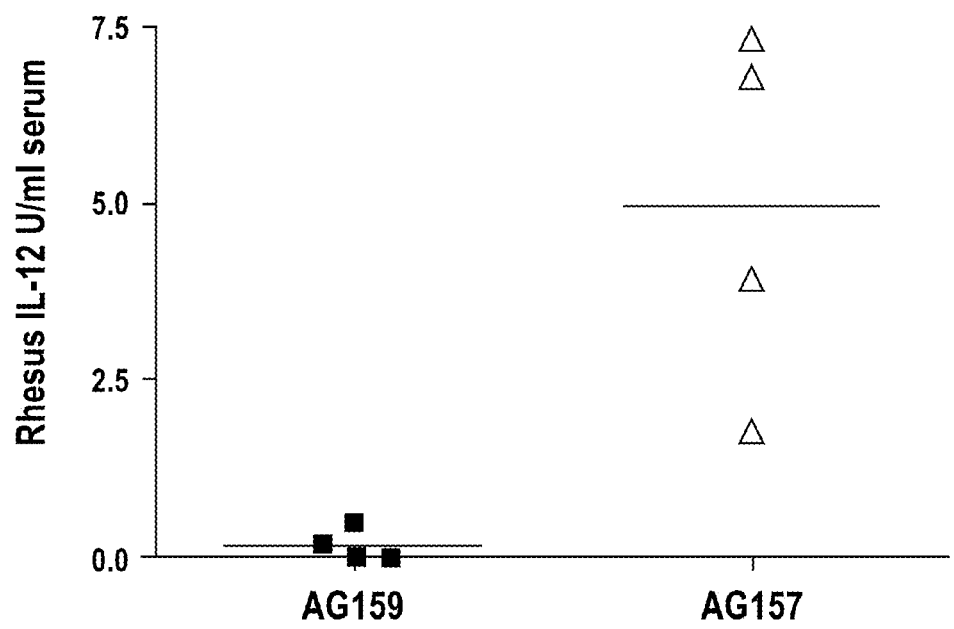
FIG. 9 illustrates expression of rhesus macaque IL-12 upon intramuscular injection of the dual expression plasmids in the macaques. 100 micrograms of either the AG157 or AG159 DNA were injected intramuscularly into the macaques. Serum levels of the rhesus macaque IL-12 (p70) were measured at day 4 by ELISA. AG157 produces about 30-fold higher levels of IL-12 p70 heterodimer in comparison to AG159.
Figure 10:
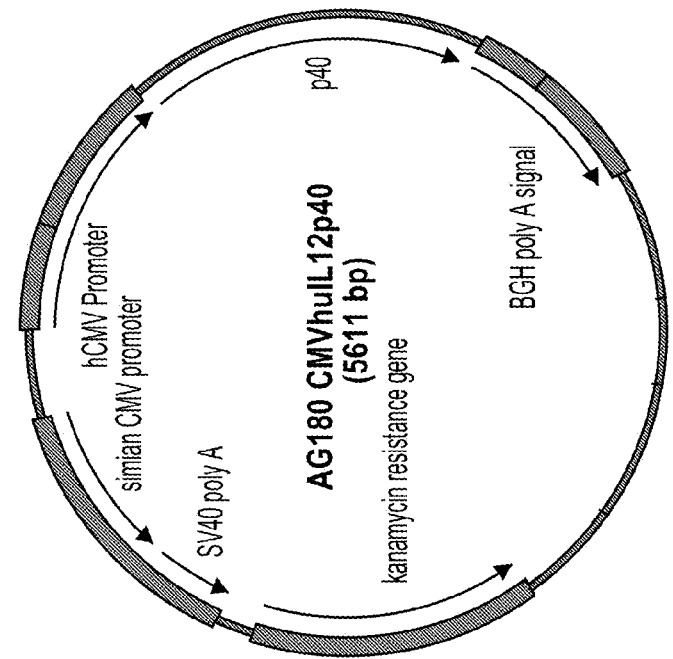
FIG. 10 illustrates that IL-23 consists of two subunits: p19 and p40 (IL-23 p40 is identical to IL-12 p40). Plasmid AG177 produces human p19 from an improved RNA nucleic acid sequence having minimized inhibitory/instability sequences (SEQ ID NO:26). The plasmid AG177 expresses human p19 under the control of the human CMV promoter and the BGH polyA signal. The improved RNA nucleic acid sequence encoding the human IL-12 p40 subunit is expressed under the control of the human CMV promoter in plasmid AG180.
Figure 10:
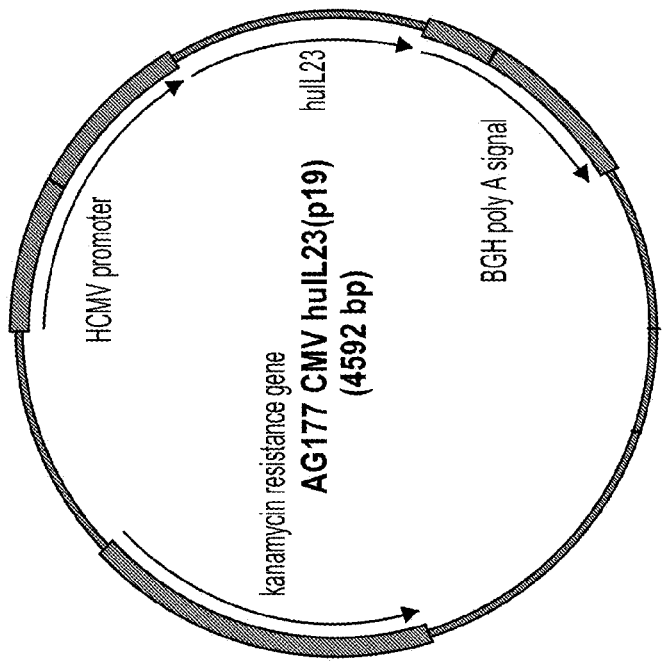
Figure 11:
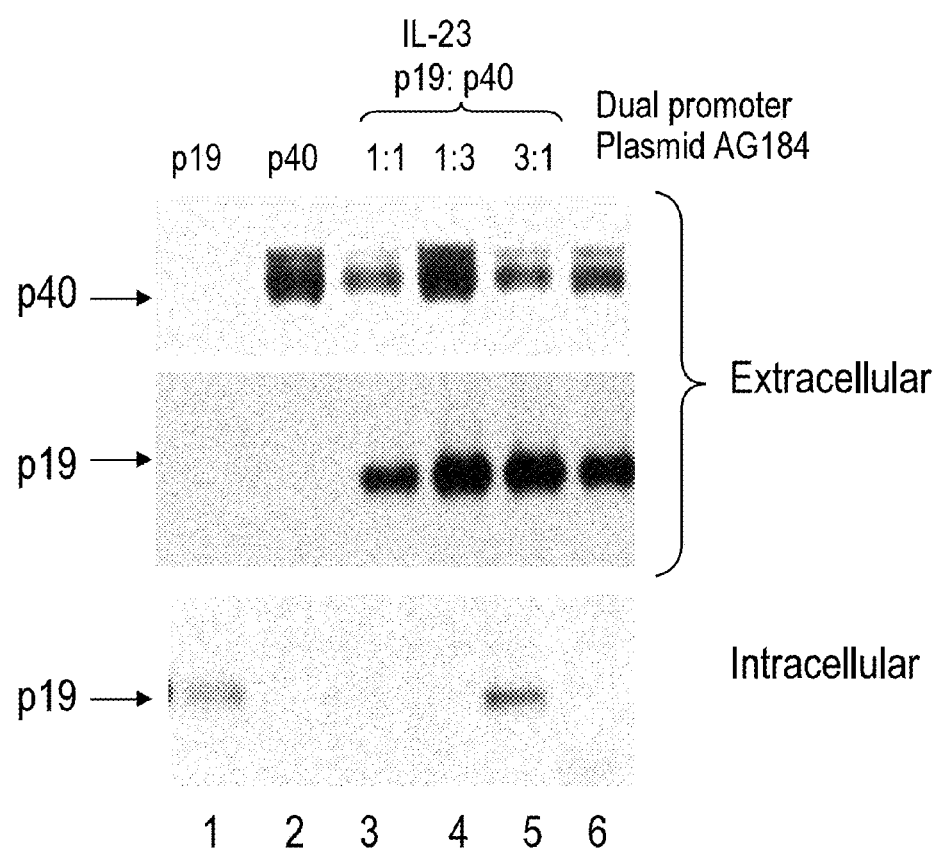
FIG. 11 illustrates more efficient human IL-23 heterodimer production in the presence of high levels of the IL-12 subunit p40. The plasmids expressing p19 (AG177) and p40 (AG180) were transfected into human 293 cells and one day later the cells were analyzed by Western immunoblot. Expression of the p19 (lane 1) and p40 (lane 2) subunits alone shows that the p19 subunit remains cell-associated when expressed alone. Co-transfection of p19 and p40 at different ratios, as indicated: p19:p40 at 1:1 (lane 3), 1:3 (lane 4) or 3:1 (lane 5) demonstrates that the presence of higher levels of p40 results in higher levels of IL-23 heterodimer production (lane 4). Lane 6 shows IL-23 heterodimer production from the dual promoter plasmid AG184 (see, FIG. 12, below).
Figure 12:
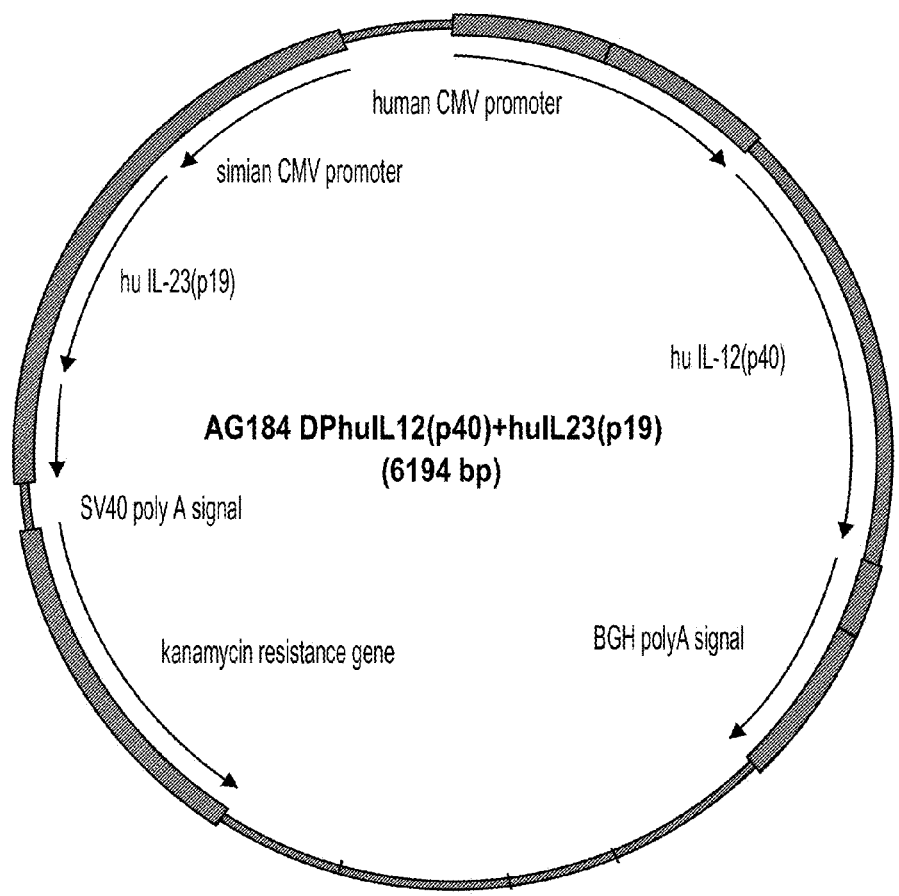
FIG. 12 illustrates a dual promoter expression plasmid AG184, for human IL-23. The p40 subunit is expressed from the stronger human CMV promoter and the p19 subunit is expressed from the weaker simian CMV promoter.
Figure 13:
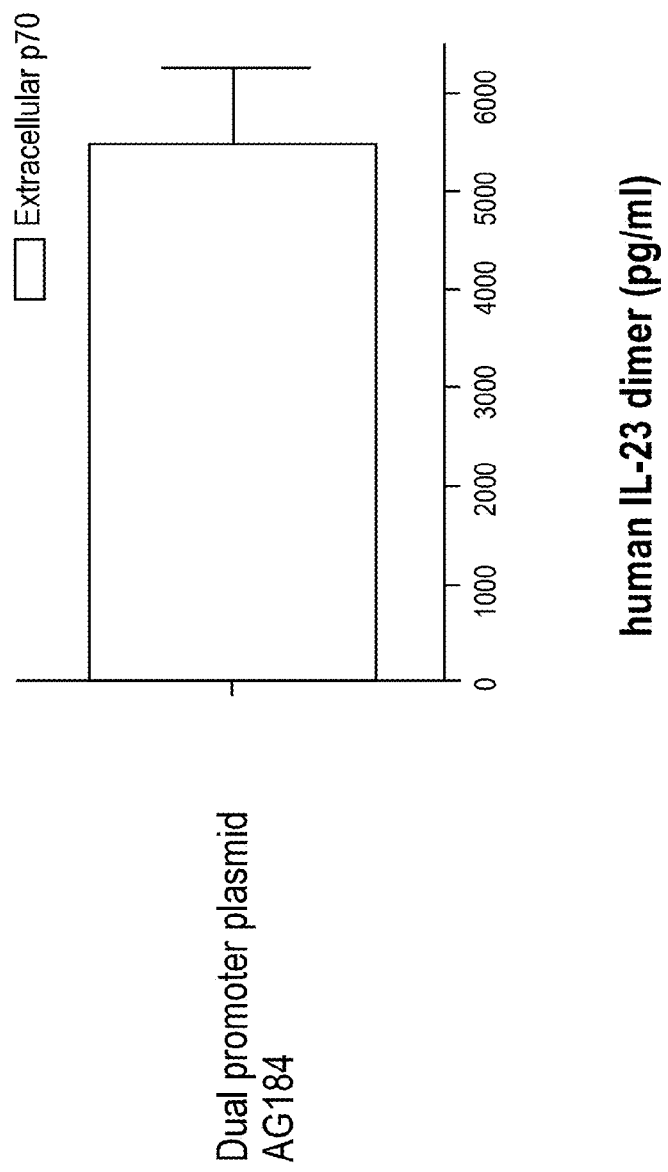
FIG. 13 illustrates quantification of human IL-23 heterodimer production from the dual promoter expression plasmid AG184. Human 293 cells were transfected with 100 ng of AG184 and IL-23 heterodimer was measured in the supernatant 2 days later by ELISA (eBioscience). Total supernatant volume was 4 ml per plate.
Figure 14:
FIG. 14 illustrates that IL-27 consists of the p28 and EBI3 subunits. Expression plasmids encoding improved RNA nucleic acid sequences (i.e., having minimized inhibitory/instability sequences) for murine IL-27 p28 (SEQ ID NO:27) and murine EBI3 (SEQ ID NO:28) were generated. The murine IL-27 p28 subunit is expressed under the control of the human CMV promoter in plasmid AG193. The murine IL-27 EBI3 subunit is expressed under the control of the human CMV promoter in plasmid AG194.
Figure 14:
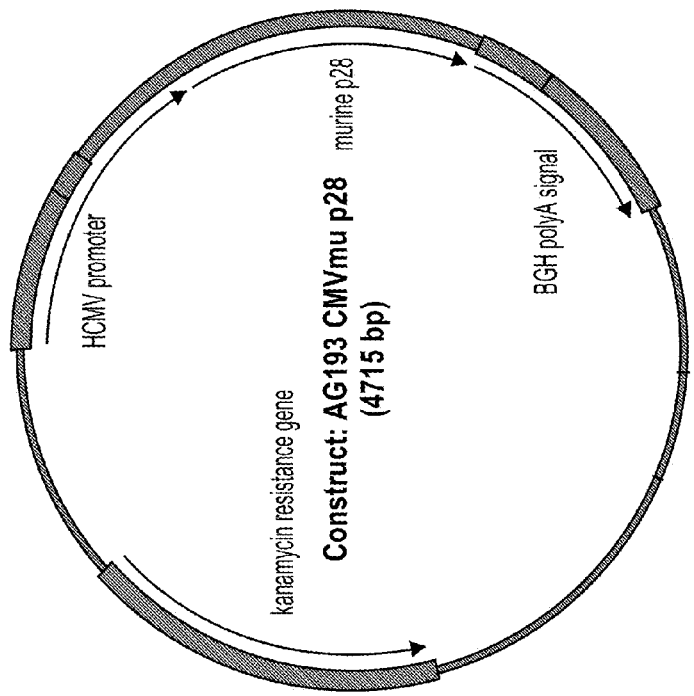
Figure 15:
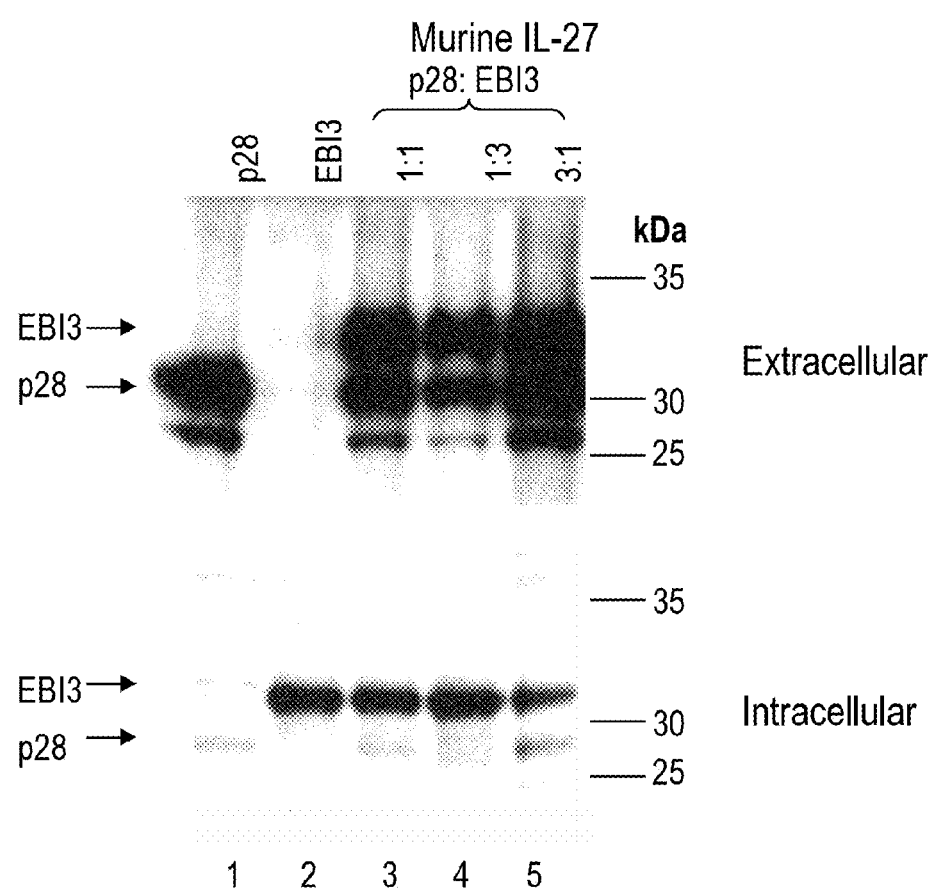
FIG. 15 illustrates expression of the murine IL-27 heterodimer from transfected human 293 cells. Expression of the p28 (lane 1) or EBI3 (lane 2) subunit alone shows that EBI3 remains cell-associated. Co-expression of the subunits (lanes 3-5) at a ratio of p28:EBI3 of 1:1 (lane 3), 1:3 (lane 4) or 3:1(lane 5) shows that higher p28 levels result in higher IL-27 heterodimer production in the supernatant. Therefore, excess of p28 promotes stabilization and secretion of EBI3.
Figure 16:
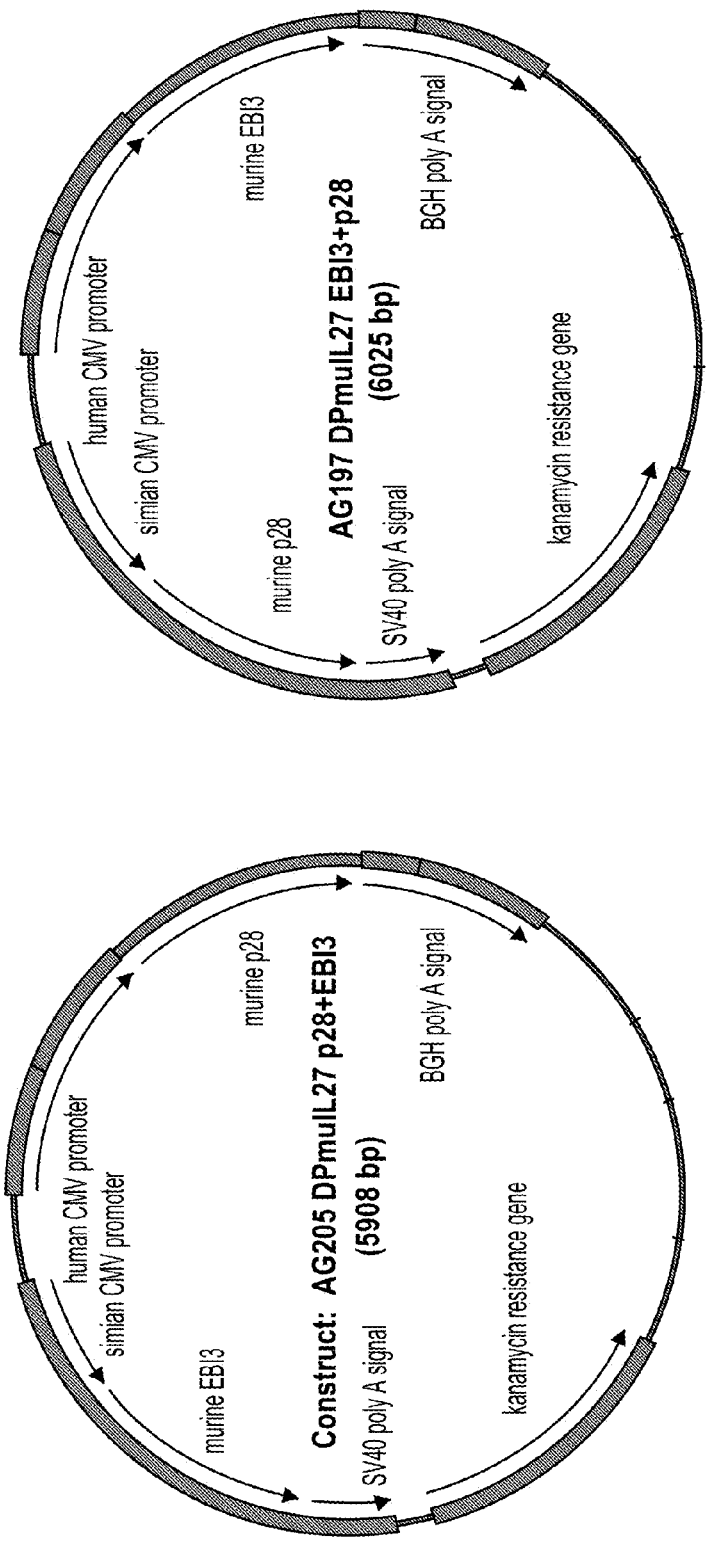
FIG. 16 illustrates dual promoter expression plasmids for murine IL-27. The p28 subunit is expressed from the stronger human CMV promoter and the EBI3 subunit is expressed from the weaker simian CMV promoter in AG205. The EBI3 subunit is expressed from the stronger human CMV promoter and the p28 subunit is expressed from the weaker simian CMV promoter in AG 197.
Figure 17:
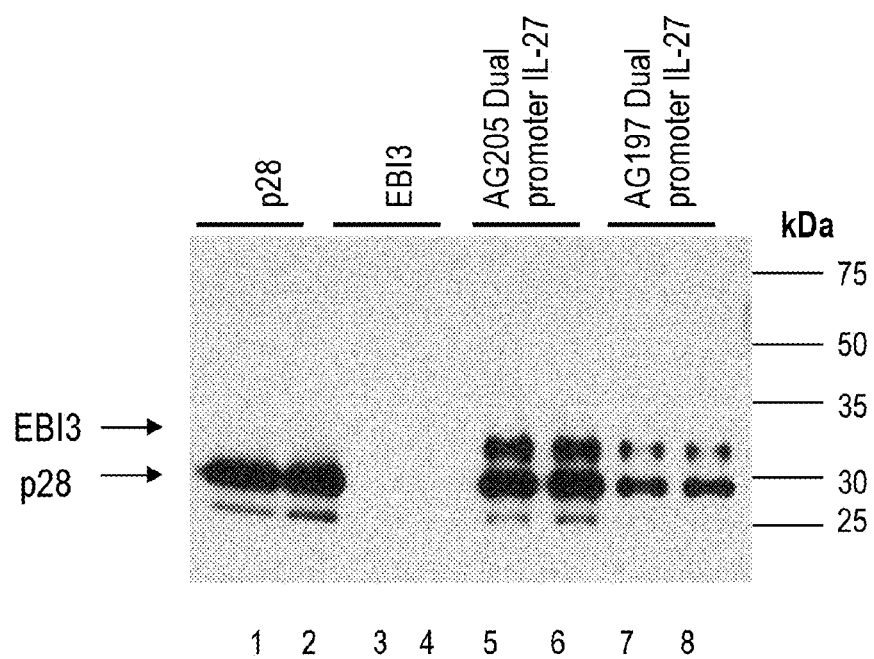
FIG. 17 illustrates more efficient murine IL-27 heterodimer production from the dual promoter expression plasmid. The plasmid expressing the p28 subunit form the human CMV promoter (AG205) (lanes 5, 6) produces higher levels of IL-27 compared to levels obtained from AG197 (lanes 7,8). The presence of both subunits is essential for IL-27 production. Expression of p28 alone (lanes 1,2) or EBI3 alone (lanes 3,4) show that in the absence of cotransfected p28, the EBI3 subunit is not secreted.
Figure 18:
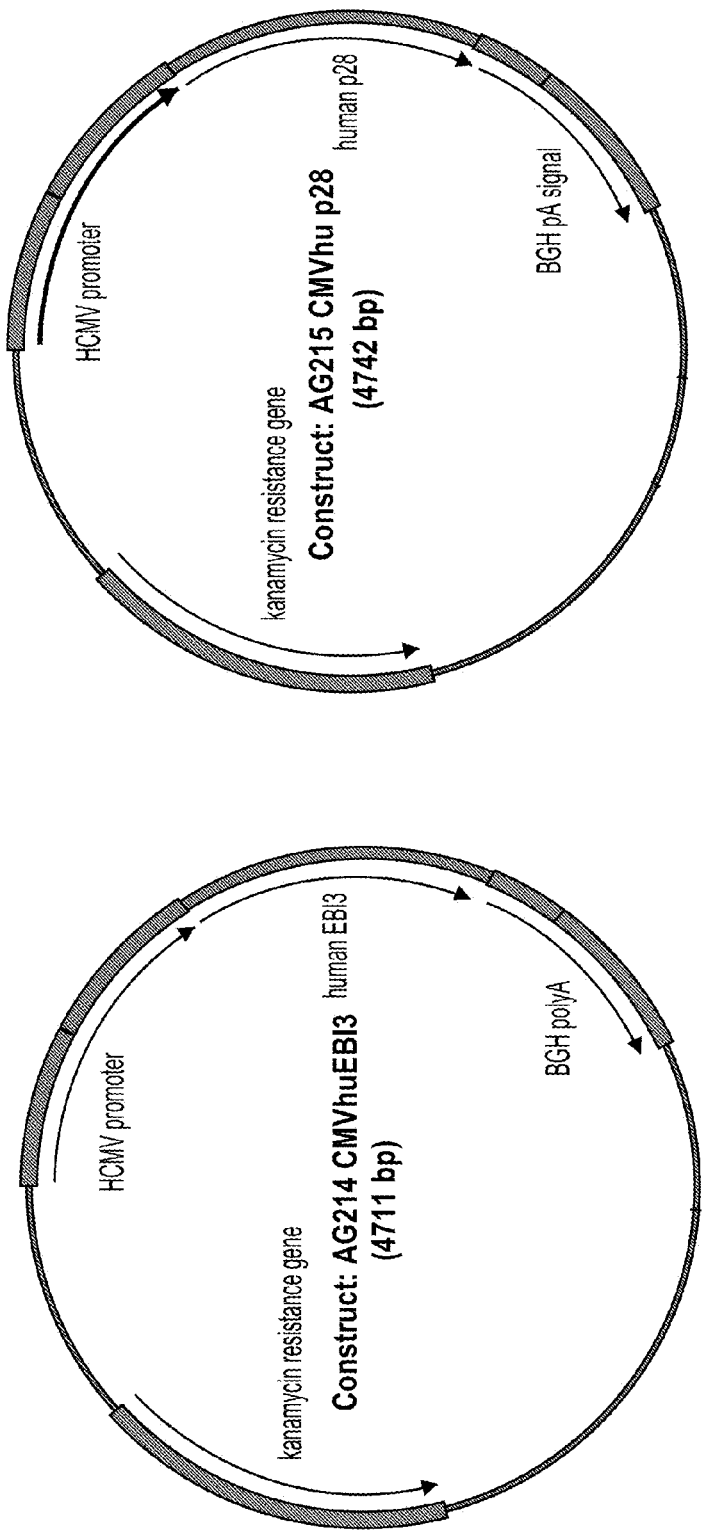
FIG. 18 illustrates expression plasmids for the EBI3 and p28 subunits of the human IL-27. Improved RNA nucleic acid sequences of the human EBI3 (SEQ ID NO:30) and human p28 (SEQ ID NO:29) genes, having minimized instability/inhibitory sequences, were inserted between the human CMV promoter and the BGH polyA signal in plasmids AG214 and AG215, respectively.
Figure 19:
FIG. 19 illustrates dual promoter expression plasmids for expression human IL-27 heterodimer. The human IL-27 p28 subunit is expressed from the stronger human CMV promoter and the EBI3 subunit is expressed from the weaker simian CMV promoter in AG216. The EBI3 subunit is expressed from the stronger human CMV promoter and the p28 subunit is expressed from the weaker simian CMV promoter in AG217.
Figure 19:
Figure 20:
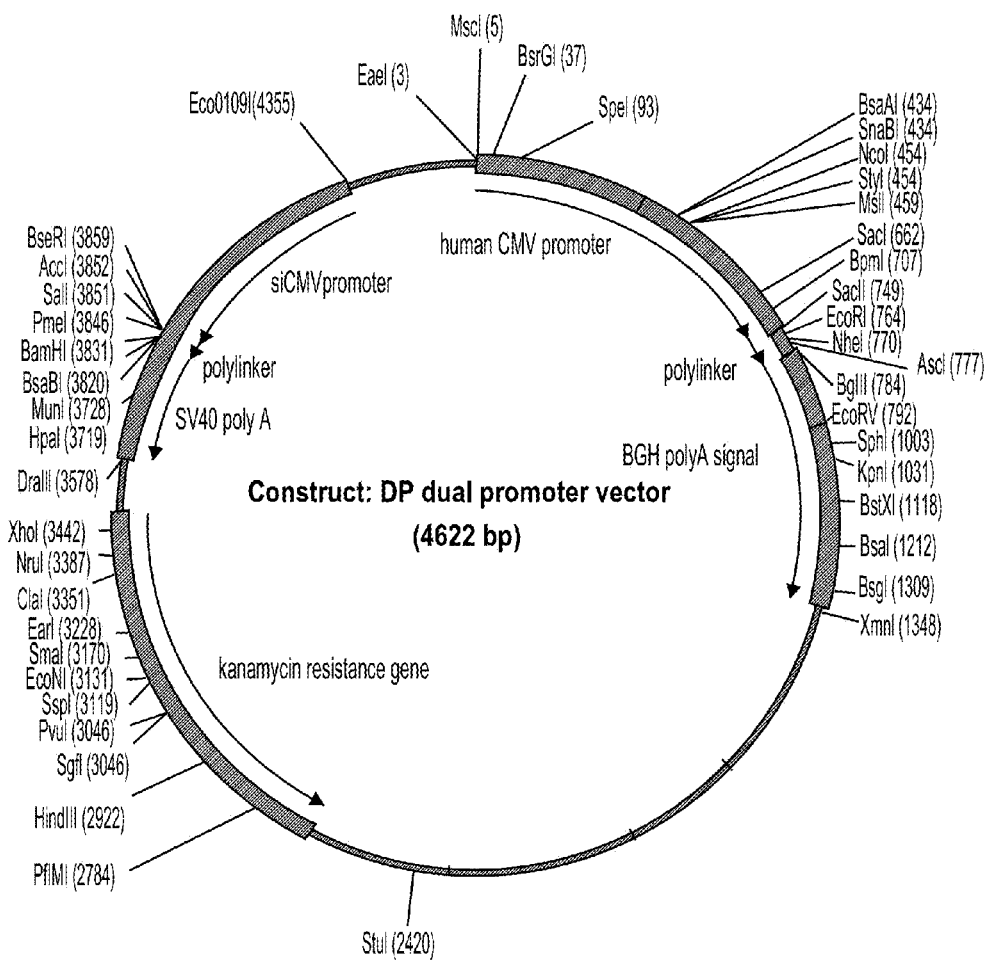
FIG. 20 illustrates schematics of vector backbones for single expression cassette vector CMVkan (SEQ ID NO:31) and dual expression promoter DP (SEQ ID NO:32), comprising a first expression cassette for expression a first subunit of a heterodimeric protein from the relatively stronger human CMV promoter and a second expression cassette for expression of a second subunit of a heterodimeric protein from the relatively weaker simian CMV promoter.
Figure 20:
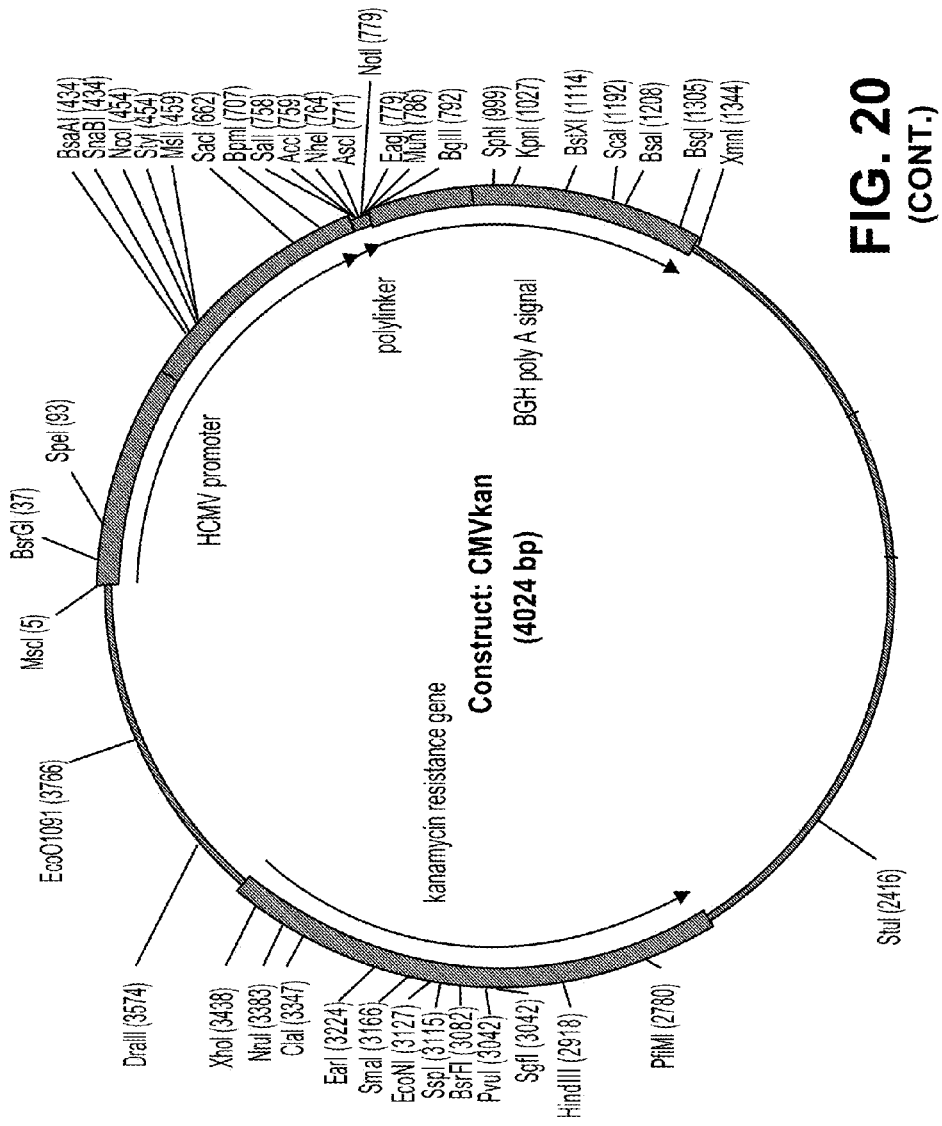

Dual-promoter expression vectors for the concurrent expression of two polypeptide chains in a mammalian cell are commercially available, for example, the pVITRO vector from InvivoGen (San Diego, Calif.). Exemplified dual-promoter expression vectors are shown in FIGS. 2, 6, 12, 16, 19 and 20 and as SEQ ID NOS:1, 3, 7, 10, 14 and 32.

As discussed below, the expression vectors can also be viral vectors.

4. Mammalian Host Cells

The expression vectors of the invention can be expressed in mammalian host cells. The host cells can be in vivo in a host or in vitro. For example, expression vectors containing high-level expressing IL-12 family cytokine nucleic acid sequences can be transfected into cultured mammalian host cells in vitro, or delivered to a mammalian host cell in a mammalian host in vivo.

Exemplary host cells that can be used to express improved IL-12 nucleic acid sequences include mammalian primary cells and established mammalian cell lines, including COS, CHO, HeLa, NIH3T3, HEK 293-T, RD and PC12 cells. Mammalian host cells for expression of IL-12 family cytokine subunits polypeptides are commercially available from, for example, the American Type Tissue Collection (ATCC), Manassas, Va. Protocols for in vitro culture of mammalian cells is also well known in the art. See, for example, *Handbook of Industrial Cell Culture: Mammalian, Microbial, and Plant Cells*, Vinci, et al., eds., 2003, Humana Press; and *Mammalian Cell Culture: Essential Techniques*, Doyle and Griffiths, eds., 1997, John Wiley & Sons.

Protocols for transfecting mammalian host cells in vitro and expressing recombinant nucleic acid sequences are well known in the art. See, for example, Sambrook and Russell, and Ausubel, et al, supra; *Gene Delivery to Mammalian Cells: Nonviral Gene Transfer Techniques*, Methods in Molecular Biology series, Heiser, ed., 2003, Humana Press; and Makrides, *Gene Transfer and Expression in Mammalian Cells*, New Comprehensive Biochemistry series, 2003, Elsevier Science. Mammalian host cells modified to express the improved IL-12 family cytokine nucleic acid sequences can be transiently or stably transfected with a recombinant vector. The improved IL-12 family cytokine sequences can remain epigenetic or become chromasomally integrated.

5. Vaccine Adjuvants

The high level expression improved IL-12 family cytokine nucleic acid sequences are suitable for use as an adjuvant co-delivered with a vaccine antigen. The use of IL-12 family cytokines as adjuvants in antimicrobial therapy, anticancer therapy and for stimulating mucosal immunity is known in the art. See, for example, Tomioka, *Curr Pharm Des* (2004) 10:3297; El-Aneed, *Eur J Pharmacol* (2004) 498:1; Stevceva and Ferrari, *Curr Pharm Des* (2005) 11:801; Toka, et al., *Immunol Rev* (2004) 199:100; Overwijk, et al., *J Immunol.* (2006) 176(9): 5213-5222; Matsui, et al. *Journal of Virology*, (2004) 78(17):9093-9104; Goldberg, et al., *J Immunol*, (2004) 173:1171-1178).

In a preferred embodiment, high level expressing improved IL-12 family cytokine nucleic acid sequences are co-administered with one or more vaccine antigens, with at least the improved IL-12 family cytokine nucleic acid sequences delivered as naked DNA. The antigen can be delivered as one or more polypeptide antigens or a nucleic acid encoding one or more antigens. Naked DNA vaccines are generally known in the art; see, Wolff, et al., *Science* (1990) 247:1465; Brower, *Nature Biotechnology* (1998) 16:1304-130; and Wolff, et al., *Adv Genet* (2005) 54:3. Methods for the use of nucleic acids as DNA vaccines are well known to one of ordinary skill in the art. See, *DNA Vaccines*, Ertl, ed., 2003, Kluwer Academic Pub and *DNA Vaccines: Methods and Protocols*, Lowrie and Whalen, eds., 1999, Humana Press. The methods include placing a nucleic acid encoding one or more antigens under the control of a promoter for expression in a patient. Co-administering high level expressing improved IL-12 family cytokine nucleic acid sequences further enhances the immune response against the one or more antigens. Without being bound by theory, following expression of the polypeptide encoded by the DNA vaccine, cytotoxic T-cells, helper T-cells and antibodies are induced which recognize and destroy or eliminate cells or pathogens expressing the antigen.

The invention contemplates compositions comprising improved IL-12 family cytokine nucleic acid sequences in a physiologically acceptable carrier. While any suitable carrier known to those of ordinary skill in the art may be employed in the pharmaceutical compositions of this invention, the type of carrier will vary depending on the mode of administration. For parenteral administration, including subcutaneous or intramuscular injection, the carrier preferably comprises water, saline, and optionally an alcohol, a fat, a polymer, a wax, one or more stabilizing amino acids or a buffer. General formulation technologies are known to those of skill in the art (see, for example, *Remington: The Science and Practice of Pharmacy* (20th edition), Gennaro, ed., 2000, Lippincott Williams & Wilkins; *Injectable Dispersed Systems: Formulation, Processing And Performance*, Burgess, ed., 2005, CRC Press; and *Pharmaceutical Formulation Development of Peptides and Proteins*, Frkjr et al., eds., 2000, Taylor & Francis).

Naked DNA can be delivered in solution (e.g., a phosphate-buffered saline solution) by injection, usually by an intra-arterial, intravenous, subcutaneous or intramuscular route. In general, the dose of a naked nucleic acid composition is from about 10 μg to 10 mg for a typical 70 kilogram patient. Subcutaneous or intramuscular doses for naked nucleic acid (typically DNA encoding a fusion protein) will range from 0.1 mg to 50 mg for a 70 kg patient in generally good health.

DNA vaccinations can be administered once or multiple times. In some embodiments, the improved IL-12 family cytokine nucleic acid sequences are administered more than once, for example, 2, 3, 4, 5, 6, 7, 8, 10, 15, 20 or more times as needed to induce the desired response (e.g., specific antigenic response). Multiple administrations can be administered, for example, bi-weekly, weekly, bi-monthly, monthly, or more or less often, as needed, for a time period sufficient to achieve the desired response.

In some embodiments, the improved IL-12 family cytokine nucleic acid compositions are administered by liposome-based methods, electroporation or biolistic particle acceleration. A delivery apparatus (e.g., a "gene gun") for delivering DNA into cells in vivo can be used. Such an apparatus is commercially available (e.g., BioRad, Hercules, Calif., Chiron Vaccines, Emeryville, Calif.). Naked DNA can also be introduced into cells by complexing the DNA to a cation, such as polylysine, which is coupled to a ligand for a cell-surface receptor (see, for example, Wu, G. and Wu, C. H. (1988) *J. Biol. Chem.* 263:14621; Wilson et al. (1992) *J. Biol. Chem.* 267:963-967; and U.S. Pat. Nos. 5,166,320; 6,846,809; 6,733,777; 6,720,001; 6,290,987). Liposome formulations for delivery of naked DNA to mammalian host cells are commercially available from, for example, Encapsula NanoSciences, Nashville, Tenn. An electroporation apparatus for use in delivery of naked DNA to mammalian host cells is commercially available from, for example, Inovio Biomedical Corporation, San Diego, Calif.

The improved IL-12 family cytokine nucleic acid vaccine compositions are administered to a mammalian host (i.e., individual, patient). The mammalian host usually is a human or a primate. In some embodiments, the mammalian host can be a domestic animal, for example, canine, feline, lagomorpha, rodentia, rattus, hamster, murine. In other embodiment, the mammalian host is an agricultural animal, for example, bovine, ovine, porcine, equine, etc.

6. Methods of Improving Expression of IL-12 Family Cytokines

The methods of the present invention provide for expressing an IL-12 family cytokine from an improved coding sequence in a mammalian cell by introducing a recombinant vector into the cell to express the high level improved alpha and beta nucleic acid sequences described herein. The transfected mammalian cell can be in vitro or in vivo in a mammalian host.

The alpha and beta subunits of the IL-12 family cytokines are co-expressed in a host cell to determine the relative ratio of expression of the alpha and beta subunits that achieves an increased, e.g., in some instances the highest, level and stability of extracellular expression. The host cell can be prokaryotic or eukaryotic. In some embodiments, the host cell for expression is a eukaryotic cell, e.g., a mammalian cell (as described above), an insect cell, a plant cell, etc. Test host cell populations are co-transfected with nucleic acids encoding the alpha and beta subunits of an IL-12 family cytokine at different relative ratios, e.g., relative ratios in the range of about 15:1 to about 1:15 (excluding equimolar ratios, i.e., a 1:1 ratio), for example, about 15:1, 12:1, 10:1, 8:1, 5:1, 4:1, 3:1, 2:1, 1:2, 1:3, 1:4, 1:5, 1:8, 1:10, 1:12, 1:15, etc. The desired ratio can be the ratio that produces the highest level of expression, or can be a ratio that produces less than the highest level of expression, depending on the context of use of the IL-12 family cytokine The desired ratio or the highest ratio may be different depending on the context of expression of the IL-12 family cytokine, e.g., in vitro expression versus in vivo expression; in vivo expression in mice, primate or human.

The expression levels of the alpha and beta subunits, e.g., in the extracellular space, in cell culture media, in serum, are then quantified employing any method known in the art. For example, the relative ratios can be quantified by Western immunoblot or by ELISA. Antibodies against IL-12, IL-23 and IL-27 are commercially available, for example, from AbCam, Cambridge, Mass.; BioLegend, San Diego, Calif.; GenWay Biotech, San Diego, Calif.; Lifespan Biosciences, Seattle, Wash.; Novus Biologicals, Littleton, Colo.; R&D Systems, Minneapolis, Minn.; Peprotech, Rocky Hill, N.J.; and Biosource Intl., Camarillo, Calif. See also, Coligan, et al., *Current Methods in Immunology*, 1991-2006, John Wiley & Sons; Harlow and Lane, *Using Antibodies: A Laboratory Manual*, 1998, Cold Spring Harbor Laboratory Press; and *The ELISA Guidebook*, Crowther, ed., 2000, Humana Press.

Upon determination of the relative ratios of expression of the alpha and beta subunits that result in the desired (e.g., highest) levels and stability of expression of the IL-12 family cytokines, host cells are then transfected with one or more polynucleotides in a manner sufficient to express the alpha and beta subunits at the appropriate relative ratios. Expression of the alpha and beta subunits at a desired relative ratio can be achieved using any method known in the art.

For example, host cells can be co-transfected with a first polynucleotide encoding the alpha subunit and a second polynucleotide encoding the beta subunit, wherein the first and second polynucleotides are co-transfected at a relative molar ratio that corresponds to the desired relative ratio of expression of the alpha and beta subunits, e.g., at molar ratios in the range of about 15:1 to about 1:15 (excluding equimolar ratios, i.e., a 1:1 ratio), for example, about 15:1, 12:1, 10:1, 8:1, 5:1, 4:1, 3:1, 2:1, 1:2, 1:3, 1:4, 1:5, 1:8, 1:10, 1:12, 1:15, etc.

In another embodiment, the host cells can be transfected with a single polynucleotide having first and second expression cassettes, the first expression cassette comprising a first promoter that controls expression of a nucleic acid encoding the alpha subunit, and the second expression cassette comprising a second promoter that controls expression of a nucleic acid encoding the beta subunits. The strengths of the first and second promoters are selected such that the desired relative ratio of expression of the alpha and beta subunits, e.g., molar ratios in the range of about 15:1 to about 1:15, excluding equimolar (1:1 ratio) expression, for example, about 15:1, 12:1, 10:1, 8:1, 5:1, 4:1, 3:1, 2:1, 1:2, 1:3, 1:4, 1:5, 1:8, 1:10, 1:12, 1:15, etc., are achieved. For example, in a mammalian host cell, the human CMV promoter is stronger than the simian CMV promoter. Accordingly, the subunit to be expressed at relatively higher levels is placed under the control of the human CMV promoter, and the subunit to be expressed at relatively lower levels is placed under the control of the simian CMV promoter.

In a further embodiment, the host cells can be transfected with a bicistronic polynucleotide that comprises a single promoter and two ribosomal entry sites, a first ribosomal entry site proximal to the promoter and a second or internal ribosomal entry site that is distal from the promoter (i.e., separated by the coding sequence of an alpha or beta subunit). The coding sequence of the subunit to be expressed at relatively higher levels is located proximal to the promoter, or relatively 5' in the bicistronic polynucleotide. The coding sequence of the subunit to be expressed at relatively lower levels is located distal to the promoter, or relatively 3' in the bicistronic polynucleotide, e.g., 3' to the internal ribosomal entry site.

Introduction of Expression Vectors into Cells

As discussed herein, standard transfection methods are used to introduce the polynucleotides, expression cassettes and/or expression vectors encoding IL-12 family cytokine subunits into cells. The expression vectors can be plasmid expression vectors or other commonly used expression vectors including viral expression vectors. In some embodiments, naked mRNA coding sequences are delivered into the cells. See, e.g., Pascolo, *Handb Exp Pharmacol.* (2008) 183:221-35; Weide, et al., *Immunol Lett.* (2008) 115(1):33-42; and Van Tendeloo, *Curr Opin Mol Ther.* (2007) 9(5): 423-31. Gene transfer techniques include the use of calcium phosphate transfection, polybrene, protoplast fusion, electroporation, liposomes, microinjection, plasma vectors, viral vectors and any of the other well known methods for introducing heterologous nucleic acids into a host cell (see, e.g., Sambrook, supra). The vectors can be used for in vitro experiments or in vivo.

The cells are typically mammalian cells, e.g., human cells. Cells into which the vectors are introduced can be primary cells as well as cell lines. Exemplary cell types include circulating cells such as peripheral blood cells, monocytes, lymphocytes, and cells of these lineages, including $CD4^+$ T cells, and the like; muscle cells, epidermal cells, neuronal cell types, fibroblasts, hepatocytes, cardiac cells, mammary cells, prostate cells, pancreatic cells, lung cells, endocrine cells, splenocytes, and the like. Such cells may be normal or cancerous.

Non-Viral Delivery Methods

Methods of non-viral delivery of DNA or RNA polynucleotides encoding IL-12 family cytokine heterodimers include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. Nos. 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells either in vitro or in vivo. Delivery can be by injection (e.g., intramuscular), by inhalation or any other appropriate route that allows expression in a targeted host cell.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Viral Delivery Method

The use of RNA or DNA viral based systems for the delivery of vectors, e.g., comprising the nucleic acids encoding IL-12 family cytokine subunits, are known in the art. Conventional viral based systems include without limitation lentivirus, retroviral, adenoviral, adeno-associated, herpes simplex virus, and various other viral vectors for gene transfer. The polynucleotides encoding the alpha and beta subunits of the IL-12 family cytokine can be in the same viral vector or in different viral vectors.

In many applications, it is desirable a vector be delivered with a high degree of specificity to a cell type, e.g., for delivery in vivo. A viral vector can be modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g. Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Vectors can be delivered in vivo by administration to an individual patient, typically by systemic administration (e.g., intravenous, intraperitoneal, intramuscular, intranasally, inhalationally, subdermal, or intracranial infusion) or topical application, as described below. Alternatively, vectors can also be delivered to cells in vitro. Such methods include ex vivo methods, e.g., for introducing DNA into cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism (e.g., mammal, human), transfected with expression vectors comprising the nucleic acids encoding IL-12 family cytokine heterodimer and re-infused back into the subject organism (e.g., mammal, human). Various cell types suitable for ex vivo transfection are well known to those of skill in the art (see, e.g., Freshney et al., Culture of Animal Cells, A Manual of Basic Technique (5th ed. 2005), Wiley-Liss) and the references cited therein for a discussion of how to isolate and culture cells from patients, e.g., mammals, humans).

Vectors (e.g., lentiviruses, retroviruses, adenoviruses, liposomes, etc.) containing therapeutic nucleic acids can also be administered directly to an organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

The data obtained from cell culture assays and animal studies can be used to formulate a dosage range for use in humans. The dosage can vary within this range depending upon the dosage form employed and the route of administration.

When administering a viral vector, the amount of virus (number of virions) per dose will vary depending on results of different titrations used in clinical trials. The range can range, e.g., from only a few infectious units, to about $10^4$ to $10^{10}$ infectious units (i.e., virions) per dose. Protocols and means to determine safety and efficacy used for other attenuated vaccines can be adapted and used with the novel reagents provided by the invention; see, e.g., Belshe (1998) *N. Engl. J. Med.* 338:1405-1412; Gruber (1997) *Vaccine* 15:1379-1384; Tingle (1997) *Lancet* 349:1277-1281; Varis (1996) *J. Infect. Dis.* 174:S330-S334; Gruber (1996) *J. Infect. Dis.* 173:1313-1319.

The vaccine can be administered in conjunction with other treatment regimens, e.g., it can be coadministered or administered before or after any anti-viral pharmaceutical (see, e.g., Moyle (1998) *Drugs* 55:383-404) or a killed (completely inactivated) anti-HIV vaccine. The vaccine can be administered in any form of schedule regimen, e.g., in a single dose, or, using several doses (e.g., boosters) at dosages and time intervals to be determined by clinical trials.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., Remington: The Science and Practice of Pharmacy, University of the Sciences in Philadelphia, 21st edition, 2005, Lippincott, Williams and Wilkins).

EXAMPLES

The following examples are offered to illustrate, but not to limit the claimed invention.

Example 1

The strategy for introducing nucleotide changes into IL-12 family cytokine sequences is to simultaneously rectify several factors affecting mRNA traffic, stability and expression. Codons are altered to change the overall mRNA AT(AU)-content or to remove any other inhibitory signals within the RNA such as all potential splice sites (computer programs predicting potential splice sites can be found for example at web sites such as fruitfly.org/seq_tools/splice.html, or sunl.softberry.com/berry.phtml) and also to alter sequences such as runs of A or T/U nucleotides, AATAAA, ATTTA and closely related variant sequences, known to negatively affect mRNA. By substituting codons with a different codon encoding the identical amino acid, the chosen codon can be more GC-rich, or can have a different sequence that is sufficient to alter the RNA structure. This approach has been described in several patents, each of which is hereby incorporated herein by reference in their entirety: U.S. Pat. Nos. 5,965,726; 5,972,596; 6,174,666; 6,291,664; 6,414,132; 6,794,498, WO 07/084,364 and WO 07/084,342.

Standard lab techniques are used to generate, purify and sequence plasmid DNAs. One microgram (1 μg) of the plasmids containing the indicated IL-12 family cytokine coding sequence were transfected into human 293 or RD cells seeded into 60 mm plates the day before with $10^6$ cells using calcium coprecipitation technique (293 cells) and the SuperFect Reagent protocol (Qiagen) for RD4 cells. 2-3 days later, intracellular and extracellular and total IL-12 family protein was measured using commercial kits.

DNA Plasmids

The backbone vector used for the generation of all the constructs, pCMVkan, contains the human cytomegalovirus promoter, the bovine growth hormone polyadenylation site, and the kanamycin resistance gene (Rosati, et al., (2005) J. Virol. 79:8480-8492 and Schneider, et al., (1997) J. Virol. 71:4892-4903). The IL-12, IL-23 and IL-27 cytokines were RNA/codon-optimized by introducing multiple silent point mutations that result in more stable mRNA. For the in vivo studies, highly purified, endotoxin-free DNA plasmid preparations were produced using Qiagen EndoFree Giga kit (Hilden, Germany).

In Vitro Transient Transfection and Protein Expression

Human 293 cells were transfected by the calcium phosphate coprecipitation technique using 0.1 μg of each plasmid, and cells were harvested after 24 or 48 h. Co-transfection of 0.05 μg of the GFP expression vector pFRED143 (Stauber, et al., (1995) *Virology* 213, 439-449) served as internal control. GFP variation in the different samples was less than 50%.

Levels of expressed IL-12, IL-23 or IL-27 were measured by ELISA or by Western immunoblot. Human IL-12 was measured using as primary antibody polyclonal Goat Anti Human IL-12 p70 Neutralizing Ab (R&D Systems; AF219; 1:5000); and as secondary antibody Donkey Anti Goat IgG-HRP (R&D Systems; HAF109; 1:1000). Human IL-23 was measured using as primary antibodies a mixture of Polyclonal Goat Anti Human IL-12 p28 Neutralizing Ab (1:3000) and mouse anti-human p19 antibody (capture Ab from eBioscience HuIL23 ELISA KIT; 1:1250); and as secondary antibodies a mixture of Donkey Anti Goat IgG-HRP (R&D Systems; HAF109; 1:1000) and Anti-Mouse IgG-HRP (GE Healthcare; NA934V; 1:5000). Murine IL-27 was measured using as primary antibodies a mixture of Polyclonal Goat Anti Mouse IL-27 p28 Neutralizing Ab (R&D Systems; AF1834; 1: 1000) and Rabbit anti-mouse EBI3 (M-75) antibody (Santa Cruz Biotechnology, Inc.; sc-32869; 1:1000); and as secondary antibodies a mixture of Donkey Anti Goat IgG-HRP (R&D Systems; HAF109; 1:1000) and Donkey Anti-Rabbit IgG-HRP (GE Healthcare; NA934V; 1:5000). Protein bands were visualized on immunoblots by enhanced chemiluminescence (GE Healthcare).

In Vivo Hydrodynamic DNA Delivery

Six-week-old female BALB/c mice were obtained from Charles River Laboratories, Inc. (Frederick, Md.). Hydrodynamic injection of the plasmid DNA (Liu, et al., (1999) *Gene Ther.* 6, 1258-1266) encoding IL-12, IL-23 or IL-27 was performed essentially as described in Ortaldo, et al., (2005) *J. Immunol.* 175, 693-699. Briefly, the plasmid(s) in 1.6 ml of sterile 0.9% NaCl were injected into mice through the tail vein within 7 s using a 27.5-gauge needle. Mice were bled at day 1 and day 3 after injection, and the serum levels of IL-12, IL-23 or IL-27 were measured by immunoassay. Three days after injection, mice were sacrificed, and liver, lungs, spleen, and mesenteric lymph nodes were collected and analyzed.

Spleen, Lung, and Liver Cell Analysis

To make single cell suspensions, spleens were gently squeezed through a 100-μm Cell Strainer (Thomas) and washed in RPMI 1640 medium (Invitrogen) to remove any remaining organ stroma. The cells were resuspended in RPMI 1640 medium containing 10% fetal calf serum and counted using acridine orange (Molecular Probes)/ethidium bromide (Fisher) dye. Lung and liver were minced and incubated with 200 units/ml of collagenase (Sigma) and 30 units/ml of DNase (Roche Applied Science) for 1 h at 37° C., and single cells were then collected and resuspended in complete RPMI 1640 medium with 10% fetal calf serum.

Example 2

Comparison of Human IL-12 Expression and Secretion Using Different Ratios of Improved DNA Expression Vectors Human 293 cells were transfected as described with a mix of 2 different expression vectors for IL-12 subunits p35 and p40. The amount of p35 was kept the same (100 ng) and increasing amounts of p40 plasmid were provided to the specified ratios below. Supernatants of transfected cells were assayed for human IL-12 p70 expression using a commercial ELISA (eBioscience). The results (average of two plates of cells per point) indicate that ratios of up to 1:10 result in increased expression of IL-12. See, Table 3.

TABLE 3

| | human IL-12 subunits: | |
|---|---|---|
| p35:p40 ratio | vectors | P70 ng/ml in cell supernatant |
| 1:3 | AG182 + AG180 (1:3) | 5243.8 |
| 1:5 | AG182 + AG180 (1:5) | 4236.9 |
| 1:8 | AG182 + AG180 (1:8) | 18175.5 |
| 1:10 | AG182 + AG180 (1:10) | 35485.0 |
| 1:20 | AG182 + AG180 (1:20) | 2984.2 |
| no p35, negative control | AG177 + AG180 (1:1) | 0.6 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications and sequence accession numbers cited herein are hereby incorporated by reference in their entirety for all purposes.

INFORMAL SEQUENCE LISTING

```
SEQ ID NO: 1-AG181
flanking sequences in lower case; coding sequences underlined
human IL-12 heterodimer expressed; p40 from human CMV promoter
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGGcgcgcgtcgaggaatt
tcgagaagaaATGTGCCACCAGCAGCTGGTCATCAGCTGGTTCAGCCTCGTTTTCCTCGCCTCG
CCGCTGGTCGCCATATGGGAGCTCAAGAAGGACGTATACGTGGTGGAGCTGGACTGGTACCCCG
ACGCGCCGGGCGAGATGGTCGTCCTGACGTGCGACACGCCGGAGGAGGACGGCATCACGTGGAC
GCTGGACCAGTCCAGCGAGGTCCTCGGCTCCGGCAAGACGCTGACGATCCAGGTCAAGGAGTTC
GGCGACGCGGGCCAGTACACCGTGCCACAAGGGCGGCGAGGTCCTGAGCCACTCCCTCCTCCTGC
TACACAAGAAGGAGGACGGGATCTGGAGCACGGACATCCTCAAGGACCAGAAGGAGCCGAAGAA
CAAGACCTTCCTGCGCTGCGAGGCGAAGAATTACTCGGGCCGGTTCACGTGCTGGTGGCTCACC
ACGATCAGCACGGACCTGACGTTCTCGGTCAAGTCGTCGCGGGGCTCGTCGGACCCCCAGGGGG
TGACCTGCGGCGCGGCGACGCTGTCGGCGGAGCGGGTGCGGGGCGACAACAAGGAGTACGAGTA
CTCGGTCGAGTGCCAGGAGGACTCGGCGTGCCCGGCGGCGGAGGAGTCGCTGCCGATCGAGGTG
ATGGTCGACGCGGTCCACAAGCTGAAGTACGAGAACTACACGTCGTCGTTCTTCATCCGGGACA
TCATCAAGCCGGACCCGCCGAAGAACCTGCAGCTGAAGCCGCTGAAGAACTCGCGGCAGGTCGA
GGTCTCGTGGGAGTACCCGGACACGTGGTCGACGCCGCACTCGTACTTCTCGCTGACGTTCTGC
GTCCAAGTGCAGGGCAAGTCGAAGCGGGAGAAGAAGGACCGGGTGTTCACCGACAAGACGAGCG
CGACGGTGATCTGCCGGAAGAACGCGTCGATCTCGGTGCGGGCGCAGGACCGGTACTACTCGTC
GTCGTGGTCGGAGTGGGCGTCGGTGCCGTGCAGCTAGacctaggggcgcgccagatctgatatc
ggatctgCTGTGCCTTCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAATTGCATCGCATTGTCT
GAGTAGGTGTCATTCTATTCTGGGGGGTGGGGTGGGGCAGGACAGCAAGGGGGAGGATTGGGAA
GACAATAGCAGGCATGCTGGGGATGCGGTGGGCTCTATGGGTACCCAGGTGCTGAAGAATTGAC
CCGGTTCCTCCTGGGCCAGAAAGAAGCAGGCACATCCCCTTCTCTGTGACACACCCTGTCCACG
CCCCTGGTTCTTAGTTCCAGCCCCACTCATAGGACACTCATAGCTCAGGAGGGCTCCGCCTTCA
ATCCCACCCGCTAAAGTACTTGGAGCGGTCTCTCCCTCCCTCATCAGCCCACCAAACCAAACCT
AGCCTCCAAGAGTGGGAAGAAATTAAAGCAAGATAGGCTATTAAGTGCAGAGGGAGAGAAAATG
CCTCCAACATGTGAGGAAGTAATGAGAGAAATCATAGAATTTCTTCCGCTTCCTCGCTCACTGA
CTCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAG
```

-continued

INFORMAL SEQUENCE LISTING

CCACTGGTAACAGGATTAGCAGAGCGAGGTATGTAGGCGGTGCTACAGAGTTCTTGAAGTGGTG
GCCTAACTACGGCTACACTAGAAGAACAGTATTTGGTATCTGCGCTCTGCTGAAGCCAGTTACC
TTCGGAAAAAGAGTTGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTG
TCTATTTCGTTCATCCATAGTTGCCTGACTCGGGGGGGGGGGGCGCTGAGGTCTGCCTCGTGAA
GAAGGTGTTGCTGACTCATACCAGGCCTGAATCGCCCCATCATCCAGCCAGAAAGTGAGGGAGC
CACGGTTGATGAGAGCTTTGTTGTAGGTGGACCAGTTGGTGATTTTGAACTTTTGCTTTGCCAC
GGAACGGTCTGCGTTGTCGGGAAGATGCGTGATCTGATCCTTCAACTCAGCAAAAGTTCGATTT
ATTCAACAAAGCCGCCGTCCCGTCAAGTCAGCGTAATGCTCTGCCAGTGTTACAACCAATTAAC
CAATTCTGATTAGAAAAACTCATCGAGCATCAAATGAAACTGCAATTTATTCATATCAGGATTA
TCAATACCATATTTTTGAAAAAGCCGTTTCTGTAATGAAGGAGAAAACTCACCGAGGCAGTTCC
ATAGGATGGCAAGATCCTGGTATCGGTCTGCGATTCCGACTCGTCCAACATCAATACAACCTAT
TAATTTCCCCTCGTCAAAAATAAGGTTATCAAGTGAGAAATCACCATGAGTGACGACTGAATCC
GGTGAGAATGGCAAAAGCTTATGCATTTCTTTCCAGACTTGTTCAACAGGCCAGCCATTACGCT
CGTCATCAAAATCACTCGCATCAACCAAACCGTTATTCATTCGTGATTGCGCCTGAGCGAGACG
AAATACGCGATCGCTGTTAAAAGGACAATTACAAACAGGAATCGAATGCAACCGGCGCAGGAAC
ACTGCCAGCGCATCAACAATATTTTCACCTGAATCAGGATATTCTTCTAATACCTGGAATGCTG
TTTTCCCGGGGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTAACATCATTG
GCAACGCTACCTTTGCCATGTTTCAGAAACAACTCTGGCGCATCGGGCTTCCCATACAATCGAT
AGATTGTCGCACCTGATTGCCCGACATTATCGCGAGCCCATTTATACCCATATAAATCAGCATC
CATGTTGGAATTTAATCGCGGCCTCGAGCAAGACGTTTCCCGTTGAATATGGCTCATAACACCC
CTTGTATTACTGTTTATGTAAGCAGACAGTTTTATTGTTCATGATGATATATTTTTATCTTGTG
CAATGTAACATCAGAGATTTTGAGACACAACGTGGATCATCCAGACATGATAAGATACATTGAT
GAGTTTGGACAAACCACAACTAGAATGCAGTGAAAAAAATGCTTTATTTGTGAAATTTGTGATG
CTATTGCTTTATTTGTAACCATTATAAGCTGCAATAAACAAGTTAACAACAACAATTGCATTCA
TTTTATGTTTCAGGTTCAGGGGGAGGTGTGGGAGGTTTTTTAAAGCAAGTAAAACCTCTACAAA
TGTGGTATGGCTGATTATGATCgtcgaggatccggcgccggtttcgcgtcgatatcTTACGAAG
CGTTCAGGTACGACATCACCCGGTCGATCGTCACCGCCCGGATCCGGAAAGCGTGCAGCAGGAT
GCAGAGCTTGATCTTCGTCTTGTAGAAGTCCGGCTCCTCGAGCGACGACTTCTGCGGCACCGTC
TCGCTGTTGAAGTTGAGCGCCTGCATGAGCTCGTCGATCACCGCCAGCATGTTCTGGTCGAGGA
AGATCTGCCGCTTCGGGTCCATCAGCAGCTTCGCGTTCATCGTCTTGAACTCCACCTGGTACAT
CTTCAGGTCCTCGTAGATCGACGACAGGCACAGCGCCATCATGAACGACGTCTTCCGCGACGCC
AGGCACGACCCGTTCGTGATGAACGACGTCTCCCTCGAGTTCAGGCACGACTCGTTCTTCGTCA
GCTCCAGCGGCAGGCACGCCTCCACCGTGCTGGTCTTGTCCTTCGTGATGTCCTCGTGGTCGAT
CTCCTCGCTCGTGCACGGGTAGAACTCCAGCGTCTGCCGCGCCTTCTGCAGCATGTTCGACACC
GCCCGCAGCAGGTTCTGGCTGTGGTGCAGGCACGGGAACATCCCCGGGTCCGGCGTCGCCACCG
GCAGGTTCCGCGCCAGGCTCAGGTGGTCGAGCAGGACCAGCGTCGCCACGAGCAGCAGGGAGCG
CGCCGGGCACATttctttctagaaacgtcgacagatccAAACGCTCCTCCGACGTCCCCAGGCA
GAATGGCGGTTCCCTAAACGAGCATTGCTTATATAGACCTCCCATTAGGCACGCCTACCGCCCA
TTTACGTCAATGGAACGCCCATTTGCGTCATTGCCCCTCCCCATTGACGTCAATGGGGATGTAC
TTGGCAGCCATCGCGGGCCATTTACCGCCATTGACGTCAATGGGAGTACTGCCAATGTACCCTG
GCGTACTTCCAATAGTAATGTACTTGCCAAGTTACTATTAATAGATATTGATGTACTGCCAAGT
GGGCCATTTACCGTCATTGACGTCAATAGGGGGCGTGAGAACGGATATGAATGGGCAATGAGCC
ATCCCATTGACGTCAATGGTGGGTGGTCCTATTGACGTCAATGGGCATTGAGCCAGGCGGGCCA
TTTACCGTAATTGACGTCAATGGGGGAGGCGCCATATACGTCAATAGGACCGCCCATATGACGT
CAATAGGTAAGACCATGAGGCCCTTTCGTCTCGCGCGTTTCGGTGATGACGGTGAAAACCTCTG
ACACATGCAGCTCCCGGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACTATGCGGCATCAGAGC
AGATTGTACTGAGAGTGCACCATATGCGGTGTGAAATACCGCACAGATGCGTAAGGAGAAAATA
CCGCATCAGATTGGCTATTGG SEQ ID NO: 2-AG183
flanking sequences in lower case; coding sequences underlined
human IL-12 heterodimer expressed; p40 from simian CMV promoter
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGGcgcgcgtcgaggaatt
cgctagaaagaaATGTGCCCGGCGCGCTCCCTGCTGCTCGTGGCGACGCTGGTCCTGCTCGACC
ACCTGAGCCTGGCGCGGAACCTGCCGGTGGCGACGCCGGACCCGGGGATGTTCCCGTGCCTGCA
CCACAGCCAGAACCTGCTGCGGGCGGTGTCGAACATGCTGCAGAAGGCGCGGCAGACGCTGGAG
TTCTACCCGTGCACGAGCGAGGAGATCGACCACGAGGACATCACGAAGGACAAGACCAGCACGG
TGGAGGCGTGCCTGCCGCTGGAGCTGACGAAGAACGAGTCGTGCCTGAACTCGAGGGAGACGTC
GTTCATCACGAACGGGTCGTGCCTGGCGTCGCGGAAGACGTCGTTCATGATGGCGCTGTGCCTG
TCGTCGATCTACGAGGACCTGAAGATGTACCAGGTGGAGTTCAAGACGATGAACGCGAAGCTGC

INFORMAL SEQUENCE LISTING

```
TGATGGACCCGAAGCGGCAGATCTTCCTCGACCAGAACATGCTGGCGGTGATCGACGAGCTCAT
GCAGGCGCTCAACTTCAACAGCGAGACGGTGCCGCAGAAGTCGTCGCTCGAGGAGCCGGACTTC
TACAAGACGAAGATCAAGCTCTGCATCCTGCTGCACGCTTTCCGGATCCGGGCGGTGACGATCG
ACCGGGTGATGTCGTACCTGAACGCTTCGTAAgatatcgacgcgccagatctgatatcggatct
GCTGTGCCTTCTAGTTGCCAGCCATCTGTTGTTTGCCCCTCCCCCGTGCCTTCCTTGACCCTGG
AAGGTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAGACAAT
AGCAGGCATGCTGGGGATGCGGTGGGCTCTATGGGTACCCAGGTGCTGAAGAATTGACCCGGTT
CCTCCTGGGCCAGAAAGAAGCAGGCACATCCCCTTCTCTGTGACACACCCTGTCCACGCCCCTG
GTTCTTAGTTCCAGCCCCACTCATAGGACACTCATAGCTCAGGAGGGCTCCGCCTTCAATCCCA
CCCGCTAAAGTACTTGGAGCGGTCTCTCCCTCCCTCATCAGCCCACCAAACCAAACCTAGCCTC
CAAGAGTGGGAAGAAATTAAAGCAAGATAGGCTATTAAGTGCAGAGGGAGAGAAAATGCCTCCA
ACATGTGAGGAAGTAATGAGAGAAATCATAGAATTTCTTCCGCTTCCTCGCTCACTGACTCGCT
GCGCTCGGTCGTTCGGCTGCGGCGAGCGGTATCAGCTCACTCAAAGGCGGTAATACGGTTATCC
ACAGAATCAGGGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTCCGCCTTTC
TCCCTTCGGGAAGCGTGGCGCTTTCTCAATGCTCACGCTGTAGGTATCTCAGTTCGGTGTAGGT
CGTTCGCTCCAAGCTGGGCTGTGTGCACGAACCCCCCGTTCAGCCCGACCGCTGCGCCTTATCC
GGTAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCCTAA
CTACGGCTACACTAGAAGAACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTTTTCTACGGG
GTCTGACGCTCAGTGGAACGAAAACTCACGTTAAGGGATTTTGGTCATGAGATTATCAAAAAGG
ATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATT
TCGTTCATCCATAGTTGCCTGACTCGGGGGGGGGGGCGCTGAGGTCTGCCTCGTGAAGAAGGT
GTTGCTGACTCATACCAGGCCTGAATCGCCCCATCATCCAGCCAGAAAGTGAGGGAGCCACGGT
TGATGAGAGCTTTGTTGTAGGTGGACCAGTTGGTGATTTTGAACTTTTGCTTTGCCACGGAACG
GTCTGCGTTGTCGGGAAGATGCGTGATCTGATCCTTCAACTCAGCAAAAGTTCGATTTATTCAA
CAAAGCCGCCGTCCCGTCAAGTCAGCGTAATGCTCTGCCAGTGTTACAACCAATTAACCAATTC
TGATTAGAAAAACTCATCGAGCATCAAATGAAACTGCAATTTATTCATATCAGGATTATCAATA
CCATATTTTTGAAAAAGCCGTTTCTGTAATGAAGGAGAAAACTCACCGAGGCAGTTCCATAGGA
TGGCAAGATCCTGGTATCGGTCTGCGATTCCGACTCGTCCAACATCAATACAACCTATTAATTT
CCCCTCGTCAAAAATAAGGTTATCAAGTGAGAAATCACCATGAGTGACGACTGAATCCGGTGAG
AATGGCAAAAGCTTATGCATTTCTTTCCAGACTTGTTCAACAGGCCAGCCATTACGCTCGTCAT
CAAAATCACTCGCATCAACCAAACCGTTATTCATTCGTGATTGCGCCTGAGCGAGACGAAATAC
GCGATCGCTGTTAAAAGGACAATTACAAACAGGAATCGAATGCAACCGGCGCAGGAACACTGCC
AGCGCATCAACAATATTTTCACCTGAATCAGGATATTCTTCTAATACCTGGAATGCTGTTTTCC
CGGGGATCGCAGTGGTGAGTAACCATGCATCATCAGGAGTACGGATAAAATGCTTGATGGTCGG
AAGAGGCATAAATTCCGTCAGCCAGTTTAGTCTGACCATCTCATCTGTAACATCATTGGCAACG
CTACCTTTGCCATGTTTCAGAAACAACTCTGGCGCATCGGGCTTCCCATACAATCGATAGATTG
TCGCACCTGATTGCCCGACATTATCGCGAGCCCATTTATACCCATATAAATCAGCATCCATGTT
GGAATTTAATCGCGGCCTCGAGCAAGACGTTTCCCGTTGAATATGGCTCATAACACCCCTTGTA
TTACTGTTTATGTAAGCAGACAGTTTTATTGTTCATGATGATATATTTTTATCTTGTGCAATGT
AACATCAGAGATTTTGAGACACAACGTGGATCATCCAGACATGATAAGATACATTGATGAGTTT
GGACAAACCACAACTAGAATGCAGTGAAAAAAATGCTTTATTTGTGAAATTTGTGATGCTATTG
CTTTATTTGTAACCATTATAAGCTGCAATAAACAAGTTAACAACAACAATTGCATTCATTTTAT
GTTTCAGGTTCAGGGGGAGGTGTGGGAGGTTTTTTAAAGCAAGTAAAACCTCTACAAATGTGGT
ATGGCTGATTATGATCgtcgaggatccggcgccggtttgatccggcgcgccctaggtCTAGCT
GCACGGCACCGACGCCCACTCCGACCACGACGACGAGTAGTACCGGTCCTGCGCCCGCACCGAG
ATCGACGCGTTCTTCCGGCAGATCACCGTCGCGCTCGTCTTGTCGGTGAACACCCGGTCCTTCT
TCTCCCGCTTCGACTTGCCCTGCACTTGGACGCAGAACGTCAGCGAGAAGTACGAGTGCGGCGT
CGACCACGTGTCCGGGTACTCCCACGAGACCTCGACCTGCCGCGAGTTCTTCAGCGGCTTCAGC
TGCAGGTTCTTCGGCGGGTCCGGCTTGATGATGTCCCGGATGAAGAACGACGACGTGTAGTTCT
CGTACTTCAGCTTGTGGACCGCGTCGACCATCACCTCGATCGGCAGCGACTCCTCCGCCGCCGG
GCACGCCGAGTCCTCCTGGCACTCGACCGAGTACTCGTACTCCTTGTTGTCGCCCCGCACCCGC
TCCGCCGACAGCGTCGCCGCGCCGCAGGTCACCCCCTGGGGGTCCGACGAGCCCCGCGACGACT
TGACCGAGAACGTCAGGTCCGTGCTGATCGTGGTGAGCCACCAGCACGTGAACCGGCCCGAGTA
ATTCTTCGCCTCGCAGCGCAGGAAGGTCTTGTTCTTCGGCTCCTTCTGGTCCTTGAGGATGTCC
GTGCTCCAGATCCCGTCCTCCTTCTTGTGTAGCAGGAGGAGGGAGTGGCTCAGGACCTCGCCGC
CCTTGTGGCACGTGTACTGGCCCGCGTCGCCGAACTCCTTGACCTGGATCGTCAGCGTCTTGCC
GGAGCCGAGGACCTCGCTGGACTGGTCCAGCGTCCACGTGATGCCGTCCTCCTCCGGCGTGTCG
CACGTCAGGACGACCATCTCGCCCGGCGCGTCGGGGTACCAGTCCAGCTCCACCACGTATACGT
CCTTCTTGAGCTCCCATATGGCGACCAGCGGCGAGGCGAGGAAAACGAGGCTGAACAGCTGAT
GACCAGCTGCTGGTGGCACATttcttctcgacagatccAAAGCTCCTCCGACGTCCCCAGGCA
GAATGGCGGTTCCCTAAACGAGCATTGCTTATATAGACCTCCCATTAGGCACGCCTACCGCCCA
TTTACGTCAATGGAACGCCCATTTGCGTCATTGCCCCTCCCCATTGACGTCAATGGGGATGTAC
TTGGCAGCCATCGCGGGCCATTTACCGCCATTGACGTCAATGGGAGTACTGCCAATGTACCCTG
GCGTACTTCCAATAGTAATGTACTTGCCAAGTTACTATTAATAGATATTGATGTACTGCCAAGT
GGGCCATTTACCGTCATTGACGTCAATAGGGGGCGTGAGAACGGATATGAATGGGCAATGAGCC
ATCCCATTGACGTCAATGGTGGTGGTCCTATTGACGTCAATGGGCATTGAGCCAGGCGGGCCA
TTTACCGTAATTGACGTCAATGGGGAGGCGCCATATACGTCAATAGGACCGCCCATATGACGT
CAATAGGTAAAGACCATGAGGCCCTTTCGTCTCGCGCGTTTCGGTGATGACGGTGAAAACCTCT
GACACATGCAGCTCCCGGAGACGGTCACAGCTTGTCTGTAAGCGGATGCCGGGAGCAGACAAGC
```

| INFORMAL SEQUENCE LISTING |
| --- |
| CCGTCAGGGCGCGTCAGCGGGTGTTGGCGGGTGTCGGGGCTGGCTTAACTATGCGGCATCAGAG
CAGATTGTACTGAGAGTGCACCATATGCGGTGTGAAATACCGCACAGATGCGTAAGGAGAAAAT
ACCGCATCAGATTGGCTATTGG

SEQ ID NO: 3-AG157
flanking sequences in lower case; coding sequences underlined
rhesus IL-12 heterodimer expressed; p40 from human CMV promoter
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGgcgcgcgtcgaggaatt
aaacctcgagaagaaATGTGCCACCAGCAGCTGGTGATCAGCTGGTTCAGCCTGGTGTTCCTGG
CCAGCCCCCTGATGGCCATCTGGGAGCTGAAGAAGGACGTATACGTGGTGGAGCTGGACTGGTA
TCCCGACGCGCCTGGCGAGATGGTGGTGCTGACCTGCGACACCCCCGAGGAGGACGGCATCACC
TGGACCCTGGACCAGAGCGGCGAAGTGCTGGGCAGCGGCAAGACCCTGACGATCCAGGTCAAGG
AGTTCGGCGACGCCGGCCAGTACACCTGCCACAAGGGCGGCGAGGTCCTGAGCCACAGCCTGCT
GCTGCTGCACAAGAAGGAGGACGGGATCTGGAGCACCGACGTGCTGAAGGACCAGAAGGAGCCC
AAGAACAAGACCTTCCTGCGCTGCGAGGCCAAGAATTACAGCGGCCGGTTCACCTGTTGGTGGC
TGACCACCATCAGCACCGACCTGACCTTCAGCGTGAAGAGCAGCAGAGGCAGCAGCAACCCCCA
GGGCGTGACCTGTGGCGCCGTGACCCTGAGCGCCGAGAGAGTGAGAGGCGACAACAAGGAGTAC
GAGTACAGCGTGGAGTGCCAGGAGGACAGCGCCTGCCCTGCCGCCGAGGAGAGACTGCCCATCG
AAGTGATGGTGGACGCCATCCACAAGCTGAAGTACGAGAACTACACCAGCTCCTTCTTCATCCG
GGACATCATCAAGCCCGACCCCCCCAAGAACCTGCAGCTGAAGCCCCTGAAGAACAGCAGGCAG
GTGGAAGTGAGCTGGGAGTACCCCGACACCTGGAGCACCCCTCACAGCTACTTCAGCCTGACCT
TCTGCATCCAAGTGCAGGGCAAGAGCAAGCGGGAGAAGAAGGACCGGATCTTCACCGATAAGAC
CAGCGCCACCGTGATCTGCCGGAAGAACGCCAGCTTCAGCGTGCAGGCCCAGGACAGATACTAC
AGCAGCAGCTGGAGCGAGTGGGCCAGCGTGCCTTGCAGCTGATGAacctaggggcgcgccagat
ctgatatcggatctGCTGTGCCTTCTAGTTGCCAGCCATCTGTTGTTTGCCCCTCCCCCGTGCC
TTCCTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGGCAGGACAGCAAGGGGGAGG
ATTGGGAAGACAATAGCAGGCATGCTGGGGATGCGGTGGGCTCTATGGGTACCCAGGTGCTGAA
GAATTGACCCGGTTCCTCCTGGGCCAGAAAGAAGCAGGCACATCCCCTTCTCTGTGACACACCC
TGTCCACGCCCCTGGTTCTTAGTTCCAGCCCCACTCATAGGACACTCATAGCTCAGGAGGGCTC
CGCCTTCAATCCCACCCGCTAAAGTACTTGGAGCGGTCTCTCTCCCTCCTCATCAGCCCACCAA
CCAAACCTAGCCTCCAAGAGTGGGAAGAAATTAAAGCAAGATAGGCTATTAAGTGCAGAGGGAG
AGAAAATGCCTCCAACATGTGAGGAAGTAATGAGAGAAATCATAGAATTTCTTCCGCTTCCTCG
CTCACTGACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAAGATACC
AGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTC
AGTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAGAGTTCTTG
AAGTGGTGGCCTAACTACGGCTACACTAGAAGAACAGTATTTGGTATCTGCGCTCTGCTGAAGC
CAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGA
GATTATCAAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACCTATCTCA
GCGATCTGTCTATTTCGTTCATCCATAGTTGCCTGACTCGGGGGGGGGGGCGCTGAGGTCTGC
CTCGTGAAGAAGGTGTTGCTGACTCATACCAGGCCTGAATCGCCCCATCATCCAGCCAGAAAGT
GAGGGAGCCACGGTTGATGAGAGCTTTGTTGTAGGTGGACCAGTTGGTGATTTTGAACTTTTGC
TTTGCCACGGAACGGTCTGCGTTGTCGGGAAGATGCGTGATCTGATCCTTCAACTCAGCAAAAG
TTCGATTTATTCAACAAAGCCGCCGTCCCGTCAAGTCAGCGTAATGCTCTGCCAGTGTTACAAC
CAATTAACCAATTCTGATTAGAAAAACTCATCGAGCATCAAATGAAACTGCAATTTATTCATAT
CAGGATTATCAATACCATATTTTTGAAAAAGCCGTTTCTGTAATGAAGGAGAAAACTCACCGAG
GCAGTTCCATAGGATGGCAAGATCCTGGTATCGGTCTGCGATTCCGACTCGTCCAACATCAATA
CAACCTATTAATTTCCCCTCGTCAAAAATAAGGTTATCAAGTGAGAAATCACCATGAGTGACGA
CTGAATCCGGTGAGAATGGCAAAAGCTTATGCATTTCTTTCCAGACTTGTTCAACAGGCCAGCC
ATTACGCTCGTCATCAAAATCACTCGCATCAACCAAACCGTTATTCATTCGTGATTGCGCCTGA
GCGAGACGAAATACGCGATCGCTGTTAAAAGGACAATTACAACAGGAATCGAATGCAACCGGCG
CAGGAACACTGCCAGCGCATCAACAATATTTTCACCTGAATCAGGATATTCTTCTAATACCTG
GAATGCTGTTTTCCCGGGGATCGCAGTGGTGAGTAACCATGCATCATCAGGAGTACGGATAAAA
TGCTTGATGGTCGGAAGAGGCATAAATTCCGTCAGCCAGTTTAGTCTGACCATCTCATCTGTAA
CATCATTGGCAACGCTACCTTTGCCATGTTTCAGAAACAACTCTGGCGCATCGGGCTTCCCATA
CAATCGATAGATTGTCGCACCTGATTGCCCGACATTATCGCGAGCCCATTTATACCCATATAAA
TCAGCATCCATGTTGGAATTTAATCGCGGCCTCGAGCAAGACGTTTCCCGTTGAATATGGCTCA |

TAACACCCCTTGTATTACTGTTTATGTAAGCAGACAGTTTTATTGTTCATGATGATATATTTTT
ATCTTGTGCAATGTAACATCAGAGATTTTGAGACACAACGTGGATCATCCAGACATGATAAGAT
ACATTGATGAGTTTGGACAAACCACAACTAGAATGCAGTGAAAAAAATGCTTTATTTGTGAAAT
TTGTGATGCTATTGCTTTATTTGTAACCATTATAAGCTGCAATAAACAAGTTAACAACAACAAT
TGCATTCATTTTATGTTTCAGGTTCAGGGGGAGGTGTGGGAGGTTTTTTAAAGCAAGTAAAACC
TCTACAAATGTGGTATGGCTGATTATGATCgtcgaggatcatcTTATCAGCTGGCGTTCAGGTA
GCTCATCACTCTGTCGATGGTCACGGCCCTGATCGGAAGGCGTGCAGCAGGATGCACAGCTTG
ATCTTGGTCTTGTAGAAGTCGGGCTCCTCCAGGCTGCTCTTCTGAGGCACGGTCTCGCTGTTGA
AGTTCAGGGCCTGCATCAGCTCGTCGATCACGCCCAGGATGTTCTGGTCCAGGAAGATCTGCCT
CTTGGGGTCCCTCAGCAGCTTGGCGTTCATGGTCTTGAACTCCACCTGGTACATCTTCAGGTCC
TCGTAGATGCTCCTCAGGCACAGGGCCATCATGAAGGAGGTCTTTCTGCTGGCCAGGCAGCTGC
CGTTGGTGATGAAGCTGGTCTCCCTCGAGTTCAGGCACGACTCGTTCTTGATCAGCTCCAGCGG
CAGGCACGCCTCCACCGTGCTGGTCTTGTCCTTCGTGATGTCCTCGTGGTCGATCTCCTCGCTC
GTGCACGGGTAGAACTCCAGGATCTGCCGCGCCTTCTGCAGCGTGTTCGACGCCGCCTTCAGCA
GGTTCTGGCTGTGGTGCAGGCACGGGAACATCTCCGGTCCCGGGGTCGCCACCGACAGGTTCCG
CGCCAGGCTCAGGTAGTCGAGGCAGGACCAGCGTCGCCACGAGCAGCAGGGAGCGCGCCGGGCAC
ATttctttctagacgtcgacagatccAAACGCTCCTCCGACGTCCCCAGGCAGAATGGCGGTTC
CCTAAACGAGCATTGCTTATATAGACCTCCCATTAGGCACGCCTACCGCCCATTTACGTCAATG
GAACGCCCATTTGCGTCATTGCCCCTCCCCATTGACGTCAATGGGGATGTACTTGGCAGCCATC
GCGGGCCATTTACCGCCATTGACGTCAATGGGAGTACTGCCAATGTACCCTGGCGTACTTCCAA
TAGTAATGTACTTGCCAAGTTACTATTAATAGATATTGATGTACTGCCAAGTGGGCATTTACC
GTCATTGACGTCAATAGGGGGCGTGAGAACGGATATGAATGGGCAATGAGCCATCCCATTGACG
TCAATGGTGGGTGGTCCTATTGACGTCAATGGGCATTGAGCCAGGCGGGCCATTTACCGTAATT
GACGTCAATGGGGAGGCGCCATATACGTCAATAGGACGCCCCATATGACGTCAATAGGTAAGA
CCATGAGGCCCTTTCGTCTCGCGCGTTTCGGTGATGACGGTGAAAACCTCTGACACATGCAGCT
CCCGGAGACGGTCACAGCTTGTCTGTAAGCGGATGCCGGGAGCAGACAAGCCCGTCAGGGCGCG
TCAGCGGGTGTTGGCGGGTGTCGGGGCTGGCTTAACTATGCGGCATCAGAGCAGATTGTACTGA
GAGTGCACCATATGCGGTGTGAAATACCGCACAGATGCGTAAGGAGAAAATACCGCATCAGATT
GGCTATTGG SEQ ID NO: 4-AG159
flanking sequences in lower case; coding sequences underlined
rhesus IL-12 heterodimer expressed; p40 from simian CMV promoter
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGgcgcgcgtcgaggaatt
cgctagaaagaaATGTGCCCGGCGCGCTCCCTGCTGCTCGTGGCGACGCTGGTCCTGCTCGACT
ACCTGAGCCTGGCGCGGAACCTGTCGGTGGCGACCCCGGGACCGGAGATGTTCCCGTGCCTGCA
CCACAGCCAGAACCTGCTGAAGGCGGCGTCGAACACGCTGCAGAAGGCGCGGCAGATCCTGGAG
TTCTACCCGTGCACGAGCGAGGAGATCGACCACGAGGACATCACGAAGGACAAGACCAGCACGG
TGGAGGCGTGCCTGCCGCTGGAGCTGATCAAGAACGAGTCGTGCCTGAACTCGAGGGAGACCAG
CTTCATCACCAACGGCAGCTGCCTGGCCAGCAGAAAGACCTCCTTCATGATGGCCCTGTGCCTG
AGGAGCATCTACGAGGACCTGAAGATGTACCAGGTGGAGTTCAAGACCATGAACGCCAAGCTGC
TGAGGGACCCCAAGAGGCAGATCTTCCTGGACCAGAACATGCTGGGCGTGATCGACGAGCTGAT
GCAGGCCCTGAACTTCAACAGCGAGACCGTGCCTCAGAAGAGCAGCCTGGAGGAGCCCGACTTC
TACAAGACCAAGATCAAGCTGTGCATCCTGCTGCACGCCTTCCGGATCAGGGCCGTGACCATCG
ACAGAGTGATGAGCTACCTGAACGCCAGCTGATAAgatatcggatctatcggatctGCTGTGCC
TTCTAGTTGCCAGCCATCTGTTGTTTGCCCCTCCCCGTGCCTTCCTTGACCCTGGAAGGTGCC
ACTCCCACTGTCCTTTCCTAATAAAATGAGGAAATTGCATCGCATTGTCTGAGTAGGTGTCATT
CTATTCTGGGGGGTGGGTGGGGCAGGACAGCAAGGGGGAGGATTGGGAAGACAATAGCAGGCA
TGCTGGGGATGCGGTGGGCTCTATGGGTACCCAGGTGCTGAAGAATTGACCCGGTTCCTCCTGG
GCCAGAAAGAAGCAGGCACATCCCCTTCTCTGTGACACACCTGTCCACGCCCCTGGTTCTTAG
TTCCAGCCCCACTCATAGGACACTCATAGCTCAGGAGGGCTCCGCCTTCAATCCCACCCGCTAA
AGTACTTGGAGCGGTCTCTCCCTCCCTCATCAGCCCACCAAACCAAACCTAGCCTCCAAGAGTG
GGAAGAAATTAAAGCAAGATAGGCTATTAAGTGCAGAGGGAGAGAAAATGCCTCCAACATGTGA
GGAAGTAATGAGAGAAATCATAGAATTTCTTCCGCTTCCTCGCTCACTGACTCGCTGCGCTCGG
TCGTTCGGCTGCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAACCGTAAAAAG
GCCGCGTTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTATCCGGTAACTA
TCGTCTTGAGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTGCAAGCAG
CAGATTACGCGCAGAAAAAAAGGATCTCAAGAAGATCCTTTGATCTTTTCTACGGGGTCTGACG -continued

| INFORMAL SEQUENCE LISTING |
|---|
| CTCAGTGGAACGAAAACTCACGTTAAGGGATTTTGGTCATGAGATTATCAAAAAGGATCTTCAC |
| CTAGATCCTTTTAAATTAAAAATGAAGTTTTAAATCAATCTAAAGTATATATGAGTAAACTTGG |
| TCTGACAGTTACCAATGCTTAATCAGTGAGGCACCTATCTCAGCGATCTGTCTATTTCGTTCAT |
| CCATAGTTGCCTGACTCGGGGGGGGGGGCGCTGAGGTCTGCCTCGTGAAGAAGGTGTTGCTGA |
| CTCATACCAGGCCTGAATCGCCCCATCATCCAGCCAGAAAGTGAGGGAGCCACGGTTGATGAGA |
| GCTTTGTTGTAGGTGGACCAGTTGGTGATTTTGAACTTTTGCTTTGCCACGGAACGGTCTGCGT |
| TGTCGGGAAGATGCGTGATCTGATCCTTCAACTCAGCAAAAGTTCGATTTATTCAACAAAGCCG |
| CCGTCCCGTCAAGTCAGCGTAATGCTCTGCCAGTGTTACAACCAATTAACCAATTCTGATTAGA |
| AAAACTCATCGAGCATCAAATGAAACTGCAATTTATTCATATCAGGATTATCAATACCATATTT |
| TTGAAAAAGCCGTTTCTGTAATGAAGGAGAAAACTCACCGAGGCAGTTCCATAGGATGGCAAGA |
| TCCTGGTATCGGTCTGCGATTCCGACTCGTCCAACATCAATACAACCTATTAATTTCCCCTCGT |
| CAAAAATAAGGTTATCAAGTGAGAAATCACCCATGAGTGACGACTGAATCCGGTGAGAATGGCAA |
| AAGCTTATGCATTTCTTTCCAGACTTGTTCAACAGGCCAGCCATTACGCTCGTCATCAAAATCA |
| CTCGCATCAACCAAACCGTTATTCATTCGTGATTGCGCCTGAGCGAGACGAAATACGCGATCGC |
| TGTTAAAAGGACAATTACAAACAGGAATCGAATGCAACCGGCCAGGAACACTGCCAGCGCATC |
| AACAATATTTTCACCTGAATCAGGATATTCTTCTAATACCTGGAATGCTGTTTTCCCGGGGATC |
| GCAGTGGTGAGTAACCATGCATCATCAGGAGTACGGATAAAATGCTTGATGGTCGGAAGAGGCA |
| TAAATTCCGTCAGCCAGTTTAGTCTGACCATCTCATCTGTAACATCATTGGCAACGCTACCTTT |
| GCCATGTTTCAGAAACAACTCTGGCGCATCGGGCTTCCCATACAATCGATAGATTGTCGCACCT |
| GATTGCCCGACATTATCGCGAGCCCATTTATACCCATATAAATCAGCATCCATGTTGGAATTTA |
| ATCGCGGCCTCGAGCAAGACGTTTCCCGTTGAATATGGCTCATAACACCCCTTGTATTACTGTT |
| TATGTAAGCAGACAGTTTTATTGTTCATGATGATATATTTTTATCTTGTGCAATGTAACATCAG |
| AGATTTTGAGACACAACGTGGATCATCCAGACATGATAAGATACATTGATGAGTTTGGACAAAC |
| CACAACTAGAATGCAGTGAAAAAAATGCTTTATTTGTGAAATTTGTGATGCTATTGCTTTATTT |
| GTAACCATTATAAGCTGCAATAAACAAGTTAACAACAACAATTGCATTCATTTTATGTTTCAGG |
| TTCAGGGGAGGTGTGGGAGGTTTTTTAAAGCAAGTAAAACCTCTACAAATGTGGTATGGCTGA |
| TTATGATCgtcgaggatccggcgccggtttcgcgcccctaggt<u>TCATCAGCTGCAAGGCACGCT</u> |
| <u>GGCCCACTCGCTCCAGCTGCTGCTGTAGTATCTGTCCTGGGCGCTGAAGCTGGCGTTC</u> |
| <u>TTCCGGCAGATCACGGTGGCGCTGGTCTTATCGGTGAAGATCCGGTCCTTCTTCTCCCGCTTGC</u> |
| <u>TCTTGCCCTGCACTTGGATGCAGAAGGTCAGGCTGAAGTAGCTGTGAGGGGTGCTCCAGGTGTC</u> |
| <u>GGGGTACTCCCAGCTCACTTCCACCTGCCTGCTGTTCTTCAGGGGCTTCAGCTGCAGGTTCTTG</u> |
| <u>GGGGGGTCGGGCTTGATGATGTCCCGGATGAAGAAGGAGCTGGTGTAGTTCTCGTACTTCAGCT</u> |
| <u>TGTGGATGGCGTCCACCATCACTTCGATGGGCAGTCTCTCCTCGGCGGCAGGGCAGGCGCTGTC</u> |
| <u>CTCCTGGCACTCCACGCTGTACTCGTACTCCTTGTTGTCGCCTCTCACTCTCGGCGCTCAGG</u> |
| <u>GTCACGGCGCCACAGGTCACGCCCTGGGGGTTGCTGCTGCCTCTGCTGCTCTTCACGCTGAAGG</u> |
| <u>TCAGGTCGGTGCTGATGGTGGTCAGCCACCAACAGGTGAACCGGCCGCTGTAATTCTTGGCCTC</u> |
| <u>GCAGCGCAGGAAGGTCTTGTTCTTGGGCTCCTTCTGGTCCTTCAGCACGTCGGTGCTCCAGATC</u> |
| <u>CCGTCCTCCTTCTTGTGCAGCAGCAGCAGGCTGTGGCTCAGGGCCTCGCCGCCCTTGTGGCAGG</u> |
| <u>TGTACTGGCCGGCGTCGCCGAACTCCTTGACCTGGATCGTCAGGGTCTTGCCGCTGCCCAGCAC</u> |
| <u>TTCGCCGCTCTGGTCCAGGGTCCAGGTGATGCCGTCCTCCTCGGGGGTGTCGCAGGTCAGCACC</u> |
| <u>ACCATCTCGCCAGGCGCGTCGGGATACCAGTCCAGCTCCACACGTATACGTCCTTCTTCAGCT</u> |
| <u>CCCAGATGGCCATCAGGGGGCTGGCCAGGAACACCAGGCTGAACCAGCTGATCACCAGCTGCTG</u> |
| <u>GTGGCACAT</u>ttcttctcgacagatccAAACGCTCCTCCGACGTCCCCAGGCAGAATGGCGGTTC |
| CCTAAACGAGCATTGCTTATATAGACCTCCCATTAGGCACGCCTACCGCCCATTTACGTCAATG |
| GAACGCCCATTTGCGTCATTGCCCCTCCCCATTGACGTCAATGGGGATGTACTTGGCAGCCATC |
| GCGGGCCATTTACCGCCATTGACGTCAATGGGAGTACTGCCAATGTACCCTGGCGTACTTCCAA |
| TAGTAATGTACTTGCCAAGTTACTATTAATAGATATTGATGTACTGCCAAGTGGGCCATTTACC |
| GTCATTGACGTCAATAGGGGGCGTGAGAACGGATATGAATGGGCAATGAGCCATCCCATTGACG |
| TCAATGGTGGGTGGTCCTATTGACGTCAATGGGCATTGAGCCAGGCGGGCCATTTACCGTAATT |
| GACGTCAATGGGGGAGGCGCCATATACGTCAATAGGACCGCCATATGACGTCAATAGGTAAGA |
| CCATGAGGCCCTTTCGTCTCGCGCGTTTCGGTGATGACGGTGAAAACCTCTGACACATGCAGCT |
| CCCGGAGACGGTCACAGCTTGTCTGTAAGCGGATGCCGGGAGCAGACAAGCCCGTCAGGGCGCG |
| TCAGCGGGTGTTGGCGGGTGTCGGGGCTGGCTTAACTATGCGGCATCAGAGCAGATTGTACTGA |
| GAGTGCACCATATGCGGTGTGAAATACCGCACAGATGCGTAAGGAGAAAATACCGCATCAGATT |
| GGCTATTGG |

SEQ ID NO: 5-AG177
flanking sequences in lower case; coding sequences underlined
expresses p19 subunit of human IL-23
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGcgcgcgtcgactctag
aaagaa<u>ATGCTGGGGACGCGCGGTCATGCTGCTCTTGCTGCTCCCCTGGACGGCCCAGGGCC</u>
<u>GGGCGGTGCCCGGGGGCTCGAGCCCGGCCTGGACGCAGTGCCAGCAGCTCAGCCAGAAGCTCTG</u>
<u>CACCCTGGCCTGGTCGGCCCACCCGCTCGTGGGCCACATGGACCTCGGGAGGAGGGCGACGAG</u>
<u>GAGACGACCAACGACGTCCCCCACATCCAGTGCGGCGACGGCTGCGACCCCCAGGGCCTCCGGG</u>
<u>ACAACTCGCAGTTCTGCCTGCAGCGCATCCACCAGGGCCTGATCTTCTACGAGAAGCTGCTCGG</u>
<u>CTCGGACATCTTCACGGGGGAGCCGTCGCTGCTCCCGGACAGCCCGGTGGGCCAGCTCCACGCC</u>

| INFORMAL SEQUENCE LISTING |
|---|
| <u>TCCCTCCTGGGCCTCTCGCAACTTCTGCAACCGGAGGGCCACCACTGGGAGACGCAGCAGATCC</u> |
| <u>CGAGCCTCTCGCCCAGCCAGCCGTGGCAGCGGCTCCTGCTCAGATTCAAGATCTTGCGCTCCCT</u> |
| <u>CCAAGCCTTCGTGGCGGTCGCCGCCCGGGTCTTCGCCCACGGCGCCACCCTGAGCCCCTGA</u> |
| <u>TAA</u>gatatcggatccaGATCTGCTGTGCCTTCTAGTTGCCAGCCATCTGTTGTTTGCCCCTCCC |
| CCGTGCCTTCCTTGACCCTGGAAGGTGCCACTCCCACTGTCCTTTCCTAATAAAATGAGGAAAT |
| TGCATCGCATTGTCTGAGTAGGTGTCATTCTATTCTGGGGGGTGGGGTGGGGCAGGACAGCAAG |
| GGGGAGGATTGGGAAGACAATAGCAGGCATGCTGGGGATGCGGTGGGCTCTATGGGTACCCAGG |
| TGCTGAAGAATTGACCCGGTTCCTCCTGGGCCAGAAAGAAGCAGGCACATCCCCTTCTCTGTGA |
| CACACCCTGTCCACGCCCCTGGTTCTTAGTTCCAGCCCCACTCATAGGACACTCATAGCTCAGG |
| AGGGCTCCGCCTTCAATCCCACCCGCTAAAGTACTTGGAGCGGTCTCTCCCTCCCTCATCAGCC |
| CACCAAACCAAACCTAGCCTCCAAGAGTGGGAAGAAATTAAAGCAAGATAGGCTATTAAGTGCA |
| GAGGGAGAGAAAATGCCTCCAACATGTGAGGAAGTAATGAGAGAAATCATAGAATTTCTTCCGC |
| TTCCTCGCTCACTGACTCGCTGCGCTCGGTCGTTCGGCTGCGGCGAGCGGTATCAGCTCACTCA |
| AAGGCGGTAATACGGTTATCCACAGAATCAGGGGATAACGCAGGAAAGAACATGTGAGCAAAAG |
| GCCAGCAAAAGGCCAGGAACCGTAAAAAGGCCGCGTTGCTGGCGTTTTTCCATAGGCTCCGCCC |
| CCCTGACGAGCATCACAAAAATCGACGCTCAAGTCAGAGGTGGCGAAACCCGACAGGACTATAA |
| AGATACCAGGCGTTTCCCCCTGGAAGCTCCCTCGTGCGCTCTCCTGTTCCGACCCTGCCGCTTA |
| CCGGATACCTGTCCGCCTTTCTCCCTTCGGGAAGCGTGGCGCTTTCTCATAGCTCACGCTGTAG |
| GTATCTCAGTTCGGTGTAGGTCGTTCGCTCCAAGCTGGGCTGTGTGCACGAACCCCCCGTTCAG |
| CCCGACCGCTGCGCCTTATCCGGTAACTATCGTCTTGAGTCCAACCCGGTAAGACACGACTTAT |
| CGCCACTGGCAGCAGCCACTGGTAACAGGATTAGCAGAGCGAGGTATGTAGGCGGTGCTACAGA |
| GTTCTTGAAGTGGTGGCCTAACTACGGCTACACTAGAAGAACAGTATTTGGTATCTGCGCTCTG |
| CTGAAGCCAGTTACCTTCGGAAAAAGAGTTGGTAGCTCTTGATCCGGCAAACAAACCACCGCTG |
| GTAGCGGTGGTTTTTTTGTTTGCAAGCAGCAGATTACGCGCAGAAAAAAAGGATCTCAAGAAGA |
| TCCTTTGATCTTTTCTACGGGGTCTGACGCTCAGTGGAACGAAAACTCACGTTAAGGGATTTTG |
| GTCATGAGATTATCAAAAAGGATCTTCACCTAGATCCTTTTAAATTAAAAATGAAGTTTTAAAT |
| CAATCTAAAGTATATATGAGTAAACTTGGTCTGACAGTTACCAATGCTTAATCAGTGAGGCACC |
| TATCTCAGCGATCTGTCTATTTCGTTCATCCATAGTTGCCTGACTCGGGGGGGGGGGGCGCTGA |
| GGTCTGCCTCGTGAAGAAGGTGTTGCTGACTCATACCAGGCCTGAATCGCCCCATCATCCAGCC |
| AGAAAGTGAGGGAGCCACGGTTGATGAGAGCTTTGTTGTAGGTGGACCAGTTGGTGATTTTGAA |
| CTTTTGCTTTGCCACGGAACGGTCTGCGTTGTCGGGAAGATGCGTGATCTGATCCTTCAACTCA |
| GCAAAAGTTCGATTTATTCAACAAAGCCGCCGTCCCGTCAAGTCAGCGTAATGCTCTGCCAGTG |
| TTACAACCAATTAACCAATTCTGATTAGAAAAACTCATCGAGCATCAAATGAAACTGCAATTTA |
| TTCATATCAGGATTATCAATACCATATTTTTGAAAAAGCCGTTTCTGTAATGAAGGAGAAAACT |
| CACCGAGGCAGTTCCATAGGATGGCAAGATCCTGGTATCGGTCTGCGATTCCGACTCGTCCAAC |
| ATCAATACAACCTATTAATTTCCCCTCGTCAAAAATAAGGTTATCAAGTGAGAAATCACCATGA |
| GTGACGACTGAATCCGGTGAGAATGGCAAAAGCTTATGCATTTCTTTCCAGACTTGTTCAACAG |
| GCCAGCCATTACGCTCGTCATCAAAATCACTCGCATCAACCAAACCGTTATTCATTCGTGATTG |
| CGCCTGAGCGAGACGAAATACGCGATCGCTGTTAAAAGGACAATTACAAACAGGAATCGAATGC |
| AACCGGCGCAGGAACACTGCCAGCGCATCAACAATATTTTCACCTGAATCAGGATATTCTTCTA |
| ATACCTGGAATGCTGTTTTCCCGGGGATCGCAGTGGTGAGTAACCATGCATCATCAGGAGTACG |
| GATAAAATGCTTGATGGTCGGAAGAGGCATAAATTCCGTCAGCCAGTTTAGTCTGACCATCTCA |
| TCTGTAACATCATTGGCAACGCTACCTTTGCCATGTTTCAGAAACAACTCTGGCGCATCGGGCT |
| TCCCATACAATCGATAGATTGTCGCACCTGATTGCCCGACATTATCGCGAGCCCATTTATACCC |
| ATATAAATCAGCATCCATGTTGGAATTTAATCGCGGCCTCGAGCAAGACGTTTCCCGTTGAATA |
| TGGCTCATAACACCCCTTGTATTACTGTTTATGTAAGCAGACAGTTTTATTGTTCATGATGATA |
| TATTTTTATCTTGTGCAATGTAACATCAGAGATTTTGAGACACAACGTGGCTTTCCCCCCCCCC |
| CCATTATTGAAGCATTTATCAGGGTTATTGTCTCATGAGCGGATACATATTTGAATGTATTTAG |
| AAAAATAAACAAATAGGGGTTCCGCGCACATTTCCCCGAAAAGTGCCACCTGACGTCTAAGAAA |
| CCATTATTATCATGACATTAACCTATAAAAATAGGCGTATCACGAGGCCCTTTCGTCTCGCGCG |
| TTTCGGTGATGACGGTGAAAACCTCTGACACATGCAGCTCCCGGAGACGGTCACAGCTTGTCTG |
| TAAGCGGATGCCGGGAGCAGACAAGCCCGTCAGGGCGCGTCAGCGGGTGTTGGCGGGTGTCGGG |
| GCTGGCTTAACTATGCGGCATCAGAGCAGATTGTACTGAGAGTGCACCATATGCGGTGTGAAAT |
| ACCGCACAGATGCGTAAGGAGAAAATACCGCATCAGATTGGCTATTGG |

SEQ ID NO: 6-AG180
flanking sequences in lower case; coding sequences underlined
expresses p40 subunit of human IL-12

CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGcgcgcgtcgaggaatt
cgagaagaa<u>ATGTGCCACCAGCAGCTGGTCATCAGCTGGTTCAGCCTCGTTTTCCTCGCCTCG</u>
<u>CCGCTGGTCGCCATATGGGAGCTCAAGAAGGACGTATACGTGGTGGAGCTGGACTGGTACCCCG</u>
<u>ACGCGCCGGGCGAGATGGTCGTCCTGACGTGCGACACGCCGGAGGAGGACGGCATCACGTGGAC</u>
<u>GCTGGACCAGTCCAGCGAGGTCCTCGGCTCCGGCAAGACGCTGACGATCCAGGTCAAGGAGTTC</u>
<u>GGCGACGCGGGCCAGTACACGTGCCACAAGGGCGGCGAGGTCCTGAGCCACTCCCTCCTCCTGC</u>
<u>TACACAAGAAGGAGGACGGGATCTGGAGCACGGACATCCTCAAGGACCAGAAGGAGCCGAAGAA</u>
<u>CAAGACCTTCCTGCGCTGCGAGGCGAAGAATTACTCGGGCCGGTTCACGTGCTGGTGGCTCACC</u>

INFORMAL SEQUENCE LISTING

<u>ACGATCAGCACGGACCTGACGTTCTCGGTCAAGTCGTCGCGGGGCTCGTCGGACCCCCAGGGGG
TGACCTGCGGCGCGGCGACGCTGTCGGCGGAGCGGGTGCGGGGCGACAACAAGGAGTACGAGTA
CTCGGTCGAGTGCCAGGAGGACTCGGCGTGCCCGGCGGCGGAGGAGTCGCTGCCGATCGAGGTG
ATGGTCGACGCGGTCCACAAGCTGAAGTACGAGAACTACACGTCGTCGTTCTTCATCCGGGACA
TCATCAAGCCGGACCCGCCGAAGAACCTGCAGCTGAAGCCGCTGAAGAACTCGCGGCAGGTCGA
GGTCTCGTGGGAGTACCCGGACACGTGGTCGACGCCGCACTCGTACTTCTCGCTGACGTTCTGC
GTCCAAGTGCAGGGCAAGTCGAAGCGGGAGAAGAAGGACCGGGTGTTCACCGACAAGACGAGCG
CGACGGTGATCTGCCGGAAGAACGCGTCGATCTCGGTGCGGGCGCAGGACCGGTACTACTCGTC
GTCGTGGTCGGAGTGGGCGTCGGTGCCGTGCAGCTAG</u>acctaggggcgcgccagatctgatatc
ggatctGCTGTGCCTTCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAATTGCATCGCATTGTCT
GAGTAGGTGTCATTCTATTCTGGGGGGTGGGGTGGGGCAGGACAGCAAGGGGGAGGATTGGGAA
GACAATAGCAGGCATGCTGGGGATGCGGTGGGCTCTATGGGTACCCAGGTGCTGAAGAATTGAC
CCGGTTCCTCCTGGGCCAGAAAGAAGCAGGCACATCCCCTTCTCTGTGACACACCCTGTCCACG
CCCCTGGTTCTTAGTTCCAGCCCCACTCATAGGACACTCATAGCTCAGGAGGGCTCCGCCTTCA
ATCCCACCCGCTAAAGTACTTGGAGCGGTCTCTCCCTCCCTCATCAGCCCACCAAACCAAACCT
AGCCTCCAAGAGTGGGAAGAAATTAAAGCAAGATAGGCTATTAAGTGCAGAGGGAGAGAAAATG
CCTCCAACATGTGAGGAAGTAATGAGAGAAATCATAGAATTTCTTCCGCTTCCTCGCTCACTGA
CTCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAAGTGGTG
GCCTAACTACGGCTACACTAGAAGAACAGTATTTGGTATCTGCGCTCTGCTGAAGCCAGTTACC
TTCGGAAAAAGAGTTGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTG
TCTATTTCGTTCATCCATAGTTGCCTGACTCGGGGGGGGGGGCGCTGAGGTCTGCCTCGTGAA
GAAGGTGTTGCTGACTCATACCAGGCCTGAATCGCCCCATCATCCAGCCAGAAAGTGAGGGAGC
CACGGTTGATGAGAGCTTTGTTGTAGGTGGACCAGTTGGTGATTTTGAACTTTTGCTTTGCCAC
GGAACGGTCTGCGTTGTCGGGAAGATGCGTGATCTGATCCTTCAACTCAGCAAAAGTTCGATTT
ATTCAACAAAGCCGCCGTCCCGTCAAGTCAGCGTAATGCTCTGCCAGTGTTACAACCAATTAAC
CAATTCTGATTAGAAAACTCATCGAGCATCAAATGAAACTGCAATTTATTCATATCAGGATTA
TCAATACCATATTTTTGAAAAAGCCGTTTCTGTAATGAAGGAGAAAACTCACCGAGGCAGTTCC
ATAGGATGGCAAGATCCTGGTATCGGTCTGCGATTCCGACTCGTCCAACATCAATACAACCTAT
TAATTTCCCCTCGTCAAAAATAAGGTTATCAAGTGAGAAATCACCATGAGTGACGACTGAATCC
GGTGAGAATGGCAAAAGCTTATGCATTTCTTTCCAGACTTGTTCAACAGGCCAGCCATTACGCT
CGTCATCAAAATCACTCGCATCAACCAAACCGTTATTCATTCGTGATTGCGCCTGAGCGAGACG
AAATACGCGATCGCTGTTAAAAGGACAATTACAAACAGGAATCGAATGCAACCGGCGCAGGAAC
ACTGCCAGCGCATCAACAATATTTTCACCTGAATCAGGATATTCTTCTAATACCTGGAATGCTG
TTTTCCCGGGGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTAACATCATTG
GCAACGCTACCTTTGCCATGTTTCAGAAACAACTCTGGCGCATCGGGCTTCCCATACAATCGAT
AGATTGTCGCACCTGATTGCCCGACATTATCGCGAGCCCATTTATACCCATATAAATCAGCATC
CATGTTGGAATTTAATCGCGGCCTCGAGCAAGACGTTTCCCGTTGAATATGGCTCATAACACCC
CTTGTATTACTGTTTATGTAAGCAGACAGTTTTATTGTTCATGATGATATATTTTTATCTTGTG
CAATGTAACATCAGAGATTTTGAGACACAACGTGGATCATCCAGACATGATAAGATACATTGAT
GAGTTTGGACAAACCACAACTAGAATGCAGTGAAAAAATGCTTTATTTGTGAAATTTGTGATG
CTATTGCTTTATTTGTAACCATTATAAGCTGCAATAAACAAGTTAACAACAACAATTGCATTCA
TTTTATGTTTCAGGTTCAGGGGGAGGTGTGGGAGGTTTTTTAAAGCAAGTAAAACCTCTACAAA
TGTGGTATGGCTGATTATGATCGTCGAGGATCCGGCGCGGTTTAAACGTCGACAGATCCAAAC
GCTCCTCCGACGTCCCAGGCAGAATGGCGGTTCCCTAAACGAGCATTGCTTATATAGACCTCC
CATTAGGCACGCCTACCGCCCATTTACGTCAATGGAACGCCCATTTGCGTCATTGCCCCTCCCC
ATTGACGTCAATGGGGATGTACTTGGCAGCCATCGCGGGCCATTTACCGCCATTGACGTCAATG
GGAGTACTGCCAATGTACCCTGGCGTACTTCCAATAGTAATGTACTTGCCAAGTTACTATTAAT
AGATATTGATGTACTGCCAAGTGGGCCATTTACCGTCATTGACGTCAATAGGGGGCGTGAGAAC
GGATATGAATGGGCAATGAGCCATCCCATTGACGTCAATGGTGGTGGTCCTATTGACGTCAAT
GGGCATTGAGCCAGGCGGGCCATTTACCGTAATTGACGTCAATGGGGAGGCGCATATACGTC
AATAGGACCGCCCATATGACGTCAATAGGTAAGACCATGAGGCCCTTCGTCTCGCGCGTTTCG
GTGATGACGGTGAAAACCTCTGACACATGCAGCTCCCGGAGACGGTCACAGCTTGTCTGTAAGC
GGATGCCGGGAGCAGACAAGCCCGTCAGGGCGCGTCAGCGGGTGTTGGCGGGTGTCGGGGCTGG
CTTAACTATGCGGCATCAGAGCAGATTGTACTGAGAGTGCACCATATGCGGTGTGAAATACCGC
ACAGATGCGTAAGGAGAAAATACCGCATCAGATTGGCTATTGG SEQ ID NO: 7-AG184
flanking sequences in lower case; coding sequences underlined
expresses p40 subunit of human IL-12 under control of hCMV and
p19 subunit of human IL-23 under control of siCMV
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC

INFORMAL SEQUENCE LISTING

```
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGGcgcgcgtcgaggaatt
cgagaagaaATGTGCCACCAGCAGCTGGTCATCAGCTGGTTCAGCCTCGTTTTCCTCGCCTCG
CCGCTGGTCGCCATATGGGAGCTCAAGAAGGACGTATACGTGGTGGAGCTGGACTGGTACCCCG
ACGCGCCGGGCGAGATGGTCGTCCTGACGTGCGACACGCCGGAGGAGGACGGCATCACGTGGAC
GCTGGACCAGTCCAGCGAGGTCCTCGGCTCCGGCAAGACGCTGACGATCCAGGTCAAGGAGTTC
GGCGACGCGGGCCAGTACACGTGCCACAAGGGCGGCGAGGTCCTGAGCCACTCCCTCCTCCTGC
TACACAAGAAGGAGGACGGGATCTGGAGCACGGACATCCTCAAGGACCAGAAGGAGCCGAAGAA
CAAGACCTTCCTGCGCTGCGAGGCGAAGAATTACTCGGGCCGGTTCACGTGCTGGTGGCTCACC
ACGATCAGCACGGACCTGACGTTCTCGGTCAAGTCGTCGCGGGGCTCGTCGGACCCCCAGGGGG
TGACCTGCGGCGCGGCGACGCTGTCGGCGGAGCGGGTGCGGGGCGACAACAAGGAGTACGAGTA
CTCGGTCGAGTGCCAGGAGGACTCGGCGTGCCCGGCGGCGGAGGAGTCGCTGCCGATCGAGGTG
ATGGTCGACGCGGTCCACAAGCTGAAGTACGAGAACTACACGTCGTCGTTCTTCATCCGGGACA
TCATCAAGCCGGACCCGCCGAAGAACCTGCAGCTGAAGCCGCTGAAGAACTCGCGGCAGGTCGA
GGTCTCGTGGGAGTACCCGGACACGTGGTCGACGCCGCACTCGTACTTCTCGCTGACGTTCTGC
GTCCAAGTGCAGGGCAAGTCGAAGCGGGAGAAGAAGGACCGGGTGTTCACCGACAAGACGAGCG
CGACGGTGATCGCCGGAAGAACGCGTCGATCTCGGTGCGGGCGCAGGACCGGTACTACTCGTC
GTCGTGGTCGGAGTGGGCGTCGGTGCCGTGCAGCTAGacctaggggcgcgccagatctgatatc
ggatctGCTGTGCCTTCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAATTGCATCGCATTGTCT
GAGTAGGTGTCATTCTATTCTGGGGGGTGGGGTGGGGCAGGACAGCAAGGGGGAGGATTGGGAA
GACAATAGCAGGCATGCTGGGGATGCGGTGGGCTCTATGGGTACCCAGGTGCTGAAGAATTGAC
CCGGTTCCTCCTGGGCCAGAAAGAAGCAGGCACATCCCCTTCTCTGTGACACACCCTGTCCACG
CCCCTGGTTCTTAGTTCCAGCCCCACTCATAGGACACTCATAGCTCAGGAGGGCTCCGCCTTCA
ATCCCACCCGCTAAAGTACTTGGAGCGGTCTCTCCCTCCCTCATCAGCCCACCAAACCAAACCT
AGCCTCCAAGAGTGGGAAGAAATTAAAGCAAGATAGGCTATTAAGTGCAGAGGGAGAGAAAATG
CCTCCAACATGTGAGGAAGTAATGAGAGAAATCATAGAATTTCTTCCGCTTCCTCGCTCACTGA
CTCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAAGTGGTG
GCCTAACTACGGCTACACTAGAAGAACAGTATTTGGTATCTGCGCTCTGCTGAAGCCAGTTACC
TTCGGAAAAAGAGTTGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTG
TCTATTTCGTTCATCCATAGTTGCCTGACTCGGGGGGGGGGGCGCTGAGGTCTGCCTCGTGAA
GAAGGTGTTGCTGACTCATACCAGGCCTGAATCGCCCCATCATCCAGCCAGAAAGTGAGGGAGC
CACGGTTGATGAGAGCTTTGTTGTAGGTGGACCAGTTGGTGATTTTGAACTTTTGCTTTGCCAC
GGAACGGTCTGCGTTGTCGGGAAGATGCGTGATCTGATCCTTCAACTCAGCAAAAGTTCGATTT
ATTCAACAAAGCCGCCGTCCCGTCAAGTCAGCGTAATGCTCTGCCAGTGTTACAACCAATTAAC
CAATTCTGATTAGAAAAACTCATCGAGCATCAAATGAAACTGCAATTTATTCATATCAGGATTA
TCAATACCATATTTTTGAAAAGCCGTTTCTGTAATGAAGGAGAAAACTCACCGAGGCAGTTCC
ATAGGATGGCAAGATCCTGGTATCGGTCTGCGATTCCGACTCGTCCAACATCAATACAACCTAT
TAATTTCCCCTCGTCAAAAATAAGGTTATCAAGTGAGAAATCACCATGAGTGACGACTGAATCC
GGTGAGAATGGCAAAAGCTTATGCATTTCTTTCCAGACTTGTTCAACAGGCCAGCCATTACGCT
CGTCATCAAAATCACTCGCATCAACCAAACCGTTATTCATTCGTGATTGCGCCTGAGCGAGACG
AAATACGCGATCGCTGTTAAAAGGACAATTACAAACAGGAATCGAATGCAACCGGCGCAGGAAC
ACTGCCAGCGCATCAACAATATTTTCACCTGAATCAGGATATTCTTCTAATACCTGGAATGCTG
TTTTCCCGGGGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTAACATCATTG
GCAACGCTACCTTTGCCATGTTTCAGAAACAACTCTGGCGCATCGGGCTTCCCATACAATCGAT
AGATTGTCGCACCTGATTGCCCGACATTATCGCGAGCCCATTTATACCCATATAAATCAGCATC
CATGTTGGAATTTAATCGCGGCCTCGAGCAAGACGTTTCCCGTTGAATATGGCTCATAACACCC
CTTGTATTACTGTTTATGTAAGCAGACAGTTTTATTGTTCATGATGATATATTTTTATCTTGTG
CAATGTAACATCAGAGATTTTGAGACACAACGTGGATCATCCAGACATGATAAGATACATTGAT
GAGTTTGGACAAACCACAACTAGAATGCAGTGAAAAAAATGCTTTATTTGTGAAATTTGTGATG
CTATTGCTTTATTTGTAACCATTATAAGCTGCAATAAACAAGTTAACAACAACAATTGCATTCA
TTTTATGTTTCAGGTTCAGGGGGAGGTGTGGGAGGTTTTTTAAAGCAAGTAAAACCTCTACAAA
TGTGGTATGGCTGATTATGATCgtcgaggatccgatatcTTATCAGGGGCTCAGGGTGGCCGCG
CCGTGGGCGAAGACCCGGGCGGCGACCGCCACGAAGGCTTGAGGGAGCGCAAGATCTTGAATC
TGAGCAGGAGCCGCTGCCACGGCTGGCTGGGCGAGAGGCTCGGGATCTGCTGCGTCTCCCAGTC
GTGGCCCTCCGGTTGCAGAAGTTGCGAGAGGCCCAGGAGGGAGGCGTGGAGCTGGCCCACCGGG
CTGTCCGGGAGCAGCGACGGCTCCCCCGTGAAGATGTCCGAGCCGAGCAGCTTCTCGTAGAAGA
```

-continued

| INFORMAL SEQUENCE LISTING |
|---|
| TCAGGCCCTGGTGGATGCGCTGCAGGCAGAACTGCGAGTTGTCCCGGAGGCCCTGGGGGTCGCA |
| GCCGTCGCCGCACTGGATGTGGGGGACGTCGTTGGTCGTCTCCTCGTCGCCCTCCTCCCGGAGG |
| TCCATGTGGCCCACGAGCGGGTGGGCCGACCAGGCCAGGGTGCAGAGCTTCTGGCTGAGCTGCT |
| GGCACTGCGTCCAGGCCGGGCTCGAGCCCCGGGCACCGCCCGGCCCTGGGCCGTCAGGGGAG |
| CAGCAAGAGCAGCATGACCGCGCGGCTCCCCAGCATTtctttctagagtcaaacgtcgacagat |
| ccAAACGCTCCTCCGACGTCCCCAGGCAGAATGGCGGTTCCCTAAACGAGCATTGCTTATATAG |
| ACCTCCCATTAGGCACGCCTACCGCCCATTTACGTCAATGGAACGCCCATTTGCGTCATTGCCC |
| CTCCCCATTGACGTCAATGGGGATGTACTTGGCAGCCATCGCGGGCCATTTACCGCCATTGACG |
| TCAATGGGAGTACTGCCAATGTACCCTGGCGTACTTCCAATAGTAATGTACTTGCCAAGTTACT |
| ATTAATAGATATTGATGTACTGCCAAGTGGGCCATTTACCGTCATTGACGTCAATAGGGGGCGT |
| GAGAACGGATATGAATGGGCAATGAGCCATCCCATTGACGTCAATGGTGGGTGGTCCTATTGAC |
| GTCAATGGGCATTGAGCCAGGCGGGCCATTTACCGTAATTGACGTCAATGGGGGAGGCGCCATA |
| TACGTCAATAGGACCGCCCATATGACGTCAATAGGTAAAGACCATGAGGCCCTTTCGTCTCGCG |
| CGTTTCGGTGATGACGGTGAAAACCTCTGACACATGCAGCTCCCGGAGACGGTCACAGCTTGTC |
| TGTAAGCGGATGCCGGGAGCAGACAAGCCCGTCAGGGCGCGTCAGCGGGTGTTGGCGGGTGTCG |
| GGGCTGGCTTAACTATGCGGCATCAGAGCAGATTGTACTGAGAGTGCACCATATGCGGTGTGAA |
| ATACCGCACAGATGCGTAAGGAGAAAATACCGCATCAGATTGGCTATTGG |

SEQ ID NO: 8-AG193
flanking sequences in lower case; coding sequences underlined
expresses murine IL-27 p28

| CCTGGCCATTGCATACGTTGTATCCATATCATAATATGTACATTTATATTGGCTCATGTCCAAC |
|---|
| ATTACCGCCATGTTGACATTGATTATTGACTAGTTATTAATAGTAATCAATTACGGGGTCATTA |
| GTTCATAGCCCATATATGGAGTTCCGCGTTACATAACTTACGGTAAATGGCCCGCCTGGCTGAC |
| CGCCCAACGACCCCCGCCCATTGACGTCAATAATGACGTATGTTCCCATAGTAACGCCAATAGG |
| GACTTTCCATTGACGTCAATGGGTGGAGTATTTACGGTAAACTGCCCACTTGGCAGTACATCAA |
| GTGTATCATATGCCAAGTACGCCCCCTATTGACGTCAATGATGGTAAATGGCCCGCCTGGCATT |
| ATGCCCAGTACATGACCTTATGGGACTTTCCTACTTGGCAGTACATCTACGTATTAGTCATCGC |
| TATTACCATGGTGATGCGGTTTTGGCAGTACATCAATGGGCGTGGATAGCGGTTTGACTCACGG |
| GGATTTCCAAGTCTCCACCCCATTGACGTCAATGGGAGTTTGTTTTGGCACCAAAATCAACGGG |
| ACTTTCCAAAATGTCGTAACAACTCCGCCCCATTGACGCAAATGGGCGGTAGGCGTGTACGGTG |
| GGAGGTCTATATAAGCAGAGCTCGTTTAGTGAACCGtcagatcgcctggagacgccatccacgc |
| tgttttgacctccatagaagacaccgggaccgatccagcctcgcgggcgcgtcgacaagaa |
| ATGGGCCAGGTCACCGGGGACCTCGGGTGCGCCTGTCGCTCCTGCTCCTGCCCCTCCTCCTGG |
| TCCAAGCGGGGAGCTGGGGCTTCCCCACGGATCCCCTGAGCCTCCAGGAGCTGCGCAGGGAGTT |
| CACCGTCAGCCTGTACCTCGCCGGAAGCTGCTCTCCGAGGTCCAGGGCTACGTCCACAGCTTC |
| GCCGAGTCGCGCCTGCCCGGCGTGAACCTGGACCTCCTGCCCCTGGGCTACCACCTCCCCAACG |
| TCTCCCTGACGTTCCAAGCCTGGCACCACCTCTCCGACTCCGAGCGCCTCTGCTTCCTCGCCAC |
| CACGCTCCGGCCGTTCCCGGCCATGCTGGGCGGGCTGGGGACCCAGGGGACCTGGACCAGCTCC |
| GAGAGGGAGCAGCTGTGGGCCATGAGGCTGGACCTCCGGGACCTGCACAGGCACCTCCGCTTCC |
| AAGTCCTGGCCGCGGGCTTCAAGTGCTCCAAGGAGGAGGAGGACAAGGAGGAAGAGGAAGAGGA |
| GGAAGAAGAGGAAAAGAAGCTGCCCCTCGGGGCCCTGGGCGGCCCCAACCAGGTGTCCTCCCAA |
| GTGTCCTGGCCCCAGCTGCTCTACACCTACCAGCTCCTCCACTCCCTGGAGCTGGTCCTGAGCC |
| GGGCGGTGCGGGACCTGCTCCTGCTGTCCCTGCCCCGGCGCCCGGGCTCGGCCTGGGACTCCTA |
| ATGAtctagaaGATCTGCTGTGCCTTCTAGTTGCCAGCCATCTGTTGTTTGCCCCTCCCCCGTG |
| CCTTCCTTGACCCTGGAAGGTGCCACTCCCACTGTCCTTTCCTAATAAAATGAGGAAATTGCAT |
| CGCATTGTCTGAGTAGGTGTCATTCTATTCTGGGGGGTGGGGTGGGCAGGACAGCAAGGGGA |
| GGATTGGGAAGACAATAGCAGGCATGCTGGGGATGCGGTGGGCTCTATGGGTACCCAGGTGCTG |
| AAGAATTGACCCGGTTCCTCCTGGGCCAGAAAGAAGCAGGCACATCCCCTTCTCTGTGACACAC |
| CCTGTCCACGCCCCTGGTTCTTAGTTCCAGCCCCACTCATAGGACACTCATAGCTCAGGAGGC |
| TCCGCCTTCAATCCCACCCGCTAAAGTACTTGGAGCGGTCTCTCCCTCCCTCATCAGCCCACCA |
| AACCAAACCTAGCCTCCAAGAGTGGGAAGAAATTAAAGCAAGATAGGCTATTAAGTGCAGAGGG |
| AGAGAAAATGCCTCCAACATGTGAGGAAGTAATGAGAGAAATCATAGAATTTCTTCCGCTTCCT |
| CGCTCACTGACTCGCTGCGCTCGGTCGTTCGGCTGCGGCGAGCGGTATCAGCTCACTCAAAGGC |
| GGTAATACGGTTATCCACAGAATCAGGGGATAACGCAGGAAAGAACATGTGAGCAAAAGGCCAG |
| CAAAAGGCCAGGAACCGTAAAAAGGCCGCGTTGCTGGCGTTTTTCCATAGGCTCCGCCCCCCTG |
| ACGAGCATCACAAAAATCGACGCTCAAGTCAGAGGTGGCGAAACCCGACAGGACTATAAAGATA |
| CCAGGCGTTTCCCCCTGGAAGCTCCCTCGTGCGCTCTCCTGTTCCGACCCTGCCGCTTACCGGA |
| TACCTGTCCGCCTTTCTCCCTTCGGGAAGCGTGGCGCTTTCTCATAGCTCACGCTGTAGGTATC |
| TCAGTTCGGTGTAGGTCGTTCGCTCCAAGCTGGGCTGTGTGCACGAACCCCCCGTTCAGCCCGA |
| CCGCTGCGCCTTATCCGGTAACTATCGTCTTGAGTCCAACCCGGTAAGACACGACTTATCGCCA |
| CTGGCAGCAGCCACTGGTAACAGGATTAGCAGAGCGAGGTATGTAGGCGGTGCTACAGAGTTCT |
| TGAAGTGGTGGCCTAACTACGGCTACACTAGAAGAACAGTATTTGGTATCTGCGCTCTGCTGAA |
| GCCAGTTACCTTCGGAAAAAGAGTTGGTAGCTCTTGATCCGGCAAACAAACCACCGCTGGTAGC |
| GGTGGTTTTTTTGTTTGCAAGCAGCAGATTACGCGCAGAAAAAAAGGATCTCAAGAAGATCCTT |
| TGATCTTTTCTACGGGGTCTGACGCTCAGTGGAACGAAAACTCACGTTAAGGGATTTTGGTCAT |
| GAGATTATCAAAAAGGATCTTCACCTAGATCCTTTTAAATTAAAAATGAAGTTTTAAATCAATC |
| TAAAGTATATATGAGTAAACTTGGTCTGACAGTTACCAATGCTTAATCAGTGAGGCACCTATCT |
| CAGCGATCTGTCTATTTCGTTCATCCATAGTTGCCTGACTCGGGGGGGGGGGCGCTGAGGTCT |
| GCCTCGTGAAGAAGGTGTTGCTGACTCATACCAGGCCTGAATCGCCCCATCATCCAGCCAGAAA |
| GTGAGGGAGCCACGGTTGATGAGAGCTTTGTTGTAGGTGGACCAGTTGGTGATTTTGAACTTTT |
| GCTTTGCCACGGAACGGTCTGCGTTGTCGGGAAGATGCGTGATCTGATCCTTCAACTCAGCAAA |
| AGTTCGATTTATTCAACAAAGCCGCCGTCCCGTCAAGTCAGCGTAATGCTCTGCCAGTGTTACA |
| ACCAATTAACCAATTCTGATTAGAAAAACTCATCGAGCATCAAATGAAACTGCAATTTATTCAT |
| ATCAGGATTATCAATACCATATTTTTGAAAAAGCCGTTTCTGTAATGAAGGAGAAAACTCACCG |
| AGGCAGTTCCATAGGATGGCAAGATCCTGGTATCGGTCTGCGATTCCGACTCGTCCAACATCAA |
| TACAACCTATTAATTTCCCCTCGTCAAAAATAAGGTTATCAAGTGAGAAATCACCATGAGTGAC |

| INFORMAL SEQUENCE LISTING |
| --- |
| GACTGAATCCGGTGAGAATGGCAAAAGCTTATGCATTTCTTTCCAGACTTGTTCAACAGGCCAG<br>CCATTACGCTCGTCATCAAAATCACTCGCATCAACCAAACCGTTATTCATTCGTGATTGCGCCT<br>GAGCGAGACGAAATACGCGATCGCTGTTAAAAGGACAATTACAAACAGGAATCGAATGCAACCG<br>GCGCAGGAACACTGCCAGCGCATCAACAATATTTTCACCTGAATCAGGATATTCTTCTAATACC<br>TGGAATGCTGTTTTCCCGGGGATCGCAGTGGTGAGTAACCATGCATCATCAGGAGTACGGATAA<br>AATGCTTGATGGTCGGAAGAGGCATAAATTCCGTCAGCCAGTTTAGTCTGACCATCTCATCTGT<br>AACATCATTGGCAACGCTACCTTTGCCATGTTTCAGAAACAACTCTGGCGCATCGGGCTTCCCA<br>TACAATCGATAGATTGTCGCACCTGATTGCCCGACATTATCGCGAGCCCATTTATACCCATATA<br>AATCAGCATCCATGTTGGAATTTAATCGCGGCCTCGAGCAAGACGTTTCCCGTTGAATATGGCT<br>CATAACACCCCTTGTATTACTGTTTATGTAAGCAGACAGTTTTATTGTTCATGATGATATATTT<br>TTATCTTGTGCAATGTAACATCAGAGATTTTGAGACACAACGTGGCTTTCCCCCCCCCCCCATT<br>ATTGAAGCATTTATCAGGGTTATTGTCTCATGAGCGGATACATATTTGAATGTATTTAGAAAAA<br>TAAACAAATAGGGGTTCCGCGCACATTTCCCCGAAAAGTGCCACCTGACGTCTAAGAAACCATT<br>ATTATCATGACATTAACCTATAAAAATAGGCGTATCACGAGGCCCTTTCGTCTCGCGCGTTTCG<br>GTGATGACGGTGAAAACCTCTGACACATGCAGCTCCCGGAGACGGTCACAGCTTGTCTGTAAGC<br>GGATGCCGGGAGCAGACAAGCCCGTCAGGGCGCGTCAGCGGGTGTTGGCGGGTGTCGGGGCTGG<br>CTTAACTATGCGGCATCAGAGCAGATTGTACTGAGAGTGCACCATATGCGGTGTGAAATACCGC<br>ACAGATGCGTAAGGAGAAAATACCGCATCAGATTGGCTATTGG |

SEQ ID NO: 9-AG194
flanking sequences in lower case; coding sequences underlined
expresses murine IL-27 EBI3
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGtcagatcgcctggagacgccatccacgc
tgttttgacctccatagaagacaccgggaccgatccagcctccgcggcacgtgaagaaATGTCG
<ins>AAGCTCCTGTTCCTGAGCCTGGCGCTCTGGGCCAGCCGCTCGCCGGGGTATACCGAGACGGCGC
TCGTGGCCCTGAGCCAGCCCCGGGTGCAGTGCCACGCCTCGCGCTACCCCGTGGCCGTGGACTG
CTCCTGGACCCCGCTGCAAGCGCCCAACTCCACCAGGTCCACGTCCTTCATCGCCACGTACCGG
CTCGGCGTGGCCACCCAGCAGCAGAGCCAGCCCTGCCTGCAGCGGAGCCCCCAGGCCTCCCGCT
GCACCATCCCCGACGTGCACCTGTTCTCCACGGTGCCCTACATGCTCAACGTCACGGCGGTGCA
CCCGGGCGGCGCCAGCAGCAGCCTCCTGGCCTTCGTGGCGGAGCGGATCATCAAGCCGGACCCG
CCGGAGGGCGTGCGCCTGCGCACGGCGGGCCAGCGCCTGCAGGTGCTCTGGCACCCCCCGGCCT
CCTGGCCCTTCCCGGACATCTTCTCGCTCAAGTACCGCCTCCGCTACCGGCCGCCGAGGCGCCTC
CCACTTCCGCCAAGTCGGCCCCATCGAGGCCACGACCTTCACCCTCCGGAACTCGAAGCCCCAC
GCCAAGTACTGCATCCAGGTGTCGGCGCAGGACCTCACCGACTACGGGAAGCCCAGCGACTGGA
GCCTCCCGGGGCAGGTCGAGAGCGCTCCCCACAAGCCCTAATGA</ins>gaattcgcggatatcggtta
acggatccaGATCTGCTGTGCCTTCTAGTTGCCAGCCATCTGTTGTTTGCCCCTCCCCCGTGCC
TTCCTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGCAGGACAGCAAGGGGGAGG
ATTGGGAAGACAATAGCAGGCATGCTGGGGATGCGGTGGGCTCTATGGGTACCCAGGTGCTGAA
GAATTGACCCGGTTCCTCCTGGGCCAGAAAGAAGCAGGCACATCCCCTTCTCTGTGACACACCC
TGTCCACGCCCTGGTTCTTAGTTCCAGCCCCACTCATAGGACACTCATAGCTCAGGAGGGCTC
CGCCTTCAATCCCACCCGCTAAAGTACTTGGAGCGGTCTCTCCCTCCCTCATCAGCCCACCCAA
CCAAACCTAGCCTCCAAGAGTGGGAAGAAATTAAAGCAAGATAGGCTATTAAGTGCAGAGGGAG
AGAAAATGCCTCCAACATGTGAGGAAGTAATGAGAGAAATCATAGAATTCTTCCGCTTCCTCG
CTCACTGACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAAGATACC
AGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTC
AGTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAGAGTTCTTG
AAGTGGTGGCCTAACTACGGCTACACTAGAAGAACAGTATTTGGTATCTGCGCTCTGCTGAAGC
CAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGA
GATTATCAAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACCTATCTCA
GCGATCTGTCTATTTCGTTCATCCATAGTTGCCTGACTCGGGGGGGGGGGCGCTGAGGTCTGC
CTCGTGAAGAAGGTGTTGCTGACTCATACCAGGCCTGAATCGCCCCATCATCCAGCCAGAAAGT
GAGGGAGCCACGGTTGATGAGAGCTTTGTTGTAGGTGGACCAGTTGGTGATTTTGAACTTTTGC
TTTGCCACGGAACGGTCTGCGTTGTCGGGAAGATGCGTGATCTGATCCTTCAACTCAGCAAAAG
TTCGATTTATTCAACAAAGCCGCCGTCCCGTCAAGTCAGCGTAATGCTCTGCCAGTGTTACAAC
CAATTAACCAATTCTGATTAGAAAACTCATCGAGCATCAAATGAAACTGCAATTTATTCATAT
CAGGATTATCAATACCATATTTTTGAAAAAGCCGTTTCTGTAATGAAGGAGAAAACTCACCGAG
GCAGTTCCATAGGATGGCAAGATCCTGGTATCGGTCTGCGATTCCGACTCGTCCAACATCAATA

INFORMAL SEQUENCE LISTING

```
CAACCTATTAATTTCCCCTCGTCAAAAATAAGGTTATCAAGTGAGAAATCACCATGAGTGACGA
CTGAATCCGGTGAGAATGGCAAAAGCTTATGCATTTCTTTCCAGACTTGTTCAACAGGCCAGCC
ATTACGCTCGTCATCAAAATCACTCGCATCAACCAAACCGTTATTCATTCGTGATTGCGCCTGA
GCGAGACGAAATACGCGATCGCTGTTAAAAGGACAATTACAAACAGGAATCGAATGCAACCGGC
GCAGGAACACTGCCAGCGCATCAACAATATTTTCACCTGAATCAGGATATTCTTCTAATACCTG
GAATGCTGTTTTCCCGGGGATCGCAGTGGTGAGTAACCATGCATCATCAGGAGTACGGATAAAA
TGCTTGATGGTCGGAAGAGGCATAAATTCCGTCAGCCAGTTTAGTCTGACCATCTCATCTGTAA
CATCATTGGCAACGCTACCTTTGCCATGTTTCAGAAACAACTCTGGCGCATCGGGCTTCCCATA
CAATCGATAGATTGTCGCACCTGATTGCCCGACATTATCGCGAGCCCATTTATACCCATATAAA
TCAGCATCCATGTTGGAATTTAATCGCGGCCTCGAGCAAGACGTTTCCCGTTGAATATGGCTCA
TAACACCCCTTGTATTACTGTTTATGTAAGCAGACAGTTTTATTGTTCATGATGATATATTTTT
ATCTTGTGCAATGTAACATCAGAGATTTTGAGACACAACGTGGCTTTCCCCCCCCCCCCATTAT
TGAAGCATTTATCAGGGTTATTGTCTCATGAGCGGATACATATTTGAATGTATTTAGAAAAATA
AACAAATAGGGGTTCCGCGCACATTTCCCCGAAAAGTGCCACCTGACGTCTAAGAAACCATTAT
TATCATGACATTAACCTATAAAAATAGGCGTATCACGAGGCCCTTTCGTCTCGCGCGTTTCGGT
GATGACGGTGAAAACCTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCAC
AGATGCGTAAGGAGAAAATACCGCATCAGATTGGCTATTGG

SEQ ID NO: 10-AG205
flanking sequences in lower case; coding sequences underlined
expresses murine IL-27 p28 subunit (under control of hCMV) and
murine IL-27 EBI3 subunit (under control of siCMV)
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGAG
ACTTTCCAAAATGTCGTAACAACTCCGCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGCcgcgcgtcgaggaatt
cgctagtcgacaagaaATGGGCCAGGTCACCGGGGACCTCGGGTGGCGCCTGTCGCTCCTGCTC
CTGCCCCTCCTCCTGGTCCAAGCGGGGAGCTGGGGCTTCCCCACGGATCCCTGAGCCTCCAGG
AGCTGCGCAGGGAGTTCACCGTCAGCCTGTACCTCGCCCGGAAGCTGCTCTCCGAGGTCAGGG
CTACGTCCACAGCTTCGCCGAGTCGCGCCTGCCCGGCGTGAACCTGGACCTCCTGCCCCTGGGC
TACCACCTCCCCAACGTCTCCCTGACGTTCCAAGCCTGGCACCACCTCTCCGACTCCGAGCGCC
TCTGCTTCCTCGCCACCACGCTCCGGCCGTTCCCGGCCATGCTGGGCGGGCTGGGGACCCAGGG
GACCTGGACCAGCTCCGAGAGGGAGCAGCTGTGGGCATGAGGCTGGACCTCCGGGACCTGCAC
AGGCACCTCCGCTTCCAAGTCCTGGCCGCGGGCTTCAAGTGCTCCAAGGAGGAGGAGGACAAGG
AGGAAGAGGAAGAGGAGGAAGAAGAGGAAAAAGAAGCTGCCCCTCGGGACCCTGGGCGGCCCAA
CCAGGTGTCCTCCCAAGTGTCCTGGCCCCAGCTGCTCTACACCTACCAGCTCCTCCACTCCCTG
GAGCTGGTCCTGAGCCGGGCGGTGCGGGACCTGCTCCTGCTGTCCCTGCCCCGGCGCCCGGGCT
CGGCCTGGGACTCCTAATGAtctagaagatctgatatcggatctGCTGTGCCTTCTAGTTGCCA
GCCATCTGTTGTTTGCCCCTCCCCCGTGCCTTCCTTGACCCTGGAAGGTGCCACTCCCACTGTC
CTTTCCTAATAAAATGAGGAAATTGCATCGCATTGTCTGAGTAGGTGTCATTCTATTCTGGGGG
GTGGGGTGGGGCAGGACAGCAAGGGGGAGGATTGGGAAGACAATAGCAGGCATGCTGGGGATGC
GGTGGGCTCTATGGGTACCCAGGTGCTGAAGAATTGACCCGGTTCCTCCTGGGCCAGAAAGAAG
CAGGCACATCCCCTTCTCTGTGACACACCCTGTCCACGCCCCTGGTTCTTAGTTCCAGCCCCAC
TCATAGGACACTCATAGCTCAGGAGGGCTCCGCCTTCAATCCCACCCGCTAAAGTACTTGGAGC
GGTCTCTCCCTCCCTCATCAGCCCACCAAACCAAACCTAGCCTCCAAGAGTGGGAAGAAATTAA
AGCAAGATAGGCTATTAAGTGCAGAGGGAGAGAAAATGCCTCCAACATGTGAGGAAGTAATGAG
AGAAATCATAGAATTTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTC
TCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAACTATCGTCTTGAGTC
CAACCCGGTAAGACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTACACTAGAAGAA
CAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTGACGCTCAGTGGAACG
AAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTAC
CAATGCTTAATCAGTGAGGCACCTATCTCAGCGATCTGTCTATTTCGTTCATCCATAGTTGCCT
GACTCGGGGGGGGGGCGCTGAGGTCTGCCTCGTGAAGAAGGTGTTGCTGACTCATACCAGGC
CTGAATCGCCCCATCATCCAGCCAGAAAGTGAGGGAGCCACGGTTGATGAGAGCTTTGTTGTAG
GTGGACCAGTTGGTGATTTTGAACTTTTGCTTTGCCACGGAACGGTCTGCGTTGTCGGGAAGAT
GCGTGATCTGATCCTTCAACTCAGCAAAGTTCGATTTATTCAACAAAGCCGCCGTCCCGTCAA
GTCAGCGTAATGCTCTGCCAGTGTTACAACCAATTAACCAATTCTGATTAGAAAAACTCATCGA
```

| INFORMAL SEQUENCE LISTING |
|---|
| GCATCAAATGAAACTGCAATTTATTCATATCAGGATTATCAATACCATATTTTTGAAAAAGCCG
TTTCTGTAATGAAGGAGAAAACTCACCGAGGCAGTTCCATAGGATGGCAAGATCCTGGTATCGG
TCTGCGATTCCGACTCGTCCAACATCAATACAACCTATTAATTTCCCCTCGTCAAAAATAAGGT
TATCAAGTGAGAAATCACCCATGAGTGACGACTGAATCCGGTGAGAATGGCAAAAGCTTATGCAT
TTCTTTCCAGACTTGTTCAACAGGCCAGCCATTACGCTCGTCATCAAATCACTCGCATCAACC
AAACCGTTATTCATTCGTGATTGCGCCTGAGCGAGACGAAATACGCGATCGCTGTTAAAAGGAC
AATTACAAACAGGAATCGAATGCAACCGGCGCAGGAACACTGCCAGCGCATCAACAATATTTC
ACCTGAATCAGGATATTCTTCTAATACCTGGAATGCTGTTTTCCCGGGGATCGCAGTGGTGAGT
AACCATGCATCATCAGGAGTACGGATAAAATGCTTGATGGTCGGAAGAGGCATAAATTCCGTCA
GCCAGTTTAGTCTGACCATCTCATCTGTAACATCATTGGCAACGCTACCTTTGCCATGTTTCAG
AAACAACTCTGGCGCATCGGGCTTCCCATACAATCGATAGATTGTCGCACCTGATTGCCCGACA
TTATCGCGAGCCCATTTATACCCATATAAATCAGCATCCATGTTGGAATTTAATCGCGGCCTCG
AGCAAGACGTTTCCCGTTGAATATGGCTCATAACACCCCTTGTATTACTGTTTATGTAAGCAGA
CAGTTTTATTGTTCATGATGATATATTTTATCTTGTGCAATGTAACATCAGAGATTTTGAGAC
ACAACGTGGATCATCCAGACATGATAAGATACATTGATGAGTTTGGACAAACCACAACTAGAAT
GCAGTGAAAAAAATGCTTTATTTGTGAAATTTGTGATGCTATTGCTTTATTTGTAACCATTATA
AGCTGCAATAAACAAGTTAACAACAACAATTGCATTCATTTTATGTTTCAGGTTCAGGGGGAGG
TGTGGGAGGTTTTTTAAAGCAAGTAAAACCTCTACAAATGTGGTATGGCTGATTATGATCgtcg
aggatccgttaaccgatatccgcgaattc<u>TCATTAGGGCTTGTGGGGAGCGCTCTCGACCTGCC
CCGGGAGGCTCCAGTCGCTGGGCTTCCCGTAGTCGGTGAGGTCCTGCGCCGACACCTGGATGCA
GTACTTGGCGTGGGGCTTCGAGTTCCGGAGGGTGAAGGTCGTGGCCTCGATGGGGCCGACTTGG
CGGAAGTGGGAGGCGCCTCGGCGCCGGTAGCGGAGGCGGTACTTGAGCGAGAAGATGTCCGGGA
AGGGCCAGGAGGCCGGGGGGTGCCAGAGCACCTGCAGGCGCTGGCCCGCCGTGCGCAGGCGCAC
GCCCTCCGGCGGGTCCGGCTTGATGATCCGCTCCGCCACGAAGGCCAGGAGGCTGCTGCTGGCG
CCGCCCGGGTGCACCGCCGTGACGTTGAGCATGTAGGGCACCGTGGAGAACAGGTGCACGTCGG
GGATGGTGCAGCGGGAGGCCTGGGGGCTCCGCTGCAGGCAGGGCTGGCTCTGCTGCTGGGTGGC
CACGCCGAGCCGGTACGTGGCGATGAAGGACGTGGACCTGGTGGAGTTGGGCGCTTGCAGCGGG
GTCCAGGAGCAGTCCACGGCCACGGGGTAGCGCGAGGCGTGCACTGCACCCGGGGCTGGCTCA
GGGCCACGAGCGCCGTCTCGGTATACCCCGGCGAGCGGCTGGCCCAGAGCGCCAGGCTCAGGAA
CAGGAGCTTCGACAT</u>ttcttcacaaacgtcgacagatccAAACGCTCCTCCGACGTCCCCAGGC
AGAATGGCGGTTCCCTAAACGAGCATTGCTTATATAGACCTCCCATTAGGCACGCCTACCGCCC
ATTTACGTCAATGGAACGCCCATTTGCGTCATTGCCCCTCCCCATTGACGTCAATGGGGATGTA
CTTGGCAGCCATCGCGGGCCATTTACCGCCATTGACGTCAATGGGAGTACTGCCAATGTACCCT
GGCGTACTTCCAATAGTAATGTACTTGCCAAGTTACTATTAATAGATATTGATGTACTGCCAAG
TGGGCCATTTACCGTCATTGACGTCAATAGGGGGCGTGAGAACGGATATGAATGGGCAATGAGC
CATCCTAAAGACCATGAGGCCCTTTCGTCTCGCGCGTTTCGGTGATGACGGTGAAAACCTCTGA
CACATGCAGCTCCCGGAGACGGTCACAGCTTGTCTGTAAGCGGATGCCGGGAGCAGACAAGCCC
GTCAGGGCGCGTCAGCGGGTGTTGGCGGGTGTCGGGGCTGGCTTAACTATGCGGCATCAGAGCA
GATTGTACTGAGAGTGCACCATATGCGGTGTGAAATACCGCACAGATGCGTAAGGAGAAAATAC
CGCATCAGATTGGCTATTGG SEQ ID NO: 11-AG197
flanking sequences in lower case; coding sequences underlined
expresses murine IL-27 EBI3 subunit (under control of hCMV) and
murine IL-27 p28 subunit (under control of siCMV)
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGcacgtgaagaa<u>ATGTCG
AAGCTCCTGTTCCTGAGCCTGGCGCTCTGGGCCAGCCGCTCGCCGGGGTATACCGAGACGGCGC
TCGTGGCCCTGAGCCAGCCCCGGGTGCAGTGCCACGCCTCGCGCTACCCCGTGGCCGTGGACTG
CTCCTGGACCCCGCTGCAAGCGCCCAACTCCACCAGGTCCACGTCCTTCATCGCCACGTACCGG
CTCGGCGTGGCCACCCAGCAGCAGAGCCAGCCCTGCCTGCAGCGGAGCCCCCAGGCCTCCCGCT
GCACCATCCCCGACGTGCACCTGTTCTCCACGGTGCCCTACATGCTCAACGTCACGGCGGTGCA
CCCGGGCGGCGCCAGCAGCAGCCTCCTGGCCTTCGTGGCGGAGCGGATCATCAAGCCGGACCCG
CCGGAGGGCGTGCGCCTGCGCACGGCGGGCCAGCGCCTGCAGGTGCTCTGGCACCCCCCGGCCT
CCTGGCCCTTCCCGGACATCTTCTCGCTCAAGTACCGCCTCCGCTACCGGCCGAGGCGCCTC
CCACTTCCGCCAAGTCGGCCCCATCGAGGCCACGACCTTCACCCTCCGGAACTCGAAGCCCCAC
GCCAAGTACTGCATCCAGGTGTCGGCGCAGGACCTCACCGACTACGGGAAGCCCAGCGACTGGA
GCCTCCCGGGGCAGGTCGAGAGCGCTCCCCACAAGCCCTAATGA</u>ggaattcgctagcggcgcgc
cagatctgatatcggatctGCTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATGAGGAAATTG
CATCGCATTGTCTGAGTAGGTGTCATTCTATTCTGGGGGGTGGGGTGGGGCAGGACAGCAAGGG
GGAGGATTGGGAAGACAATAGCAGGCATGCTGGGGATGCGGTGGGCTCTATGGGTACCCAGGTG
CTGAAGAATTGACCCGGTTCCTCCTGGGCCAGAAAGAAGCAGGCACATCCCCTTCTCTGTGACA
CACCCTGTCCACGCCCCTGGTTCTTAGTTCCAGCCCCACTCATAGGACACTCATAGCTCAGGAG
GGCTCCGCCTTCAATCCCACCCGCTAAAGTACTTGGAGCGGTCTCTCCCTCCCTCATCAGCCCA
CCAAACCAAACCTAGCCTCCAAGAGTGGGAAGAAATTAAAGCAAGATAGGCTATTAAGTGCAGA
GGGAGAGAAAATGCCTCCAACATGTGAGGAAGTAATGAGAGAAATCATAGAATTTCTTCCGCTT |

INFORMAL SEQUENCE LISTING

```
CCTCGCTCACTGACTCGCTGCGCTCGGTCGTTCGGCTGCGGCGAGCGGTATCAGCTCACTCAAA
GGCGGTAATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAAGACACGACTTATCG
CCACTGGCAGCAGCCACTGGTAACAGGATTAGCAGAGCGAGGTATGTAGGCGGTGCTACAGAGT
TCTTGAAGTGGTGGCCTAACTACGGCTACACTAGAAGAACAGTATTTGGTATCTGCGCTCTGCT
GAAGCCAGTTACCTTCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAGGATCTCAAGAAGATC
CTTTGATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAAATCA
ATCTAAAGTATATATGAGTAAACTTGGTCTGACAGTTACCAATGCTTAATCAGTGAGGCACCTA
TCTCAGCGATCTGTCTATTTCGTTCATCCATAGTTGCCTGACTCGGGGGGGGGGGGCGCTGAGG
TCTGCCTCGTGAAGAAGGTGTTGCTGACTCATACCAGGCCTGAATCGCCCCATCATCCAGCCAG
AAAGTGAGGGAGCCACGGTTGATGAGAGCTTTGTTGTAGGTGGACCAGTTGGTGATTTTGAACT
TTTGCTTTGCCACGGAACGGTCTGCGTTGTCGGGAAGATGCGTGATCTGATCCTTCAACTCAGC
AAAAGTTCGATTTATTCAACAAAGCCGCCGTCCCGTCAAGTCAGCGTAATGCTCTGCCAGTGTT
ACAACCAATTAACCAATTCTGATTAGAAAAACTCATCGAGCATCAAATGAAACTGCAATTTATT
CATATCAGGATTATCAATACCATATTTTTGAAAAAGCCGTTTCTGTAATGAAGGAGAAAACTCA
CCGAGGCAGTTCCATAGGATGGCAAGATCCTGGTATCGGTCTGCGATTCCGACTCGTCCAACAT
CAATACAACCTATTAATTTCCCCTCGTCAAAAATAAGGTTATCAAGTGAGAAATCACCATGAGT
GACGACTGAATCCGGTGAGAATGGCAAAAGCTTATGCATTTCTTTCCAGACTTGTTCAACAGGC
CAGCCATTACGCTCGTCATCAAAATCACTCGCATCAACCAAACCGTTATTCATTCGTGATTGCG
CCTGAGCGAGACGAAATACGCGATCGCTGTTAAAAGGACAATTACAAACAGGAATCGAATGCAA
CCGGCGCAGGAACACTGCCAGCGCATCAACAATATTTTCACCTGAATCAGGATATTCTTCTAAT
ACCTGGAATGCTGTTTTCCCGGGGATCGCAGTGGTGAGTAACCATGCATCATCAGGAGTACGGA
TAAAATGCTTGATGGTCGGAAGAGGCATAAATTCCGTCAGCCAGTTTAGTCTGACCATCTCATC
TGTAACATCATTGGCAACGCTACCTTTGCCATGTTTCAGAAACAACTCTGGCGCATCGGGCTTC
CCATACAATCGATAGATTGTCGCACCTGATTGCCCGACATTATCGCGAGCCCATTTATACCCAT
ATAAATCAGCATCCATGTTGGAATTTAATCGCGGCCTCGAGCAAGACGTTTCCCGTTGAATATG
GCTCATAACACCCCTTGTATTACTGTTTATGTAAGCAGACAGTTTTATTGTTCATGATGATATA
TTTTTATCTTGTGCAATGTAACATCAGAGATTTTGAGACACAACGTGGATCATCCAGACATGAT
AAGATACATTGATGAGTTTGGACAAACCACAACTAGAATGCAGTGAAAAAAATGCTTTATTTGT
GAAATTTGTGATGCTATTGCTTTATTTGTAACCATTATAAGCTGCAATAAACAAGTTAACAACA
ACAATTGCATTCATTTTATGTTTCAGGTTCAGGGGGAGGTGTGGGAGGTTTTTTAAAGCAAGTA
AAACCTCTACAAATGTGGTATGGCTGATTATGATCgtcgaggatctgtttaaactctagaTCAT
TAGGAGTCCCAGGCCGAGCCCGGGCGCCGGGGCAGGGACAGCAGGAGCAGGTCCCGCACCGCCC
GGCTCAGGACCAGCTCCAGGGAGTGGAGGAGCTGGTAGGTGTAGAGCAGCTGGGGCCAGGACAC
TTGGGAGGACACCTGGTTGGGGCCGCCCAGGGCCCCGAGGGGCAGCTTCTTTTCCTCTTCTTCC
TCCTCTTCCTCTTCCTCCTTGTCCTCCTCCTCCTTGGAGCACTTGAAGCCCGCGGCCAGGACTT
GGAAGCGGAGGTGCCTGTGCAGGTCCCGGAGGTCCAGCCTCATGCCCACAGCTGCTCCCTCTC
GGAGCTGGTCCAGGTCCCCTGGGTCCCAGCCCGCCCAGCATGGCCGGGAACGGCCGGAGCGTG
GTGGCGAGGAAGCAGAGGCGCTCGGAGTCGGAGAGGTGGTGCCAGGCTTGGAACGTCAGGGAGA
CGTTGGGGAGGTGGTAGCCCAGGGCAGGAGGTCCAGGTTCACGCCGGGCAGGCGCGACTCGGC
GAAGCTGTGGACGTAGCCCTGGACCTCGGAGAGCAGCTTCCGGGCGAGGTACAGGCTGACGGTG
AACTCCCTGCGCAGCTCCTGGAGGCTCAGGGGaTccGTGGGGAAGCCCCAGCTCCCCGCTTGGA
CCAGGAGGAGGGGCAGGAGCAGGAGCGACAGGCGCCACCCGAGGTCCCCGGTGACCTGGCCCAT
ttcttgtcgacagatccAAACGCTCCTCCGACGTCCCCAGGCAGAATGGCGGTTCCCTAAACGA
GCATTGCTTATATAGACCTCCCATTAGGCACGCCTACCGCCCATTTACGTCAATGGAACGCCCA
TTTGCGTCATTGCCCCTCCCCATTGACGTCAATGGGATGTTACTTGGCAGCCATCGCGGGCCAT
TTACCGCCATTGACGTCAATGGGAGTACTGCCAATGTACCCTGGCGTACTTCCAATAGTAATGT
ACTTGCCAAGTTACTATTAATAGATATTGATGTACTGCCAAGTGGGCCATTTACCGTCATTGAC
GTCAATAGGGGCGTGAGAACGGATATGAATGGGCAATGAGCCATCCCATTGACGTCAATGGTG
GGTGGTCCTATTGACGTCAATGGGCATTGAGCCAGGCGGGCCATTTACCGTAATTGACGTCAAT
GGGGGAGGCGCCATATACGTCAATAGGACCGCCCATATGACGTCAATAGGTAAGACCATGAGGC
CCTTTCGTCTCGCGCGTTTCGGTGATGACGGTGAAAACCTCTGACACATGCAGCTCCCGGAGAC
GGTCACAGCTTGTCTGTAAGCGGATGCCGGGAGCAGACAAGCCCGTCAGGGCGCGTCAGCGGGT
GTTGGCGGGTGTCGGGGCTGGCTTAACTATGCGGCATCAGAGCAGATTGTACTGAGAGTGCACC
ATATGCGGTGTGAAATACCGCACAGATGCGTAAGGAGAAAATACCGCATCAGATTGGCTATTGG
CATTATGCC SEQ ID NO: 12-AG214
flanking sequences in lower case; coding sequences underlined
expresses human IL-27 EBI3
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
```

INFORMAL SEQUENCE LISTING

```
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGGaagaaATGACGCCGCA
GCTGCTTCTGGCTCTGGTCCTCTGGGCCAGCTGCCCTCCGTGCAGCGGACGCAAGGGTCCTCCA
GCTGCCCTGACCCTGCCCAGAGTGCAGTGCAGAGCCTCGCGCTACCCCATCGCTGTGGACTGCT
CCTGGACCCTTCCACCTGCACCCAACTCCACCTCCCCTGTCTCCTTCATCGCCACGTACCGGCT
CGGCATGGCCGCTAGGGGTCACAGCTGGCCCTGCCTGCAGCAGACGCCCACATCTACTTCCTGC
ACCATCACTGACGTGCAGCTGTTCTCCATGGCTCCCTACGTCCTCAACGTCACGGCGGTGCACC
CGTGGGGCTCTTCAAGCAGCTTCGTCCCTTTCATCACTGAGCACATCATCAAGCCGGACCCACC
GGAGGGAGTGCGCCTGTCTCCTCTCGCGGAGCGCCAGCTGCAGGTGCAGTGGGAGCCCCCAGGT
TCCTGGCCCTTCCCGGAGATCTTCTCGCTCAAGTACTGGATCAGATACAAGCGCCAGGGCGCCG
CTAGATTCCACAGAGTCGGCCCCATCGAGGCCACGTCTTTCATCCTCCGAGCGGTCCGACCCAG
AGCCCGATACTACGTGCAGGTGGCTGCGCAGGACCTCACCGACTACGGGGAGCTTAGCGACTGG
AGCCTCCCGGCTACAGCAACTATGAGTTTGGGAAAGTAATGAgaattcgcggatatcggttaac
ggatccaGATCTGCTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATCGCA
TTGTCTGAGTAGGTGTCATTCTATTCTGGGGGGTGGGGTGGGGCAGGACAGCAAGGGGGAGGAT
TGGGAAGACAATAGCAGGCATGCTGGGGATGCGGTGGGCTCTATGGGTACCCAGGTGCTGAAGA
ATTGACCCGGTTCCTCCTGGGCCAGAAAGAAGCAGGCACATCCCCTTCTCTGTGACACACCCTG
TCCACGCCCCTGGTTCTTAGTTCCAGCCCCACTCATAGGACACTCATAGCTCAGGAGGGCTCCG
CCTTCAATCCCACCCGCTAAAGTACTTGGAGCGGTCTCTCCCTCCCTCATCAGCCCACCAAACC
AAACCTAGCCTCCAAGAGTGGGAAGAAATTAAAGCAAGATAGGCTATTAAGTGCAGAGGGAGAG
AAAATGCCTCCAACATGTGAGGAAGTAATGAGAGAAATCATAGAATTTCTTCCGCTTCCTCGCT
CACTGACTCGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTACCGGATACC
TGTCCGCCTTTCTCCCTTCGGGAAGCGTGGCGCTTTCTCATAGCTCACGCTGTAGGTATCTCAG
TTCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTGAA
GTGGTGGCCTAACTACGGCTACACTAGAAGGACAGTATTTGGTATCTGCGCTCTGCTGAAGCCA
GTTACCTTCGGAAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAGATCCTTTGAT
CTTTTCTACGGGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGC
GATCTGTCTATTTCGTTCATCCATAGTTGCCTGACTCGGGGGGGGGGGGCGCTGAGGTCTGCCT
CGTGAAGAAGGTGTTGCTGACTCATACCAGGCCTGAATCGCCCCATCATCCAGCCAGAAAGTGA
GGGAGCCACGGTTGATGAGAGCTTTGTTGTAGGTGGACCAGTTGGTGATTTTGAACTTTTGCTT
TGCCACGGAACGGTCTGCGTTGTCGGGAAGATGCGTGATCTGATCCTTCAACTCAGCAAAAGTT
CGATTTATTCAACAAAGCCGCCGTCCCGTCAAGTCAGCGTAATGCTCTGCCAGTGTTACAACCA
ATTAACCAATTCTGATTAGAAAAACTCATCGAGCATCAAATGAAACTGCAATTTATTCATATCA
GGATTATCAATACCATATTTTTGAAAAAGCCGTTTCTGTAATGAAGGAGAAAACTCACCGAGGC
AGTTCCATAGGATGGCAAGATCCTGGTATCGGTCTGCGATTCCGACTCGTCCAACATCAATACA
ACCTATTAATTTCCCCTCGTCAAAAATAAGGTTATCAAGTGAGAAATCACCATGAGTGACGACT
GAATCCGGTGAGAATGGCAAAAGCTTATGCATTTCTTTCCAGACTTGTTCAACAGGCCAGCCAT
TACGCTCGTCATCAAAATCACTCGCATCAACCAAACCGTTATTCATTCGTGATTGCGCCTGAGC
GAGACGAAATACGCGATCGCTGTTAAAAGGACAATTACAAACAGGAATCGAATGCAACCGGCGC
AGGAACACTGCCAGCGCATCAACAATATTTTCACCTGAATCAGGATATTCTTCTAATACCTGGA
ATGCTGTTTTCCCGGGGATCGCAGTGGTGAGTAACCATGCATCATCAGGAGTACGGATAAAATG
CTTGATGGTCGGAAGAGGCATAAATTCCGTCAGCCAGTTTAGTCTGACCATCTCATCTGTAACA
TCATTGGCAACGCTACCTTTGCCATGTTTCAGAAACAACTCTGGCGCATCGGGCTTCCCATACA
ATCGATAGATTGTCGCACCTGATTGCCCGACATTATCGCGAGCCCATTTATACCCATATAAATC
AGCATCCATGTTGGAATTTAATCGCGGCCTCGAGCAAGACGTTTCCCGTTGAATATGGCTCATA
ACACCCCTTGTATTACTGTTTATGTAAGCAGACAGTTTTATTGTTCATGATGATATATTTTTAT
CTTGTGCAATGTAACATCAGAGATTTTGAGACACAACGTGGCTTTCCCCCCCCCCCCATTATTG
AAGCATTTATCAGGGTTATTGTCTCATGAGCGGATACATATTTGAATGTATTTAGAAAAATAAA
CAAATAGGGGTTCCGCGCACATTTCCCCGAAAAGTGCCACCTGACGTCTAAGAAACCATTATTA
TCATGACATTAACCTATAAAAATAGGCGTATCACGAGGCCCTTTCGTCTCGCGCGTTTCGGTGA
TGACGGTGAAAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGGGGCTGGCTTA
ACTATGCGGCATCAGAGCAGATTGTACTGAGAGTGCACCATATGCGGTGTGAAATACCGCACAG
ATGCGTAAGGAGAAAATACCGCATCAGATTGGCTATTGG
```

SEQ ID NO: 13-AG215
flanking sequences in lower case; coding sequences underlined
expresses human IL-27 p28

```
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
```

| INFORMAL SEQUENCE LISTING |
|---|
| ACTTTCCAAAATGTCGTAACAACTCCGCCCCATTGACGCAAATGGGCGGTAGCGTGTACGGTG |
| GGAGGTCTATATAAGCAGAGCTCGTTTAGTGAACCGTCAGATCGCCTGGAGACGCCATCCACGC |
| TGTTTTGACCTCCATAGAAGACACCGGGACCGATCCAGCCTCCGCGGGcgcgcgtcgacaagaa |
| <u>ATGGGCCAGACGGCGGGGGACCTCGGGTGGCGCCTGTCGCTTCTGCTACTGCCCCTACTTCTGG</u> |
| <u>TCCAAGCGGGAGTCTGGGGCTTCCCACGTCCACCCGGCAGACCGCAGCTGAGCCTCCAGGAGCT</u> |
| <u>TCGCAGGGAGTTCACCGTCAGCCTGCACCTCGCCCGGAAGCTGTTGTCCGAAGTCAGAGGCCAG</u> |
| <u>GCGCACCGGTTCGCCGAGTCGCACCTTCCAGGCGTGAACCTGTACCTCTTGCCCCTTGGCGAGC</u> |
| <u>AGCTCCCCGACGTCTCCCTGACGTTCCAAGCCTGGCGACGGCTCTCCGACCCGGAGCGCCTCTG</u> |
| <u>CTTCATCTCGACCACGCTCCAGCCGTTCCACGCCCTCCTTGGCGGGTTGGGGACCCAGGGGAGG</u> |
| <u>TGGACCAACATGGAGAGGATGCAGCTGTGGGCCATGAGGCTTGACCTCCGGGACCTGCAGAGGC</u> |
| <u>ACCTCCGCTTCCAAGTCCTTGCCGCTGGCTTCAACCTCCCTGAGGAGGAGGAAGAAGAGGAGA</u> |
| <u>AGAGGAAGAGGAGGAACGGAAGGGGCTGCTCCCAGGTGCCCTGGGCTCGGCGCTGCAGGGACCG</u> |
| <u>GCACAGGTGTCTTGGCCCCAGCTGCTCTCGACCTACCGGCTCCTTCACTCCCTGGAGCTGGTCC</u> |
| <u>TGAGCCGGGCGGTGCGGGAGCTGCTTCTGTTGTCCAAAGCGGGCCACTCGGTCTGGCCGCTTGG</u> |
| <u>ATTCCCCACCCTCTCGCCCCAGCCGTAATGA</u>ggatccaGATCTGCTGTGCCTTCTAGTTGCCAG |
| CCATCTGTTGTTTGCCCCTCCCCCGTGCCTTCCTTGACCCTGGAAGGTGCCACTCCCACTGTCC |
| TTTCCTAATAAAATGAGGAAATTGCATCGCATTGTCTGAGTAGGTGTCATTCTATTCTGGGGGG |
| TGGGGTGGGGCAGGACAGCAAGGGGGAGGATTGGGAAGACAATAGCAGGCATGCTGGGGATGCG |
| GTGGGCTCTATGGGTACCCAGGTGCTGAAGAATTGACCCGGTTCCTCCTGGGCCAGAAAGAAGC |
| AGGCACATCCCCTTCTCTGTGACACACCCTGTCCACGCCCCTGGTTCTTAGTTCCAGCCCCACT |
| CATAGGACACTCATAGCTCAGGAGGGCTCCGCCTTCAATCCCACCCGCTAAAGTACTTGGAGCG |
| GTCTCTCCCTCCCTCATCAGCCCACCCAAACCAAACCTAGCCTCCAAGAGTGGGAAGAAATTAA |
| GCAAGATAGGCTATTAAGTGCAGAGGGAGAGAAAATGCCTCCAACATGTGAGGAAGTAATGAGA |
| GAAATCATAGAATTTCTTCCGCTTCCTCGCTCACTGACTCGCTGCGCTCGGTCGTTCGGCTGCG |
| GCGAGCGGTATCAGCTCACTCAAAGGCGGTAATACGGTTATCCACAGAATCAGGGGATAACGCA |
| GGAAAGAACATGTGAGCAAAAGGCCAGCAAAAGGCCAGGAACCGTAAAAAGGCCGCGTTGCTGG |
| CGTTTTTCCATAGGCTCCGCCCCCCTGACGAGCATCACAAAAATCGACGCTCAAGTCAGAGGTG |
| GCGAAACCCGACAGGACTATAAAGATACCAGGCGTTTCCCCCTGGAAGCTCCCTCGTGCGCTCT |
| CCTGTTCCGACCCTGCCGCTTACCGGATACCTGTCCGCCTTTCTCCCTTCGGGAAGCGTGGCGC |
| TTTCTCATAGCTCACGCTGTAGGTATCTCAGTTCGGTGTAGGTCGTTCGCTCCAAGCTGGGCTG |
| TGTGCACGAACCCCCCGTTCAGCCCGACCGCTGCGCCTTATCCGGTAACTATCGTCTTGAGTCC |
| AACCCGGTAAGACACGACTTATCGCCACTGGCAGCAGCCACTGGTAACAGGATTAGCAGAGCGA |
| GGTATGTAGGCGGTGCTACAGAGTTCTTGAAGTGGTGGCCTAACTACGGCTACACTAGAAGAAC |
| AGTATTTGGTATCTGCGCTCTGCTGAAGCCAGTTACCTTCGGAAAAAGAGTTGGTAGCTCTTGA |
| TCCGGCAAACAAACCACCGCTGGTAGCGGTGGTTTTTTTGTTTGCAAGCAGCAGATTACGCGCA |
| GAAAAAAAGGATCTCAAGAAGATCCTTTGATCTTTTCTACGGGGTCTGACGCTCAGTGGAACGA |
| AAACTCACGTTAAGGGATTTTGGTCATGAGATTATCAAAAAGGATCTTCACCTAGATCCTTTTA |
| AATTAAAAATGAAGTTTTAAATCAATCTAAAGTATATATGAGTAAACTTGGTCTGACAGTTACC |
| AATGCTTAATCAGTGAGGCACCTATCTCAGCGATCTGTCTATTTCGTTCATCCATAGTTGCCTG |
| ACTCGGGGGGGGGGGCGCTGAGGTCTGCCTCGTGAAGAAGGTGTTGCTGACTCATACCAGGCC |
| TGAATCGCCCCATCATCCAGCCAGAAAGTGAGGGAGCCACGGTTGATGAGAGCTTTGTTGTAGG |
| TGGACCAGTTGGTGATTTTGAACTTTTGCTTTGCCACGGAACGGTCTGCGTTGTCGGGAAGATG |
| CGTGATCTGATCCTTCAACTCAGCAAAAGTTCGATTTATTCAACAAAGCCGCCGTCCCGTCAAG |
| TCAGCGTAATGCTCTGCCAGTGTTACAACCAATTAACCAATTCTGATTAGAAAAACTCATCGAG |
| CATCAAATGAAACTGCAATTTATTCATATCAGGATTATCAATACCATATTTTTGAAAAAGCCGT |
| TTCTGTAATGAAGGAGAAAACTCACCGAGGCAGTTCCATAGGATGGCAAGATCCTGGTATCGGT |
| CTGCGATTCCGACTCGTCCAACATCAATACAACCTATTAATTTCCCCTCGTCAAAAATAAGGTT |
| ATCAAGTGAGAAATCACCATGAGTGACGACTGAATCCGGTGAGAATGGCAAAAGCTTATGCATT |
| TCTTTCCAGACTTGTTCAACAGGCCAGCCATTACGCTCGTCATCAAAATCACTCGCATCAACCA |
| AACCGTTATTCATTCGTGATTGCGCCTGAGCGAGACGAAATACGCGATCGCTGTTAAAAGGACA |
| ATTACAAACAGGAATCGAATGCAACCGGCGCAGGAACACTGCCAGCGCATCAACAATATTTTCA |
| CCTGAATCAGGATATTCTTCTAATACCTGGAATGCTGTTTTCCCGGGGATCGCAGTGGTGAGTA |
| ACCATGCATCATCAGGAGTACGGATAAAATGCTTGATGGTCGGAAGAGGCATAAATTCCGTCAG |
| CCAGTTTAGTCTGACCATCTCATCTGTAACATCATTGGCAACGCTACCTTTGCCATGTTTCAGA |
| AACAACTCTGGCGCATCGGGCTTCCCATACAATCGATAGATTGTCGCACCTGATTGCCCGACAT |
| TATCGCGAGCCCATTTATACCCATATAAATCAGCATCCATGTTGGAATTTAATCGCGGCCTCGA |
| GCAAGACGTTTCCCGTTGAATATGGCTCATAACACCCCTTGTATTACTGTTTATGTAAGCAGAC |
| AGTTTTATTGTTCATGATGATATATTTTTATCTTGTGCAATGTAACATCAGAGATTTTGAGACA |
| CAACGTGGCTTTCCCCCCCCCCCCATTATTGAAGCATTTATCAGGGTTATTGTCTCATGAGCGG |
| ATACATATTTGAATGTATTTAGAAAAATAAACAAATAGGGGTTCCGCGCACATTTCCCCGAAAA |
| GTGCCACCTGACGTCTAAGAAACCATTATTATCATGACATTAACCTATAAAAATAGGCGTATCA |
| CGAGGCCCTTTCGTCTCGCGCGTTTCGGTGATGACGGTGAAAACCTCTGACACATGCAGCTCCC |
| GGAGACGGTCACAGCTTGTCTGTAAGCGGATGCCGGGAGCAGACAAGCCCGTCAGGGCGCGTCA |
| GCGGGTGTTGGCGGGTGTCGGGGCTGGCTTAACTATGCGGCATCAGAGCAGATTGTACTGAGAG |
| TGCACCATATGCGGTGTGAAATACCGCACAGATGCGTAAGGAGAAAATACCGCATCAGATTGGC |
| TATTGG |

SEQ ID NO: 14-AG216
flanking sequences in lower case; coding sequences underlined
expresses human IL-27 p28 subunit (under control of hCMV) and
human IL-27 EBI3 subunit (under control of siCMV)
CCTGGCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT

INFORMAL SEQUENCE LISTING

```
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGcgtcgacaagaaATGGG
CCAGACGGCGGGGGACCTCGGGTGGCGCCTGTCGCTTCTGCTACTGCCCCTACTTCTGGTCCAA
GCGGGAGTCTGGGGCTTCCCACGTCCACCCGGCAGACCGCAGCTGAGCCTCCAGGAGCTTCGCA
GGGAGTTCACCGTCAGCCTGCACCTCGCCCGGAAGCTGTTGTCCGAAGTCAGAGGCCAGGCGCA
CCGGTTCGCCGAGTCGCACCTTCCAGGCGTGAACCTGTACCTCTTGCCCCTTGGCGAGCAGCTC
CCCGACGTCTCCCTGACGTTCCAAGCCTGGCGACGGCTCTCCGACCCGGAGCGCCTCTGCTTCA
TCTCGACCACGCTCCAGCCGTTCCACGCCCTCCTTGGCGGGTTGGGGACCCAGGGGAGGTGGAC
CAACATGGAGAGGATGCAGCTGTGGGCATGAGGCTTGACCTCCGGGACCTGCAGAGGCACCTC
CGCTTCCAAGTCCTTGCCGCTGGCTTCAACCTCCCTGAGGAGGAGGAAGAAGAGGAAGAAGAGG
AAGAGGAGGAACGGAAGGGGCTGCTCCCAGGTGCCCTGGGCTCGGCGCTGCAGGGACCGGCACA
GGTGTCTTGGCCCCAGCTGCTCTCGACCTACCGGCTCCTTCACTCCCTGGAGCTGGTCCTGAGC
CGGGCGGTGCGGGAGCTGCTTCTGTTGTCCAAAGCGGGCCACTCGGTCTGGCCGCTTGGATTCC
CCACCCTCTCGCCCCAGCCGTAATGAggatctgatatcggatctGCTGTGCCTTCTAGTTGCCA
GCCATCTGTTGTTTGCCCCTCCCCCGTGCCTTCCTTGACCCTGGAAGGTGCCACTCCCACTGTC
CTTTCCTAATAAAATGAGGAAATTGCATCGCATTGTCTGAGTAGGTGTCATTCTATTCTGGGGG
GTGGGGTGGGGCAGGACAGCAAGGGGGAGGATTGGGAAGACAATAGCAGGCATGCTGGGGATGC
GGTGGGCTCTATGGGTACCCAGGTGCTGAAGAATTGACCCGGTTCCTCCTGGGCCAGAAAGAAG
CAGGCACATCCCCTTCTCTGTGACACACCCTGTCCACGCCCCTGGTTCTTAGTTCCAGCCCCAC
TCATAGGACACTCATAGCTCAGGAGGGCTCCGCCTTCAATCCCACCCGCTAAAGTACTTGGAGG
GGTCTCTCCCTCCCTCATCAGCCCACCAAACCAAACCTAGCCTCCAAGAGTGGGAAGAAATTAA
AGCAAGATAGGCTATTAAGTGCAGAGGGAGAGAAAATGCCTCCAACATGTGAGGAAGTAATGAG
AGAAATCATAGAATTTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGCCGCGTTGCTG
GCGTTTTTCCATAGGCTCCGCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTC
TCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAACTATCGTCTTGAGTC
CAACCCGGTAAGACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTACACTAGAAGAA
CAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTGACGCTCAGTGGAACG
AAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTAC
CAATGCTTAATCAGTGAGGCACCTATCTCAGCGATCTGTATTTCGTTCATCCATAGTTGCCT
GACTCGGGGGGGGGGCGCTGAGGTCTGCCTCGTGAAGAAGGTGTTGCTGACTCATACCAGGC
CTGAATCGCCCCATCATCCAGCCAGAAAGTGAGGGAGCCACGGTTGATGAGAGCTTTGTTGTAG
GTGGACCAGTTGGTGATTTTGAACTTTTGCTTTGCCACGGAACGGTCTGCGTTGTCGGGAAGAT
GCGTGATCTGATCCTTCAACTCAGCAAAAGTTCGATTTATTCAACAAAGCCGCCGTCCCGTCAA
GTCAGCGTAATGCTCTGCCAGTGTTACAACCAATTAACCAATTCTGATTAGAAAACTCATCGA
GCATCAAATGAAACTGCAATTTATTCATATCAGGATTATCAATACCATATTTTTGAAAAAGCCG
TTTCTGTAATGAAGGAGAAAACTCACCGAGGCAGTTCCATAGGATGGCAAGATCCTGGTATCGG
TCTGCGATTCCGACTCGTCCAACATCAATACAACCTATTAATTTCCCCTCGTCAAAAATAAGGT
TATCAAGTGAGAAATCACCATGAGTGACGACTGAATCCGGTGAGAATGGCAAAAGCTTATGCAT
TTCTTTCCAGACTTGTTCAACAGGCCAGCCATTACGCTCGTCATCAAAATCACTCGCATCAACC
AAACCGTTATTCATTCGTGATTGCGCCTGAGCGAGACGAAATACGCGATCGCTGTTAAAAGGAC
AATTACAAACAGGAATCGAATGCAACCGGCGCAGGAACACTGCCAGCGCATCAACAATATTTTC
ACCTGAATCAGGATATTCTTCTAATACCTGGAATGCTGTTTTCCCGGGGATCGCAGTGGTGAGT
AACCATGCATCATCAGGAGTACGGATAAAATGCTTGATGGTCGGAAGAGGCATAAATTCCGTCA
GCCAGTTTAGTCTGACCATCTCATCTGTAACATCATTGGCAACGCTACCTTTGCCATGTTTCAG
AAACAACTCTGGCGCATCGGGCTTCCCATACAATCGATAGATTGTCGCACCTGATTGCCCGACA
TTTATCGCGAGCCCATTTATACCCATATAAATCAGCATCCATGTTGGAATTTAATCGCGGCTCG
AGCAAGACGTTTCCCGTTGAATATGGCTCATAACACCCCTTGTATTACTGTTTATGTAAGCAGA
CAGTTTTATTGTTCATGATGATATATTTTTATCTTGTGCAATGTAACATCAGAGATTTTGAGAC
ACAACGTGGATCATCCAGACATGATAAGATACATTGATGAGTTTGGACAAACCACAACTAGAAT
GCAGTGAAAAAAATGCTTTATTTGTGAAATTTGTGATGCTATTGCTTTATTTGTAACCATTATA
AGCTGCAATAAACAAGTTAACAACAACAATTGCATTCATTTTATGTTTCAGGTTCAGGGGGAGG
TGTGGGAGGTTTTTTAAAGCAAGTAAAACCTCTACAAATGTGGTATGGCTGATTATGATCgtcg
aggatcccTCATTACTTTCCCAAACTCATAGTTGCTGTAGCCGGGAGGCTCCGCTCCTAAGCT
CCCCGTAGTCGGTGAGGTCCTGCGCAGCCACCTGCACGTAGTACTCGGGCTCTGGGTCGGACCGC
TCGGAGGATGAAAGACGTGGCCTCGATGGGGCCGACTCTGTGGAATCTAGCGGCGCCCTGGCGC
TTGTATCTGATCCAGTACTTGAGCGAGAAGATCTCCGGGAAGGGCCAGGAACCTGGGGGCTCCC
ACTGCACCTGCAGCTGGCGCTCCGCGAGAGGAGACAGGCGCACTCCCTCCGGTGGGTCCGGCTT
GATGATGTGCTCAGTGATGAAAGGGACGAAGCTGCTTGAAGAGCCCCACGGGTGCACCGCCGTG
ACGTTGAGGACGTAGGGAGCCATGGAGAACAGCTGCACGTCAGTGATGGTGCAGGAAGTAGATG
TGGGCGTCTGCTGCAGGCAGGGCCAGCTGTGACCCCTAGCGGCCATGCCGAGCCGGTACGTGGC
GATGAAGGAGACAGGGGAGGTGGAGTTGGGTGCAGGTGGAAGGGTCCAGGAGCAGTCCACAGCG
ATGGGGTAGCGCGAGGCTCTGCACTGCACTCTGGGCAGGGTCAGGGCAGCTGGAGGACCCTTGC
GTCCGCTGCACGGAGGGCAGCTGGCCCAGAGGACCAGAGCCAGAAGCAGCTGCGCGTCATttc
ttgtttaaacgtcgacagatccAAACGCTCCTCCGACGTCCCCAGGCAGAATGGCGGTTCCCTA
```

| INFORMAL SEQUENCE LISTING |
|---|
| AACGAGCATTGCTTATATAGACCTCCCATTAGGGCACGCCTACCGCCCATTTACGTCAATGGAAC
GCCCATTTGCGTCATTGCCCCTCCCCATTGACGTCAATGGGGATGTACTTGGCAGCCATCGCGG
GCCATTTACCGCCATTGACGTCAATGGGAGTACTGCCAATGTACCCTGGCGTACTTCCAATAGT
AATGTACTTGCCAAGTTACTATTAATAGATATTGATGTACTGCCAAGTGGGCCATTTACCGTCA
TTGACGTCAATAGGGGCGTGAGAACGGATATGAATGGGCAATGAGCCATCCCATTGACGTCAA
TGGTGGGTGGTCCTATTGACGTCAATGGGCATTGAGCCAGGCGGGCCATTTACCGTAATTGACG
TCAATGGGGAGGCGCCATATACGTCAATAGGACCGCCCATATGACGTCAATAGGTAAGACCAT
GAGGGCCCTTTCGTCTCGCGCGTTTCGGTGATGACGGTGAAAACCTCTGACACATGCAGCTCCCG
GAGACGGTCACAGCTTGTCTGTAAGCGGATGCCGGGAGCAGACAAGCCCGTCAGGGCGCGTCAG
CGGGTGTTGGCGGGTGTCGGGGCTGGCTTAACTATGCGGCATCAGAGCAGATTGTACTGAGAGT
GCACCATATGCGGTGTGAAATACCGCACAGATGCGTAAGGAGAAAATACCGCATCAGATTGGCT
ATTGGCATTATGCC |

SEQ ID NO: 15-AG217
flanking sequences in lower case; coding sequences underlined
expresses human IL-27 EBI3 subunit (under control of hCMV) and
human IL-27 p28 subunit (under control of siCMV)

CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGgcgcgcgtcgaaagaaA
TGACGCCGCAGCTGCTTCTGGCTCTGGTCCTCTGGGCCAGCTGCCCTCCGTGCAGCGGACGCAA
GGGTCCTCCAGCTGCCCTGACCCTGCCCAGAGTGCAGTGCAGAGCCTCGCGCTACCCCATCGCT
GTGGACTGCTCCTGGACCCTTCCACCTGCACCCAACTCCACCTCCCCTGTCTCCTTCATCGCCA
CGTACCGGCTCGGCATGGCCGCTAGGGGTCACAGCTGGCCCTGCCTGCAGCAGACGCCCACATC
TACTTCCTGCACCATCACTGACGTGCAGCTGTTCTCCATGGCTCCCTACGTCCTCAACGTCACG
GCGGTGCACCCGTGGGGCTCTTCAAGCAGCTTCGTCCCTTTCATCACTGAGCACATCATCAAGC
CGGACCCACCGGAGGGAGTGCGCCTGTCTCCTCGCGGAGCGCCAGCTGCAGGTGCAGTGGGA
GCCCCCAGGTTCCTGGCCCTTCCCGGAGATCTTCTCGCTCAAGTACTGGATCAGATACAAGCGC
CAGGGCGCCGCTAGATTCCACAGAGTCGGCCCCATCGAGGCCACGTCTTTCATCCTCCGAGCGG
TCCGACCCAGAGCCCGATACTACGTGCAGGTGGCTGCGCAGGACCTCACCGACTACGGGGAGCT
TAGCGACTGGAGCCTCCCGGCTACAGCAACTATGAGTTTGGGAAAGTAATGAggaattcgctag
cggcgcgccagatctgatatcggatctGCTGTGCCTTCTAGTTGCCAGCCATCTGTTGTTTGCC
CCTCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGTGGGGCAGGAC
AGCAAGGGGGAGGATTGGGAAGACAATAGCAGGCATGCTGGGGATGCGGTGGGCTCTATGGGTA
CCCAGGTGCTGAAGAATTGACCCGGTTCCTCCTGGGCCAGAAAGAAGCAGGCACATCCCCTTCT
CTGTGACACACCCTGTCCACGCCCTGGTTCTTAGTTCCAGCCCCACTCATAGGACACTCATAG
CTCAGGAGGGCTCCGCCTTCAATCCCACCCGCTAAAGTACTTGGAGCGGTCTCTCCCTCCCTCA
TCAGCCCACCAAACCAAACCTAGCCTCCAAGAGTGGGAAGAAATTAAAGCAAGATAGGCTATTA
AGTGCAGAGGGAGAGAAAATGCCTCCAACATGTGAGGAAGTAATGAGAAGAAATCATAGAATTTC
TTCCGCTTCCTCGCTCACTGACTCGCTGCGCTCGGTCGTTCGGCTGCGGCGAGCGGTATCAGCT
CACTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGGCT
CCGCCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGC
TACAGAGTTCTTGAAGTGGTGGCCTAACTACGGCTACACTAGAAGAACAGTATTTGGTATCTGC
GCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCA
AGAAGATCCTTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTAAAAATGAAGTT
TTAAATCAATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCGGGGGGGGGGG
CGCTGAGGTCTGCCTCGTGAAGAAGGTGTTGCTGACTCATACCAGGCCTGAATCGCCCCATCAT
CCAGCCAGAAAGTGAGGGAGCCACGGTTGATGAGAGCTTTGTTGTAGGTGGACCAGTTGGTGAT
TTTGAACTTTTGCTTTGCCACGGAACGGTCTGCGTTGTCGGGAAGATGCGTGATCTGATCCTTC
AACTCAGCAAAAGTTCGATTTATTCAACAAAGCCGCCGTCCCGTCAAGTCAGCGTAATGCTCTG
CCAGTGTTACAACCAATTAACCAATTCTGATTAGAAAAACTCATCGAGCATCAAATGAAACTGC
AATTTATTCATATCAGGATTATCAATACCATATTTTTGAAAAAGCCGTTTCTGTAATGAAGGAG
AAAACTCACCGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGTGAGAAATCA
CCATGAGTGACGACTGAATCCGGTGAGAATGGCAAAAGCTTATGCATTTCTTTCCAGACTTGTT
CAACAGGCCAGCCATTACGCTCGTCATCAAAATCACTCGCATCAACCAAACCGTTATTCATTCG
TGATTGCGCCTGAGCGAGACGAAATACGCGATCGCTGTTAAAAGGACAATTACAAACAGGAATC
GAATGCAACCGGCGCAGGAACACTGCCAGCGCATCAACAATATTTTCACCTGAATCAGGATATT

```
CTTCTAATACCTGGAATGCTGTTTTCCCGGGGATCGCAGTGGTGAGTAACCATGCATCATCAGG
AGTACGGATAAAATGCTTGATGGTCGGAAGAGGCATAAATTCCGTCAGCCAGTTTAGTCTGACC
ATCTCATCTGTAACATCATTGGCAACGCTACCTTTGCCATGGTTCAGAAACAACTCTGGCGCAT
CGGGCTTCCCATACAATCGATAGATTGTCGCACCTGATTGCCCGACATTATCGCGAGCCCATTT
ATACCCATATAAATCAGCATCCATGTTGGAATTTAATCGCGGCCTCGAGCAAGACGTTTCCCGT
TGAATATGGCTCATAACACCCCTTGTATTACTGTTTATGTAAGCAGACAGTTTTATTGTTCATG
ATGATATATTTTTATCTTGTGCAATGTAACATCAGAGATTTTGAGACACAACGTGGATCATCCA
GACATGATAAGATACATTGATGAGTTTGGACAAACCACAACTAGAATGCAGTGAAAAAAATGCT
TTATTTGTGAAATTTGTGATGCTATTGCTTTATTTGTAACCATTATAAGCTGCAATAAACAAGT
TAACAACAACAATTGCATTCATTTTATGTTTCAGGTTCAGGGGGAGGTGTGGGAGGTTTTTTAA
AGCAAGTAAAACCTCTACAAATGTGGTATGGCTGATTATGATCgtcgaggatccggcgccgttt
aaacTCATTACGGCTGGGGCGAGAGGGTGGGGAATCCAAGCGGCCAGACCGAGTGGCCCGCTTT
GGACAACAGAAGCAGCTCCCGCACCGCCCGGCTCAGGACCAGCTCCAGGGAGTGAAGGAGCCGG
TAGGTCGAGAGCAGCTGGGGCAAGACACCTGTGCCGGTCCCTGCAGCGCCGAGCCCAGGGCAC
CTGGGAGCAGCCCCTTCCGTTCCTCCTCTTCCTCTTCTTCCTCTTCTTCCTCCTCCTCAGGGAG
GTTGAAGCCAGCGGCAAGGACTTGGAAGCGGAGGTGCCTCTGCAGGTCCCGGAGGTCAAGCCTC
ATGGCCCACAGCTGCATCCTCTCCATGTTGGTCCACCTCCCCTGGGTCCCCAACCCGCCAAGGA
GGGCGTGGAACGGCTGGAGCGTGGTCGAGATGAAGCAGAGGCGCTCCGGGTCGGAGAGCCGTCG
CCCAGGCTTGGAACGTCAGGGAGACGTCGGGGAGCTGCTCGCCAAGGGGCAAGAGGTACAGGTTC
ACGCCTGGAAGGTGCGACTCGGCGAACCGGTGCGCCTGGCCTCTGACTTCGGACAACAGCTTCC
GGGCGAGGTGCAGGCTGACGGTGAACTCCCTGCGAAGCTCCTGGAGGCTCAGCTGCGGTCTGCC
GGGTGGACGTGGGAAGCCCCAGACTCCCGCTTGGACCAGAAGTAGGGGCAGTAGCAGAAGCGAC
AGGCGCCACCCGAGGTCCCCCGCCGTCTGGCCCATttcttgtcgacagatccAAACGCTCCTCC
GACGTCCCCAGGCAGAATGGCCGGTTCCCTAAACGAGCATTGCTTATATAGACCTCCCATTAGGC
ACGCCTACCGCCCATTTACGTCAATGGAACGCCCATTTGCGTCATTGCCCCTCCCCATTGACGT
CAATGGGGATGTACTTGGCAGCCATCGCGGGCCATTTACCGCCATTGACGTCAATGGGAGTACT
GCCAATGTACCCTGGCGTACTTCCAATAGTAATGTACTTGCCAAGTTACTATTAATAGATATTG
ATGTACTGCCAAGTGGGCCATTTACCGTCATTGACGTCAATAGGGGCGTGAGAACGGATATGA
ATGGGCAATGAGCCATCCCATTGACGTCAATGGTGGGTGGTCCTATTGACGTCAATGGGCATTG
AGCCAGGCGGGCCATTTACCGTAATTGACGTCAATGGGGAGGCGCCATATACGTCAATAGGAC
CGCCCATATGACGTCAATAGGTAAGACCATGAGGCCCTTTCGTCTCGCGTTTCGGTGATGAC
GGTGAAAACCTCTGACACATGCAGCTCCCGGAGACGGTCACAGCTTGTCTGTAAGCGGATGCCG
GGAGCAGACAAGCCCGTCAGGGCGCGTCAGCGGGTGTTGGCGGGTGTCGGGGCTGGCTTAACTA
TGCGGCATCAGAGCAGATTGTACTGAGAGTGCACCATATGCGGTGTGAAATACCGCACAGATGC
GTAAGGAGAAAATACCGCATCAGATTGGCTATTGGCATTATGCC SEQ ID NO: 16-human IL-23 (p19) nucleotide sequence wildtype
GenBank NM_016584.
Atgctggggagcagagctgtaatgctgctgttgctgctgccctggacagctcagggcagagctg
tgcctggggcagcagccctgcctggactcagtgccagcagctttcacagaagctctgcacact
ggcctggagtgcacatccactagtgggacacatggatctaagagaagagggagatgaagagact
acaaatgatgttccccatatccagtgtggagatggctgtgaccccccaaggactcagggacaaca
gtcagttctgcttgcaaaggatccaccagggtctgattttttatgagaagctgctaggatcgga
tattttcaggggagccttctctgctccctgatagccctgtgggccagcttcatgcctccta
ctgggcctcagccaactcctgcagcctgagggtcaccactgggagactcagcagattccaagcc
tcagtcccagccagccatggcagcgtctcctttctccgcttcaaaatccttcgcagcctccaggc
ctttgtggctgtagccgccgggtcttttgcccatggagcagcaaccctgagtccctaa SEQ ID NO: 17-human IL-23 (p19) protein sequence
GenBank NP_057668.
M L G S R A V M L L L L L P W T A Q G R A V
P G G S S P A W T Q C Q Q L S Q K L C T L A
W S A H P L V G H M D L R E E G D E E T T N
D V P H I Q C G D G C D P Q G L R D N S Q F
C L Q R I H Q G L I F Y E K L L G S D I F T
G E P S L L P D S P V G Q L H A S L L G L S
Q L L Q P E G H H W E T Q Q I P S L S P S Q
P W Q R L L L R F K I L R S L Q A F V A V A
A R V F A H G A A T L S P *

SEQ ID NO: 18-murine p28 nucleotide sequence wildtype
GenBank NM_145636.
Atgggccaggtgacaggagaccttggctggcggctcagcctgttgctgctaccttgcttctgg
tacaagctggttcctgggggttcccaacagacccctgagccttcaagagctgcgcagggaatt
cacagtcagcctgtaccttgccaggaagctgctctctgaggttcagggctatgtccacagcttt
gctgaatctcgattgccaggagtgaacctggacctcctgccctgggataccatcttcccaatg
tttccctgactttccaggcatggcatcacctctctgactctgagagactctgcttcctcgctac
cacacttcggcccttccctgccatgctgggagggctggggacccaggggacctggaccagctca
gagagggagcagctgtgggccatgaggctggatctccgggacctgcaggcacctccgctttc
aggtgctggctgcaggattcaaatgttcaaaggaggaggaggacaaggaggaagaggaagagga
ggaagaagaagaaagaagctgcccctaggggctctgggtggcccaatcaggtgtcatcccaa
gtgtcctggcccagctgctctataccctaccagctccttcactccctggagcttgtcctgtctc
gggctgttcgggacctgctgctgctgtccctgcccaggcgcccaggctcagcctgggattccta
a
```

| INFORMAL SEQUENCE LISTING |
| --- |

SEQ ID NO: 19-murine p28 protein sequence
MGQVTGDLGWRLSLLLLPLLLVQAGSWGFPTDPLSLQELRREFTVSLYLARKLLSEVQGYVHSF
AESRLPGVNLDLLPLGYHLPNVSLTFQAWHHLSDSERLCFLATTLRPFPAMLGGLGTQGTWTSS
EREQLWAMRLDLRDLHRHLRFQVLAAGFKCSKEEEDKEEEEEEEEEKKLPLGALGGPNQVSSQ
VSWPQLLYTYQLLHSLELVLSRAVRDLLLLSLPRRPGSAWDS SEQ ID NO: 20-murine EBI3 nucleotide sequence wildtype
Genbank NM_015766
Atgtccaagctgctcttcctgtcacttgccctctgggccagccgctcccctggttacactgaaa
cagctctcgtggctctaagccagcccagagtgcaatgccatgcttctcggtatcccgtggccgt
ggactgctcctggactcctctccaggctcccaactccaccagatccacgtccttcattgccact
tacaggctcggtgtggccacccagcagcagagccagccctgcctacaacggaccccccaggcct
cccgatgcaccatccccgacgtgcacctgttctccacggtgcccatacatgctaaatgtcactgc
agtgcacccaggcggccagcagcagcctcctagcctttgtggctgagcgaatcatcaagccg
gaccctccggaaggcgtgcgcctgcgcacagcgggacagcgcctgcaggtgctctggcatcccc
ctgcttcctggcccttcccggacatcttctctctcaagtaccgactccgctaccggcgccgagg
agcctctcacttccgccaggtgggacccattgaagccacgactttcaccctcaggaactcgaaa
ccccatgccaagtattgcatccaggtgtcagctcaggacctcacagattatgggaaaccaagtg
actggagcctccctgggcaagtagaaagtgcaccccataagccc SEQ ID NO: 21-murine EBI3 protein sequence wildtype
Genbank NP_056581
M S K L L F L S L A L W A S R S P G Y T E T
A L V A L S Q P R V Q C H A S R Y P V A V D
C S W T P L Q A P N S T R S T S F I A T Y R
L G V A T Q Q Q S Q P C L Q R S P Q A S R C
T I P D V H L F S T V P Y M L N V T A V H P
G G A S S S L L A F V A E R I I K P D P P E
G V R L R T A G Q R L Q V L W H P P A S W P
F P D I F S L K Y R L R Y R R R G A S H F R
Q V G P I E A T T F T L R N S K P H A K Y C
I Q V S A Q D L T D Y G K P S D W S L P G Q
V E S A P H K P SEQ ID NO: 22-human EBI3 nucleotide sequence wildtype
Genbank CCDS12123.1 (also, NM_005755)
ATGACCCCGCAGCTTCTCCTGGCCCTTGTCCTCTGGGCCAGCTGCCCGCCCTGCAGTGGAAGGA
AAGGGCCCCAGCAGCTCTGACACTGCCCCGGGTGCAATGCCGAGCCTCTCGGTACCCGATCGC
CGTGGATTGCTCCTGGACCCTGCCGCCTGCTCCAAACTCCACCAGCCCCGTGTCCTTCATTGCC
ACGTACAGGCTCGGCATGGCTGCCCGGGGCCACAGCTGGCCCTGCCTGCAGCAGACGCCAACGT
CCACCAGCTGCACCATCACGGATGTCCAGCTGTTCTCCATGGCTCCCTACGTGCTCAATGTCAC
CGCCGTCCACCCCTGGGGCTCCAGCAGCAGCTTCGTGCCTTTCATAACAGAGCACATCATCAAG
CCCGACCCTCCAGAAGGCGTGCGCCTAAGCCCCCTCGCTGAGCGCCAGCTACAGGTGCAGTGG
AGCCTCCCGGGTCCTGGCCCTTCCCAGAGATCTTCTCACTGAAGTACTGGATCCGTTACAAGCG
TCAGGGAGCTGCGCGCTTCCACCGGGTGGGGCCCATTGAAGCCACGTCCTTCATCCTCAGGGCT
GTGCGGCCCCGAGCCAGGTACTACGTCCAAGTGGCGGCTCAGGACCTCACAGACTACGGGGAAC
TGAGTGACTGGAGTCTCCCCGCCACTGCCACAATGAGCCTGGGCAAG SEQ ID NO: 23-human EBI3 protein sequence
M T P Q L L L A L V L W A S C P P C S G R K
G P P A A L T L P R V Q C R A S R Y P I A V
D C S W T L P P A P N S T S P V S F I A T Y
R L G M A A R G H S W P C L Q Q T P T S T S
C T I T D V Q L F S M A P Y V L N V T A V H
P W G S S S F V P F I T E H I I K P D P P
E G V R L S P L A E R Q L Q V Q W E P P G S
W P F P E I F S L K Y W I R Y K R Q G A A R
F H R V G P I E A T S F I L R A V R P R A R
Y Y V Q V A A Q D L T D Y G E L S D W S L P
A T A T M S L G K SEQ ID NO: 24 human IL-27 p28 nucleotide sequence
Genbank NM_145659.
Atgggccagacggcaggcgaccttggctggcggctcagcctgttgctgcttcccttgctcctgg
ttcaagctggtgtctggggattcccaaggccccagggaggccccagctgagcctgcaggagct
gcggagggagttcacagtcagcctgcatctcgccaggaagctgctctccgaggttcggggccag
gcccaccgctttgcggaatctcacctgccaggagtgaacctgtacctcctgcccctgggagagc
agctccctgatgtttccctgaccttccaggcctggcgccgcctctctgacccggagcgtctctg
cttcatctccaccacgcttcagccccttccatgccctgctgggagggctgggacccagggccgc
tggaccaacatggagaggatgcagctgtgggccatgaggctggacctccgcgatctgcagcggc
acctccgcttccaggtgctggctgcaggattcaacctcccggaggaggaggaggaggaagagga
ggaggaggaggagaggaaggggctgctcccaggggcactgggcagcgccttacagggccgg
gcccaggtgtcctggccccagctcctctccacctaccgcctgctgcactccttggagctcgtct
tatctcgggccgtgcgggagttgctgctgctgtcaaggctgggcactcagtctggcccttggg
gttcccaacattgagccccagccctga

| INFORMAL SEQUENCE LISTING |
| --- |

SEQ ID NO: 25 human IL-27 p28 protein sequence
Genbank NP_663634.
```
M G Q T A G D L G W R L S L L L L P L L L V
Q A G V W G F P R P P G R P Q L S L Q E L R
R E F T V S L H L A R K L L S E V R G Q A H
R F A E S H L P G V N L Y L L P L G E Q L P
D V S L T F Q A W R R L S D P E R L C F I S
T T L Q P F H A L L G G L G T Q G R W T N M
E R M Q L W A M R L D L R D L Q R H L R F Q
V L A A G F N L P E E E E E E E E E E E E E
R K G L L P G A L G S A L Q G P A Q V S W P
Q L L S T Y R L L H S L E L V L S R A V R E
L L L L S K A G H S V W P L G F P T L S P Q
P .
```

SEQ ID NO: 26-human IL-23 p19
RNA improved nucleotide sequence
ATGCTGGGGAGCCGCGCGGTCATGCTGCTCTTGCTGCTCCCCTGGACGGCCCAGGGCCGGGCGG
TGCCCGGGGGCTCGAGCCCGGCCTGGACGCAGTGCCAGCAGCTCAGCCAGAAGCTCTGCACCCT
GGCCTGGTCGGCCCACCCGCTCGTGGGCCACATGGACCTCCGGGAGGAGGGCGACGAGGAGACG
ACCAACGACGTCCCCCACATCCAGTCGGCGACGGCTGCGACCCCCAGGGCCTCCGGGACAACT
CGCAGTTCTGCCTGCAGCGCATCCACCAGGGCCTGATCTTCTACGAGAAGCTGCTCGGCTCGGA
CATCTTCACGGGGGAGCCGTCGCTGCTCCCGGACAGCCCGGTGGCCAGCTCCACGCCTCCCTC
CTGGGCCTCTCGCAACTTCTGCAACCGGAGGGCCACCACTGGGAGACGCAGCAGATCCCGAGC
TCTCGCCCAGCCAGCCGTGGCAGCGGCTCCTGCTCAGATTCAAGATCTTGCGCTCCCTCCAAGC
CTTCGTGGCGGTCGCCGCCCGGGTCTTCGCCCACGGCGCGGCCACCCTGAGCCCCTGATAA SEQ ID NO: 27-murine IL-27 p28
RNA improved nucleotide sequence
ATGGGCCAGGTCACCGGGGACCTCGGGTGGCGCGCCTGTCGCTCCTGCTCCTGCCCCTCCTCCTGG
TCCAAGCGGGGAGCTGGGGCTTCCCCACGGATCCCCTGAGCCTCCAGGAGCTGCGCAGGGAGTT
CACCGTCAGCCTGTACCTCGCCCGGAAGCTGCTCTCCGAGGTCCAGGGCTACGTCCACAGCTTC
GCCGAGTCGCGCCTGCCCGGCGTGAACCTGGACCTCCTGCCCCTGGGCTACCACCTCCCCAACG
TCTCCCTGACGTTCCAAGCCTGGCACCACCTCTCCGACTCCGAGCGCCTCTGCTTCCTCGCCAC
CACGCTCCGGCCGTTCCCGGCCATGCTGGGCGGGCTGGGGACCCAGGGGACCTGGACCAGCTCC
GAGAGGGAGCAGCTGTGGGCCATGAGGCTGGACCTCCGGGACCTGCACAGGCACCTCCGCTTCC
AAGTCCTGGCCGCGGGCTTCAAGTGCTCCAAGGAGGAGGAGGACAAGGAGGAAGAGGAAGAGGA
GGAAGAAGAGGAAAAGAAGCTGCCCCTCGGGGCCCTGGGCGGCCCCAACCAGGTGTCCTCCCAA
GTGTCCTGGCCCCAGCTGCTCTACACCTACCAGCTCCTCCACTCCCTGGAGCTGGTCCTGAGCC
GGGCGGTGCGGGACCTGCTCCTGCTGTCCCTGCCCCGGCGCCCGGGCTCGGCCTGGGACTCCTA
ATGA SEQ ID NO: 28-murine IL-27 EBI3
RNA improved nucleotide sequence
ATGTCGAAGCTCCTGTTCCTGAGCCTGGCGCTCTGGGCCAGCCGCTCGCCGGGGTATACCGAGA
CGGCGCTCGTGGCCCTGAGCCAGCCCCGGGTGCAGTGCCACGCCTCGCGCTACCCCGTGGCCGT
GGACTGCTCCTGGACCCCGCTGCAAGCGCCCAACTCCACCAGGTCCACGTCCTTCATCGCCACG
TACCGGCTCGGCGTGGCCACCCAGCAGCAGAGCCAGCCCTGCCTGCAGCGGAGCCCCCAGGCCT
CCCGCTGCACCATCCCCGACGTGCACCTGTTCTCCACGGTGCCCTACATGCTCAACGTCACGGC
GGTGCACCCGGGCGGCGCCAGCAGCAGCTCCTGGCCTTCGTGGCGGAGCGGATCATCAAGCCG
GACCCGCCGGAGGGCGTGCGCCTGCGCACGGCGGGCCAGCGCCTGCAGGTGCTCTGGCACCCCC
CGGCCTCCTGGCCCTTCCCGGACATCTTCTCGCTCAAGTACGCCTCCGCTACCGGCGCCGAGG
CGCCTCCCACTTCCGCAAGTCGGCCCCATCGAGGCGCACGACCTTCCGGAACTCGAAG
CCCCACGCCAAGTACTGCATCCAGGTGTCGGCGCAGGACCTCACCGACTACGGGAAGCCCAGCG
ACTGGAGCCTCCCGGGGCAGGTCGAGAGCGCTCCCCACAAGCCCTAATGA SEQ ID NO: 29-human IL-27 p28
RNA improved nucleotide sequence
ATGGGCCAGACGGCGGGGGACCTCGGGTGGCGCGCCTGTCGCTTCTGCTACTGCCCCTACTTCTGG
TCCAAGCGGGAGTCTGGGGCTTCCCACGTCCACCCGGCAGACCGCAGCTGAGCCTCCAGGAGCT
TCGCAGGGAGTTCACCGTCAGCCTGCACCTCGCCCGGAAGCTGTTGTCCGAAGTCAGAGGCCAG
GCGCACCGGTTCGCCGAGTCGCACCTTCCAGGCGTGAACCTGTACCTCTTGCCCCTTGGCGAGC
AGCTCCCCGACGTCTCCCTGACGTTCCAAGCCTGGCGACGGCTCTCCGACCCGGAGCGCCTCTG
CTTCATCTCGACCACGCTCCAGCCGTTCCACGCCCTCCTTGGCGGGTTGGGGACCCAGGGGAGG
TGGACCAACATGGAGAGGATGCAGCTGTGGGCCATGAGGCTTGACCTCCGGGACCTGCAGAGGC
ACCTCCGCTTCCAAGTCCTTGCCGCTGGCTTCAACCTCCCTGAGGAGGAGAAGAAGGAAGGAAGA
AGAGGAAGAGGAGGAACGAAGGGGCTGCTCCCAGGTGCCCTGGGCTCGGCGCTGCAGGGACCG
GCACAGGTGTCTTGGCCCCAGCTGCTCTCGACCTACCGGCTCCTTCACTCCTGGAGCTGGTCC
TGAGCCGGGCGGTGCGGGAGCTGCTTCTGTTGTCCAAAGCGGGCCACTCGGTCTGGCCGCTTGG
ATTCCCCACCCTCTCGCCCCAGCCGTAATGA SEQ ID NO: 30-human IL-27 EBI3
RNA improved nucleotide sequence
ATGACGCCGCAGCTGCTTCTGGCTCTGGTCCTCTGGGCCAGCTGCCCTCCGTGCAGCGGACGCA
AGGGTCCTCCAGCTGCCCTGACCCTGCCCAGAGTGCAGTGCAGAGCCTCGCGCTACCCCATCGC
TGTGGACTGCTCCTGGACCCTTCCACCTGCACCCAACTCCACCTCCCCTGTCTCCTTCATCGCC
ACGTACCGGCTCGGCATGGCCGCTAGGGGTCACAGCTGGCCCTGCCTGCAGCAGACGCCCACAT

```
CTACTTCCTGCACCATCACTGACGTGCAGCTGTTCTCCATGGCTCCCTACGTCCTCAACGTCAC
GGCGGTGCACCCGTGGGGCTCTTCAAGCAGCTTCGTCCCTTTCATCACTGAGCACATCATCAAG
CCGGACCCACCGGAGGGAGTGCGCCTGTCTCCTCTCGCGGAGCGCCAGCTGCAGGTGCAGTGGG
AGCCCCCAGGTTCCTGGCCCTTCCCGGAGATCTTCTCGCTCAAGTACTGGATCAGATACAAGCG
CCAGGGCGCCGCTAGATTCCACAGAGTCGGCCCCATCGAGGCCACGTCTTTCATCCTCCGAGCG
GTCCGACCCAGAGCCCGATACTACGTGCAGGTGGCTGCGCAGGACCTCACCGACTACGGGGAGC
TTAGCGACTGGAGCCTCCCGGCTACAGCAACTATGAGTTTGGGAAAGTAATGA

SEQ ID NO: 31-CMVkan vector backbone
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAA
GTGTATCATATGCCAAGTACGCCCCCTATTGACGTCAATGATGGTAAATGGCCCGCCTGGCATT
ATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTG
GGAGGTCTATATAAGCAGAGCTCGTTTAGTGAACCGTCAGATCGCCTGGAGACGCCATCCACGC
TGTTTTGACCTCCATAGAAGACACCGGGACCGATCCAGCCTCCGCGGGCGCGCGTCGACGCTAG
CGGCGCGCCGCGGCCGCCAATTGAGATCTGCTGTGCCTTCTAGTTGCCAGCCATCTGTTGTTTG
CCCCTCCCCCGTGCCTTCCTTGACCCTGGAAGGTGCCACTCCCACTGTCCTTTCCTAATAAAAT
GAGGAAATTGCATCGCATTGTCTGAGTAGGTGTCATTCTATTCTGGGGGGTGGGGTGGGGCAGG
ACAGCAAGGGGGAGGATTGGGAAGACAATAGCAGGCATGCTGGGGATGCGGTGGGCTCTATGGG
TACCCAGGTGCTGAAGAATTGACCCGGTTCCTCCTGGGCCAGAAAGAAGCAGGCACATCCCCTT
CTCTGTGACACACCCTGTCCACGCCCCTGGTTCTTAGTTCCAGCCCCACTCATAGGACACTCAT
AGCTCAGGAGGGCTCCGCCTTCAATCCCACCCGCTAAAGTACTTGGAGCGGTCTCTCCCTCCCT
CATCAGCCCACCCAAACCAAACCTAGCCTCCAAGAGTGGGAAGAAATTAAAGCAAGATAGGCTAT
TAAGTGCAGAGGGAGAGAAAATGCCTCCAACATGTGAGGAAGTAATGAGAGAAATCATAGAATT
TCTTCCGCTTCCTCGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGACAG
GACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCCAACCCGGTAAGACA
CGACTTATCGCCACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGAACAGTATTTGGTATCT
GCGCTCTGCTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAAAGGATCT
CAAGAAGATCCTTTGATCTTTTCTACGGGGTCTGACGCTCAGTGGAACGAAAACTCACGTTAAG
GGATTTTGGTCATGAGATTATCAAAAAGGATCTTCACCTAGATCCTTTTAAATTAAAAATGAAG
TTTTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCGGGGGGGGGG
GGCGCTGAGGTCTGCCTCGTGAAGAAGGTGTTGCTGACTCATACCAGGCCTGAATCGCCCCATC
ATCCAGCCAGAAAGTGAGGGAGCCACGGTTGATGAGAGCTTTGTTGTAGGTGGACCAGTTGGTG
ATTTTGAACTTTTGCTTTGCCACGGAACGGTCTGCGTTGTCGGGAAGATGCGTGATCTGATCCT
TCAACTCAGCAAAAGTTCGATTTATTCAACAAAGCCGCCGTCCCGTCAAGTCAGCGTAATGCTC
TGCCAGTGTTACAACCAATTAACCAATTCTGATTAGAAAAACTCATCGAGCATCAAATGAAACT
GCAATTTATTCATATCAGGATTATCAATACCATATTTTTGAAAAAGCCGTTTCTGTAATGAAGG
AGAAAACTCACCGAGGCAGTTCCATAGGATGGCAAGATCCTGGTATCGGTCTGCGATTCCGACT
CGTCCAACATCAATACAACCTATTAATTTCCCCTCGTCAAAAATAAGGTTATCAAGTGAGAAAT
CACCATGAGTGACGACTGAATCCGGTGAGAATGGCAAAAGCTTATGCATTTCTTTCCAGACTTG
TTCAACAGGCCAGCCATTACGCTCGTCATCAAAATCACTCGCATCAACCAAACCGTTATTCATT
CGTGATTGCGCCTGAGCGAGACGAAATACGCGATCGCTGTTAAAAGGACAATTACAAACAGGAA
TCGAATGCAACCGGCGCAGGAACACTGCCAGCGCATCAACAATATTTTCACCTGAATCAGGATA
TTCTTCTAATACCTGGAATGCTGTTTTCCCGGGGATCGCAGTGGTGAGTAACCATGCATCATCA
GGAGTACGGATAAAATGCTTGATGGTCGGAAGAGGCATAAATTCCGTCAGCCAGTTTAGTCTGA
CCATCTCATCTGTAACATCATTGGCAACGCTACCTTTGCCATGTTTCAGAAACAACTCTGGCGC
ATCGGGCTTCCCATACAATCGATAGATTGTCGCACCTGATTGCCCGACATTATCGCGAGCCCAT
TTATACCCATATAAATCAGCATCCATGTTGGAATTTAATCGCGGCCTCGAGCAAGACGTTTCCC
GTTGAATATGGCTCATAACACCCCTTGTATTACTGTTTATGTAAGCAGACAGTTTTATTGTTCA
TGATGATATATTTTTATCTTGTGCAATGTAACATCAGAGATTTTGAGACACAACGTGGCTTTCC
CCCCCCCCCATTATTGAAGCATTTATCAGGGTTATTGTCTCATGAGCGGATACATATTTGAAT
GTATTTAGAAAAATAAACAAATAGGGGTTCCGCGCACATTTCCCCGAAAAGTGCCACCTGACGT
CTAAGAAACCATTATTATCATGACATTAACCTATAAAAATAGGCGTATCACGAGGCCCTTTCGT
CTCGCGCGTTTCGGTGATGACGGTGAAAACCTCTGACACATGCAGCTCCCGGAGACGGTCACAG
CTTGTCTGTAAGCGGATGCCGGGAGCAGACAAGCCCGTCAGGGCGCGTCAGCGGGTGTTGGCGG
GTGTCGGGGCTGGCTTAACTATGCGGCATCAGAGCAGATTGTACTGAGAGTGCACCATATGCGG
TGTGAAATACCGCACAGATGCGTAAGGAGAAAATACCGCATCAGATTGGCTATTGG SEQ ID NO: 32-DP dual promoter expression vector backbone
CCTGGCCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCTGGCTGAC
```

| INFORMAL SEQUENCE LISTING |
|---|
| CGCCCAACGACCCCCGCCCATTGACGTCAATAATGACGTATGTTCCCATAGTAACGCCAATAGG |
| GACTTTCCATTGACGTCAATGGGTGGAGTATTTACGGTAAACTGCCCACTTGGCAGTACATCAA |
| GTGTATCATATGCCAAGTACGCCCCCTATTGACGTCAATGATGGTAAATGGCCCGCCTGGCATT |
| ATGCCCAGTACATGACCTTATGGGACTTTCCTACTTGGCAGTACATCTACGTATTAGTCATCGC |
| TATTACCATGGTGATGCGGTTTTGGCAGTACATCAATGGGCGTGGATAGCGGTTTGACTCACGG |
| GGATTTCCAAGTCTCCACCCCATTGACGTCAATGGGAGTTTGTTTTGGCACCAAAATCAACGGG |
| ACTTTCCAAAATGTCGTAACAACTCCGCCCCATTGACGCAAATGGGCGGTAGGCGTGTACGGTG |
| GGAGGTCTATATAAGCAGAGCTCGTTTAGTGAACCGTCAGATCGCCTGGAGACGCCATCCACGC |
| TGTTTTGACCTCCATAGAAGACACCGGGACCGATCCAGCCTCCGCGGGCGCGCGTCGAGGAATT |
| CGCTAGCGGCGCGCCAGATCTGATATCGGATCTGCTGTGCCTTCTAGTTGCCAGCCATCTGTTG |
| TTTGCCCCTCCCCCGTGCCTTCCTTGACCCTGGAAGGTGCCACTCCCACTGTCCTTTCCTAATA |
| AAATGAGGAAATTGCATCGCATTGTCTGAGTAGGTGTCATTCTATTCTGGGGGGTGGGGTGGGG |
| CAGGACAGCAAGGGGGAGGATTGGGAAGACAATAGCAGGCATGCTGGGGATGCGGTGGGCTCTA |
| TGGGTACCCAGGTGCTGAAGAATTGACCCGGTTCCTCCTGGGCCAGAAAGAAGCAGGCACATCC |
| CCTTCTCTGTGACACACCCTGTCCACGCCCCTGGTTCTTAGTTCCAGCCCCACTCATAGGACAC |
| TCATAGCTCAGGAGGGCTCCGCCTTCAATCCCACCCGCTAAAGTACTTGGAGCGGTCTCTCCCT |
| CCCTCATCAGCCCACCCAAACCAAACCTAGCCTCCAAGAGTGGGAAGAAATTAAAGCAAGATAGG |
| CTATTAAGTGCAGAGGGAGAGAAAATGCCTCCAACATGTGAGGAAGTAATGAGAGAAATCATAG |
| AATTTCTTCCGCTTCCTCGCTCACTGACTCGCTGCGCTCGGTCGTTCGGCTGCGGCGAGCGGTA |
| TCAGCTCACTCAAAGGCGGTAATACGGTTATCCACAGAATCAGGGGATAACGCAGGAAAGAACA |
| TGTGAGCAAAAGGCCAGCAAAAGGCCAGGAACCGTAAAAAGGCCGCGTTGCTGGCGTTTTTCCA |
| TAGGCTCCGCCCCCCTGACGAGCATCACAAAAATCGACGCTCAAGTCAGAGGTGGCGAAACCCG |
| ACAGGACTATAAAGATACCAGGCGTTTCCCCCTGGAAGCTCCCTCGTGCGCTCTCCTGTTCCGA |
| CCCTGCCGCTTACCGGATACCTGTCCGCCTTTCTCCCTTCGGGAAGCGTGGCGCTTTCTCATAG |
| CTCACGCTGTAGGTATCTCAGTTCGGTGTAGGTCGTTCGCTCCAAGCTGGGCTGTGTGCACGAA |
| CCCCCCGTTCAGCCCGACCGCTGCGCCTTATCCGGTAACTATCGTCTTGAGTCCAACCCGGTAA |
| GACACGACTTATCGCCACTGGCAGCAGCCACTGGTAACAGGATTAGCAGAGCGAGGTATGTAGG |
| CGGTGCTACAGAGTTCTTGAAGTGGTGGCCTAACTACGGCTACACTAGAAGAACAGTATTTGGT |
| ATCTGCGCTCTGCTGAAGCCAGTTACCTTCGGAAAAAGAGTTGGTAGCTCTTGATCCGGCAAAC |
| AAACCACCGCTGGTAGCGGTGGTTTTTTTGTTTGCAAGCAGCAGATTACGCGCAGAAAAAAAGG |
| ATCTCAAGAAGATCCTTTGATCTTTTCTACGGGGTCTGACGCTCAGTGGAACGAAAACTCACGT |
| TAAGGGATTTTGGTCATGAGATTATCAAAAAGGATCTTCACCTAGATCCTTTTAAATTAAAAAT |
| GAAGTTTTAAATCAATCTAAAGTATATATGAGTAAACTTGGTCTGACAGTTACCAATGCTTAAT |
| CAGTGAGGCACCTATCTCAGCGATCTGTCTATTTCGTTCATCCATAGTTGCCTGACTCGGGGGG |
| GGGGGGCGCTGAGGTCTGCCTCGTGAAGAAGGTGTTGCTGACTCATACCAGGCCTGAATCGCCC |
| CATCATCCAGCCAGAAAGTGAGGGAGCCACGGTTGATGAGAGCTTTGTTGTAGGTGGACCAGTT |
| GGTGATTTTGAACTTTTGCTTTGCCACGGAACGGTCTGCGTTGTCGGGAAGATGCGTGATCTGA |
| TCCTTCAACTCAGCAAAAGTTCGATTTATTCAACAAAGCCGCCGTCCCGTCAAGTCAGCGTAAT |
| GCTCTGCCAGTGTTACAACCAATTAACCAATTCTGATTAGAAAAACTCATCGAGCATCAAATGA |
| AACTGCAATTTATTCATATCAGGATTATCAATACCATATTTTTGAAAAAGCCGTTTCTGTAATG |
| AAGGAGAAAACTCACCGAGGCAGTTCCATAGGATGGCAAGATCCTGGTATCGGTCTGCGATTCC |
| GACTCGTCCAACATCAATACAACCTATTAATTTCCCCTCGTCAAAATAAGGTTATCAAGTGAG |
| AAATCACCATGAGTGACGACTGAATCCGGTGAGAATGGCAAAAGCTTATGCATTTCTTTCCAGA |
| CTTGTTCAACAGGCCAGCCATTACGCTCGTCATCAAAATCACTCGCATCAACCAAACCGTTATT |
| CATTCGTGATTGCGCCTGAGCGAGACGAAATACGCGATCGCTGTTAAAAGGACAATTACAAACA |
| GGAATCGAATGCAACCGGCGCAGGAACACTGCCAGCGCATCAACAATATTTTCACCTGAATCAG |
| GATATTCTTCTAATACCTGGAATGCTGTTTTCCCGGGGATCGCAGTGGTGAGTAACCATGCATC |
| ATCAGGAGTACGGATAAAATGCTTGATGGTCGGAAGAGGCATAAATTCCGTCAGCCAGTTTAGT |
| CTGACCATCTCATCTGTAACATCATTGGCAACGCTACCTTTGCCATGTTTCAGAAACAACTCTG |
| GCGCATCGGGCTTCCCATACAATCGATAGATTGTCGCACCTGATTGCCCGACATTATCGCGAGC |
| CCATTTATACCCATATAAATCAGCATCCATGTTGGAATTTAATCGCGGCCTCGAGCAAGACGTT |
| TCCCGTTGAATATGGCTCATAACACCCCTTGTATTACTGTTTATGTAAGCAGACAGTTTTATTG |
| TTCATGATGATATATTTTTATCTTGTGCAATGTAACATCAGAGATTTTGAGACACAACGTGGAT |
| CATCCAGACATGATAAGATACATTGATGAGTTTGGACAAACCACAACTAGAATGCAGTGAAAAA |
| AATGCTTTATTTGTGAAATTTGTGATGCTATTGCTTTATTTGTAACCATTATAAGCTGCAATAA |
| ACAAGTTAACAACAACAATTGCATTCATTTTATGTTTCAGGTTCAGGGGGAGGTGTGGGAGGTT |
| TTTTAAAGCAAGTAAAACCTCTACAAATGTGGTATGGCTGATTATGATCGTCGAGGATCCGGCG |
| CCGTTTAAACGTCGACAGATCCAAACGCTCCTCCGACGTCCCCAGGCAGAATGGCGGTTCCCTA |
| AACGAGCATTGCTTATATAGACCTCCCATTAGGCACGCCTACCGCCCATTTACGTCAATGGAAC |
| GCCCATTTGCGTCATTGCCCTCCCCATTGACGTCAATGGGATGTACTTGGCAGCCATCGCGG |
| GCCATTTACCGCCATTGACGTCAATGGGAGTACTGCCAATGTACCCTGGCGTACTTCCAATAGT |
| AATGTACTTGCCAAGTTACTATTAATAGATATTGATGTACTGCCAAGTGGGCCATTTACCGTCA |
| TTGACGTCAATAGGGGGCGTGAGAACGGATATGAATGGGCAATGAGCCATCCCATTGACGTCAA |
| TGGTGGGTGGTCCTATTGACGTCAATGGGCATTGAGCCAGGCGGCATTTACCGTAATTGACG |
| TCAATGGGGAGGCGCCATATACGTCAATAGGACCGCCCATATGACGTCAATAGGTAAGACCAT |
| GAGGCCCTTTCGTCTCGCGCGTTTCGGTGATGACGGTGAAAACCTCTGACACATGCAGCTCCCG |
| GAGACGGTCACAGCTTGTCTGTAAGCGGATGCCGGGAGCAGACAAGCCCGTCAGGGCGCGTCAG |
| CGGGTGTTGGCGGGTGTCGGGGCTGGCTTAACTATGCGGCATCAGAGCAGATTGTACTGAGAGT |
| GCACCATATGCGGTGTGAAATACCGCACAGATGCGTAAGGAGAAAATACCGCATCAGATTGGCT |
| ATTGGCATTATGCC |

SEQ ID NO: 33
Human improved IL-12 p40 nucleic acid sequence
ATGTGCCACCAGCAGCTGGTCATCAGCTGGTTCAGCCTCGTTTTCCTCGCCTCGCCGCTGGTCG
CCATATGGGAGCTCAAGAAGGACGTATACGTGGTGGAGCTGGACTGGTACCCCGACGCGCCGGG
CGAGATGGTCGTCCTGACGTGCGACACGCCGGAGGAGGACGGCATCACGTGGACGCTGGACCAG
TCCAGCGAGGTCCTCGGCTCCGGCAAGACGCTGACGATCCAGGTCAAGGAGTTCGGCGACGCGG

| INFORMAL SEQUENCE LISTING |
|---|
| GCCAGTACACGTGCCACAAGGGCGGCGAGGTCCTGAGCCACTCCCTCCTCCTGCTACACAAGAA<br>GGAGGACGGGATCTGGAGCACGGACATCCTCAAGGACCAGAAGGAGCCGAAGAACAAGACCTTC<br>CTGCGCTGCGAGGCGAAGAATTACTCGGGCCGGTTCACGTGCTGGTGGCTCACCACGATCAGCA<br>CGGACCTGACGTTCTCGGTCAAGTCGTCGCGGGGCTCGTCGGACCCCCAGGGGGTGACCTGCGG<br>CGCGGCGACGCTGTCGGCGGAGCGGGTGCGGGGCGACAACAAGGAGTACGAGTACTCGGTCGAG<br>TGCCAGGAGGACTCGGCGTGCCCGGCGGCGGAGGAGTCGCTGCCGATCGAGGTGATGGTCGACG<br>CGGTCCACAAGCTGAAGTACGAGAACTACACGTCGTCGTTCTTCATCCGGGACATCATCAAGCC<br>GGACCCGCCGAAGAACCTGCAGCTGAAGCCGCTGAAGAACTCGCGGCAGGTCGAGGTCTCGTGG<br>GAGTACCCGGACACGTGGTCGACGCCGCACTCGTACTTCTCGCTGACGTTCTGCGTCCAAGTGC<br>AGGGCAAGTCGAAGCGGGAGAAGAAGGACCGGGTGTTCACCGACAAGACGAGCGCGACGGTGAT<br>CTGCCGGAAGAACGCGTCGATCTCGGTGCGGGCGCAGGACCGGTACTACTCGTCGTCGTGGTCG<br>GAGTGGGCGTCGGTGCCGTGCAGCTAG<br><br>SEQ ID NO: 34<br>Human improved IL-12 p35 nucleic acid sequence<br>ATGTGCCCGGCGCGCTCCCTGCTGCTCGTGGCGACGCTGGTCCTGCTCGACCACCTGAGCCTGG<br>CGCGGAACCTGCCGGTGGCGACGCCGGACCCGGGGATGTTCCCGTGCCTGCACCACAGCCAGAA<br>CCTGCTGCGGGCGGTGTCGAACATGCTGCAGAAGGCGCGGCAGACGCTGGAGTTCTACCCGTGC<br>ACGAGCGAGGAGATCGACCACGAGGACATCACGAAGGACAAGACCAGCACGGTGGAGGCGTGCC<br>TGCCGCTGGAGCTGACGAAGAACGAGTCGTGCCTGAACTCTGCAGGGGAGACGTCGTTCATCACGAA<br>CGGGTCGTGCCTGGCGTCGCGGAAGACGTCGTTCATGATGGCGTCGTGCCTGTCGTCGATCTAC<br>GAGGACCTGAAGATGTACCAGGTGGAGTTCAAGACGATGAACGCGAAGCTGCTGATGGACCCGA<br>AGCGGCAGATCTTCCTCGACCAGAACATGCTGGCGGTGATCGACGAGCTCATGCAGGCGCTCAA<br>CTTCAACAGCGAGACGGTGCCGCAGAAGTCGTCGCTCGAGGAGCCGGACTTCTACAAGACGAAG<br>ATCAAGCTCTGCATCCTGCTGCACGCTTTCCGGATCCGGGCGGTGACGATCGACCGGGTGATGT<br>CGTACCTGAACGCTTCGTAA |

---

What is claimed is:

1. A dual expression vector for expressing a first subunit and a second subunit of an IL-12 family cytokine protein, comprising a first expression cassette for expressing the first subunit and a second expression cassette for expressing the second subunit, wherein the first subunit and the second subunit are expressed from the dual expression vector at a relative ratio other than 1:1, and further, wherein the IL-12 family cytokine protein is IL 23 or IL-27.

2. The dual expression vector of claim 1, wherein the first subunit and the second subunit are expressed at a ratio in the range of about 3:1 to about 15:1.

3. The dual expression vector of claim 1, wherein the first subunit is expressed under the control of a human CMV promoter and the second subunit is expressed under the control of a simian CMV promoter.

4. The dual expression vector of claim 2, wherein the IL-12 family cytokine is IL-23, wherein the first subunit is IL-23 p40 and the second subunit is IL-23 p19.

5. The dual expression vector of claim 4, wherein the p19 subunit is encoded by a nucleic acid sequence that shares at least 95% nucleic acid sequence identity with SEQ ID NO:26 and the p40 subunit is encoded by a nucleic acid sequence hat shares at least 95% nucleic acid sequence identity with SEQ ID NO:33.

6. The dual expression vector of claim 1, wherein the IL-12 family cytokine is IL-27.

7. The dual expression vector of claim 1, wherein the IL-12 family cytokine is IL-27 and further, wherein the p28 subunit is encoded by a nucleic acid sequence that shares at least 95% sequence identity with SEQ ID NO:29 and the EBI3 subunit is encoded by a nucleic acid sequence that shares at least 95% sequence identity with SEQ ID NO:30.

8. A mammalian cell comprising the dual promoter expression vector of claim 1.

9. A composition comprising the dual expression vector of claim 1 and a pharmaceutically acceptable excipient.

10. A method of promoting the stability and secretion of an IL-27 heterodimer comprised of a p28 subunit and an EBI3 subunit, comprising expressing the p28 and the EBI3 subunit in a relative ratio that is not equimolar.

11. The method of claim 10, wherein the p28 subunit is expressed from a nucleic acid sequence that shares at least 95% sequence identity with SEQ ID NO:29 and the EBI3 subunit is expressed from a nucleic acid sequence that shares at least 95% sequence identity with SEQ ID NO:30.

12. A method of increasing the levels of expression of an IL-12 family cytokine protein, wherein the IL-12 family cytokine protein comprises an alpha subunit and a beta subunit, the method comprising:
   a) determining the ratio of the alpha subunit and the beta subunit that produces an increased level of expression; and
   b) expressing the alpha subunit and the beta subunit from a cell at the determined ratio; wherein:
      (i) the IL-12 family cytokine is cytokine is IL-12, and the alpha subunit (p35) and the beta subunit (p40) are expressed at a ratio in the range of 1:3 to about 1:15;
      (ii) the IL-12 family cytokine is IL-23, and the alpha subunit (p19) and the beta subunit (p40) are expressed at a ratio in the range of about 1:3 to about 1:15; or
      (iii) the IL-12 family cytokine is IL-27, and the alpha subunit (p28) and the beta subunit (EBI3) are expressed in non-equimolar amounts.

13. The method of claim 12, wherein the IL-12 family cytokine is IL-12, and the alpha subunit (p35) and the beta subunit (p40) are expressed at a ratio in the range of 1:3 to about 1:15.

14. The method of claim 12, wherein the IL-12 family cytokine is IL-23, and the alpha subunit (p19) and the beta subunit (p40) are expressed at a ratio in the range of about 1:3 to about 1:15.

15. The method of claim 12, wherein the IL-12 family cytokine is IL-27, and the alpha subunit (p28) and the beta subunit (EBI3) are expressed in non-equimolar amounts.

16. The method of claim 12, wherein the level of expression of the IL-12 family cytokine protein is increased at least 3-fold in comparison to expressing the alpha subunit and the beta subunit at a 1:1 ratio.

* * * * *

SEQUENCE LISTING

<160> NUMBER OF SEQ ID NOS: 34

<210> SEQ ID NO 1
<211> LENGTH: 6293
<212> TYPE: DNA
<213> ORGANISM: Artificial Sequence
<220> FEATURE:
<223> OTHER INFORMATION: synthetic dual-promoter expression vector
    plasmid AG181 for human IL-12 heterodimer expression with
    human cytomegalovirus (CMV) promoter

<400> SEQUENCE: 1
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg gcggtaggc gtgtacggtg gaggtctat ataagcagag     660 ctcgtttagt gaaccgtcag atcgcctgga gacgccatcc acgctgtttt gacctccata     720
gaagacaccg gaccgatcc agcctccgcg ggcgcgcgtc gaggaatttc gagaagaaat     780
gtgccaccag cagctggtca tcagctggtt cagcctcgtt ttcctcgcct cgccgctggt     840
cgccatatgg gagctcaaga aggacgtata cgtggtggag ctggactggt accccgacgc     900
gccgggcgag atggtcgtcc tgacgtgcga cacgccggag gaggacggca tcacgtggac     960

```
gctggaccag tccagcgagg tcctcggctc cggcaagacg ctgacgatcc aggtcaagga    1020
gttcggcgac gcgggccagt acacgtgcca caagggcggc gaggtcctga gccactccct    1080
cctcctgcta cacaagaagg aggacgggat ctggagcacg acatcctca aggaccagaa     1140 ggagccgaag aacaagacct tcctgcgctg cgaggcgaag aattactcgg ccggttcac     1200 gtgctggtgg ctcaccacga tcagcacgga cctgacgttc tcggtcaagt cgtcgcgggg    1260
ctcgtcggac ccccaggggg tgacctgcgc gcggcgacg ctgtcggcgg agcgggtgcg     1320
gggcgacaac aaggagtacg agtactcggt cgagtgccag gaggactcgg cgtgcccggc    1380
ggcggaggag tcgctgccga tcgaggtgat ggtcgacgcg gtccacaagc tgaagtacga    1440
gaactacacg tcgtcgttct tcatccggga catcatcaag ccggacccgc cgaagaacct    1500
gcagctgaag ccgctgaaga actcgcggca ggtcgaggtc tcgtgggagt acccggacac    1560
gtggtcgacg ccgcactcgt acttctcgct gacgttctgc gtccaagtgc agggcaagtc    1620
gaagcgggag aagaaggacc gggtgttcac cgacaagacg agcgcgacgg tgatctgccg    1680
gaagaacgcg tcgatctcgg tgcgggcgca ggaccggtac tactcgtcgt cgtggtcgga    1740
gtgggcgtcg gtgccgtgca gctagaccta ggggcgcgcc agatctgata tcggatctgc    1800
tgtgccttct agttgccagc catctgttgt ttgcccctcc ccgtgcctt ccttgaccct     1860 ggaaggtgcc actcccactg tcctttccta ataaaatgag gaaattgcat cgcattgtct    1920
gagtaggtgt cattctattc tggggggtgg ggtggggcag acagcaagg gggaggattg     1980 ggaagacaat agcaggcatg ctggggatgc ggtgggctct atgggtaccc aggtgctgaa    2040
gaattgaccc ggttcctcct gggccagaaa gaagcaggca catccccttc tctgtgacac    2100
accctgtcca cgcccctggt tcttagttcc agccccactc ataggacact catagctcag    2160
gagggctccg ccttcaatcc cacccgctaa agtacttgga gcggtctctc cctccctcat    2220
cagcccacca aaccaaacct agcctccaag agtgggaaga aattaaagca agataggcta    2280
ttaagtgcag agggagagaa aatgcctcca acatgtgagg aagtaatgag agaaatcata    2340
gaatttcttc cgcttcctcg ctcactgact cgctgcgctc ggtcgttcgg ctgcggcgag    2400
cggtatcagc tcactcaaag gcggtaatac ggttatccac agaatcaggg gataacgcag    2460
gaaagaacat gtgagcaaaa ggccagcaaa aggccaggaa ccgtaaaaag gccgcgttgc    2520
tggcgttttt ccataggctc cgcccccctg acgagcatca caaaaatcga cgctcaagtc    2580
agaggtggcg aaacccgaca ggactataaa gataccaggc gtttccccct ggaagctccc    2640
tcgtgcgctc tcctgttccg accctgccgc ttaccggata cctgtccgcc tttctccctt    2700
cgggaagcgt ggcgctttct catagctcac gctgtaggta tctcagttcg gtgtaggtcg    2760
ttcgctccaa gctgggctgt gtgcacgaac cccccgttca gcccgaccgc tgcgccttat    2820
ccggtaacta tcgtcttgag tccaacccgg taagacacga cttatcgcca ctggcagcag    2880
ccactggtaa caggattagc agagcgaggt atgtaggcgg tgctacagag ttcttgaagt    2940
ggtggcctaa ctacggctac actagaagaa cagtatttgg tatctgcgct ctgctgaagc    3000
cagttacctt cggaaaaaga gttggtagct cttgatccgg caaacaaacc accgctggta    3060
gcggtggttt ttttgtttgc aagcagcaga ttacgcgcag aaaaaaagga tctcaagaag    3120
atcctttgat cttttctacg gggtctgacg ctcagtggaa cgaaaactca cgttaaggga    3180
ttttggtcat gagattatca aaaaggatct tcacctagat ccttttaaat taaaaatgaa    3240
gttttaaatc aatctaaagt atatatgagt aaacttggtc tgacagttac caatgcttaa    3300
tcagtgaggc acctatctca gcgatctgtc tatttcgttc atccatagtt gcctgactcg    3360
```

```
gggggggggg gcgctgaggt ctgcctcgtg aagaaggtgt tgctgactca taccaggcct      3420
gaatcgcccc atcatccagc cagaaagtga gggagccacg gttgatgaga gctttgttgt      3480
aggtggacca gttggtgatt ttgaacttt gctttgccac ggaacggtct gcgttgtcgg       3540
gaagatgcgt gatctgatcc ttcaactcag caaaagttcg atttattcaa caaagccgcc      3600
gtcccgtcaa gtcagcgtaa tgctctgcca gtgttacaac caattaacca attctgatta      3660
gaaaaactca tcgagcatca aatgaaactg caatttattc atatcaggat tatcaatacc      3720 atattttga aaaagccgtt tctgtaatga aggagaaaac tcaccgaggc agttccatag       3780
gatggcaaga tcctggtatc ggtctgcgat tccgactcgt ccaacatcaa tacaacctat     3840
taatttcccc tcgtcaaaaa taaggttatc aagtgagaaa tcaccatgag tgacgactga      3900
atccggtgag aatggcaaaa gcttatgcat ttctttccag acttgttcaa caggccagcc     3960
attacgctcg tcatcaaaat cactcgcatc aaccaaaccg ttattcattc gtgattgcgc     4020
ctgagcgaga cgaaatacgc gatcgctgtt aaaaggacaa ttacaaacag gaatcgaatg     4080
caaccggcgc aggaacactg ccagcgcatc aacaatattt tcacctgaat caggatattc     4140
ttctaatacc tggaatgctg ttttcccggg gatcgcagtg gtgagtaacc atgcatcatc     4200
aggagtacgg ataaaatgct tgatggtcgg aagaggcata aattccgtca gccagtttag     4260
tctgaccatc tcatctgtaa catcattggc aacgctacct ttgccatgtt tcagaaacaa     4320
ctctggcgca tcgggcttcc catacaatcg atagattgtc gcacctgatt gcccgacatt     4380
atcgcgagcc catttatacc catataaatc agcatccatg ttggaattta atcgcggcct     4440
cgagcaagac gtttcccgtt gaatatggct cataacaccc cttgtattac tgtttatgta     4500
agcagacagt tttattgttc atgatgatat attttatct tgtgcaatgt aacatcagag      4560
attttgagac acaacgtgga tcatccagac atgataagat acattgatga gtttggacaa     4620
accacaacta gaatgcagtg aaaaaaatgc tttatttgtg aaatttgtga tgctattgct     4680
ttatttgtaa ccattataag ctgcaataaa caagttaaca acaacaattg cattcatttt     4740
atgtttcagg ttcaggggga ggtgtgggag gtttttaaa gcaagtaaaa cctctacaaa      4800
tgtggtatgg ctgattatga tcgtcgagga tccggcgccg gtttcgcgtc gatatcttac     4860
gaagcgttca ggtacgacat cacccggtcg atcgtcaccg cccggatccg gaaagcgtgc    4920
agcaggatgc agagcttgat cttcgtcttg tagaagtccg gctcctcgag cgacgacttc    4980
tgcggcaccg tctcgctgtt gaagttgagc gcctgcatga gctcgtcgat caccgccagc    5040
atgttctggt cgaggaagat ctgccgcttc gggtccatca gcagcttcgc gttcatcgtc    5100
ttgaactcca cctggtacat cttcaggtcc tcgtagatcg acgacaggca cagcgccatc    5160
atgaacgacg tcttccgcga cgccaggcac gacccgttcg tgatgaacga cgtctccctc    5220
gagttcaggc acgactcgtt cttcgtcagc tccagcggca ggcacgcctc caccgtgctg    5280
gtcttgtcct tcgtgatgtc ctcgtggtcg atctcctcgc tcgtgcacgg gtagaactcc    5340
agcgtctgcc gcgccttctg cagcatgttc gacaccgccc gcagcaggtt ctggctgtgg    5400
tgcaggcacg ggaacatccc cgggtccggc gtcgccaccg gcaggttccg cgccaggctc    5460
aggtggtcga gcaggaccag cgtcgccacg agcagcaggg agcgcgccgg gcacatttct    5520
ttctagaaac gtcgacagat ccaaacgctc ctccgacgtc cccaggcaga atggcggttc    5580
cctaaacgag cattgcttat atagacctcc cattaggcac gcctaccgcc catttacgtc    5640
aatggaacgc ccatttgcgt cattgcccct ccccattgac gtcaatgggg atgtacttgg    5700
```

| | |
|---|---|
| cagccatcgc gggccattta ccgccattga cgtcaatggg agtactgcca atgtaccctg | 5760 |
| gcgtacttcc aatagtaatg tacttgccaa gttactatta atagatattg atgtactgcc | 5820 |
| aagtgggcca tttaccgtca ttgacgtcaa taggggcgt gagaacggat atgaatgggc | 5880 |
| aatgagccat cccattgacg tcaatggtgg gtggtcctat tgacgtcaat gggcattgag | 5940 |
| ccaggcgggc catttaccgt aattgacgtc aatggggag gcgccatata cgtcaatagg | 6000 |
| accgcccata tgacgtcaat aggtaagacc atgaggccct ttcgtctcgc gcgtttcggt | 6060 |
| gatgacggtg aaaacctctg acacatgcag ctcccggaga cggtcacagc ttgtctgtaa | 6120 |
| gcggatgccg ggagcagaca gcccgtcag ggcgcgtcag cgggtgttgg cgggtgtcgg | 6180 |
| ggctggctta actatgcggc atcagagcag attgtactga gagtgcacca tatgcggtgt | 6240 |
| gaaataccgc acagatgcgt aaggagaaaa taccgcatca gattggctat tgg | 6293 |

<210> SEQ ID NO 2
<211> LENGTH: 6293
<212> TYPE: DNA
<213> ORGANISM: Artificial Sequence
<220> FEATURE:
<223> OTHER INFORMATION: synthetic dual-promoter expression vector
      plasmid AG183 for human IL-12 heterodimer expression with
      simian cytomegalovirus (CMV) promoter

<400> SEQUENCE: 2

| | |
|---|---|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gaccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg ggaggtctat ataagcagag | 660 |
| ctcgtttagt gaaccgtcag atcgcctgga gacgccatcc acgctgtttt gacctccata | 720 |
| gaagacaccg ggaccgatcc agcctccgcg gcgcgcgtc gaggaattcg ctagaaagaa | 780 |
| atgtgcccgg cgcgctccct gctgctcgtg gcgacgctgg tcctgctcga ccacctgagc | 840 |
| ctggcgcgga acctgccggt ggcgacgccg gacccgggga tgttcccgtg cctgcaccac | 900 |
| agccagaacc tgctgcgggc ggtgtcgaac atgctgcaga aggcgcggca gacgctggag | 960 |
| ttctacccgt gcacgagcga ggagatcgac cacgaggaca tcacgaagga caagaccagc | 1020 |
| acggtggagg cgtgcctgcc gctggagctg acgaagaacg agtcgtgcct gaactcgagg | 1080 |
| gagacgtcgt tcatcacgaa cgggtcgtgc ctggcgtcgc ggaagacgtc gttcatgatg | 1140 |
| gcgctgtgcc tgtcgtcgat ctacgaggac ctgaagatgt accaggtgga gttcaagacg | 1200 |
| atgaacgcga agctgctgat ggacccgaag cggcagatct tcctcgacca gaacatgctg | 1260 |
| gcggtgatcg acgagctcat gcaggcgctc aacttcaaca gcgagacggt gccgcagaag | 1320 |
| tcgtcgctcg aggagccgga cttctacaag acgaagatca gctctgcat cctgctgcac | 1380 |
| gctttccgga tccgggcggt gacgatcgac cgggtgatgt cgtacctgaa cgcttcgtaa | 1440 |

```
gatatcgacg cgccagatct gatatcggat ctgctgtgcc ttctagttgc cagccatctg   1500
ttgtttgccc ctcccccgtg ccttccttga ccctggaagg tgccactccc actgtccttt   1560
cctaataaaa tgaggaaatt gcatcgcatt gtctgagtag gtgtcattct attctggggg   1620
gtggggtggg gcaggacagc aaggggagg attgggaaga caatagcagg catgctgggg   1680
atgcggtggg ctctatgggt acccaggtgc tgaagaattg acccggttcc tcctgggcca   1740
gaaagaagca ggcacatccc cttctctgtg acacaccctg tccacgcccc tggttcttag   1800
ttccagcccc actcatagga cactcatagc tcaggagggc tccgccttca atcccacccg   1860
ctaaagtact tggagcggtc tctccctccc tcatcagccc accaaaccaa acctagcctc   1920
caagagtggg aagaaattaa agcaagatag gctattaagt gcagagggag agaaaatgcc   1980
tccaacatgt gaggaagtaa tgagagaaat catagaattt cttccgcttc ctcgctcact   2040
gactcgctgc gctcggtcgt tcggctgcgg cgagcggtat cagctcactc aaaggcggta   2100
atacggttat ccacagaatc aggggataac gcaggaaaga acatgtgagc aaaaggccag   2160
caaaaggcca ggaaccgtaa aaaggccgcg ttgctggcgt ttttccatag gctccgcccc   2220
cctgacgagc atcacaaaaa tcgacgctca agtcagaggt ggcgaaaccc gacaggacta   2280
taaagatacc aggcgtttcc ccctggaagc tccctcgtgc gctctcctgt tccgaccctg   2340
ccgcttaccg gatacctgtc cgcctttctc ccttcgggaa gcgtggcgct ttctcatagc   2400
tcacgctgta ggtatctcag ttcggtgtag gtcgttcgct ccaagctggg ctgtgtgcac   2460
gaaccccccg ttcagcccga ccgctgcgcc ttatccggta actatcgtct tgagtccaac   2520
ccggtaagac acgacttatc gccactggca gcagccactg gtaacaggat tagcagagcg   2580
aggtatgtag gcggtgctac agagttcttg aagtggtggc ctaactacgg ctacactaga   2640
agaacagtat ttggtatctg cgctctgctg aagccagtta ccttcggaaa aagagttggt   2700
agctcttgat ccggcaaaca aaccaccgct ggtagcggtg gtttttttgt ttgcaagcag   2760
cagattacgc gcagaaaaaa aggatctcaa gaagatcctt tgatcttttc tacggggtct   2820
gacgctcagt ggaacgaaaa ctcacgttaa gggattttgg tcatgagatt atcaaaaagg   2880
atcttcacct agatcctttt aaattaaaaa tgaagtttta aatcaatcta agtatatat    2940 gagtaaactt ggtctgacag ttaccaatgc ttaatcagtg aggcacctat ctcagcgatc   3000
tgtctatttc gttcatccat agttgcctga ctcgggggg ggggcgctg aggtctgcct   3060 cgtgaagaag gtgttgctga ctcataccag gcctgaatcg ccccatcatc agccagaaa   3120 gtgagggagc cacggttgat gagagctttg ttgtaggtgg accagttggt gattttgaac   3180
ttttgctttg ccacggaacg gtctgcgttg tcgggaagat gcgtgatctg atccttcaac   3240
tcagcaaaag ttcgatttat tcaacaaagc cgccgtcccg tcaagtcagc gtaatgctct   3300
gccagtgtta caaccaatta accaattctg attagaaaaa ctcatcgagc atcaaatgaa   3360
actgcaattt attcatatca ggattatcaa taccatattt ttgaaaaagc cgtttctgta   3420
atgaaggaga aaactcaccg aggcagttcc ataggatggc aagatcctgg tatcggtctg   3480
cgattccgac tcgtccaaca tcaatacaac ctattaattt cccctcgtca aaataaggt    3540 tatcaagtga gaaatcacca tgagtgacga ctgaatccgg tgagaatggc aaaagcttat   3600
gcatttcttt ccagacttgt tcaacaggcc agccattacg ctcgtcatca aaatcactcg   3660
catcaaccaa accgttattc attcgtgatt gcgcctgagc gagacgaaat acgcgatcgc   3720
tgttaaaagg acaattacaa acaggaatcg aatgcaaccg gcgcaggaac actgccagcg   3780
```

```
catcaacaat attttcacct gaatcaggat attcttctaa tacctggaat gctgttttcc    3840
cggggatcgc agtggtgagt aaccatgcat catcaggagt acggataaaa tgcttgatgg    3900
tcggaagagg cataaattcc gtcagccagt ttagtctgac catctcatct gtaacatcat    3960
tggcaacgct acctttgcca tgtttcagaa acaactctgg cgcatcgggc ttcccataca    4020
atcgatagat tgtcgcacct gattgcccga cattatcgcg agcccattta tacccatata    4080
aatcagcatc catgttggaa tttaatcgcg gcctcgagca agacgtttcc cgttgaatat    4140
ggctcataac accccttgta ttactgttta tgtaagcaga cagttttatt gttcatgatg    4200
atatatttt atcttgtgca atgtaacatc agagattttg agacacaacg tggatcatcc    4260
agacatgata agatacattg atgagtttgg acaaaccaca actagaatgc agtgaaaaaa    4320
atgctttatt tgtgaaattt gtgatgctat tgctttattt gtaaccatta taagctgcaa    4380
taaacaagtt aacaacaaca attgcattca ttttatgttt caggttcagg gggaggtgtg    4440
ggaggttttt taaagcaagt aaaacctcta caaatgtggt atggctgatt atgatcgtcg    4500
aggatccggc gccggtttga tccggcgcgc cctaggtct agctgcacgg caccgacgcc    4560
cactccgacc acgacgacga gtagtaccgg tcctgcgccc gcaccgagat cgacgcgttc    4620
ttccggcaga tcaccgtcgc gctcgtcttg tcggtgaaca cccggtcctt cttctcccgc    4680
ttcgacttgc cctgcacttg gacgcagaac gtcagcgaga agtacgagtg cggcgtcgac    4740
cacgtgtccg ggtactccca cgagacctcg acctgccgcg agttcttcag cggcttcagc    4800
tgcaggttct tcggcgggtc cggcttgatg atgtcccgga tgaagaacga cgacgtgtag    4860
ttctcgtact tcagcttgtg gaccgcgtcg accatcacct cgatcggcag cgactcctcc    4920
gccgccgggc acgccgagtc ctcctggcac tcgaccgagt actcgtactc cttgttgtcg    4980
ccccgcaccc gctccgccga cagcgtcgcc gcgccgcagg tcacccctg ggggtccgac    5040
gagccccgcg acgacttgac cgagaacgtc aggtccgtgc tgatcgtggt gagccaccag    5100
cacgtgaacc ggcccgagta attcttcgcc tcgcagcgca ggaaggtctt gttcttcggc    5160
tccttctggt ccttgaggat gtccgtgctc cagatcccgt cctccttctt gtgtagcagg    5220
aggagggagt ggctcaggac ctcgccgccc ttgtggcacg tgtactggcc cgcgtcgccg    5280
aactccttga cctggatcgt cagcgtcttg ccggagccga ggacctcgct ggactggtcc    5340
agcgtccacg tgatgccgtc ctcctccggc gtgtcgcacg tcaggacgac catctcgccc    5400
ggcgcgtcgg ggtaccagtc cagctccacc acgtatacgt ccttcttgag ctcccatatg    5460
gcgaccagcg gcgaggcgag gaaaacgagg ctgaaccagc tgatgaccag ctgctggtgg    5520
cacatttctt ctcgacagat ccaaacgctc ctccgacgtc cccaggcaga atggcggttc    5580
cctaaacgag cattgcttat atagacctcc cattaggcac gcctaccgcc catttacgtc    5640
aatggaacgc ccatttgcgt cattgcccct ccccattgac gtcaatgggg atgtacttgg    5700
cagccatcgc gggccattta ccgccattga cgtcaatggg agtactgcca atgtaccctg    5760
gcgtacttcc aatagtaatg tacttgccaa gttactatta atagatattg atgtactgcc    5820
aagtgggcca tttaccgtca ttgacgtcaa tagggggcgt gagaacggat atgaatgggc    5880
aatgagccat cccattgacg tcaatggtgg gtggtcctat tgacgtcaat gggcattgag    5940
ccaggcgggc catttaccgt aattgacgtc aatggggag gcgccatata cgtcaatagg    6000
accgcccata tgacgtcaat aggtaagacc atgaggccct tcgtctcgc gcgtttcggt    6060
gatgacggtg aaaacctctg acacatgcag ctcccgagga cggtcacagc ttgtctgtaa    6120
gcggatgccg ggagcagaca agcccgtcag ggcgcgtcag cgggtgttgg cgggtgtcgg    6180
```

-continued

| | |
|---|---|
| ggctggctta actatgcggc atcagagcag attgtactga gagtgcacca tatgcggtgt | 6240 |
| gaaataccgc acagatgcgt aaggagaaaa taccgcatca gattggctat tgg | 6293 |

<210> SEQ ID NO 3
<211> LENGTH: 6281
<212> TYPE: DNA
<213> ORGANISM: Artificial Sequence
<220> FEATURE:
<223> OTHER INFORMATION: synthetic dual-promoter expression vector plasmid AG157 for rhesus IL-12 heterodimer expression with human cytomegalovirus (CMV) promoter

<400> SEQUENCE: 3
cctggccatt gcatacgttg tatccatatc ataatatgta catttatatt ggctcatgtc 60
caacattacc gccatgttga cattgattat tgactagtta ttaatagtaa tcaattacgg 120
ggtcattagt tcatagccca tatatggagt tccgcgttac ataacttacg gtaaatggcc 180
cgcctggctg accgcccaac gacccccgcc cattgacgtc aataatgacg tatgttccca 240
tagtaacgcc aatagggact ttccattgac gtcaatgggt ggagtattta cggtaaactg 300
cccacttggc agtacatcaa gtgtatcata tgccaagtac gccccctatt gacgtcaatg 360
atggtaaatg gcccgcctgg cattatgccc agtacatgac cttatgggac tttcctactt 420
ggcagtacat ctacgtatta gtcatcgcta ttaccatggt gatgcggttt tggcagtaca 480
tcaatgggcg tggatagcgg tttgactcac ggggatttcc aagtctccac cccattgacg 540
tcaatgggag tttgttttgg caccaaaatc aacgggactt tccaaaatgt cgtaacaact 600
ccgccccatt gacgcaaatg ggcggtaggc gtgtacggtg ggaggtctat ataagcagag 660
ctcgtttagt gaaccgtcag atcgcctgga gacgccatcc acgctgtttt gacctccata 720
gaagacaccg ggaccgatcc agcctccgcg ggcgcgcgtc gaggaattaa acctcgagaa 780
gaaatgtgcc accagcagct ggtgatcagc tggttcagcc tggtgttcct ggccagcccc 840
ctgatggcca tctgggagct gaagaaggac gtatacgtgg tggagctgga ctggtatccc 900
gacgcgcctg gcgagatggt ggtgctgacc tgcgacaccc ccgaggagga cggcatcacc 960
tggaccctgg accagagcgg cgaagtgctg ggcagcggca agaccctgac gatccaggtc 1020
aaggagttcg gcgacgccgg ccagtacacc tgccacaagg gcggcgaggc cctgagccac 1080
agcctgctgc tgctgcacaa gaaggaggac gggatctgga gcaccgacgt gctgaaggac 1140
cagaaggagc ccaagaacaa gaccttcctg cgctgcgagg ccaagaatta cagcggccgg 1200
ttcacctgtt ggtggctgac caccatcagc accgacctga ccttcagcgt gaagagcagc 1260
agaggcagca gcaaccccca gggcgtgacc tgtggcgccg tgaccctgag cgccgagaga 1320
gtgagaggcg acaacaagga gtacgagtac agcgtggagt gccaggagga cagcgcctgc 1380
cctgccgccg aggagagact gcccatcgaa gtgatggtgg acgccatcca caagctgaag 1440
tacgagaact acaccagctc cttcttcatc cgggacatca tcaagcccga ccccccccaag 1500 aacctgcagc tgaagcccct gaagaacagc aggcaggtgg aagtgagctg ggagtacccc 1560
gacacctgga gcacccctca cagctacttc agcctgacct tctgcatcca agtgcagggc 1620
aagagcaagc gggagaagaa ggaccggatc ttcaccgata agaccagcgc caccgtgatc 1680
tgccggaaga acgccagctt cagcgtgcag gcccaggaca gatactacag cagcagctgg 1740
agcgagtggg ccagcgtgcc ttgcagctga tgaacctagg ggcgcgccag atctgatatc 1800
ggatctgctg tgccttctag ttgccagcca tctgttgttt gcccctcccc cgtgccttcc 1860

-continued

```
ttgaccctgg aagtgccac tcccactgtc ctttcctaat aaaatgagga aattgcatcg    1920
cattgtctga gtaggtgtca ttctattctg gggggtgggg tggggcagga cagcaagggg    1980
gaggattggg aagacaatag caggcatgct ggggatgcgg tgggctctat gggtacccag    2040
gtgctgaaga attgacccgg ttcctcctgg gccagaaaga agcaggcaca tccccttctc    2100
tgtgacacac cctgtccacg cccctggttc ttagttccag ccccactcat aggacactca    2160
tagctcagga gggctccgcc ttcaatccca cccgctaaag tacttggagc ggtctctccc    2220
tccctcatca gcccaccaaa ccaaacctag cctccaagag tgggaagaaa ttaaagcaag    2280
ataggctatt aagtgcagag ggagagaaaa tgcctccaac atgtgaggaa gtaatgagag    2340
aaatcataga atttcttccg cttcctcgct cactgactcg ctgcgctcgg tcgttcggct    2400
gcggcgagcg gtatcagctc actcaaaggc ggtaatacgg ttatccacag aatcagggga    2460
taacgcagga agaacatgt gagcaaaagg ccagcaaaag gccaggaacc gtaaaaaggc    2520
cgcgttgctg gcgttttttcc ataggctccg ccccccctgac gagcatcaca aaaatcgacg    2580
ctcaagtcag aggtggcgaa acccgacagg actataaaga taccaggcgt ttccccctgg    2640
aagctccctc gtgcgctctc ctgttccgac cctgccgctt accggatacc tgtccgcctt    2700
tctcccttcg ggaagcgtgg cgctttctca gctcacgc tgtaggtatc tcagttcggt    2760
gtaggtcgtt cgctccaagc tgggctgtgt gcacgaaccc cccgttcagc ccgaccgctg    2820
cgccttatcc ggtaactatc gtcttgagtc aacccggta agacacgact tatcgccact    2880
ggcagcagcc actggtaaca ggattagcag agcgaggtat gtaggcggtg ctacagagtt    2940
cttgaagtgg tggcctaact acggctacac tagaagaaca gtatttggta tctgcgctct    3000
gctgaagcca gttaccttcg gaaaaagagt ggtagctct tgatccggca acaaaccac    3060
cgctggtagc ggtggttttt ttgtttgcaa gcagcagatt acgcgcagaa aaaaggatc    3120
tcaagaagat cctttgatct tttctacggg gtctgacgct cagtggaacg aaaactcacg    3180
ttaagggatt ttggtcatga gattatcaaa aaggatcttc acctagatcc ttttaaatta    3240
aaaatgaagt tttaaatcaa tctaaagtat atatgagtaa acttggtctg acagttacca    3300
atgcttaatc agtgaggcac ctatctcagc gatctgtcta tttcgttcat ccatagttgc    3360
ctgactcggg ggggggggc gctgaggtct gcctcgtgaa gaaggtgttg ctgactcata    3420
ccaggcctga atcgccccat catccagcca gaaagtgagg gagccacggt tgatgagagc    3480
tttgttgtag gtggaccagt tggtgatttt gaacttttgc tttgccacgg aacggtctgc    3540
gttgtcggga agatgcgtga tctgatcctt caactcagca aaagttcgat ttattcaaca    3600
aagccgccgt cccgtcaagt cagcgtaatg ctctgccagt gttacaacca attaaccaat    3660
tctgattaga aaaactcatc gagcatcaaa tgaaactgca atttattcat atcaggatta    3720
tcaataccat atttttgaaa aagccgtttc tgtaatgaag gagaaaactc accgaggcag    3780
ttccatagga tggcaagatc ctggtatcgg tctgcgattc cgactcgtcc aacatcaata    3840
caacctatta atttccctc gtcaaaaata aggttatcaa gtgagaaatc accatgagtg    3900
acgactgaat ccggtgagaa tggcaaaagc ttatgcattt ctttccagac ttgttcaaca    3960
ggccagccat tacgctcgtc atcaaaatca ctcgcatcaa ccaaaccgtt attcattcgt    4020
gattgcgcct gagcgagacg aaatacgcga tcgctgttaa aaggacaatt acaaacagga    4080
atcgaatgca accggcgcag gaacactgcc agcgcatcaa caatattttc acctgaatca    4140
ggatattctt ctaatacctg gaatgctgtt ttcccgggga tcgcagtggt gagtaaccat    4200
gcatcatcag gagtacggat aaaatgcttg atggtcggaa gaggcataaa ttccgtcagc    4260
```

```
cagtttagtc tgaccatctc atctgtaaca tcattggcaa cgctacctt gccatgtttc   4320 agaaacaact ctggcgcatc gggcttccca tacaatcgat agattgtcgc acctgattgc   4380
ccgacattat cgcgagccca tttatacca tataaatcag catccatgtt ggaatttaat   4440
cgcggcctcg agcaagacgt ttccgttga atatggctca taacacccct tgtattactg   4500
tttatgtaag cagacagttt tattgttcat gatgatatat ttttatcttg tgcaatgtaa   4560
catcagagat tttgagacac aacgtggatc atccagacat gataagatac attgatgagt   4620
ttggacaaac cacaactaga atgcagtgaa aaaatgctt tatttgtgaa atttgtgatg   4680
ctattgcttt atttgtaacc attataagct gcaataaaca agttaacaac aacaattgca   4740
ttcattttat gtttcaggtt caggggggagg tgtgggaggt tttttaaagc aagtaaaacc   4800
tctacaaatg tggtatggct gattatgatc gtcgaggatc atcttatcag ctggcgttca   4860
ggtagctcat cactctgtcg atggtcacgg ccctgatccg gaaggcgtgc agcaggatgc   4920
acagcttgat cttggtcttg tagaagtcgg gctcctccag gctgctcttc tgaggcacgg   4980
tctcgctgtt gaagttcagg gcctgcatca gctcgtcgat cacgcccagg atgttctggt   5040
ccaggaagat ctgcctcttg gggtccctca gcagcttggc gttcatggtc ttgaactcca   5100
cctggtacat cttcaggtcc tcgtagatgc tcctcaggca cagggccatc atgaaggagg   5160
tctttctgct ggccaggcag ctgccgttgg tgatgaagct ggtctccctc gagttcaggc   5220
acgactcgtt cttgatcagc tccagcggca ggcacgcctc caccgtgctg gtcttgtcct   5280
tcgtgatgtc ctcgtggtcg atctcctcgc tcgtgcacgg gtagaactcc aggatctgcc   5340
gcgccttctg cagcgtgttc gacgccgcct tcagcaggtt ctggctgtgg tgcaggcacg   5400
ggaacatctc cggtcccggg gtcgccaccg acaggttccg cgccaggctc aggtagtcga   5460
gcaggaccag cgtcgccacg agcagcaggg agcgcgccgg gcacatttct ttctagacgt   5520
cgacagatcc aaacgctcct ccgacgtccc caggcagaat ggcggttccc taaacgagca   5580
ttgcttatat agacctccca ttaggcacgc ctaccgccca tttacgtcaa tggaacgccc   5640
atttgcgtca ttgcccctcc ccattgacgt caatggggat gtacttggca gccatcgcgg   5700
gccatttacc gccattgacg tcaatgggag tactgccaat gtaccctggc gtacttccaa   5760
tagtaatgta cttgccaagt tactattaat agatattgat gtactgccaa gtgggccatt   5820
taccgtcatt gacgtcaata gggggcgtga aacggatat gaatgggcaa tgagccatcc   5880
cattgacgtc aatggtgggt ggtcctattg acgtcaatgg gcattgagcc aggcgggcca   5940
tttaccgtaa ttgacgtcaa tggggaggc gccatatacg tcaataggac cgcccatatg   6000
acgtcaatag gtaagaccat gaggcccttt cgtctcgcgc gtttcggtga tgacggtgaa   6060
aacctctgac acatgcagct cccggagacg gtcacagctt gtctgtaagc ggatgccggg   6120
agcagacaag cccgtcaggg cgcgtcagcg ggtgttggcg ggtgtcgggg ctggcttaac   6180
tatgcggcat cagagcagat tgtactgaga gtgcaccata tgcggtgtga ataccgcac    6240 agatgcgtaa ggagaaaata ccgcatcaga ttggctattg                         6281
```

<210> SEQ ID NO 4
<211> LENGTH: 6281
<212> TYPE: DNA
<213> ORGANISM: Artificial Sequence
<220> FEATURE:
<223> OTHER INFORMATION: synthetic dual-promoter expression vector plasmid AG159 for rhesus IL-12 heterodimer expression with simian cytomegalovirus (CMV) promoter

<400> SEQUENCE: 4

```
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg gaggtctat ataagcagag      660
ctcgtttagt gaaccgtcag atcgcctgga gacgccatcc acgctgtttt gacctccata     720
gaagacaccg ggaccgatcc agcctccgcg gccgcgcgtc gaggaattcg ctagaaagaa     780
atgtgcccgg cgcgctccct gctgctcgtg gcgacgctgg tcctgctcga ctacctgagc     840
ctggcgcgga acctgtcggt ggcgaccccg ggaccggaga tgttcccgtg cctgcaccac     900
agccagaacc tgctgaaggc ggcgtcgaac acgctgcaga aggcgcggca gatcctggag     960
ttctacccgt gcacgagcga ggagatcgac cacgaggaca tcacgaagga caagaccagc    1020
acggtggagg cgtgcctgcc gctggagctg atcaagaacg agtcgtgcct gaactcgagg    1080
gagaccagct tcatcaccaa cggcagctgc ctggcagca gaaagacctc cttcatgatg    1140
gccctgtgcc tgaggagcat ctacgaggac ctgaagatgt accaggtgga gttcaagacc    1200
atgaacgcca agctgctgag ggaccccaag aggcagatct tcctggacca gaacatcctg    1260
ggcgtgatcg acgagctgat gcaggccctg aacttcaaca gcgagaccgt gcctcagaag    1320
agcagcctgg aggagcccga cttctacaag accaagatca gctgtgcat cctgctgcac    1380
gccttccgga tcagggccgt gaccatcgac agagtgatga gctacctgaa cgccagctga    1440
taagatatcg gatctatcgg atctgctgtg ccttctagtt gccagccatc tgttgtttgc    1500
ccctccccg tgccttcctt gaccctggaa ggtgccactc ccactgtcct ttcctaataa    1560
aatgaggaaa ttgcatcgca ttgtctgagt aggtgtcatt ctattctggg gggtggggtg    1620
gggcaggaca gcaaggggga ggattgggaa gacaatagca ggcatgctgg ggatgcggtg    1680
ggctctatgg gtacccaggt gctgaagaat tgacccggtt cctcctgggc cagaaagaag    1740
caggcacatc cccttctctg tgacacaccc tgtccacgcc cctggttctt agttccagcc    1800
ccactcatag gacactcata gctcaggagg gctccgcctt caatcccacc cgctaaagta    1860
cttggagcgg tctctcccctc cctcatcagc ccaccaaacc aaacctagcc tccaagagtg    1920
ggaagaaatt aaagcaagat aggctattaa gtgcagaggg agagaaaatg cctccaacat    1980
gtgaggaagt aatgagagaa atcatagaat ttcttccgct tcctcgctca ctgactcgct    2040
gcgctcggtc gttcggctgc ggcgagcggt atcagctcac tcaaaggcgg taatacggtt    2100
atccacagaa tcaggggata acgcaggaaa gaacatgtga gcaaaaggcc agcaaaaggc    2160
caggaaccgt aaaaaggccg cgttgctggc gttttccat aggctccgcc cccctgacga    2220
gcatcacaaa aatcgacgct caagtcagag gtggcgaaac ccgacaggac tataaagata    2280
ccaggcgttt ccccctggaa gctccctcgt gcgctctcct gttccgaccc tgccgcttac    2340
```

```
cggatacctg tccgcctttc tcccttcggg aagcgtggcg ctttctcata gctcacgctg    2400
taggtatctc agttcggtgt aggtcgttcg ctccaagctg ggctgtgtgc acgaacccccc   2460 cgttcagccc gaccgctgcg ccttatccgg taactatcgt cttgagtcca acccggtaag    2520
acacgactta tcgccactgg cagcagccac tggtaacagg attagcagag cgaggtatgt    2580
aggcggtgct acagagttct tgaagtggtg gcctaactac ggctacacta agaacagt     2640 atttggtatc tgcgctctgc tgaagccagt taccttcgga aaaagagttg gtagctcttg    2700
atccggcaaa caaaccaccg ctggtagcgg tggttttttt gtttgcaagc agcagattac    2760
gcgcagaaaa aaggatctca agaagatcc tttgatcttt tctacggggt ctgacgctca    2820
gtggaacgaa aactcacgtt aagggatttt ggtcatgaga ttatcaaaaa ggatcttcac    2880
ctagatcctt ttaaattaaa aatgaagttt taaatcaatc taaagtatat atgagtaaac    2940
ttggtctgac agttaccaat gcttaatcag tgaggcacct atctcagcga tctgtctatt    3000
tcgttcatcc atagttgcct gactcggggg ggggggggcgc tgaggtctgc ctcgtgaaga    3060
aggtgttgct gactcatacc aggcctgaat cgccccatca tccagccaga aagtgaggga    3120
gccacggttg atgagagctt tgttgtaggt ggaccagttg gtgattttga acttttgctt    3180
tgccacggaa cggtctgcgt tgtcgggaag atgcgtgatc tgatccttca actcagcaaa    3240
agttcgattt attcaacaaa gccgccgtcc cgtcaagtca gcgtaatgct ctgccagtgt    3300
tacaaccaat taaccaattc tgattagaaa aactcatcga gcatcaaatg aaactgcaat    3360
ttattcatat caggattatc aataccatat ttttgaaaaa gccgtttctg taatgaagga    3420
gaaaactcac cgaggcagtt ccataggatg gcaagatcct ggtatcggtc tgcgattccg    3480
actcgtccaa catcaataca acctattaat ttccctcgt caaaataag gttatcaagt     3540 gagaaatcac catgagtgac gactgaatcc ggtgagaatg gcaaaagctt atgcatttct    3600
ttccagactt gttcaacagg ccagccatta cgctcgtcat caaaatcact cgcatcaacc    3660
aaaccgttat tcattcgtga ttgcgcctga gcgagacgaa atacgcgatc gctgttaaaa    3720
ggacaattac aaacaggaat cgaatgcaac cggcgcagga acactgccag cgcatcaaca    3780 atatttttcac ctgaatcagg atattcttct aatacctgga atgctgtttt cccggggatc    3840
gcagtggtga gtaaccatgc atcatcagga gtacggataa aatgcttgat ggtcggaaga    3900
ggcataaatt ccgtcagcca gtttagtctg accatctcat ctgtaacatc attggcaacg    3960
ctacctttgc catgtttcag aaacaactct ggcgcatcgg gcttcccata caatcgatag    4020
attgtcgcac ctgattgccc gacattatcg cgagcccatt tatacccata taatcagca    4080 tccatgttgg aatttaatcg cggcctcgag caagacgttt cccgttgaat atggctcata    4140 acacccctg tattactgtt tatgtaagca gacagttttta ttgttcatga tgatatattt    4200
ttatcttgtg caatgtaaca tcagagattt tgagacacaa cgtggatcat ccagacatga    4260
taagatacat tgatgagttt ggacaaacca caactagaat gcagtgaaaa aaatgcttta    4320
tttgtgaaat ttgtgatgct attgctttat ttgtaaccat tataagctgc aataaacaag    4380
ttaacaacaa caattgcatt cattttatgt ttcaggttca gggggaggtg tgggaggttt    4440
tttaaagcaa gtaaacctc tacaaatgtg gtatggctga ttatgatcgt cgaggatccg    4500
gcgccggttt cgcgccccta ggttcatcag ctgcaaggca cgctggccca ctcgctccag    4560
ctgctgctgt agtatctgtc ctgggcctgc acgctgaagc tggcgttctt ccggcagatc    4620
acggtggcgc tggtcttatc ggtgaagatc cggtccttct tctcccgctt gctcttgccc    4680
```

```
tgcacttgga tgcagaaggt caggctgaag tagctgtgag gggtgctcca ggtgtcgggg    4740
tactcccagc tcacttccac ctgcctgctg ttcttcaggg gcttcagctg caggttcttg    4800 gggggggtcgg gcttgatgat gtcccggatg aagaaggagc tggtgtagtt ctcgtacttc    4860
agcttgtgga tggcgtccac catcacttcg atgggcagtc tctcctcggc ggcagggcag    4920
gcgctgtcct cctggcactc cacgctgtac tcgtactcct tgttgtcgcc tctcactctc    4980
tcggcgctca gggtcacggc gccacaggtc acgccctggg ggttgctgct gcctctgctg    5040
ctcttcacgc tgaaggtcag gtcggtgctg atggtggtca gccaccaaca ggtgaaccgg    5100
ccgctgtaat tcttggcctc gcagcgcagg aaggtcttgt tcttgggctc cttctggtcc    5160
ttcagcacgt cggtgctcca gatcccgtcc tccttcttgt gcagcagcag caggctgtgg    5220
ctcagggcct cgccgccctt gtggcaggtg tactggccgg cgtcgccgaa ctccttgacc    5280
tggatcgtca gggtcttgcc gctgccagc acttcgccgc tctggtccag gtccaggtg    5340 atgccgtcct cctcggggt gtcgcaggtc agcaccacca tctcgccagg cgcgtcggga    5400
taccagtcca gctccaccac gtatacgtcc ttcttcagct cccagatggc catcaggggg    5460
ctggccagga acaccaggct gaaccagctg atcaccagct gctggtggca catttcttct    5520
cgacagatcc aaacgctcct ccgacgtccc caggcagaat ggcggttccc taaacgagca    5580
ttgcttatat agacctccca ttaggcacgc ctaccgccca tttacgtcaa tggaacgccc    5640
atttgcgtca ttgcccctcc ccattgacgt caatggggat gtacttggca gccatcgcgg    5700
gccatttacc gccattgacg tcaatgggag tactgccaat gtaccctggc gtacttccaa    5760
tagtaatgta cttgccaagt tactattaat agatattgat gtactgccaa gtgggccatt    5820
taccgtcatt gacgtcaata gggggcgtga aacggatat gaatgggcaa tgagccatcc    5880
cattgacgtc aatggtgggt ggtcctattg acgtcaatgg gcattgagcc aggcgggcca    5940
tttaccgtaa ttgacgtcaa tgggggaggc gccatatacg tcaataggac gcccatatg    6000 acgtcaatag gtaagaccat gaggcccttt cgtctcgcgc gtttcggtga tgacggtgaa    6060
aacctctgac acatgcagct cccggagacg gtcacagctt gtctgtaagc ggatgccggg    6120
agcagacaag cccgtcaggg cgcgtcagcg ggtgttggcg ggtgtcgggg ctggcttaac    6180
tatgcggcat cagagcagat tgtactgaga gtgcaccata tgcggtgtga ataccgcac    6240 agatgcgtaa ggagaaaata ccgcatcaga ttggctattg g                       6281
```

<210> SEQ ID NO 5
<211> LENGTH: 4592
<212> TYPE: DNA
<213> ORGANISM: Artificial Sequence
<220> FEATURE:
<223> OTHER INFORMATION: synthetic expression vector plasmid AG177 for
      human IL-23 p19 alpha subunit expression

<400> SEQUENCE: 5

```
cctggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
```

```
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg gcgcgcgtc gactctagaa agaaatgctg     780
gggagccgcg cggtcatgct gctcttgctg ctcccctgga cggcccaggg ccgggcggtg    840
cccgggggct cgagcccggc ctggacgcag tgccagcagc tcagccagaa gctctgcacc    900
ctggcctggt cggcccaccc gctcgtgggc cacatggacc tccgggagga gggcgacgag    960
gagacgacca acgacgtccc ccacatccag tgcggcgacg gctgcgaccc caggggcctc   1020
cgggacaact cgcagttctg cctgcagcgc atccaccagg gcctgatctt ctacgagaag   1080
ctgctcggct cggacatctt cacggggag ccgtcgctgc tcccggacag cccggtgggc   1140
cagctccacg cctccctcct gggcctctcg caacttctgc aaccgagggg ccaccactgg   1200
gagacgcagc agatcccgag cctctcgccc agccagccgt ggcagcggct cctgctcaga   1260
ttcaagatct tgcgctccct ccaagccttc gtggcggtcg ccgcccgggt cttcgcccac   1320
ggcgcggcca ccctgagccc ctgataagat atcggatcca gatctgctgt gccttctagt   1380
tgccagccat ctgttgtttg cccctccccc gtgccttcct tgaccctgga aggtgccact   1440
cccactgtcc tttcctaata aaatgaggaa attgcatcgc attgtctgag taggtgtcat   1500
tctattctgg ggggtggggt ggggcaggac agcaaggggg aggattggga agacaatagc   1560
aggcatgctg gggatgcggt gggctctatg ggtacccagg tgctgaagaa ttgacccggt   1620
tcctcctggg ccagaaagaa gcaggcacat ccccttctct gtgacacacc ctgtccacgc   1680
ccctggttct tagttccagc cccactcata ggacactcat agctcaggag ggctccgcct   1740
tcaatcccac ccgctaaagt acttggagcg gtctctccct ccctcatcag cccaccaaac   1800
caaacctagc ctccaagagt gggaagaaat taaagcaaga taggctatta agtgcagagg   1860
gagagaaaat gcctccaaca tgtgaggaag taatgagaga aatcatagaa tttcttccgc   1920
ttcctcgctc actgactcgc tgcgctcggt cgttcggctg cggcgagcgg tatcagctca   1980
ctcaaaggcg gtaatacggt tatccacaga atcaggggat aacgcaggaa agaacatgtg   2040
agcaaaaggc cagcaaaagg ccaggaaccg taaaaaggcc gcgttgctgg cgttttttcca  2100 taggctccgc cccctgacg agcatcacaa aaatcgacgc tcaagtcaga ggtggcgaaa    2160
cccgacagga ctataaagat accaggcgtt tccccctgga agctccctcg tgcgctctcc   2220
tgttccgacc ctgccgctta ccggatacct gtccgccttt ctcccttcgg gaagcgtggc   2280
gctttctcat agctcacgct gtaggtatct cagttcggtg taggtcgttc gctccaagct   2340
gggctgtgtg cacgaacccc ccgttcagcc cgaccgctgc gccttatccg gtaactatcg   2400
tcttgagtcc aacccggtaa gacacgactt atcgccactg gcagcagcca ctggtaacag   2460
gattagcaga gcgaggtatg taggcggtgc tacagagttc ttgaagtggt ggcctaacta   2520
cggctacact agaagaacag tatttggtat ctgcgctctg ctgaagccag ttaccttcgg   2580
aaaaagagtt ggtagctctt gatccggcaa acaaaccacc gctggtagcg gtggtttttt   2640
tgtttgcaag cagcagatta cgcgcagaaa aaaaggatct caagaagatc ctttgatctt   2700
ttctacgggg tctgacgctc agtggaacga aaactcacgt taagggattt tggtcatgag   2760
attatcaaaa aggatcttca cctagatcct tttaaattaa aaatgaagtt ttaaatcaat   2820
```

```
ctaaagtata tatgagtaaa cttggtctga cagttaccaa tgcttaatca gtgaggcacc    2880
tatctcagcg atctgtctat ttcgttcatc catagttgcc tgactcgggg gggggggggcg   2940 ctgaggtctg cctcgtgaag aaggtgttgc tgactcatac caggcctgaa tcgccccatc    3000
atccagccag aaagtgaggg agccacggtt gatgagagct ttgttgtagg tggaccagtt    3060
ggtgattttg aactttttgct ttgccacgga acggtctgcg ttgtcgggaa gatgcgtgat   3120
ctgatccttc aactcagcaa aagttcgatt tattcaacaa agccgccgtc ccgtcaagtc    3180
agcgtaatgc tctgccagtg ttacaaccaa ttaaccaatt ctgattagaa aaactcatcg    3240
agcatcaaat gaaactgcaa tttattcata tcaggattat caataccata tttttgaaaa    3300
agccgtttct gtaatgaagg agaaaactca ccgaggcagt tccataggat ggcaagatcc    3360
tggtatcggt ctgcgattcc gactcgtcca acatcaatac aacctattaa tttcccctcg    3420
tcaaaaataa ggttatcaag tgagaaatca ccatgagtga cgactgaatc cggtgagaat    3480
ggcaaaagct tatgcatttc tttccagact tgttcaacag gccagccatt acgctcgtca    3540
tcaaaatcac tcgcatcaac caaaccgtta ttcattcgtg attgcgcctg agcgagacga    3600
aatacgcgat cgctgttaaa aggacaatta caaacaggaa tcgaatgcaa ccggcgcagg    3660
aacactgcca gcgcatcaac aatatttttca cctgaatcag gatattcttc taatacctgg    3720
aatgctgttt tcccggggat cgcagtggtg agtaaccatg catcatcagg agtacggata    3780
aaatgcttga tggtcggaag aggcataaat tccgtcagcc agtttagtct gaccatctca    3840
tctgtaacat cattggcaac gctacctttg ccatgtttca gaaacaactc tggcgcatcg    3900
ggcttcccat acaatcgata gattgtcgca cctgattgcc cgacattatc gcgagcccat    3960
ttatacccat ataaatcagc atccatgttg gaatttaatc gcggcctcga gcaagacgtt    4020
tcccgttgaa tatggctcat aacaccccctt gtattactgt ttatgtaagc agacagtttt    4080
attgttcatg atgatatatt tttatcttgt gcaatgtaac atcagagatt ttgagacaca    4140
acgtggcttt cccccccccc ccattattga agcatttatc agggttattg tctcatgagc    4200
ggatacatat ttgaatgtat ttagaaaaat aaacaaatag gggttccgcg cacatttccc    4260
cgaaaagtgc cacctgacgt ctaagaaacc attattatca tgacattaac ctataaaaat    4320
aggcgtatca cgaggccctt tcgtctcgcg cgtttcggtg atgacggtga aaacctctga    4380
cacatgcagc tcccggagac ggtcacagct tgtctgtaag cggatgccgg gagcagacaa    4440
gcccgtcagg gcgcgtcagc gggtgttggc gggtgtcggg gctggcttaa ctatgcggca    4500
tcagagcaga ttgtactgag agtgcaccat atgcggtgtg aaataccgca cagatgcgta    4560
aggagaaaat accgcatcag attggctatt gg                                 4592
```

<210> SEQ ID NO 6
<211> LENGTH: 5611
<212> TYPE: DNA
<213> ORGANISM: Artificial Sequence
<220> FEATURE:
<223> OTHER INFORMATION: synthetic expression vector plasmid AG180 for human IL-12 p40 beta subunit expression

<400> SEQUENCE: 6

```
cctggccatt gcatacgttg tatccatatc ataatatgta catttatatt ggctcatgtc    60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
```

```
tagtaacgcc aatagggact ttccattgac gtcaatgggt ggagtattta cggtaaactg    300
cccacttggc agtacatcaa gtgtatcata tgccaagtac gcccctatt gacgtcaatg    360 atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg gcggtaggc gtgtacggtg ggaggtctat ataagcagag    660
ctcgtttagt gaaccgtcag atcgcctgga cgccatcc acgctgtttt gacctccata    720
gaagacaccg ggaccgatcc agcctccgcg gccgcgcgtc gaggaatttc gagaagaaat    780
gtgccaccag cagctggtca tcagctggtt cagcctcgtt ttcctcgcct cgccgctggt    840
cgccatatgg gagctcaaga aggacgtata cgtggtggag ctggactggt accccgacgc    900
gccgggcgag atggtcgtcc tgacgtgcga cacgccggag gaggacggca tcacgtggac    960
gctggaccag tccagcgagg tcctcggctc cggcaagacg ctgacgatcc aggtcaagga    1020
gttcggcgac gcgggccagt acacgtgcca agggcggc gaggtcctga gccactccct    1080
cctcctgcta cacaagaagg aggacgggat ctggagcacg acatcctca aggaccagaa    1140 ggagccgaag aacaagacct tcctgcgctg cgaggcgaag aattactcgg gccggttcac    1200
gtgctggtgg ctcaccacga tcagcacgga cctgacgttc tcggtcaagt cgtcgcgggg    1260
ctcgtcggac cccagggggg tgacctgcgg cgcggcgacg ctgtcggcgg agcgggtgcg    1320
gggcgacaac aaggagtacg agtactcggt cgagtgccag gaggactcgg cgtgcccggc    1380
ggcggaggag tcgctgccga tcgaggtgat ggtcgacgcg gtccacaagc tgaagtacga    1440
gaactacacg tcgtcgttct tcatccggga catcatcaag ccggaccccgc cgaagaacct    1500 gcagctgaag ccgctgaaga actcgcggca ggtcgaggtc tcgtgggagt acccggacac    1560
gtggtcgacg ccgcactcgt acttctcgct gacgttctgc gtccaagtgc agggcaagtc    1620
gaagcgggag aagaaggacc gggtgttcac cgacaagacg agcgcgacgg tgatctgccg    1680
gaagaacgcg tcgatctcgg tgcgggcgca ggaccggtac tactcgtcgt cgtggtcgga    1740
gtgggcgtcg gtgccgtgca gctagaccta ggggcgcgcc agatctgata tcggatctgc    1800
tgtgccttct agttgccagc catctgttgt ttgcccctcc cccgtgcctt ccttgaccct    1860
ggaaggtgcc actcccactg tcctttccta ataaaatgag gaaattgcat cgcattgtct    1920
gagtaggtgt cattctattc tggggggtgg ggtggggcag gacagcaagg gggaggattg    1980
ggaagacaat agcaggcatg ctggggatgc ggtgggctct atgggtaccc aggtgctgaa    2040
gaattgaccc ggttcctcct gggccagaaa gaagcaggca catccccttc tctgtgacac    2100
accctgtcca cgcccctggt tcttagttcc agccccactc ataggacact catagctcag    2160
gagggctccg ccttcaatcc cacccgctaa agtacttgga gcggtctctc cctccctcat    2220
cagcccacca aaccaaacct agcctccaag agtgggaaga aattaaagca agataggcta    2280
ttaagtgcag agggagagaa aatgcctcca acatgtgagg aagtaatgag agaaatcata    2340
gaatttcttc cgcttcctcg ctcactgact cgctgcgctc ggtcgttcgg ctgcggcgag    2400
cggtatcagc tcactcaaag gcggtaatac ggttatccac agaatcaggg gataacgcag    2460
gaaagaacat gtgagcaaaa ggccagcaaa aggccaggaa ccgtaaaaag gccgcgttgc    2520
tggcgttttt ccataggctc cgcccccctg acgagcatca caaaaatcga cgctcaagtc    2580
```

```
agaggtggcg aaacccgaca ggactataaa gataccaggc gtttccccct ggaagctccc    2640
tcgtgcgctc tcctgttccg accctgccgc ttaccggata cctgtccgcc tttctccctt    2700
cgggaagcgt ggcgctttct catagctcac gctgtaggta tctcagttcg gtgtaggtcg    2760
ttcgctccaa gctgggctgt gtgcacgaac cccccgttca gcccgaccgc tgcgccttat    2820
ccggtaacta tcgtcttgag tccaacccgg taagacacga cttatcgcca ctggcagcag    2880
ccactggtaa caggattagc agagcgaggt atgtaggcgg tgctacagag ttcttgaagt    2940
ggtggcctaa ctacggctac actagaagaa cagtatttgg tatctgcgct ctgctgaagc    3000
cagttacctt cggaaaaaga gttggtagct cttgatccgg caaacaaacc accgctggta    3060
gcggtggttt ttttgtttgc aagcagcaga ttacgcgcag aaaaaaagga tctcaagaag    3120
atcctttgat cttttctacg gggtctgacg ctcagtggaa cgaaaactca cgttaaggga    3180
ttttggtcat gagattatca aaaaggatct tcacctagat ccttttaaat taaaaatgaa    3240
gttttaaatc aatctaaagt atatatgagt aaacttggtc tgacagttac caatgcttaa    3300
tcagtgaggc acctatctca gcgatctgtc tatttcgttc atccatagtt gcctgactcg    3360 ggggggggg gcgctgaggt ctgcctcgtg aagaaggtgt tgctgactca taccaggcct    3420
gaatcgcccc atcatccagc cagaaagtga gggagccacg gttgatgaga gctttgttgt    3480
aggtggacca gttggtgatt ttgaactttt gctttgccac ggaacggtct gcgttgtcgg    3540
gaagatgcgt gatctgatcc ttcaactcag caaaagttcg atttattcaa caaagccgcc    3600
gtcccgtcaa gtcagcgtaa tgctctgcca gtgttacaac caattaacca attctgatta    3660
gaaaaactca tcgagcatca aatgaaactg caatttattc atatcaggat tatcaatacc    3720
atatttttga aaaagccgtt tctgtaatga aggagaaaac tcaccgaggc agttccatag    3780
gatggcaaga tcctggtatc ggtctgcgat tccgactcgt ccaacatcaa tacaacctat    3840
taatttcccc tcgtcaaaaa taaggttatc aagtgagaaa tcaccatgag tgacgactga    3900
atccggtgag aatggcaaaa gcttatgcat ttctttccag acttgttcaa caggccagcc    3960
attacgctcg tcatcaaaat cactcgcatc aaccaaaccg ttattcattc gtgattgcgc    4020
ctgagcgaga cgaaatacgc gatcgctgtt aaaaggacaa ttacaaacag gaatcgaatg    4080
caaccggcgc aggaacactg ccagcgcatc aacaatattt tcacctgaat caggatattc    4140
ttctaatacc tggaatgctg ttttcccggg gatcgcagtg gtgagtaacc atgcatcatc    4200
aggagtacgg ataaaatgct tgatggtcgg aagaggcata aattccgtca gccagtttag    4260
tctgaccatc tcatctgtaa catcattggc aacgctacct ttgccatgtt tcagaaacaa    4320
ctctggcgca tcgggcttcc catacaatcg atagattgtc gcacctgatt gcccgacatt    4380
atcgcgagcc catttatacc catataaatc agcatccatg ttggaattta atcgcggcct    4440
cgagcaagac gtttcccgtt gaatatggct cataacaccc cttgtattac tgtttatgta    4500
agcagacagt tttattgttc atgatgatat ttttttatct tgtgcaatgt aacatcagag    4560
attttgagac acaacgtgga tcatccagac atgataagat acattgatga gtttggacaa    4620
accacaacta gaatgcagtg aaaaaaatgc tttatttgtg aaatttgtga tgctattgct    4680
ttatttgtaa ccattataag ctgcaataaa caagttaaca acaacaattg cattcatttt    4740
atgtttcagg ttcaggggga ggtgtgggag gttttttaaa gcaagtaaaa cctctacaaa    4800
tgtggtatgg ctgattatga tcgtcgagga tccggcgccg gtttaaacgt cgacagatcc    4860
aaacgctcct ccgacgtccc caggcagaat ggcggttccc taaacgagca ttgcttatat    4920
agacctccca ttaggcacgc ctaccgccca tttacgtcaa tggaacgccc atttgcgtca    4980
```

```
ttgcccctcc ccattgacgt caatggggat gtacttggca gccatcgcgg gccatttacc    5040
gccattgacg tcaatgggag tactgccaat gtaccctggc gtacttccaa tagtaatgta    5100
cttgccaagt tactattaat agatattgat gtactgccaa gtgggccatt taccgtcatt    5160
gacgtcaata gggggcgtga aacggatat gaatgggcaa tgagccatcc cattgacgtc    5220
aatggtgggt ggtcctattg acgtcaatgg gcattgagcc aggcgggcca tttaccgtaa    5280
ttgacgtcaa tggggaggc gccatatacg tcaataggac cgcccatatg acgtcaatag    5340
gtaagaccat gaggcccttt cgtctcgcgc gtttcggtga tgacggtgaa aacctctgac    5400
acatgcagct cccggagacg tcacagctt gtctgtaagc ggatgccggg agcagacaag    5460
cccgtcaggg cgcgtcagcg ggtgttggcg ggtgtcgggg ctggcttaac tatgcggcat    5520
cagagcagat tgtactgaga gtgcaccata tgcggtgtga ataccgcac agatgcgtaa    5580 ggagaaaata ccgcatcaga ttggctattg g                                   5611

<210> SEQ ID NO 7
<211> LENGTH: 6194
<212> TYPE: DNA
<213> ORGANISM: Artificial Sequence
<220> FEATURE:
<223> OTHER INFORMATION: synthetic dual-promoter expression vector
      plasmid AG184 with human cytomegalovirus (CMV) promoter for human
      IL-12 p40 beta subunit expression and simian CMV promoter for
      human IL-23 p19 alpha subunit expression

<400> SEQUENCE: 7
cctggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg gcggtaggc gtgtacggtg gaggtctat ataagcagag    660 ctcgtttagt gaaccgtcag atcgcctgga gacgccatcc acgctgtttt gacctccata    720
gaagacaccg ggaccgatcc agcctccgcg gccgcgcgtc gaggaatttc gagaagaaat    780
gtgccaccag cagctggtca tcagctggtt cagcctcgtt ttcctcgcct cgccgctggt    840
cgccatatgg gagctcaaga aggacgtata cgtggtggag ctggactggt accccgacgc    900
gccgggcgag atggtcgtcc tgacgtgcga cacgccggag gaggacggca tcacgtggac    960
gctggaccag tccagcgagg tcctcggctc cggcaagacg ctgacgatcc aggtcaagga   1020
gttcggcgac gcgggccagt acacgtgcca caagggcggc gaggtcctga gccactccct   1080
cctcctgcta cacaagaagg aggacgggat ctggagcacg acatcctca aggaccagaa   1140 ggagccgaag aacaagacct tcctgcgctg cgaggcgaag aattactcgg gccggttcac   1200
gtgctggtgg ctcaccacga tcagcacgga cctgacgttc tcggtcaagt cgtcgcgggg   1260
ctcgtcggac ccccaggggg tgacctgcgg cgcggcgacg ctgtcggcgg agcgggtgcg   1320
```

-continued

```
gggcgacaac aaggagtacg agtactcggt cgagtgccag gaggactcgg cgtgcccggc   1380
ggcggaggag tcgctgccga tcgaggtgat ggtcgacgcg gtccacaagc tgaagtacga   1440
gaactacacg tcgtcgttct tcatccggga catcatcaag ccggacccgc cgaagaacct   1500
gcagctgaag ccgctgaaga actcgcggca ggtcgaggtc tcgtgggagt acccggacac   1560
gtggtcgacg ccgcactcgt acttctcgct gacgttctgc gtccaagtgc agggcaagtc   1620
gaagcgggag aagaaggacc gggtgttcac cgacaagacg agcgcgacgg tgatctgccg   1680
gaagaacgcg tcgatctcgg tgcgggcgca ggaccggtac tactcgtcgt cgtggtcgga   1740
gtgggcgtcg gtgccgtgca gctagaccta ggggcgcgcc agatctgata tcggatctgc   1800
tgtgccttct agttgccagc catctgttgt ttgcccctcc ccgtgccttc cttgaccct    1860
ggaaggtgcc actcccactg tcctttccta ataaaatgag gaaattgcat cgcattgtct   1920
gagtaggtgt cattctattc tggggggtgg ggtggggcag gacagcaagg gggaggattg   1980
ggaagacaat agcaggcatg ctggggatgc ggtgggctct atgggtaccc aggtgctgaa   2040
gaattgaccc ggttcctcct gggccagaaa gaagcaggca catccccttc tctgtgacac   2100
accctgtcca cgcccctggt tcttagttcc agccccactc ataggacact catagctcag   2160
gagggctccg ccttcaatcc cacccgctaa agtacttgga gcggtctctc cctccctcat   2220
cagcccacca aaccaaacct agcctccaag agtgggaaga aattaaagca agataggcta   2280
ttaagtgcag agggagagaa aatgcctcca acatgtgagg aagtaatgag agaaatcata   2340
gaatttcttc cgcttcctcg ctcactgact cgctgcgctc ggtcgttcgg ctgcggcgag   2400
cggtatcagc tcactcaaag gcggtaatac ggttatccac agaatcaggg gataacgcag   2460
gaaagaacat gtgagcaaaa ggccagcaaa aggccaggaa ccgtaaaaag gccgcgttgc   2520
tggcgttttt ccataggctc cgcccccctg acgagcatca caaaaatcga cgctcaagtc   2580
agaggtggcg aaacccgaca ggactataaa gataccaggc gtttccccct ggaagctccc   2640
tcgtgcgctc tcctgttccg accctgccgc ttaccggata cctgtccgcc tttctccctt   2700
cgggaagcgt ggcgctttct catagctcac gctgtaggta tctcagttcg gtgtaggtcg   2760
ttcgctccaa gctgggctgt gtgcacgaac cccccgttca gcccgaccgc tgcgccttat   2820
ccggtaacta tcgtcttgag tccaacccgg taagacacga cttatcgcca ctggcagcag   2880
ccactggtaa caggattagc agagcgaggt atgtaggcgg tgctacagag ttcttgaagt   2940
ggtggcctaa ctacggctac actagaagaa cagtatttgg tatctgcgct ctgctgaagc   3000
cagttacctt cggaaaaaga gttggtagct cttgatccgg caaacaaacc accgctggta   3060
gcggtggttt ttttgtttgc aagcagcaga ttacgcgcag aaaaaaagga tctcaagaag   3120
atcctttgat cttttctacg gggtctgacg ctcagtggaa cgaaaactca cgttaaggga   3180
ttttggtcat gagattatca aaaaggatct tcacctagat ccttttaaat taaaaatgaa   3240
gttttaaatc aatctaaagt atatatgagt aaacttggtc tgacagttac caatgcttaa   3300
tcagtgaggc acctatctca gcgatctgtc tatttcgttc atccatagtt gcctgactcg   3360
gggggggggg gcgctgaggt ctgcctcgtg aagaaggtgt tgctgactca taccaggcct   3420
gaatcgcccc atcatccagc cagaaagtga gggagcacg gttgatgaga ctttgttgt    3480
aggtggacca gttggtgatt ttgaacttt  gctttgccac ggaacggtct cgttgtcgg    3540
gaagatgcgt gatctgatcc ttcaactcag caaaagttcg atttattcaa caaagccgcc   3600
gtcccgtcaa gtcagcgtaa tgctctgcca gtgttacaac caattaacca attctgatta   3660
```

```
gaaaaactca tcgagcatca aatgaaactg caatttattc atatcaggat tatcaatacc      3720 atattttga aaaagccgtt tctgtaatga aggagaaaac tcaccgaggc agttccatag       3780
gatggcaaga tcctggtatc ggtctgcgat tccgactcgt ccaacatcaa tacaacctat      3840
taatttcccc tcgtcaaaaa taaggttatc aagtgagaaa tcaccatgag tgacgactga      3900
atccggtgag aatggcaaaa gcttatgcat ttctttccag acttgttcaa caggccagcc      3960
attacgctcg tcatcaaaat cactcgcatc aaccaaaccg ttattcattc gtgattgcgc      4020
ctgagcgaga cgaaatacgc gatcgctgtt aaaaggacaa ttacaaacag gaatcgaatg      4080
caaccggcgc aggaacactg ccagcgcatc aacaatattt tcacctgaat caggatattc      4140
ttctaatacc tggaatgctg ttttcccggg gatcgcagtg gtgagtaacc atgcatcatc      4200
aggagtacgg ataaaatgct tgatggtcgg aagaggcata aattccgtca gccagtttag      4260
tctgaccatc tcatctgtaa catcattggc aacgctacct ttgccatgtt tcagaaacaa      4320
ctctggcgca tcgggcttcc catacaatcg atagattgtc gcacctgatt gcccgacatt      4380
atcgcgagcc catttatacc catataaatc agcatccatg ttggaattta atcgcggcct      4440
cgagcaagac gtttcccgtt gaatatggct cataacaccc cttgtattac tgtttatgta      4500
agcagacagt tttattgttc atgatgatat attttatct tgtgcaatgt aacatcagag       4560
attttgagac acaacgtgga tcatccagac atgataagat acattgatga gtttggacaa      4620
accacaacta gaatgcagtg aaaaaaatgc tttatttgtg aaatttgtga tgctattgct      4680
ttatttgtaa ccattataag ctgcaataaa caagttaaca acaacaattg cattcatttt      4740
atgtttcagg ttcaggggga ggtgtgggag gttttttaaa gcaagtaaaa cctctacaaa      4800
tgtggtatgg ctgattatga tcgtcgagga tccgatatct tatcaggggc tcagggtggc      4860
cgcgccgtgg gcgaagaccc gggcggcgac cgccacgaag gcttggaggg agcgcaagat      4920
cttgaatctg agcaggagcc gctgccacgg ctggctgggc gagaggctcg ggatctgctg      4980
cgtctcccag tggtggccct ccggttgcag aagttgcgag aggcccagga gggaggcgtg      5040
gagctggccc accgggctgt ccgggagcag cgacggctcc cccgtgaaga tgtccgagcc      5100
gagcagcttc tcgtagaaga tcaggccctg gtggatgcgc tgcaggcaga actgcgagtt      5160
gtcccggagg ccctgggggt cgcagccgtc gccgcactgg atgtggggga cgtcgttggt      5220
cgtctcctcg tcgccctcct cccggaggtc catgtggccc acgagcgggt gggccgacca      5280
ggccagggtg cagagcttct ggctgagctg ctggcactgc gtccaggccg ggctcgagcc      5340
cccgggcacc gccggccct gggccgtcca ggggagcagc aagagcagca tgaccgcgcg       5400
gctccccagc atttctttct agagtcaaac gtcgacagat ccaaacgctc ctccgacgtc      5460
cccaggcaga atggcggttc cctaaacgag cattgcttat atagacctcc cattaggcac      5520
gcctaccgcc catttacgtc aatggaacgc ccatttgcgt cattgcccct cccattgac       5580 gtcaatgggg atgtacttgg cagccatcgc gggccattta ccgccattga cgtcaatggg      5640
agtactgcca atgtaccctg gcgtacttcc aatagtaatg tacttgccaa gttactatta      5700
atagatattg atgtactgcc aagtgggcca tttaccgtca ttgacgtcaa taggggggcgt      5760 gagaacggat atgaatgggc aatgagccat cccattgacg tcaatggtgg gtggtcctat      5820
tgacgtcaat gggcattgag ccaggcgggc catttaccgt aattgacgtc aatggggggag      5880 gcgccatata cgtcaatagg accgccata tgacgtcaat aggtaaagac catgaggccc       5940
tttcgtctcg cgcgtttcgg tgatgacggt gaaaacctct gacacatgca gctcccggag      6000
acggtcacag cttgtctgta agcggatgcc gggagcagac aagcccgtca gggcgcgtca      6060
```

```
gcgggtgttg gcgggtgtcg gggctggctt aactatgcgg catcagagca gattgtactg    6120
agagtgcacc atatgcggtg tgaaataccg cacagatgcg taaggagaaa ataccgcatc    6180
agattggcta ttgg                                                      6194

<210> SEQ ID NO 8
<211> LENGTH: 4715
<212> TYPE: DNA
<213> ORGANISM: Artificial Sequence
<220> FEATURE:
<223> OTHER INFORMATION: synthetic expression vector plasmid AG193 for
      murine IL-27 p28 alpha subunit expression

<400> SEQUENCE: 8
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg gaggtctat ataagcagag      660 ctcgtttagt gaaccgtcag atcgcctgga cgccatcc acgctgtttt gacctccata      720
gaagacaccg ggaccgatcc agcctccgcg ggcgcgcgtc gacaagaaat gggccaggtc     780
accggggacc tcgggtggcg cctgtcgctc ctgctcctgc ccctcctcct ggtccaagcg     840
gggagctggg gcttccccac ggatccctg agcctccagg agctgcgcag ggagttcacc      900
gtcagcctgt acctcgcccg gaagctgctc tccgaggtcc agggctacgt ccacagcttc     960
gccgagtcgc gcctgcccgg cgtgaacctg gacctcctgc ccctgggcta ccacctcccc    1020
aacgtctccc tgacgttcca agcctggcac cacctctccg actccgagcg cctctgcttc    1080
ctcgccacca cgctccggcc gttcccggcc atgctgggcg gctggggac ccaggggacc     1140 tggaccagct ccgagaggga gcagctgtgg gccatgaggc tggacctccg ggacctgcac    1200
aggcacctcc gcttccaagt cctggccgcg ggcttcaagt gctccaagga ggaggaggac    1260
aaggaggaag aggaagagga ggaagaagag gaaaagaagc tgcccctcgg ggccctgggc    1320
ggccccaacc aggtgtcctc ccaagtgtcc tggccccagc tgctctacac ctaccagctc    1380
ctccactccc tggagctggt cctgagccgg gcggtgcggg acctgctcct gctgtccctg    1440
ccccggcgcc cgggctcggc ctgggactcc taatgatcta aagatctgc tgtgccttct    1500 agttgccagc catctgttgt ttgccctcc cccgtgcctt ccttgaccct ggaaggtgcc    1560
actcccactg tcctttccta ataaaatgag gaaattgcat cgcattgtct gagtaggtgt    1620
cattctattc tggggggtgg ggtggggcag gacagcaagg gggaggattg ggaagacaat    1680
agcaggcatg ctggggatgc ggtgggctct atgggtaccc aggtgctgaa gaattgaccc    1740
ggttcctcct gggccagaaa gaagcaggca catcccttc tctgtgacac accctgtcca    1800 cgccctggt tcttagttcc agccccactc ataggacact catagctcag gagggctccg    1860
```

```
ccttcaatcc cacccgctaa agtacttgga gcggtctctc cctccctcat cagcccacca    1920
aaccaaacct agcctccaag agtgggaaga aattaaagca agataggcta ttaagtgcag    1980
agggagagaa aatgcctcca acatgtgagg aagtaatgag agaaatcata gaatttcttc    2040
cgcttcctcg ctcactgact cgctgcgctc ggtcgttcgg ctgcggcgag cggtatcagc    2100
tcactcaaag gcggtaatac ggttatccac agaatcaggg gataacgcag gaaagaacat    2160
gtgagcaaaa ggccagcaaa aggccaggaa ccgtaaaaag gccgcgttgc tggcgttttt    2220
ccataggctc cgcccccctg acgagcatca caaaaatcga cgctcaagtc agaggtggcg    2280
aaacccgaca ggactataaa gataccaggc gtttccccct ggaagctccc tcgtgcgctc    2340
tcctgttccg accctgccgc ttaccggata cctgtccgcc tttctccctt cgggaagcgt    2400
ggcgctttct catagctcac gctgtaggta tctcagttcg gtgtaggtcg ttcgctccaa    2460
gctgggctgt gtgcacgaac cccccgttca gcccgaccgc tgcgccttat ccggtaacta    2520
tcgtcttgag tccaacccgg taagacacga cttatcgcca ctggcagcag ccactggtaa    2580
caggattagc agagcgaggt atgtaggcgg tgctacagag ttcttgaagt ggtggcctaa    2640
ctacggctac actagaagaa cagtatttgg tatctgcgct ctgctgaagc cagttacctt    2700
cggaaaaaga gttggtagct cttgatccgg caaacaaacc accgctggta gcggtggttt    2760
ttttgtttgc aagcagcaga ttacgcgcag aaaaaaagga tctcaagaag atcctttgat    2820
cttttctacg gggtctgacg ctcagtggaa cgaaaactca cgttaaggga ttttggtcat    2880
gagattatca aaaaggatct tcacctagat ccttttaaat taaaaatgaa gttttaaatc    2940
aatctaaagt atatatgagt aaacttggtc tgacagttac caatgcttaa tcagtgaggc    3000
acctatctca gcgatctgtc tatttcgttc atccatagtt gcctgactcg ggggggggg    3060 gcgctgaggt ctgcctcgtg aagaaggtgt tgctgactca taccaggcct gaatcgcccc    3120
atcatccagc cagaaagtga gggagccacg gttgatgaga gctttgttgt aggtggacca    3180
gttggtgatt ttgaactttt gctttgccac ggaacggtct gcgttgtcgg aagatgcgt    3240 gatctgatcc ttcaactcag caaaagttcg atttattcaa caaagccgcc gtcccgtcaa    3300
gtcagcgtaa tgctctgcca gtgttacaac caattaacca attctgatta gaaaaactca    3360
tcgagcatca aatgaaactg caatttattc atatcaggat tatcaatacc atattttga    3420 aaaagccgtt tctgtaatga aggagaaaac tcaccgaggc agttccatag gatggcaaga    3480
tcctggtatc ggtctgcgat tccgactcgt ccaacatcaa tacaacctat taatttcccc    3540
tcgtcaaaaa taaggttatc aagtgagaaa tcaccatgag tgacgactga atccggtgag    3600
aatggcaaaa gcttatgcat ttctttccag acttgttcaa caggccagcc attacgctcg    3660
tcatcaaaat cactcgcatc aaccaaaccg ttattcattc gtgattgcgc ctgagcgaga    3720
cgaaatacgc gatcgctgtt aaaaggacaa ttacaaacag gaatcgaatg caaccggcgc    3780
aggaacactg ccagcgcatc aacaatattt tcacctgaat caggatattc ttctaatacc    3840
tggaatgctg ttttcccggg gatcgcagtg gtgagtaacc atgcatcatc aggagtacgg    3900
ataaaatgct tgatggtcgg aagaggcata aattccgtca gccagtttag tctgaccatc    3960
tcatctgtaa catcattggc aacgctacct ttgccatgtt tcagaaacaa ctctggcgca    4020
tcgggcttcc catacaatcg atagattgtc gcacctgatt gcccgacatt atcgcgagcc    4080
catttatacc catataaatc agcatccatg ttggaattta atcgcggcct cgagcaagac    4140
gtttcccgtt gaatatggct cataacaccc cttgtattac tgtttatgta agcagacagt    4200
```

```
tttattgttc atgatgatat attttttatct tgtgcaatgt aacatcagag attttgagac      4260
acaacgtggc tttccccccc cccccattat tgaagcattt atcagggtta ttgtctcatg      4320
agcggataca tatttgaatg tatttagaaa aataaacaaa taggggttcc gcgcacattt      4380
ccccgaaaag tgccacctga cgtctaagaa accattatta tcatgacatt aacctataaa      4440
aataggcgta tcacgaggcc ctttcgtctc gcgcgtttcg gtgatgacgg tgaaaacctc      4500
tgacacatgc agctcccgga gacggtcaca gcttgtctgt aagcggatgc cgggagcaga      4560
caagcccgtc agggcgcgtc agcgggtgtt ggcgggtgtc ggggctggct taactatgcg      4620
gcatcagagc agattgtact gagagtgcac catatgcggt gtgaaatacc gcacagatgc      4680
gtaaggagaa ataccgcat cagattggct attgg                                  4715

<210> SEQ ID NO 9
<211> LENGTH: 4713
<212> TYPE: DNA
<213> ORGANISM: Artificial Sequence
<220> FEATURE:
<223> OTHER INFORMATION: synthetic expression vector plasmid AG194 for
      murine IL-27 Epstein-Barr virus-induced gene 3 (EBI3)
      beta subunit expression

<400> SEQUENCE: 9
cctggccatt gcatacgttg tatccatatc ataatatgta catttatatt ggctcatgtc        60
caacattacc gccatgttga cattgattat tgactagtta ttaatagtaa tcaattacgg       120
ggtcattagt tcatagccca tatatggagt tccgcgttac ataacttacg gtaaatggcc       180
cgcctggctg accgcccaac gacccccgcc cattgacgtc aataatgacg tatgttccca       240
tagtaacgcc aatagggact ttccattgac gtcaatgggt ggagtattta cggtaaactg       300
cccacttggc agtacatcaa gtgtatcata tgccaagtac gccccctatt gacgtcaatg       360
atggtaaatg gcccgcctgg cattatgccc agtacatgac cttatgggac tttcctactt       420
ggcagtacat ctacgtatta gtcatcgcta ttaccatggt gatgcggttt tggcagtaca       480
tcaatgggcg tggatagcgg tttgactcac ggggatttcc aagtctccac cccattgacg       540
tcaatgggag tttgttttgg caccaaaatc aacgggactt tccaaaatgt cgtaacaact       600
ccgccccatt gacgcaaatg ggcggtaggc gtgtacggtg ggaggtctat ataagcagag       660
ctcgtttagt gaaccgtcag atcgcctgga cgccatcc acgctgtttt gacctccata       720
gaagacaccg ggaccgatcc agcctccgcg gcacgtgaag aaatgtcgaa gctcctgttc       780
ctgagcctgg cgctctgggc cagccgctcg ccggggtata ccgagacggc gctcgtggcc       840
ctgagccagc ccgggtgca gtgccacgcc tcgcgctacc ccgtggccgt ggactgctcc       900 tggacccgc tgcaagcgcc caactccacc aggtccacgt ccttcatcgc cacgtaccgg       960
ctcggcgtgg ccacccagca gcagagccag ccctgcctgc agcggagccc ccaggcctcc      1020
cgctgcacca tccccgacgt gcacctgttc tccacggtgc cctacatgct caacgtcacg      1080
gcggtgcacc cggcggcgc cagcagcagc ctcctggcct tcgtggcgga gcggatcatc      1140
aagccggacc cgccggaggg cgtgcgcctg cgcacggcgg ccagcgcct gcaggtgctc      1200 tggcaccccc cggcctcctg gccttcccg gacatcttct cgctcaagta ccgcctccgc      1260
taccggcgcc gaggcgcctc ccacttccgc caagtcggcc ccatcgaggc cacgaccttc      1320
accctccgga actcgaagcc ccacgccaag tactgcatca aggtgtcggc gcaggacctc      1380
accgactacg ggaagcccag cgactggagc tcccggggac aggtcgagag cgctccccac      1440
aagccctaat gagaattcgc ggatatcggt taacggatcc agatctgctg tgccttctag      1500
```

```
ttgccagcca tctgttgttt gcccctcccc cgtgccttcc ttgaccctgg aaggtgccac    1560
tcccactgtc ctttcctaat aaaatgagga aattgcatcg cattgtctga gtaggtgtca    1620
ttctattctg gggggtgggg tgggcagga cagcaagggg gaggattggg aagacaatag    1680
caggcatgct ggggatgcgg tgggctctat gggtacccag gtgctgaaga attgacccgg    1740
ttcctcctgg gccagaaaga agcaggcaca tccccttctc tgtgacacac cctgtccacg    1800
cccctggttc ttagttccag ccccactcat aggacactca tagctcagga gggctccgcc    1860
ttcaatccca cccgctaaag tacttggagc ggtctctccc tccctcatca gcccaccaaa    1920
ccaaacctag cctccaagag tgggaagaaa ttaaagcaag ataggctatt aagtgcagag    1980
ggagagaaaa tgcctccaac atgtgaggaa gtaatgagag aaatcataga atttcttccg    2040
cttcctcgct cactgactcg ctgcgctcgg tcgttcggct gcggcgagcg gtatcagctc    2100
actcaaaggc ggtaatacgg ttatccacag aatcagggga taacgcagga agaacatgt    2160 gagcaaaagg ccagcaaaag gccaggaacc gtaaaaaggc cgcgttgctg gcgttttcc    2220 ataggctccg ccccccctgac gagcatcaca aaaatcgacg ctcaagtcag aggtggcgaa    2280
acccgacagg actataaaga taccaggcgt ttccccctgg aagctccctc gtgcgctctc    2340
ctgttccgac cctgccgctt accggatacc tgtccgcctt tctcccttcg ggaagcgtgg    2400
cgctttctca tagctcacgc tgtaggtatc tcagttcggt gtaggtcgtt cgctccaagc    2460
tgggctgtgt gcacgaaccc cccgttcagc ccgaccgctg cgccttatcc ggtaactatc    2520
gtcttgagtc caacccggta agacacgact tatcgccact ggcagcagcc actggtaaca    2580
ggattagcag agcgaggtat gtaggcggtg ctacagagtt cttgaagtgg tggcctaact    2640
acggctacac tagaagaaca gtatttggta tctgcgctct gctgaagcca gttaccttcg    2700
gaaaaagagt tggtagctct tgatccggca acaaaccac cgctggtagc ggtggttttt    2760
ttgtttgcaa gcagcagatt acgcgcagaa aaaaggatc tcaagaagat cctttgatct    2820
tttctacggg gtctgacgct cagtggaacg aaaactcacg ttaagggatt ttggtcatga    2880
gattatcaaa aaggatcttc acctagatcc ttttaaatta aaatgaagt tttaaatcaa    2940 tctaaagtat atatgagtaa acttggtctg acagttacca atgcttaatc agtgaggcac    3000
ctatctcagc gatctgtcta tttcgttcat ccatagttgc ctgactcggg ggggggggc    3060 gctgaggtct gcctcgtgaa gaaggtgttg ctgactcata ccaggcctga atcgccccat    3120
catccagcca gaaagtgagg gagccacggt tgatgagagc tttgttgtag gtggaccagt    3180
tggtgatttt gaacttttgc tttgccacgg aacggtctgc gttgtcggga agatgcgtga    3240
tctgatcctt caactcagca aaagttcgat ttattcaaca agccgccgt cccgtcaagt    3300 cagcgtaatg ctctgccagt gttacaacca attaaccaat tctgattaga aaaactcatc    3360
gagcatcaaa tgaaactgca atttattcat atcaggatta tcaataccat attttttgaaa    3420 aagccgtttc tgtaatgaag gagaaaactc accgaggcag ttccatagga tgcaagatc    3480 ctggtatcgg tctgcgattc cgactcgtcc aacatcaata aacctatta atttcccctc    3540 gtcaaaaata aggttatcaa gtgagaaatc accatgagtg acgactgaat ccggtgagaa    3600
tggcaaaagc ttatgcattt cttccagac ttgttcaaca ggccagccat tacgctcgtc    3660
atcaaaatca ctcgcatcaa ccaaaccgtt attcattcgt gattgcgcct gagcgagacg    3720
aaatacgcga tcgctgttaa aaggacaatt acaaacagga tcgaatgca accggcgcag    3780 gaacactgcc agcgcatcaa caatattttc acctgaatca ggatattctt ctaatacctg    3840
```

```
gaatgctgtt ttcccgggga tcgcagtggt gagtaaccat gcatcatcag gagtacggat      3900
aaaatgcttg atggtcggaa gaggcataaa ttccgtcagc cagtttagtc tgaccatctc      3960
atctgtaaca tcattggcaa cgctaccttt gccatgtttc agaaacaact ctggcgcatc      4020
gggcttccca tacaatcgat agattgtcgc acctgattgc ccgacattat cgcgagccca      4080
tttataccca tataaatcag catccatgtt ggaatttaat cgcggcctcg agcaagacgt      4140
ttcccgttga atatggctca taacacccct tgtattactg tttatgtaag cagacagttt      4200
tattgttcat gatgatatat ttttatcttg tgcaatgtaa catcagagat tttgagacac      4260
aacgtggctt tccccccccc cccattattg aagcatttat cagggttatt gtctcatgag      4320
cggatacata tttgaatgta tttagaaaaa taaacaaata ggggttccgc gcacatttcc      4380
ccgaaaagtg ccacctgacg tctaagaaac cattattatc atgacattaa cctataaaaa      4440
taggcgtatc acgaggccct tcgtctcgc gcgtttcggt gatgacggtg aaaacctctg      4500
acacatgcag ctcccggaga cggtcacagc ttgtctgtaa gcggatgccg ggagcagaca      4560
agcccgtcag ggcgcgtcag cgggtgttgg cgggtgtcgg ggctggctta actatgcggc      4620
atcagagcag attgtactga gagtgcacca tatgcggtgt gaaataccgc acagatgcgt      4680
aaggagaaaa taccgcatca gattggctat tgg                                  4713
```

<210> SEQ ID NO 10
<211> LENGTH: 5908
<212> TYPE: DNA
<213> ORGANISM: Artificial Sequence
<220> FEATURE:
<223> OTHER INFORMATION: synthetic dual-promoter expression vector
      plasmid AG205 with human cytomegalovirus (CMV) promoter for murine
      IL-27 p28 alpha subunit expression and simian CMV promoter for
      murine IL-27 Epstein-Barr virus-induced gene 3 (EBI3) beta subunit
      expression

<400> SEQUENCE: 10

```
cctggccatt gcatacgttg tatccatatc ataatatgta catttatatt ggctcatgtc        60
caacattacc gccatgttga cattgattat tgactagtta ttaatagtaa tcaattacgg       120
ggtcattagt tcatagccca tatatggagt tccgcgttac ataacttacg gtaaatggcc       180
cgcctggctg accgcccaac gacccccgcc cattgacgtc aataatgacg tatgttccca       240
tagtaacgcc aatagggact ttccattgac gtcaatgggt ggagtattta cggtaaactg       300
cccacttggc agtacatcaa gtgtatcata tgccaagtac gccccctatt gacgtcaatg       360
atggtaaatg gcccgcctgg cattatgccc agtacatgac cttatgggac tttcctactt       420
ggcagtacat ctacgtatta gtcatcgcta ttaccatggt gatgcggttt tggcagtaca       480
tcaatgggcg tggatagcgg tttgactcac ggggatttcc aagtctccac cccattgacg       540
tcaatgggag tttgttttgg caccaaaatc aacgggactt tccaaaatgt cgtaacaact       600
ccgccccatt gacgcaaatg ggcggtaggc gtgtacggtg gaggtctat ataagcagag        660 ctcgtttagt gaaccgtcag atcgcctgga gacgccatcc acgctgtttt gacctccata       720
gaagacaccg ggaccgatcc agcctccgcg gccgcgcgtc gaggaattcg ctagtcgaca       780
agaaatgggc caggtcaccg gggacctcgg gtggcgcctg tcgctcctgc tcctgccct       840 cctcctggtc caagcgggga gctggggctt ccccacggat cccctgagcc tccaggagct       900
gcgcagggag ttcaccgtca gcctgtacct cgcccggaag ctgctctccg aggtccaggg       960
ctacgtccca agcttcgccg agtcgcgcct gccggcgtca aacctggacc tcctgcccct      1020
gggctaccac ctccccaacg tctccctgac gttccaagcc tggcaccacc tctccgactc      1080
```

-continued

```
cgagcgcctc tgcttcctcg ccaccacgct ccggccgttc ccggccatgc tgggcgggct    1140
ggggacccag gggacctgga ccagctccga gagggagcag ctgtgggcca tgaggctgga    1200
cctccgggac ctgcacaggc acctccgctt ccaagtcctg ccgcgggct tcaagtgctc     1260 caaggaggag gaggacaagg aggaagagga agaggaggaa gaagaggaaa agaagctgcc    1320
cctcggggcc ctgggcggcc ccaaccaggt gtcctcccaa gtgtcctggc cccagctgct    1380
ctacacctac cagctcctcc actccctgga gctggtcctg agccgggcgg tgcgggacct    1440
gctcctgctg tccctgcccc ggcgcccggg ctcggcctgg gactcctaat gatctagaag    1500
atctgatatc ggatctgctg tgccttctag ttgccagcca tctgttgttt gcccctcccc    1560
cgtgccttcc ttgaccctgg aaggtgccac tcccactgtc ctttcctaat aaaatgagga    1620
aattgcatcg cattgtctga gtaggtgtca ttctattctg gggggtgggg tgggcagga    1680 cagcaagggg gaggattggg aagacaatag caggcatgct ggggatgcgg tgggctctat    1740
gggtacccag gtgctgaaga attgacccgg ttcctcctgg gccagaaaga agcaggcaca    1800
tccccttctc tgtgacacac cctgtccacg cccctggttc ttagttccag ccccactcat    1860
aggacactca tagctcagga gggctccgcc ttcaatccca cccgctaaag tacttggagc    1920
ggtctctccc tccctcatca gcccaccaaa ccaaacctag cctccaagag tgggaagaaa    1980
ttaaagcaag ataggctatt aagtgcagag ggagagaaaa tgcctccaac atgtgaggaa    2040
gtaatgagag aaatcataga atttcttccg cttcctcgct cactgactcg ctgcgctcgg    2100
tcgttcggct gcggcgagcg gtatcagctc actcaaaggc ggtaatacgg ttatccacag    2160
aatcagggga taacgcagga agaacatgt gagcaaaagg ccagcaaaag gccaggaacc     2220
gtaaaaaggc cgcgttgctg gcgttttttcc ataggctccg ccccctgac gagcatcaca    2280 aaaatcgacg ctcaagtcag aggtggcgaa acccgacagg actataaaga taccaggcgt    2340
ttccccctgg aagctccctc gtgcgctctc ctgttccgac cctgccgctt accggatacc    2400
tgtccgcctt tctcccttcg ggaagcgtgg cgctttctca tagctcacgc tgtaggtatc    2460
tcagttcggt gtaggtcgtt cgctccaagc tgggctgtgt gcacgaaccc cccgttcagc    2520
ccgaccgctg cgccttatcc ggtaactatc gtcttgagtc caacccggta agacacgact    2580
tatcgccact ggcagcagcc actggtaaca ggattagcag agcgaggtat gtaggcggtg    2640
ctacagagtt cttgaagtgg tggcctaact acggctacac tagaagaaca gtatttggta    2700
tctgcgctct gctgaagcca gttaccttcg gaaaagagt tggtagctct tgatccggca    2760
aacaaaccac cgctggtagc ggtggttttt ttgtttgcaa gcagcagatt acgcgcagaa    2820
aaaaaggatc tcaagaagat cctttgatct tttctacggg gtctgacgct cagtggaacg    2880
aaaactcacg ttaagggatt ttggtcatga gattatcaaa aaggatcttc acctagatcc    2940
ttttaaatta aaaatgaagt tttaaatcaa tctaaagtat atatgagtaa acttggtctg    3000
acagttacca atgcttaatc agtgaggcac ctatctcagc gatctgtcta tttcgttcat    3060
ccatagttgc ctgactcggg gggggggggc gctgaggtct gcctcgtgaa aaggtgttg     3120 ctgactcata ccaggcctga atcgccccat catccagcca gaaagtgagg gagccacggt    3180
tgatgagagc tttgttgtag gtggaccagt tggtgatttt gaacttttgc tttgccacgg    3240
aacggtctgc gttgtcggga agatgcgtga tctgatcctt caactcagca aaagttcgat    3300
ttattcaaca aagccgccgt cccgtcaagt cagcgtaatg ctctgccagt gttacaacca    3360
attaaccaat tctgattaga aaaactcatc gagcatcaaa tgaaactgca atttattcat    3420
```

```
atcaggatta tcaataccat attttgaaa aagccgtttc tgtaatgaag gagaaactc      3480
accgaggcag ttccatagga tggcaagatc ctggtatcgg tctgcgattc cgactcgtcc   3540
aacatcaata caacctatta atttcccctc gtcaaaaata aggttatcaa gtgagaaatc   3600
accatgagtg acgactgaat ccggtgagaa tggcaaaagc ttatgcattt ctttccagac   3660
ttgttcaaca ggccagccat tacgctcgtc atcaaaatca ctcgcatcaa ccaaaccgtt   3720
attcattcgt gattgcgcct gagcgagacg aaatacgcga tcgctgttaa aaggacaatt   3780
acaaacagga atcgaatgca accggcgcag gaacactgcc agcgcatcaa caatattttc   3840
acctgaatca ggatattctt ctaatacctg gaatgctgtt ttcccgggga tcgcagtggt   3900
gagtaaccat gcatcatcag gagtacggat aaaatgcttg atggtcggaa gaggcataaa   3960
ttccgtcagc cagtttagtc tgaccatctc atctgtaaca tcattggcaa cgctaccttt   4020
gccatgtttc agaaacaact ctggcgcatc gggcttccca tacaatcgat agattgtcgc   4080
acctgattgc ccgacattat cgcgagccca tttatacccg tataaatcag catccatgtt   4140
ggaatttaat cgcggcctcg agcaagacgt ttccgttga atatggctca taacacccct   4200
tgtattactg tttatgtaag cagacagttt tattgttcat gatgatatat tttatcttg    4260
tgcaatgtaa catcagagat tttgagacac aacgtggatc atccagacat gataagatac   4320
attgatgagt ttggacaaac cacaactaga atgcagtgaa aaaatgctt tatttgtgaa    4380
atttgtgatg ctattgcttt atttgtaacc attataagct gcaataaaca agttaacaac   4440
aacaattgca ttcattttat gtttcaggtt caggggagg tgtgggaggt ttttaaagc     4500
aagtaaaacc tctacaaatg tggtatggct gattatgatc gtcgaggatc cgttaaccga   4560
tatccgcgaa ttctcattag ggcttgtggg gagcgctctc gacctgcccc gggaggctcc   4620
agtcgctggg cttcccgtag tcggtgaggt cctgcgccga cacctggatg cagtacttgg   4680
cgtggggctt cgagttccgg agggtgaagg tcgtggcctc gatggggccg acttggcgga   4740
agtgggaggc gcctcggcgc cggtagcgga ggcggtactt gagcgagaag atgtccggga   4800
agggccagga ggccgggggg tgccagagca cctgcaggcg ctggcccgcc gtgcgcaggc   4860
gcacgccctc cggcgggtcc ggcttgatga tccgctccgc cacgaaggcc aggaggctgc   4920
tgctggcgcc gcccgggtgc accgccgtga cgttgagcat gtagggcacc gtggagaaca   4980
ggtgcacgtc ggggatggtg cagcggggag cctgggggct ccgctgcagg cagggctggc   5040
tctgctgctg ggtggccacg ccgagccggt acgtggcgat gaaggacgtg gacctggtgg   5100
agttgggcgc ttgcagcggg gtccaggagc agtccacggc cacggggtag cgcgaggcgt   5160
ggcactgcac ccggggctgg ctcagggcca cgagcgccgt ctcggtatac cccggcgagc   5220
ggctggccca gagcgccagg ctcaggaaca ggagcttcga catttcttca caaacgtcga   5280
cagatccaaa cgctcctccg acgtcccag gcagaatggc ggttccctaa cgagcattg    5340
cttatataga cctcccatta ggcacgccta ccgcccattt acgtcaatgg aacgcccatt   5400
tgcgtcattg cccctcccca ttgacgtcaa tgggatgta cttggcagcc atcgcgggcc    5460
atttaccgcc attgacgtca atgggagtac tgccaatgta ccctggcgta cttccaatag   5520
taatgtactt gccaagttac tattaataga tattgatgta ctgccaagtg gccatttac    5580
cgtcattgac gtcaataggg ggcgtgagaa cggatatgaa tgggcaatga gccatcctaa   5640
agaccatgag gcccttcgt ctcgcgcgtt tcggtgatga cggtgaaaac ctctgacaca    5700
tgcagctccc ggagacggtc acagcttgtc tgtaagcgga tgccgggagc agacaagccc   5760
gtcagggcgc gtcagcgggt gttggcgggt gtcggggctg gcttaactat gcggcatcag   5820
```

```
agcagattgt actgagagtg caccatatgc ggtgtgaaat accgcacaga tgcgtaagga      5880
gaaaataccg catcagattg gctattgg                                         5908

<210> SEQ ID NO 11
<211> LENGTH: 6025
<212> TYPE: DNA
<213> ORGANISM: Artificial Sequence
<220> FEATURE:
<223> OTHER INFORMATION: synthetic dual-promoter expression vector
      plasmid AG197 with human cytomegalovirus (CMV) promoter for murine
      IL-27 Epstein-Barr virus-induced gene 3 (EBI3) beta subunit
      expression and simian CMV promoter for murine IL-27 p28 alpha
      subunit expression

<400> SEQUENCE: 11
cctggccatt gcatacgttg tatccatatc ataatatgta catttatatt ggctcatgtc        60
caacattacc gccatgttga cattgattat tgactagtta ttaatagtaa tcaattacgg       120
ggtcattagt tcatagccca tatatggagt tccgcgttac ataacttacg gtaaatggcc       180
cgcctggctg accgcccaac gacccccgcc cattgacgtc aataatgacg tatgttccca       240
tagtaacgcc aatagggact ttccattgac gtcaatgggt ggagtattta cggtaaactg       300
cccacttggc agtacatcaa gtgtatcata tgccaagtac gccccctatt gacgtcaatg       360
atggtaaatg gcccgcctgg cattatgccc agtacatgac cttatgggac tttcctactt       420
ggcagtacat ctacgtatta gtcatcgcta ttaccatggt gatgcggttt tggcagtaca       480
tcaatgggcg tggatagcgg tttgactcac ggggatttcc aagtctccac cccattgacg       540
tcaatgggag tttgttttgg caccaaaatc aacgggactt tccaaaatgt cgtaacaact       600
ccgccccatt gacgcaaatg ggcggtaggc gtgtacggtg gaggtctat ataagcagag        660 ctcgtttagt gaaccgtcag atcgcctgga gacgccatcc acgctgtttt gacctccata       720
gaagacaccg ggaccgatcc agcctccgcg gcacgtgaag aaatgtcgaa gctcctgttc       780
ctgagcctgg cgctctgggc agccgctcg ccggggtata ccgagacggc gctcgtggcc        840
ctgagccagc ccgggtgca gtgccacgcc tcgcgctacc ccgtggccgt ggactgctcc        900 tggacccgc tgcaagcgcc caactccacc aggtccacgt ccttcatcgc cacgtaccgg        960
ctcggcgtgg ccacccagca gcagagccag ccctgcctgc agcggagccc ccaggcctcc      1020
cgctgcacca tccccgacgt gcacctgttc tccacggtgc cctacatgct caacgtcacg      1080
gcggtgcacc cggcggcgc cagcagcagc ctcctggcct tcgtggcgga gcggatcatc       1140
aagccggacc gcggagggg cgtgcgcctg cgcacggcgg ccagcgcct gcaggtgctc        1200 tggcacccccc cggcctcctg gcccttcccg gacatcttct cgctcaagta ccgcctccgc      1260
taccggcgcc gaggcgcctc ccacttccgc caagtcggcc catcgaggc cacgaccttc       1320 accctccgga actcgaagcc ccacgccaag tactgcatcc aggtgtcggc gcaggacctc      1380
accgactacg ggaagcccag cgactggagc ctcccgggc aggtcgagag cgctccccac       1440
aagccctaat gaggaattcg ctagcggcgc gccagatctg atatcggatc tgctgtgcct      1500
tctagttgcc agccatctgt tgtttgcccc tccccgtgc cttccttgac cctggaaggt       1560
gccactccca ctgtcctttc ctaataaaat gaggaaattg catcgcattg tctgagtagg      1620
tgtcattcta ttctgggggg tgggtgggg caggacagca agggggagga ttgggaagac       1680
aatagcaggc atgctgggga tgcggtggc tctatgggta cccaggtgct gaagaattga       1740
cccggttcct cctgggccag aaagaagcag gcacatcccc ttctctgtga cacaccctgt      1800
```

```
ccacgcccct ggttcttagt tccagcccca ctcataggac actcatagct caggagggct    1860
ccgccttcaa tcccacccgc taaagtactt ggagcggtct ctccctccct catcagccca    1920
ccaaaccaaa cctagcctcc aagagtggga agaaattaaa gcaagatagg ctattaagtg    1980
cagagggaga gaaaatgcct ccaacatgtg aggaagtaat gagagaaatc atagaatttc    2040
ttccgcttcc tcgctcactg actcgctgcg ctcggtcgtt cggctgcggc gagcggtatc    2100
agctcactca aaggcggtaa tacggttatc cacagaatca ggggataacg caggaaagaa    2160
catgtgagca aaaggccagc aaaaggccag gaaccgtaaa aaggccgcgt tgctggcgtt    2220
tttccatagg ctccgccccc ctgacgagca tcacaaaaat cgacgctcaa gtcagaggtg    2280
gcgaaacccg acaggactat aaagatacca ggcgtttccc cctggaagct ccctcgtgcg    2340
ctctcctgtt ccgaccctgc cgcttaccgg atacctgtcc gcctttctcc cttcgggaag    2400
cgtggcgctt tctcatagct cacgctgtag gtatctcagt tcggtgtagg tcgttcgctc    2460
caagctgggc tgtgtgcacg aaccccccgt tcagcccgac cgctgcgcct tatccggtaa    2520
ctatcgtctt gagtccaacc cggtaagaca cgacttatcg ccactggcag cagccactgg    2580
taacaggatt agcagagcga ggtatgtagg cggtgctaca gagttcttga agtggtggcc    2640
taactacggc tacactagaa gaacagtatt tggtatctgc gctctgctga agccagttac    2700
cttcggaaaa agagttggta gctcttgatc cggcaaacaa accaccgctg gtagcggtgg    2760
tttttttgtt tgcaagcagc agattacgcg cagaaaaaaa ggatctcaag aagatccttt    2820
gatcttttct acggggtctg acgctcagtg gaacgaaaac tcacgttaag ggattttggt    2880
catgagatta tcaaaaagga tcttcaccta gatcctttta aattaaaaat gaagttttaa    2940
atcaatctaa agtatatatg agtaaacttg gtctgacagt taccaatgct taatcagtga    3000
ggcacctatc tcagcgatct gtctatttcg ttcatccata gttgcctgac tcggggggggg    3060
ggggcgctga ggtctgcctc gtgaagaagg tgttgctgac tcataccagg cctgaatcgc    3120
cccatcatcc agccagaaag tgagggagcc acggttgatg agagctttgt tgtaggtgga    3180
ccagttggtg attttgaact tttgctttgc cacggaacgg tctgcgttgt cgggaagatg    3240
cgtgatctga tccttcaact cagcaaaagt tcgatttatt caacaaagcc gccgtcccgt    3300
caagtcagcg taatgctctg ccagtgttac aaccaattaa ccaattctga ttagaaaaac    3360
tcatcgagca tcaaatgaaa ctgcaattta ttcatatcag gattatcaat accatatttt    3420
tgaaaaagcc gtttctgtaa tgaaggagaa aactcaccga ggcagttcca taggatggca    3480
agatcctggt atcggtctgc gattccgact cgtccaacat caatacaacc tattaatttc    3540
ccctcgtcaa aaataaggtt atcaagtgag aaatcaccat gagtgacgac tgaatccggt    3600
gagaatggca aaagcttatg catttctttc cagacttgtt caacaggcca gccattacgc    3660
tcgtcatcaa aatcactcgc atcaaccaaa ccgttattca ttcgtgattg cgcctgagcg    3720
agacgaaata cgcgatcgct gttaaaagga caattacaaa caggaatcga atgcaaccgg    3780
cgcaggaaca ctgccagcgc atcaacaata ttttcacctg aatcaggata ttcttctaat    3840
acctggaatg ctgttttccc ggggatcgca gtggtgagta accatgcatc atcaggagta    3900
cggataaaat gcttgatggt cggaagaggc ataaattccg tcagccagtt tagtctgacc    3960
atctcatctg taacatcatt ggcaacgcta cctttgccat gtttcagaaa caactctggc    4020
gcatcgggct tcccatacaa tcgatagatt gtcgcacctg attgcccgac attatcgcga    4080
gcccatttat acccatataa atcagcatcc atgttggaat ttaatcgcgg cctcgagcaa    4140
gacgtttccc gttgaatatg gctcataaca ccccttgtat tactgtttat gtaagcagac    4200
```

```
agttttattg ttcatgatga tatatttta tcttgtgcaa tgtaacatca gagattttga      4260
gacacaacgt ggatcatcca gacatgataa gatacattga tgagtttgga caaaccacaa      4320
ctagaatgca gtgaaaaaaa tgctttattt gtgaaatttg tgatgctatt gctttatttg      4380
taaccattat aagctgcaat aaacaagtta acaacaacaa ttgcattcat tttatgtttc      4440
aggttcaggg ggaggtgtgg gaggtttttt aaagcaagta aaacctctac aaatgtggta      4500
tggctgatta tgatcgtcga ggatctgttt aaactctaga tcattaggag tcccaggccg      4560
agcccgggcg ccggggcagg gacagcagga gcaggtcccg caccgcccgg ctcaggacca      4620
gctccaggga gtggaggagc tggtaggtgt agagcagctg gggccaggac acttgggagg      4680
acacctggtt ggggccgccc agggccccga ggggcagctt cttttcctct tcttcctcct      4740
cttcctcttc ctccttgtcc tcctcctcct tggagcactt gaagcccgcg gccaggactt      4800
ggaagcggag gtgcctgtgc aggtcccgga ggtccagcct catggcccac agctgctccc      4860
tctcggagct ggtccaggtc ccctgggtcc ccagcccgcc cagcatggcc gggaacggcc      4920
ggagcgtggt ggcgaggaag cagaggcgct cggagtcgga gaggtggtgc caggcttgga      4980
acgtcaggga gacgttgggg aggtggtagc ccaggggcag gaggtccagg ttcacgccgg      5040
gcaggcgcga ctcggcgaag ctgtggacgt agccctggac ctcggagagc agcttccggg      5100
cgaggtacag gctgacggtg aactccctgc gcagctcctg gaggctcagg ggatccgtgg      5160
ggaagcccca gctccccgct tggaccagga ggaggggcag gagcaggagc gacaggcgcc      5220
acccgaggtc cccggtgacc tggcccattt cttgtcgaca gatccaaacg ctcctccgac      5280
gtccccaggc agaatggcgg ttccctaaac gagcattgct tatatagacc tcccattagg      5340
cacgcctacc gcccatttac gtcaatggaa cgcccatttg cgtcattgcc cctccccatt      5400
gacgtcaatg gggatgtact tggcagccat cgcgggccat ttaccgccat tgacgtcaat      5460
gggagtactg ccaatgtacc ctggcgtact tccaatagta atgtacttgc aagttactta      5520
ttaatagata ttgatgtact gccaagtggg ccatttaccg tcattgacgt caatagggggg      5580 cgtgagaacg gatatgaatg gcaatgagc catcccattg acgtcaatgg tgggtggtcc      5640
tattgacgtc aatgggcatt gagccaggcg ggccatttac cgtaattgac gtcaatgggg      5700
gaggcgccat atacgtcaat aggaccgccc atatgacgtc aataggtaag accatgaggc      5760
cctttcgtct cgcgcgtttc ggtgatgacg gtgaaaacct ctgacacatg cagctcccgg      5820
agacggtcac agcttgtctg taagcggatg ccgggagcag acaagcccgt cagggcgcgt      5880
cagcgggtgt tggcgggtgt cggggctggc ttaactatgc ggcatcagag cagattgtac      5940
tgagagtgca ccatatgcgg tgtgaaatac cgcacagatg cgtaaggaga aaataccgca      6000
tcagattggc tattggcatt atgcc                                            6025
```

<210> SEQ ID NO 12
<211> LENGTH: 4711
<212> TYPE: DNA
<213> ORGANISM: Artificial Sequence
<220> FEATURE:
<223> OTHER INFORMATION: synthetic expression vector plasmid AG214 for
      human IL-27 Epstein-Barr virus-induced gene 3 (EBI3)
      beta subunit expression

<400> SEQUENCE: 12

```
cctggccatt gcatacgttg tatccatatc ataatatgta catttatatt ggctcatgtc        60
caacattacc gccatgttga cattgattat tgactagtta ttaatagtaa tcaattacgg       120
```

```
ggtcattagt tcatagccca tatatggagt tccgcgttac ataacttacg gtaaatggcc    180
cgcctggctg accgcccaac gaccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg gaagaaatg acgccgcagc tgcttctggc    780
tctggtcctc tgggccagct gccctccgtg cagcggacgc aagggtcctc cagctgccct    840
gaccctgccc agagtgcagt gcagagcctc gcgctacccc atcgctgtgg actgctcctg    900
gacccttcca cctgcaccca actccacctc ccctgtctcc ttcatcgcca cgtaccggct    960
cggcatggcc gctagggtc acagctggcc ctgcctgcag cagacgccca catctacttc   1020
ctgcaccatc actgacgtgc agctgttctc catggctccc tacgtcctca acgtcacggc   1080
ggtgcacccg tggggctctt caagcagctt cgtcccttc atcactgagc acatcatcaa   1140
gccggaccca ccggagggag tgcgcctgtc tcctctcgcg gagcgccagc tgcaggtgca   1200
gtgggagccc ccaggttcct ggcccttccc ggagatcttc tcgctcaagt actggatcag   1260
atacaagcgc cagggcgccg ctagattcca cagagtcggc cccatcgagg ccacgtcttt   1320
catcctccga gcggtccgac ccagagcccg atactacgtg caggtggctg cgcaggacct   1380
caccgactac ggggagctta gcgactggag cctcccggct acagcaacta tgagtttggg   1440
aaagtaatga gaattcgcgg atatcggtta acggatccag atctgctgtg ccttctagtt   1500
gccagccatc tgttgtttgc ccctccccg tgccttcctt gaccctggaa ggtgccactc   1560
ccactgtcct ttcctaataa aatgaggaaa ttgcatcgca ttgtctgagt aggtgtcatt   1620
ctattctggg gggtggggtg ggcaggaca gcaagggga ggattgggaa gacaatagca   1680
ggcatgctgg ggatgcggtg ggctctatgg gtacccaggt gctgaagaat tgacccggtt   1740
cctcctgggc cagaaagaag caggcacatc cccttctctg tgacacaccc tgtccacgcc   1800
cctggttctt agttccagcc ccactcatag gacactcata gctcaggagg gctccgcctt   1860
caatcccacc cgctaaagta cttggagcgg tctctccctc cctcatcagc ccaccaaacc   1920
aaacctagcc tccaagagtg ggaagaaatt aaagcaagat aggctattaa gtgcagaggg   1980
agagaaaatg cctccaacat gtgaggaagt aatgagagaa atcatagaat tcttccgct   2040
tcctcgctca ctgactcgct gcgctcggtc gttcggctgc ggcgagcggt atcagctcac   2100
tcaaaggcgg taatacggtt atccacagaa tcagggata cgcaggaaa gaacatgtga   2160
gcaaaaggcc agcaaaggc caggaaccgt aaaaaggccg cgttgctggc gtttttccat   2220
aggctccgcc cccctgacga gcatcacaaa aatcgacgct caagtcagag gtggcgaaac   2280
ccgacaggac tataaagata ccaggcgttt ccccctggaa gctccctcgt gcgctctcct   2340
gttccgaccc tgccgcttac cggatacctg tccgcctttc tcccttcggg aagcgtggcg   2400
ctttctcata gctcacgctg taggtatctc agttcggtgt aggtcgttcg ctccaagctg   2460
ggctgtgtgc acgaaccccc cgttcagccc gaccgctgcg ccttatccgg taactatcgt   2520
```

```
cttgagtcca acccggtaag acacgactta tcgccactgg cagcagccac tggtaacagg   2580
attagcagag cgaggtatgt aggcggtgct acagagttct tgaagtggtg gcctaactac   2640
ggctacacta gaaggacagt atttggtatc tgcgctctgc tgaagccagt taccttcgga   2700
aaaagagttg gtagctcttg atccggcaaa caaaccaccg ctggtagcgg tggtttttt    2760 gtttgcaagc agcagattac gcgcagaaaa aaggatctc aagaagatcc tttgatcttt    2820
tctacggggt ctgacgctca gtggaacgaa aactcacgtt aagggatttt ggtcatgaga   2880
ttatcaaaaa ggatcttcac ctagatcctt ttaaattaaa aatgaagttt taaatcaatc    2940 taagtatat atgagtaaac ttggtctgac agttaccaat gcttaatcag tgaggcacct    3000
atctcagcga tctgtctatt tcgttcatcc atagttgcct gactcggggg ggggggcgc    3060 tgaggtctgc ctcgtgaaga aggtgttgct gactcatacc aggcctgaat cgccccatca   3120
tccagccaga aagtgaggga gccacggttg atgagagctt tgttgtaggt ggaccagttg   3180
gtgattttga acttttgctt tgccacgaaa cggtctgcgt tgtcgggaag atgcgtgatc   3240
tgatccttca actcagcaaa agttcgattt attcaacaaa gccgccgtcc cgtcaagtca   3300
gcgtaatgct ctgccagtgt tacaaccaat taaccaattc tgattagaaa aactcatcga   3360
gcatcaaatg aaactgcaat ttattcatat caggattatc aataccatat ttttgaaaaa   3420
gccgtttctg taatgaagga gaaaactcac cgaggcagtt ccataggatg caagatcct    3480 ggtatcggtc tgcgattccg actcgtccaa catcaataca acctattaat ttccctcgt    3540 caaaaataag gttatcaagt gagaaatcac catgagtgac gactgaatcc ggtgagaatg   3600
gcaaaagctt atgcatttct ttccagactt gttcaacagg ccagccatta cgctcgtcat   3660
caaaatcact cgcatcaacc aaaccgttat tcattcgtga ttgcgcctga gcgagacgaa   3720
atacgcgatc gctgttaaaa ggacaattac aaacaggaat cgaatgcaac cggcgcagga   3780
acactgccag cgcatcaaca atattttcac ctgaatcagg atattcttct aatacctgga   3840
atgctgtttt cccggggatc gcagtggtga gtaaccatgc atcatcagga gtacggataa   3900
aatgcttgat ggtcggaaga ggcataaatt ccgtcagcca gtttagtctg accatctcat   3960
ctgtaacatc attggcaacg ctacctttgc catgtttcag aaacaactct ggcgcatcgg   4020
gcttcccata caatcgatag attgtcgcac ctgattgccc gacattatcg cgagcccatt   4080
tatacccata taaatcagca tccatgttgg aatttaatcg cggcctcgag caagacgttt   4140
cccgttgaat atggctcata acacccttg tattactgtt tatgtaagca gacagtttta   4200
ttgttcatga tgatatattt ttatcttgtg caatgtaaca tcagagattt tgagacacaa   4260
cgtggctttc ccccccccc cattattgaa gcatttatca gggttattgt ctcatgagcg   4320
gatacatatt tgaatgtatt tagaaaaata acaaataggg gttccgcgc acatttcccc    4380 gaaaagtgcc acctgacgtc taagaaacca ttattatcat gacattaacc tataaaaata   4440
ggcgtatcac gaggcccttt cgtctcgcgc gtttcggtga tgacggtgaa aacctctgac   4500
acatgcagct cccggagacg gtcacagctt gtctgtaagc ggatgccggg agcagacaag   4560
cccgtcaggg cgcgtcagcg ggtgttggcg ggtgtcgggg ctggcttaac tatgcggcat   4620
cagagcagat tgtactgaga gtgcaccata tgcggtgtga ataccgcac agatgcgtaa    4680 ggagaaaata ccgcatcaga ttggctattg g                                 4711
```

<210> SEQ ID NO 13
<211> LENGTH: 4742
<212> TYPE: DNA

<213> ORGANISM: Artificial Sequence
<220> FEATURE:
<223> OTHER INFORMATION: synthetic expression vector plasmid AG215 for human IL-27 p28 alpha subunit expression

<400> SEQUENCE: 13

```
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg gaggtctat ataagcagag      660
ctcgtttagt gaaccgtcag atcgcctgga gacgccatcc acgctgtttt gacctccata     720
gaagacaccg ggaccgatcc agcctccgcg gcgcgcgtc acaagaaat gggcagacg        780
gcggggacc tcgggtggcg cctgtcgctt ctgctactgc cctacttct ggtccaagcg       840
ggagtctggg gcttcccacg tccacccggc agaccgcagc tgagcctcca ggagcttcgc     900
agggagttca ccgtcagcct gcacctcgcc cggaagctgt tgtccgaagt cagaggccag     960
gcgcaccggt tcgccgagtc gcaccttcca ggcgtgaacc tgtacctctt gccccttggc    1020
gagcagctcc ccgacgtctc cctgacgttc aagcctggc gacggctctc cgacccggag     1080
cgcctctgct tcatctcgac cacgctccag ccgttccacg ccctccttgg cgggttgggg    1140
acccagggga ggtggaccaa catggagagg atgcagctgt gggccatgag gcttgacctc    1200
cgggacctgc agaggcacct ccgcttccaa gtccttgccg ctggcttcaa cctccctgag    1260
gaggaggaag aagaggaaga agaggaagag gaggaacgga aggggctgct cccaggtgcc    1320
ctgggctcgg cgctgcaggg accggcacag gtgtcttggc cccagctgct ctcgacctac    1380
cggctccttc actccctgga gctggtcctg agccgggcgg tgcgggagct gcttctgttg    1440
tccaaagcgg gccactcggt ctggccgctt ggattcccca ccctctcgcc ccagccgtaa    1500
tgaggatcca gatctgctgt gccttctagt tgccagccat ctgttgtttg ccctccccc     1560
gtgccttcct tgaccctgga aggtgccact cccactgtcc tttcctaata aaatgaggaa    1620
attgcatcgc attgtctgag taggtgtcat tctattctgg ggggtggggt ggggcaggac    1680
agcaaggggg aggattggga agacaatagc aggcatgctg gggatgcggt gggctctatg    1740
ggtacccagg tgctgaagaa ttgacccggt tcctcctggg ccagaaagaa gcaggcacat    1800
ccccttctct gtgacacacc ctgtccacgc ccctggttct tagttccagc cccactcata    1860
ggacactcat agctcaggag ggctccgcct tcaatcccac ccgctaaagt acttggagcg    1920
gtctctcct ccctcatcag cccaccaaac caaacctagc ctccaagagt gggaagaaat     1980
taaagcaaga taggctatta agtgcagagg gagagaaaat gcctccaaca tgtgaggaag    2040
taatgagaga aatcatagaa tttcttccgc ttcctcgctc actgactcgc tgcgctcggt    2100
cgttcggctg cggcgagcgg tatcagctca ctcaaaggcg gtaatacggt tatccacaga    2160
```

```
atcagggat  aacgcaggaa  agaacatgtg  agcaaaaggc  cagcaaaagg  ccaggaaccg    2220
taaaaaggcc  gcgttgctgg  cgttttttcca  taggctccgc  cccctgacg   agcatcacaa    2280 aaatcgacgc  tcaagtcaga  ggtggcgaaa  cccgacagga  ctataaagat  accaggcgtt    2340
tccccctgga  agctccctcg  tgcgctctcc  tgttccgacc  ctgccgctta  ccggatacct    2400
gtccgccttt  ctcccttcgg  gaagcgtggc  gctttctcat  agctcacgct  gtaggtatct    2460
cagttcggtg  taggtcgttc  gctccaagct  gggctgtgtg  cacgaacccc  ccgttcagcc    2520
cgaccgctgc  gccttatccg  gtaactatcg  tcttgagtcc  aacccggtaa  gacacgactt    2580
atcgccactg  gcagcagcca  ctggtaacag  gattagcaga  gcgaggtatg  taggcggtgc    2640
tacagagttc  ttgaagtggt  ggcctaacta  cggctacact  agaagaacag  tatttggtat    2700
ctgcgctctg  ctgaagccag  ttaccttcgg  aaaagagtt   ggtagctctt  gatccggcaa    2760
acaaaccacc  gctggtagcg  gtggtttttt  tgtttgcaag  cagcagatta  cgcgcagaaa    2820
aaaaggatct  caagaagatc  ctttgatctt  ttctacgggg  tctgacgctc  agtggaacga    2880
aaactcacgt  taagggattt  tggtcatgag  attatcaaaa  aggatcttca  cctagatcct    2940
tttaaattaa  aaatgaagtt  ttaaatcaat  ctaaagtata  tatgagtaaa  cttggtctga    3000
cagttaccaa  tgcttaatca  gtgaggcacc  tatctcagcg  atctgtctat  ttcgttcatc    3060
catagttgcc  tgactcgggg  ggggggggcg  ctgaggtctg  cctcgtgaag  aaggtgttgc    3120
tgactcatac  caggcctgaa  tcgccccatc  atccagccag  aaagtgaggg  agccacggtt    3180
gatgagagct  ttgttgtagg  tggaccagtt  ggtgattttg  aacttttgct  ttgccacgga    3240
acggtctgcg  ttgtcgggaa  gatgcgtgat  ctgatccttc  aactcagcaa  aagttcgatt    3300
tattcaacaa  agccgccgtc  ccgtcaagtc  agcgtaatgc  tctgccagtg  ttacaaccaa    3360
ttaaccaatt  ctgattagaa  aaactcatcg  agcatcaaat  gaaactgcaa  tttattcata    3420
tcaggattat  caataccata  tttttgaaaa  agccgtttct  gtaatgaagg  agaaaactca    3480
ccgaggcagt  tccataggat  ggcaagatcc  tggtatcggt  ctgcgattcc  gactcgtcca    3540
acatcaatac  aacctattaa  tttcccctcg  tcaaaaataa  ggttatcaag  tgagaaatca    3600
ccatgagtga  cgactgaatc  cggtgagaat  ggcaaaagct  tatgcatttc  tttccagact    3660
tgttcaacag  gccagccatt  acgctcgtca  tcaaaatcac  tcgcatcaac  caaaccgtta    3720
ttcattcgtg  attgcgcctg  agcgagacga  aatacgcgat  cgctgttaaa  aggacaatta    3780
caaacaggaa  tcgaatgcaa  ccggcgcagg  aacactgcca  gcgcatcaac  aatatttca    3840 cctgaatcag  gatattcttc  taatacctgg  aatgctgttt  tcccggggat  cgcagtggtg    3900
agtaaccatg  catcatcagg  agtacggata  aaatgcttga  tggtcggaag  aggcataaat    3960
tccgtcagcc  agtttagtct  gaccatctca  tctgtaacat  cattggcaac  gctacctttg    4020
ccatgtttca  gaaacaactc  tggcgcatcg  ggcttcccat  acaatcgata  gattgtcgca    4080
cctgattgcc  cgacattatc  gcgagcccat  ttatacccat  ataaatcagc  atccatgttg    4140
gaatttaatc  gcggcctcga  gcaagacgtt  tcccgttgaa  tatggctcat  aacaccctt    4200 gtattactgt  ttatgtaagc  agacagtttt  attgttcatg  atgatatatt  tttatcttgt    4260
gcaatgtaac  atcagagatt  ttgagacaca  acgtggcttt  ccccccccc   ccattattga    4320 agcatttatc  agggttattg  tctcatgagc  ggatacatat  ttgaatgtat  ttagaaaaat    4380
aaacaaatag  gggttccgcg  cacatttccc  cgaaaagtgc  cacctgacgt  ctaagaaacc    4440
attattatca  tgacattaac  ctataaaaat  aggcgtatca  cgaggccctt  tcgtctcgcg    4500
cgtttcggtg  atgacggtga  aaacctctga  cacatgcagc  tcccggagac  ggtcacagct    4560
```

```
tgtctgtaag cggatgccgg gagcagacaa gcccgtcagg gcgcgtcagc gggtgttggc    4620
gggtgtcggg gctggcttaa ctatgcggca tcagagcaga ttgtactgag agtgcaccat    4680
atgcggtgtg aaataccgca cagatgcgta aggagaaaat accgcatcag attggctatt    4740
gg                                                                  4742

<210> SEQ ID NO 14
<211> LENGTH: 6030
<212> TYPE: DNA
<213> ORGANISM: Artificial Sequence
<220> FEATURE:
<223> OTHER INFORMATION: synthetic dual-promoter expression vector
      plasmid AG216 with human cytomegalovirus (CMV) promoter for human
      IL-27 p28 alpha subunit expression and simian CMV promoter for
      human IL-27 Epstein-Barr virus-induced gene 3 (EBI3) beta subunit
      expression

<400> SEQUENCE: 14
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg gcggtaggc gtgtacggtg gaggtctat ataagcagag       660 ctcgtttagt gaaccgtcag atcgcctgga gacgccatcc acgctgtttt gacctccata     720
gaagacaccg ggaccgatcc agcctccgcg gcgtcgacaa gaaatgggcc agacggcggg     780
ggacctcggg tggcgcctgt cgcttctgct actgccccta cttctggtcc aagcgggagt     840
ctggggcttc ccacgtccac ccggcagacc gcagctgagc ctccaggagc ttcgcaggga     900
gttcaccgtc agcctgcacc tcgcccggaa gctgttgtcc gaagtcagag gccaggcgca     960
ccggttcgcc gagtcgcacc ttccaggcgt gaacctgtac ctcttgcccc ttggcgagca    1020 gctcccgac gtctccctga cgttccaagc ctggcgacgg ctctccgacc cggagcgcct     1080
ctgcttcatc tcgaccacgc tccagccgtt ccacgccctc cttggcgggt tggggaccca    1140
ggggaggtga accaacatgg agaggatgca gctgtgggcc atgaggcttg acctccggga    1200
cctgcagagg cacctccgct tccaagtcct tgccgctggc ttcaacctcc ctgaggagga    1260
ggaagaagag gaagaagagg aagaggagga acgaaggggg ctgctcccag gtgccctggg    1320
ctcggcgctg caggaccggg cacaggtgtc ttggcccag ctgctctcga cctaccggct     1380
ccttcactcc ctggagctgg tcctgagccg ggcggtgcgg agctgcttc tgttgtccaa     1440 agcgggccac tcggtctggc cgcttggatt ccccacccttc tcgccccagc cgtaatgagg    1500
atctgatatc ggatctgctg tgccttctag ttgccagcca tctgttgttt gccccctccc    1560
cgtgccttcc ttgaccctgg aaggtgccac tcccactgtc ctttcctaat aaaatgagga    1620
aattgcatcg cattgtctga gtaggtgtca ttctattctg gggggtgggg tggggcagga    1680
```

```
cagcaagggg gaggattggg aagacaatag caggcatgct ggggatgcgg tgggctctat    1740
gggtacccag gtgctgaaga attgacccgg ttcctcctgg gccagaaaga agcaggcaca    1800
tccccttctc tgtgacacac cctgtccacg cccctggttc ttagttccag ccccactcat    1860
aggacactca tagctcagga gggctccgcc ttcaatccca cccgctaaag tacttggagc    1920
ggtctctccc tccctcatca gcccaccaaa ccaaacctag cctccaagag tgggaagaaa    1980
ttaaagcaag ataggctatt aagtgcagag ggagagaaaa tgcctccaac atgtgaggaa    2040
gtaatgagag aaatcataga atttcttccg cttcctcgct cactgactcg ctgcgctcgg    2100
tcgttcggct gcggcgagcg tatcagctc actcaaaggc ggtaatacgg ttatccacag     2160
aatcagggga taacgcagga agaacatgt gagcaaaagg ccagcaaaag gccaggaacc     2220
gtaaaaaggc cgcgttgctg cgttttttcc ataggctccg ccccctgac gagcatcaca    2280 aaaatcgacg ctcaagtcag aggtggcgaa acccgacagg actataaaga taccaggcgt    2340
ttccccctgg aagctccctc gtgcgctctc ctgttccgac cctgccgctt accggatacc    2400
tgtccgcctt tctcccttcg ggaagcgtgg cgctttctca tagctcacgc tgtaggtatc    2460
tcagttcggt gtaggtcgtt cgctccaagc tgggctgtgt gcacgaaccc ccgttcagc     2520 ccgaccgctg cgccttatcc ggtaactatc gtcttgagtc caacccggta agacacgact    2580
tatcgccact ggcagcagcc actggtaaca ggattagcag agcgaggtat gtaggcggtg    2640
ctacagagtt cttgaagtgg tggcctaact acggctacac tagaagaaca gtatttggta    2700
tctgcgctct gctgaagcca gttaccttcg gaaaagagt tggtagctct tgatccggca     2760
aacaaaccac cgctggtagc ggtggttttt tgtttgcaa gcagcagatt acgcgcagaa     2820
aaaaaggatc tcaagaagat cctttgatct tttctacggg gtctgacgct cagtggaacg    2880
aaaactcacg ttaagggatt ttggtcatga gattatcaaa aaggatcttc acctagatcc    2940
ttttaaatta aaaatgaagt tttaaatcaa tctaaagtat atatgagtaa acttggtctg    3000
acagttacca atgcttaatc agtgaggcac ctatctcagc gatctgtcta tttcgttcat    3060
ccatagttgc ctgactcggg ggggggggc gctgaggtct gcctcgtgaa gaaggtgttg     3120
ctgactcata ccaggcctga atcgccccat catccagcca gaaagtgagg gagccacggt    3180
tgatgagagc tttgttgtag gtggaccagt tggtgatttt gaacttttgc tttgccacgg    3240
aacggtctgc gttgtcggga agatgcgtga tctgatcctt caactcagca aaagttcgat    3300
ttattcaaca aagccgccgt cccgtcaagt cagcgtaatg ctctgccagt gttacaacca    3360
attaaccaat tctgattaga aaaactcatc gagcatcaaa tgaaactgca atttattcat    3420
atcaggatta tcaataccat atttttgaaa aagccgtttc tgtaatgaag gagaaaactc    3480
accgaggcag ttccatagga tgcaagatc ctggtatcgg tctgcgattc cgactcgtcc     3540
aacatcaata caacctatta atttcccctc gtcaaaaata aggttatcaa gtgagaaatc    3600
accatgagtg acgactgaat ccggtgagaa tggcaaaagc ttatgcattt ctttccagac    3660
ttgttcaaca ggccagccat tacgctcgtc atcaaaatca ctcgcatcaa ccaaaccgtt    3720
attcattcgt gattgcgcct gagcgagacg aaatacgcga tcgctgttaa aaggacaatt    3780
acaaacagga atcgaatgca accggcgcag aacactgcc agcgcatcaa caatattttc     3840
acctgaatca ggatattctt ctaatacctg gaatgctgtt ttcccgggga tcgcagtggt    3900
gagtaaccat gcatcatcag gagtacggat aaaatgcttg atggtcggaa gaggcataaa    3960
ttccgtcagc cagtttagtc tgaccatctc atctgtaaca tcattggcaa cgctacctttt   4020 gccatgtttc agaaacaact ctggcgcatc gggcttccca tacaatcgat agattgtcgc    4080
```

```
acctgattgc ccgacattat cgcgagccca tttataccca tataaatcag catccatgtt    4140
ggaatttaat cgcggcctcg agcaagacgt ttcccgttga atatggctca taacacccct    4200
tgtattactg tttatgtaag cagacagttt tattgttcat gatgatatat ttttatcttg    4260
tgcaatgtaa catcagagat tttgagacac aacgtggatc atccagacat gataagatac    4320
attgatgagt ttggacaaac cacaactaga atgcagtgaa aaaaatgctt tatttgtgaa    4380
atttgtgatg ctattgcttt atttgtaacc attataagct gcaataaaca agttaacaac    4440
aacaattgca ttcattttat gtttcaggtt caggggagg tgtgggaggt tttttaaagc    4500
aagtaaaacc tctacaaatg tggtatggct gattatgatc gtcgaggatc cctcattact    4560
ttcccaaact catagttgct gtagccggga ggctccagtc gctaagctcc ccgtagtcgg    4620
tgaggtcctg cgcagccacc tgcacgtagt atcgggctct gggtcggacc gctcggagga    4680
tgaaagacgt ggcctcgatg gggccgactc tgtggaatct agcggcgccc tggcgcttgt    4740
atctgatcca gtacttgagc gagaagatct ccgggaaggg ccaggaacct gggggctccc    4800
actgcacctg cagctggcgc tccgcgagag gagacaggcg cactccctcc ggtgggtccg    4860
gcttgatgat gtgctcagtg atgaaaggga cgaagctgct tgaagagccc acgggtgca    4920
ccgccgtgac gttgaggacg tagggagcca tggagaacag ctgcacgtca gtgatggtgc    4980
aggaagtaga tgtgggcgtc tgctgcaggc agggccagct gtgaccccta gcggccatgc    5040
cgagccggta cgtggcgatg aaggagacag gggaggtgga gttgggtgca ggtggaaggg    5100
tccaggagca gtccacagcg atggggtagc gcgaggctct gcactgcact ctgggcaggg    5160
tcagggcagc tggaggaccc ttgcgtccgc tgcacggagg gcagctggcc cagaggacca    5220
gagccagaag cagctgcggc gtcatttctt gtttaaacgt cgacagatcc aaacgctcct    5280
ccgacgtccc caggcagaat ggcggttccc taaacgagca ttgcttatat agacctccca    5340
ttaggcacgc ctaccgccca tttacgtcaa tggaacgccc atttgcgtca ttgcccctcc    5400
ccattgacgt caatggggat gtacttggca gccatcgcgg gccatttacc gccattgacg    5460
tcaatgggag tactgccaat gtaccctggc gtacttccaa tagtaatgta cttgccaagt    5520
tactattaat agatattgat gtactgccaa gtgggccatt taccgtcatt gacgtcaata    5580
ggggcgtga aacggatat gaatgggcaa tgagccatcc cattgacgtc aatggtgggt    5640
ggtcctattg acgtcaatgg gcattgagcc aggcgggcca tttaccgtaa ttgacgtcaa    5700
tgggggaggc gccatatacg tcaataggac cgcccatatg acgtcaatag gtaagaccat    5760
gaggcccttt cgtctcgcgc gtttcggtga tgacggtgaa aacctctgac acatgcagct    5820
cccggagacg gtcacagctt gtctgtaagc ggatgccggg agcagacaag cccgtcaggg    5880
cgcgtcagcg ggtgttggcg ggtgtcgggg ctggcttaac tatgcggcat cagagcagat    5940
tgtactgaga gtgcaccata tgcggtgtga ataccgcac agatgcgtaa ggagaaaata    6000
ccgcatcaga ttggctattg gcattatgcc                                    6030
```

<210> SEQ ID NO 15  
<211> LENGTH: 6060  
<212> TYPE: DNA  
<213> ORGANISM: Artificial Sequence  
<220> FEATURE:  
<223> OTHER INFORMATION: synthetic dual-promoter expression vector plasmid AG217 with human cytomegalovirus (CMV) promoter for human IL-27 Epstein-Barr virus-induced gene 3 (EBI3) beta subunit expression and simian CMV promoter for human IL-27 p28 alpha subunit expression

<400> SEQUENCE: 15

```
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gaccccgcc cattgacgtc aataatgacg tatgttccca      240
tagtaacgcc aatagggact ttccattgac gtcaatgggt ggagtattta cggtaaactg     300
cccacttggc agtacatcaa gtgtatcata tgccaagtac gcccctatt gacgtcaatg      360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg gaggtctat ataagcagag      660
ctcgtttagt gaaccgtcag atcgcctgga gacgccatcc acgctgtttt gacctccata     720
gaagacaccg ggaccgatcc agcctccgcg gccgcgcgtc gaaagaaatg acgccgcagc     780
tgcttctggc tctggtcctc tgggccagct gccctccgtg cagcggacgc aagggtcctc     840
cagctgccct gaccctgccc agagtgcagt gcagagcctc gcgctacccc atcgctgtgg     900
actgctcctg gaccettcca cctgcaccca actccacctc cctgtctcc ttcatcgcca      960
cgtaccggct cggcatggcc gctaggggtc acagctggcc ctgcctgcag cagacgccca    1020
catctacttc ctgcaccatc actgacgtgc agctgttctc catggctccc tacgtcctca    1080
acgtcacggc ggtgcacccg tggggctctt caagcagctt cgtcccttc atcactgagc     1140
acatcatcaa gccggaccca ccggagggag tgcgcctgtc tcctctcgcg gagcgccagc    1200
tgcaggtgca gtgggagccc ccaggttcct ggcccttccc ggagatcttc tcgctcaagt    1260
actggatcag atacaagcgc cagggcgccg ctagattcca cagagtcggc cccatcgagg    1320
ccacgtcttt catcctccga gcggtccgac ccagagcccg atactacgtg caggtggctg    1380
cgcaggacct caccgactac ggggagctta gcgactggag cctcccggct acagcaacta    1440
tgagtttggg aaagtaatga ggaattcgct agcggcgcgc cagatctgat atcggatctg    1500
ctgtgccttc tagttgccag ccatctgttg tttgccccte cccgtgcct tccttgaccc     1560
tggaaggtgc cactcccact gtcctttcct aataaaatga ggaaattgca tcgcattgtc    1620
tgagtaggtg tcattctatt ctgggggggtg ggtggggca ggacagcaag ggggaggatt    1680
gggaagacaa tagcaggcat gctggggatg cggtgggctc tatgggtacc caggtgctga    1740
agaattgacc cggttcctcc tgggccagaa agaagcaggc acatcccctt ctctgtgaca    1800
caccctgtcc acgccctgg ttcttagttc cagccccact cataggacac tcatagctca     1860
ggagggctcc gccttcaatc ccacccgcta aagtacttgg agcggtctct ccctccctca    1920
tcagcccacc aaaccaaacc tagcctccaa gagtgggaag aaattaaagc aagataggct    1980
attaagtgca gagggagaga aaatgcctcc aacatgtgag gaagtaatga gagaaatcat    2040
agaatttctt ccgcttcctc gctcactgac tcgctgcgct cggtcgttcg gctgcggcga    2100
gcggtatcag ctcactcaaa ggcggtaata cggttatcca cagaatcagg ggataacgca    2160
ggaaagaaca tgtgagcaaa aggccagcaa aaggccagga accgtaaaaa ggccgcgttg    2220
ctggcgtttt tccataggct ccgcccccct gacgagcatc acaaaaatcg acgctcaagt    2280
cagaggtggc gaaacccgac aggactataa agataccagg cgtttccccc tggaagctcc    2340
```

```
ctcgtgcgct ctcctgttcc gaccctgccg cttaccggat acctgtccgc ctttctccct    2400
tcgggaagcg tggcgctttc tcatagctca cgctgtaggt atctcagttc ggtgtaggtc    2460
gttcgctcca agctgggctg tgtgcacgaa ccccccgttc agcccgaccg ctgcgcctta    2520
tccggtaact atcgtcttga gtccaacccg gtaagacacg acttatcgcc actggcagca    2580
gccactggta acaggattag cagagcgagg tatgtaggcg gtgctacaga gttcttgaag    2640
tggtggccta actacggcta cactagaaga acagtatttg gtatctgcgc tctgctgaag    2700
ccagttacct tcggaaaaag agttggtagc tcttgatccg gcaaacaaac caccgctggt    2760
agcggtggtt tttttgtttg caagcagcag attacgcgca gaaaaaaagg atctcaagaa    2820
gatcctttga tcttttctac ggggtctgac gctcagtgga acgaaaactc acgttaaggg    2880
attttggtca tgagattatc aaaaaggatc ttcacctaga tccttttaaa ttaaaaatga    2940
agttttaaat caatctaaag tatatatgag taaacttggt ctgacagtta ccaatgctta    3000
atcagtgagg cacctatctc agcgatctgt ctatttcgtt catccatagt tgcctgactc    3060
ccccccccgg ggcgctgagg tctgcctcgt gaagaaggtg ttgctgactc ataccaggcc    3120
tgaatcgccc catcatccag ccagaaagtg agggagccac ggttgatgag agctttgttg    3180
taggtggacc agttggtgat tttgaacttt tgctttgcca cggaacggtc tgcgttgtcg    3240
ggaagatgcg tgatctgatc cttcaactca gcaaaagttc gatttattca acaaagccgc    3300
cgtcccgtca gtcagcgta  atgctctgcc agtgttacaa ccaattaacc aattctgatt    3360
agaaaaactc atcgagcatc aaatgaaact gcaatttatt catatcagga ttatcaatac    3420 catattttg  aaaaagccgt ttctgtaatg aaggagaaaa ctcaccgagg cagttccata    3480
ggatggcaag atcctggtat cggtctgcga ttccgactcg tccaacatca atacaaccta    3540
ttaatttccc ctcgtcaaaa ataaggttat caagtgagaa atcaccatga gtgacgactg    3600
aatccggtga agtggcaaa  agcttatgca tttctttcca gacttgttca acaggccagc    3660
cattacgctc gtcatcaaaa tcactcgcat caaccaaacc gttattcatt cgtgattgcg    3720
cctgagcgag acgaaatacg cgatcgctgt taaaaggaca attacaaaca ggaatcgaat    3780
gcaaccggcg caggaacact gccagcgcat caacaatatt ttcacctgaa tcaggatatt    3840
cttctaatac ctggaatgct gttttcccgg ggatcgcagt ggtgagtaac catgcatcat    3900
caggagtacg gataaaatgc ttgatggtcg gaagaggcat aaattccgtc agccagttta    3960
gtctgaccat ctcatctgta acatcattgg caacgctacc tttgccatgt ttcagaaaca    4020
actctgcgcg atcgggcttc ccatacaatc gatagattgt cgcacctgat tgcccgacat    4080
tatcgcgagc ccatttatac ccatataaat cagcatccat gttggaattt aatcgcggcc    4140
tcgagcaaga cgtttcccgt tgaatatggc tcataacacc ccttgtatta ctgtttatgt    4200
aagcagacag ttttattgtt catgatgata tatttttatc ttgtgcaatg taacatcaga    4260
gattttgaga cacaacgtgg atcatccaga catgataaga tacattgatg agtttggaca    4320
aaccacaact agaatgcagt gaaaaaaatg ctttatttgt gaaatttgtg atgctattgc    4380
tttatttgta accattataa gctgcaataa acaagttaac aacaacaatt gcattcattt    4440
tatgtttcag gttcaggggg aggtgtggga ggttttttaa agcaagtaaa acctctacaa    4500
atgtggtatg gctgattatg atcgtcgagg atccggcgcc gtttaaactc attacggctg    4560
gggcgagagg gtggggaatc caagcggcca gaccgagtgg cccgctttgg acaacagaag    4620
cagctcccgc accgcccggc tcaggaccag ctccagggag tgaaggagcc ggtaggtcga    4680
```

```
gagcagctgg ggccaagaca cctgtgccgg tccctgcagc gccgagccca gggcacctgg      4740
gagcagcccc ttccgttcct cctcttcctc ttcttcctct tcttcctcct cctcagggag      4800
gttgaagcca gcggcaagga cttggaagcg gaggtgcctc tgcaggtccc ggaggtcaag      4860
cctcatggcc cacagctgca tcctctccat gttggtccac ctcccctggg tccccaaccc      4920
gccaaggagg gcgtggaacg gctggagcgt ggtcgagatg aagcagaggc gctccgggtc      4980
ggagagccgt cgccaggctt ggaacgtcag ggagacgtcg gggagctgct cgccaagggg      5040
caagaggtac aggttcacgc ctggaaggtg cgactcggcg aaccggtgcg cctggcctct      5100
gacttcggac aacagcttcc gggcgaggtg caggctgacg gtgaactccc tgcgaagctc      5160
ctggaggctc agctgcggtc tgccgggtgg acgtgggaag ccccagactc ccgcttggac      5220
cagaagtagg ggcagtagca gaagcgacag gcgccacccg aggtcccccg ccgtctggcc      5280
catttcttgt cgacagatcc aaacgctcct ccgacgtccc caggcagaat ggcggttccc      5340
taaacgagca ttgcttatat agacctccca ttaggcacgc ctaccgccca tttacgtcaa      5400
tggaacgccc atttgcgtca ttgcccctcc ccattgacgt caatgggat gtacttggca       5460 gccatcgcgg ccatttacc gccattgacg tcaatgggag tactgccaat gtaccctggc       5520
gtacttccaa tagtaatgta cttgccaagt tactattaat agatattgat gtactgccaa      5580
gtgggccatt taccgtcatt gacgtcaata ggggcgtga aacggatat gaatgggcaa        5640 tgagccatcc cattgacgtc aatggtgggt ggtcctattg acgtcaatgg gcattgagcc      5700
aggcgggcca tttaccgtaa ttgacgtcaa tggggaggc gccatatacg tcaataggac       5760
cgcccatatg acgtcaatag gtaagaccat gaggcccttt cgtctcgcgc gtttcggtga      5820
tgacggtgaa aacctctgac acatgcagct cccggagacg gtcacagctt gtctgtaagc      5880
ggatgccggg agcagacaag cccgtcaggg cgcgtcagcg ggtgttggcg ggtgtcgggg      5940
ctggcttaac tatgcggcat cagagcagat tgtactgaga gtgcaccata tgcggtgtga      6000
aataccgcac agatgcgtaa ggagaaaata ccgcatcaga ttggctattg cattatgcc       6060
```

<210> SEQ ID NO 16
<211> LENGTH: 570
<212> TYPE: DNA
<213> ORGANISM: Homo sapiens
<220> FEATURE:
<223> OTHER INFORMATION: human wildtype IL-23 p19 alpha subunit

<400> SEQUENCE: 16

```
atgctgggga gcagagctgt aatgctgctg ttgctgctgc cctggacagc tcagggcaga       60
gctgtgcctg ggggcagcag ccctgcctgg actcagtgcc agcagctttc acagaagctc      120
tgcacactgg cctggagtgc acatccacta gtgggacaca tggatctaag agaagaggga      180
gatgaagaga ctacaaatga tgttccccat atccagtgtg gagatggctg taccccccaa      240
ggactcaggg acaacagtca gttctgcttg caaaggatcc accagggtct gattttttat      300
gagaagctgc taggatcgga tattttcaca ggggagcctt ctctgctccc tgatagcccc      360
gtgggccagc ttcatgcctc cctactgggc ctcagccaac tcctgcagcc tgagggtcac      420
cactgggaga ctcagcagat tccaagcctc agtcccagcc agccatggca gcgtctcctt      480
ctccgcttca aaatccttcg cagcctccag gcctttgtgg ctgtagccgc ccgggtcttt      540
gcccatggag cagcaaccct gagtccctaa                                       570
```

<210> SEQ ID NO 17
<211> LENGTH: 189

<212> TYPE: PRT
<213> ORGANISM: Homo sapiens
<220> FEATURE:
<223> OTHER INFORMATION: human wildtype IL-23 p19 alpha subunit

<400> SEQUENCE: 17

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 18
<211> LENGTH: 705
<212> TYPE: DNA
<213> ORGANISM: Mus musculus
<220> FEATURE:
<223> OTHER INFORMATION: murine wildtype IL-27 p28 alpha subunit

<400> SEQUENCE: 18
atgggccagg tgacaggaga ccttggctgg cggctcagcc tgttgctgct acccttgctt      60
ctggtacaag ctggttcctg ggggttccca acagaccccc tgagccttca agagctgcgc     120
agggaattca cagtcagcct gtaccttgcc aggaagctgc tctctgaggt tcagggctat     180
gtccacagct ttgctgaatc tcgattgcca ggagtgaacc tggacctcct gccctggga      240
taccatcttc ccaatgtttc cctgactttc caggcatggc atcacctctc tgactctgag     300
agactctgct cctcgctac cacacttcgg cccttccctg ccatgctggg agggctgggg      360
acccagggga cctggaccag ctcagagagg gagcagctgt gggccatgag ctggatctc      420
cgggacctgc acaggcacct ccgctttcag gtgctggctg caggattcaa atgttcaaag    480
gaggaggagg acaaggagga agaggaagag gaggaagaag aagaaaagaa gctgccccta    540
ggggctctgg gtggccccaa tcaggtgtca tcccaagtgt cctggcccca gctgctctat    600
acctaccagc tccttcactc cctggagctt gtcctgtctc gggctgttcg ggacctgctg    660
ctgctgtccc tgcccaggcg cccaggctca gcctgggatt cctaa                    705

<210> SEQ ID NO 19

```
<211> LENGTH: 234
<212> TYPE: PRT
<213> ORGANISM: Mus musculus
<220> FEATURE:
<223> OTHER INFORMATION: murine wildtype IL-27 p28 alpha subunit

<400> SEQUENCE: 19

Met Gly Gln Val Thr Gly Asp Leu Gly Trp Arg Leu Ser Leu Leu Leu
 1               5                  10                  15

Leu Pro Leu Leu Leu Val Gln Ala Gly Ser Trp Gly Phe Pro Thr Asp
            20                  25                  30

Pro Leu Ser Leu Gln Glu Leu Arg Arg Glu Phe Thr Val Ser Leu Tyr
        35                  40                  45

Leu Ala Arg Lys Leu Leu Ser Glu Val Gln Gly Tyr Val His Ser Phe
    50                  55                  60

Ala Glu Ser Arg Leu Pro Gly Val Asn Leu Asp Leu Leu Pro Leu Gly
65                  70                  75                  80

Tyr His Leu Pro Asn Val Ser Leu Thr Phe Gln Ala Trp His His Leu
                85                  90                  95

Ser Asp Ser Glu Arg Leu Cys Phe Leu Ala Thr Thr Leu Arg Pro Phe
            100                 105                 110

Pro Ala Met Leu Gly Gly Leu Gly Thr Gln Gly Thr Trp Thr Ser Ser
        115                 120                 125

Glu Arg Glu Gln Leu Trp Ala Met Arg Leu Asp Leu Arg Asp Leu His
    130                 135                 140

Arg His Leu Arg Phe Gln Val Leu Ala Ala Gly Phe Lys Cys Ser Lys
145                 150                 155                 160

Glu Glu Glu Asp Lys Glu Glu Glu Glu Glu Glu Glu Glu Glu Glu Lys
                165                 170                 175

Lys Leu Pro Leu Gly Ala Leu Gly Gly Pro Asn Gln Val Ser Ser Gln
            180                 185                 190

Val Ser Trp Pro Gln Leu Leu Tyr Thr Tyr Gln Leu Leu His Ser Leu
        195                 200                 205

Glu Leu Val Leu Ser Arg Ala Val Arg Asp Leu Leu Leu Leu Ser Leu
    210                 215                 220

Pro Arg Arg Pro Gly Ser Ala Trp Asp Ser
225                 230

<210> SEQ ID NO 20
<211> LENGTH: 684
<212> TYPE: DNA
<213> ORGANISM: Mus musculus
<220> FEATURE:
<223> OTHER INFORMATION: murine wildtype IL-27 Epstein-Barr virus-
      induced gene 3 (EBI3) beta subunit

<400> SEQUENCE: 20
atgtccaagc tgctcttcct gtcacttgcc ctctgggcca gccgctcccc tggttacact      60
gaaacagctc tcgtggctct aagccagccc agagtgcaat gccatgcttc tcggtatccc     120
gtggccgtgg actgctcctg gactcctctc caggctccca actccaccag atccacgtcc     180
ttcattgcca cttacaggct cggtgtggcc acccagcagc agagccagcc ctgcctacaa     240
cggagccccc aggcctcccg atgcaccatc cccgacgtgc acctgttctc cacggtgccc     300
tacatgctaa atgtcactgc agtgcaccca ggcggcgcca gcagcagcct cctagccttt     360
gtggctgagc gaatcatcaa gccggaccct ccggaaggcg tgcgcctgcg cacagcggga     420
cagcgcctgc aggtgctctg catccccct gcttcctggc ccttccggga catcttctct     480
```

```
ctcaagtacc gactccgcta ccggcgccga ggagcctctc acttccgcca ggtgggaccc    540
attgaagcca cgactttcac cctcaggaac tcgaaacccc atgccaagta ttgcatccag    600
gtgtcagctc aggacctcac agattatggg aaaccaagtg actggagcct ccctgggcaa    660
gtagaaagtg cacccataa gccc                                           684
```

<210> SEQ ID NO 21
<211> LENGTH: 228
<212> TYPE: PRT
<213> ORGANISM: Mus musculus
<220> FEATURE:
<223> OTHER INFORMATION: murine wildtype IL-27 Epstein-Barr virus-
      induced gene 3 (EBI3) beta subunit

<400> SEQUENCE: 21

```
Met Ser Lys Leu Leu Phe Leu Ser Leu Ala Leu Trp Ala Ser Arg Ser
 1               5                  10                  15

Pro Gly Tyr Thr Glu Thr Ala Leu Val Ala Leu Ser Gln Pro Arg Val
            20                  25                  30

Gln Cys His Ala Ser Arg Tyr Pro Val Ala Val Asp Cys Ser Trp Thr
        35                  40                  45

Pro Leu Gln Ala Pro Asn Ser Thr Arg Ser Thr Ser Phe Ile Ala Thr
    50                  55                  60

Tyr Arg Leu Gly Val Ala Thr Gln Gln Ser Gln Pro Cys Leu Gln
65                  70                  75                  80

Arg Ser Pro Gln Ala Ser Arg Cys Thr Ile Pro Asp Val His Leu Phe
                85                  90                  95

Ser Thr Val Pro Tyr Met Leu Asn Val Thr Ala Val His Pro Gly Gly
            100                 105                 110

Ala Ser Ser Ser Leu Leu Ala Phe Val Ala Glu Arg Ile Ile Lys Pro
        115                 120                 125

Asp Pro Pro Glu Gly Val Arg Leu Arg Thr Ala Gly Gln Arg Leu Gln
    130                 135                 140

Val Leu Trp His Pro Pro Ala Ser Trp Pro Phe Pro Asp Ile Phe Ser
145                 150                 155                 160

Leu Lys Tyr Arg Leu Arg Tyr Arg Arg Gly Ala Ser His Phe Arg
                165                 170                 175

Gln Val Gly Pro Ile Glu Ala Thr Thr Phe Thr Leu Arg Asn Ser Lys
            180                 185                 190

Pro His Ala Lys Tyr Cys Ile Gln Val Ser Ala Gln Asp Leu Thr Asp
        195                 200                 205

Tyr Gly Lys Pro Ser Asp Trp Ser Leu Pro Gly Gln Val Glu Ser Ala
    210                 215                 220

Pro His Lys Pro
225
```

<210> SEQ ID NO 22
<211> LENGTH: 687
<212> TYPE: DNA
<213> ORGANISM: Homo sapiens
<220> FEATURE:
<223> OTHER INFORMATION: human wildtype IL-27 Epstein-Barr virus-induced
      gene 3 (EBI3) beta subunit

<400> SEQUENCE: 22

```
atgacccgc agcttctcct ggcccttgtc ctctgggcca gctgcccgcc ctgcagtgga    60 aggaagggc ccccagcagc tctgacactg ccccgggtgc aatgccgagc ctctcggtac   120
```

```
ccgatcgccg tggattgctc ctggaccctg ccgcctgctc caaactccac cagccccgtg      180
tccttcattg ccacgtacag gctcggcatg gctgcccggg gccacagctg gccctgcctg      240
cagcagacgc caacgtccac cagctgcacc atcacggatg tccagctgtt ctccatggct      300
ccctacgtgc tcaatgtcac cgccgtccac ccctgggggct ccagcagcag cttcgtgcct      360
ttcataacag agcacatcat caagcccgac cctccagaag gcgtgcgcct aagccccctc      420
gctgagcgcc agctacaggt gcagtgggag cctcccgggt cctggccctt ccagagatc       480 ttctcactga agtactggat ccgttacaag cgtcaggag ctgcgcgctt ccaccgggtg       540
gggcccattg aagccacgtc cttcatcctc agggctgtgc ggccccgagc caggtactac      600
gtccaagtgg cggctcagga cctcacagac tacggggaac tgagtgactg gagtctcccc      660
gccactgcca caatgagcct gggcaag                                         687
```

<210> SEQ ID NO 23
<211> LENGTH: 229
<212> TYPE: PRT
<213> ORGANISM: Homo sapiens
<220> FEATURE:
<223> OTHER INFORMATION: human wildtype IL-27 Epstein-Barr virus-induced
      gene 3 (EBI3) beta subunit <400> SEQUENCE: 23

```
Met Thr Pro Gln Leu Leu Leu Ala Leu Val Leu Trp Ala Ser Cys Pro
  1               5                  10                  15

Pro Cys Ser Gly Arg Lys Gly Pro Pro Ala Ala Leu Thr Leu Pro Arg
                 20                  25                  30

Val Gln Cys Arg Ala Ser Arg Tyr Pro Ile Ala Val Asp Cys Ser Trp
             35                  40                  45

Thr Leu Pro Pro Ala Pro Asn Ser Thr Ser Pro Val Ser Phe Ile Ala
         50                  55                  60

Thr Tyr Arg Leu Gly Met Ala Ala Arg Gly His Ser Trp Pro Cys Leu
 65                  70                  75                  80

Gln Gln Thr Pro Thr Ser Thr Ser Cys Thr Ile Thr Asp Val Gln Leu
                 85                  90                  95

Phe Ser Met Ala Pro Tyr Val Leu Asn Val Thr Ala Val His Pro Trp
            100                 105                 110

Gly Ser Ser Ser Ser Phe Val Pro Phe Ile Thr Glu His Ile Ile Lys
            115                 120                 125

Pro Asp Pro Pro Glu Gly Val Arg Leu Ser Pro Leu Ala Glu Arg Gln
        130                 135                 140

Leu Gln Val Gln Trp Glu Pro Pro Gly Ser Trp Pro Phe Pro Glu Ile
145                 150                 155                 160

Phe Ser Leu Lys Tyr Trp Ile Arg Tyr Lys Arg Gln Gly Ala Ala Arg
                165                 170                 175

Phe His Arg Val Gly Pro Ile Glu Ala Thr Ser Phe Ile Leu Arg Ala
            180                 185                 190

Val Arg Pro Arg Ala Arg Tyr Tyr Val Gln Val Ala Ala Gln Asp Leu
        195                 200                 205

Thr Asp Tyr Gly Glu Leu Ser Asp Trp Ser Leu Pro Ala Thr Ala Thr
    210                 215                 220

Met Ser Leu Gly Lys
225
```

<210> SEQ ID NO 24

```
<211> LENGTH: 732
<212> TYPE: DNA
<213> ORGANISM: Homo sapiens
<220> FEATURE:
<223> OTHER INFORMATION: human wildtype IL-27 p28 alpha subunit

<400> SEQUENCE: 24
atgggccaga cggcaggcga ccttggctgg cggctcagcc tgttgctgct tcccttgctc      60
ctggttcaag ctggtgtctg gggattccca aggcccccag ggaggcccca gctgagcctg     120
caggagctgc ggagggagtt cacagtcagc ctgcatctcg ccaggaagct gctctccgag     180
gttcggggcc aggcccaccg ctttgcggaa tctcacctgc caggagtgaa cctgtacctc     240
ctgcccctgg gagagcagct ccctgatgtt tccctgacct ccaggcctg cgccgcctc      300
tctgacccgg agcgtctctg cttcatctcc accacgcttc agcccttcca tgccctgctg     360
ggagggctgg ggacccaggg ccgctggacc aacatggaga ggatgcagct gtgggccatg     420
aggctggacc tccgcgatct gcagcggcac ctccgcttcc aggtgctggc tgcaggattc     480
aacctcccgg aggaggagga ggaggaagag gaggaggagg aggaggagag gaaggggctg     540
ctcccagggg cactgggcag cgccttacag ggccggccc aggtgtcctg ccccagctc      600
ctctccacct accgctgct gcactccttg gagctcgtct atctcgggc cgtgcgggag      660
ttgctgctgc tgtccaaggc tgggcactca gtctggccct gggggttccc aacattgagc     720
ccccagccct ga                                                         732

<210> SEQ ID NO 25
<211> LENGTH: 243
<212> TYPE: PRT
<213> ORGANISM: Homo sapiens
<220> FEATURE:
<223> OTHER INFORMATION: human wildtype IL-27 p28 alpha subunit

<400> SEQUENCE: 25

Met Gly Gln Thr Ala Gly Asp Leu Gly Trp Arg Leu Ser Leu Leu Leu
  1               5                  10                  15
Leu Pro Leu Leu Leu Val Gln Ala Gly Val Trp Gly Phe Pro Arg Pro
                 20                  25                  30
Pro Gly Arg Pro Gln Leu Ser Leu Gln Glu Leu Arg Arg Glu Phe Thr
             35                  40                  45
Val Ser Leu His Leu Ala Arg Lys Leu Leu Ser Glu Val Arg Gly Gln
         50                  55                  60
Ala His Arg Phe Ala Glu Ser His Leu Pro Gly Val Asn Leu Tyr Leu
 65                  70                  75                  80
Leu Pro Leu Gly Glu Gln Leu Pro Asp Val Ser Leu Thr Phe Gln Ala
                 85                  90                  95
Trp Arg Arg Leu Ser Asp Pro Glu Arg Leu Cys Phe Ile Ser Thr Thr
            100                 105                 110
Leu Gln Pro Phe His Ala Leu Leu Gly Gly Leu Gly Thr Gln Gly Arg
        115                 120                 125
Trp Thr Asn Met Glu Arg Met Gln Leu Trp Ala Met Arg Leu Asp Leu
    130                 135                 140
Arg Asp Leu Gln Arg His Leu Arg Phe Gln Val Leu Ala Ala Gly Phe
145                 150                 155                 160
Asn Leu Pro Glu Glu Glu Glu Glu Glu Glu Glu Glu Glu Glu Glu Glu
                165                 170                 175
Arg Lys Gly Leu Leu Pro Gly Ala Leu Gly Ser Ala Leu Gln Gly Pro
            180                 185                 190
```

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro

<210> SEQ ID NO 26
<211> LENGTH: 573
<212> TYPE: DNA
<213> ORGANISM: Artificial Sequence
<220> FEATURE:
<223> OTHER INFORMATION: synthetic human IL-23 p19 alpha subunit
      improved RNA with minimized inhibitory/instability sequences

<400> SEQUENCE: 26

```
atgctgggga gccgcgcggt catgctgctc ttgctgctcc cctggacggc ccagggccgg      60
gcggtgcccg ggggctcgag cccggcctgg acgcagtgcc agcagctcag ccagaagctc     120
tgcaccctgg cctggtcggc ccacccgctc gtgggccaca tggacctccg ggaggagggc     180
gacgaggaga cgaccaacga cgtcccccac atccagtgcg cgacggctg cgaccccag      240 ggcctccggg acaactcgca gttctgcctg cagcgcatcc accagggcct gatcttctac     300
gagaagctgc tcggctcgga catcttcacg ggggagccgt cgctgctccc ggacagcccg     360
gtgggccagc tccacgcctc cctcctgggc ctctcgcaac ttctgcaacc ggagggccac     420
cactgggaga cgcagcagat cccgagcctc tcgcccagca gccgtggca gcggctcctg     480 ctcagattca agatcttgcg ctccctccaa gccttcgtgg cggtcgccgc ccgggtcttc     540
gcccacggcg cggccaccct gagcccctga taa                                  573
```

<210> SEQ ID NO 27
<211> LENGTH: 708
<212> TYPE: DNA
<213> ORGANISM: Artificial Sequence
<220> FEATURE:
<223> OTHER INFORMATION: synthetic murine IL-27 p28 alpha subunit
      improved RNA with minimized inhibitory/instability sequences

<400> SEQUENCE: 27

```
atgggccagg tcaccgggga cctcgggtgg cgcctgtcgc tcctgctcct gcccctcctc      60
ctggtccaag cggggagctg gggcttcccc acggatcccc tgagcctcca ggagctgcgc     120
agggagttca ccgtcagcct gtacctcgcc cggaagctgc tctccgaggt ccagggctac     180
gtccacagct cgccgagtc gcgcctgccc ggcgtgaacc tggacctcct gcccctgggc     240
taccacctcc ccaacgtctc cctgacgttc aagcctggc accacctctc cgactccgag     300
cgcctctgct tcctcgccac cacgctccgg ccgttcccgg ccatgctggg cgggctgggg     360
acccagggga cctggaccag ctccgagagg gagcagctgt gggccatgag gctggacctc     420
cgggacctgc acaggcacct ccgcttccaa gtcctggccg cgggcttcaa gtgctccaag     480
gaggaggagg acaaggagga agaggaagag gaggaagaag aggaaaagaa gctgcccctc     540
ggggccctgg gcggccccaa ccaggtgtcc tccaagtgt cctggcccca gctgctctac     600
acctaccagc cctccacta cctggagctg gtcctgagcc gggcggtgcg ggacctgctc     660
ctgctgtccc tgccccggcg cccgggctcg gcctgggact cctaatga                 708
```

<210> SEQ ID NO 28
<211> LENGTH: 690
<212> TYPE: DNA
<213> ORGANISM: Artificial Sequence
<220> FEATURE:
<223> OTHER INFORMATION: synthetic murine IL-27 Epstein-Barr virus-
      induced gene 3 (EBI3) beta subunit improved RNA with minimized
      inhibitory/instability sequences

<400> SEQUENCE: 28

| | | | |
|---|---|---|---|
| atgtcgaagc tcctgttcct gagcctggcg ctctgggcca gccgctcgcc ggggtatacc | 60 |
| gagacggcgc tcgtggccct gagccagccc cgggtgcagt gccacgcctc gcgctacccc | 120 |
| gtggccgtgg actgctcctg gaccccgctg caagcgccca actccaccag gtccacgtcc | 180 |
| ttcatcgcca cgtaccggct cggcgtggcc acccagcagc agagccagcc ctgcctgcag | 240 |
| cggagccccc aggcctcccg ctgcaccatc cccgacgtgc acctgttctc cacggtgccc | 300 |
| tacatgctca cgtcacggc ggtgcacccg ggcggcgcca gcagcagcct cctggccttc | 360 |
| gtggcggagc ggatcatcaa gccggacccc cggagggcg tgcgcctgcg cacggcgggc | 420 |
| cagcgcctgc aggtgctctg cacccccg gcctcctggc ccttcccgga tcttctcg | 480 |
| ctcaagtacc gcctccgcta ccggcgccga ggcgcctccc acttccgcca agtcggcccc | 540 |
| atcgaggcca cgaccttcac cctccggaac tcgaagcccc acgccaagta ctgcatccag | 600 |
| gtgtcggcgc aggacctcac cgactacggg aagcccagcg actggagcct ccgggggcag | 660 |
| gtcgagagcg ctccccacaa gccctaatga | 690 |

<210> SEQ ID NO 29
<211> LENGTH: 735
<212> TYPE: DNA
<213> ORGANISM: Artificial Sequence
<220> FEATURE:
<223> OTHER INFORMATION: synthetic human IL-27 p28 alpha subunit
      improved RNA with minimized inhibitory/instability sequences

<400> SEQUENCE: 29

| | | | |
|---|---|---|---|
| atgggccaga cggcggggga cctcgggtgg cgcctgtcgc ttctgctact gcccctactt | 60 |
| ctggtccaag cgggagtctg gggcttccca cgtccaccg gcagaccgca gctgagcctc | 120 |
| caggagcttc gcagggagtt caccgtcagc ctgcacctcg cccggaagct gttgtccgaa | 180 |
| gtcagaggcc aggcgcaccg gttcgccgag tcgcaccttc aggcgtgaa cctgtacctc | 240 |
| ttgccccttg gcgagcagct ccccgacgtc tccctgacgt tccaagcctg gcgacggctc | 300 |
| tccgacccgg agcgcctctg cttcatctcg accacgctcc agccgttcca cgccctcctt | 360 |
| ggcgggttgg ggacccaggg gaggtggacc aacatggaga ggatgcagct gtgggccatg | 420 |
| aggcttgacc tccgggacct gcagaggcac ctccgcttcc aagtccttgc cgctggcttc | 480 |
| aacctccctg aggaggagga agaagaggaa gaagaggaag aggaggaacg gaaggggctg | 540 |
| ctcccaggtg ccctgggctc ggcgctgcag ggaccggcac aggtgtcttg gccccagctg | 600 |
| ctctcgacct accggctcct tcactccctg gagctggtcc tgagccgggc ggtgcgggag | 660 |
| ctgcttctgt tgtccaaagc gggccactcg gtctggccgc ttggattccc caccctctcg | 720 |
| ccccagccgt aatga | 735 |

<210> SEQ ID NO 30
<211> LENGTH: 693
<212> TYPE: DNA
<213> ORGANISM: Artificial Sequence
<220> FEATURE:
<223> OTHER INFORMATION: synthetic human IL-27 Epstein-Barr virus-induced gene 3 (EBI3) beta subunit improved RNA with minimized
inhibitory/instability sequences

<400> SEQUENCE: 30

```
atgacgccgc agctgcttct ggctctggtc ctctgggcca gctgccctcc gtgcagcgga      60
cgcaagggtc ctccagctgc cctgaccctg cccagagtgc agtgcagagc ctcgcgctac     120
cccatcgctg tggactgctc ctggacccct ccacctgcac ccaactccac ctcccctgtc     180
tccttcatcg ccacgtaccg gctcggcatg ccgctaggg gtcacagctg ccctgcctg      240
cagcagacgc ccacatctac ttcctgcacc atcactgacg tgcagctgtt ctccatggct     300
ccctacgtcc tcaacgtcac ggcggtgcac ccgtggggct cttcaagcag cttcgtccct     360
ttcatcactg agcacatcat caagccggac ccaccggagg gagtgcgcct gtctcctctc     420
gcggagcgcc agctgcaggt gcagtgggag cccccaggtt cctggccctt cccggagatc     480
ttctcgctca gtactggat cagatacaag cgccagggcg ccgctagatt ccacagagtc      540
ggcccccatcg aggccacgtc tttcatcctc cgagcggtcc gacccagagc ccgatactac    600
gtgcaggtgg ctgcgcagga cctcaccgac tacggggagc ttagcgactg gagcctcccg    660
gctacagcaa ctatgagttt gggaaagtaa tga                                   693
```

<210> SEQ ID NO 31
<211> LENGTH: 4024
<212> TYPE: DNA
<213> ORGANISM: Artificial Sequence
<220> FEATURE:
<223> OTHER INFORMATION: synthetic single expression cassette vector
      CMVkan vector backbone

<400> SEQUENCE: 31

```
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg gaggtctat ataagcagag      660
ctcgtttagt gaaccgtcag atcgcctgga gacgccatcc acgctgtttt gacctccata     720
gaagacaccg ggaccgatcc agcctccgcg gccgcgcgtc gacgctagcg gcgcgccgcg     780
gccgccaatt gagatctgct gtgccttcta gttgccagcc atctgttgtt tgcccctccc     840
ccgtgccttc cttgaccctg gaaggtgcca ctcccactgt cctttcctaa taaaatgagg     900
aaattgcatc gcattgtctg agtaggtgtc attctattct ggggggtggg gtggggcagg     960
acagcaaggg ggaggattgg gaagacaata gcaggcatgc tggggatgcg gtgggctcta    1020
tgggtaccca ggtgctgaag aattgacccg gttcctcctg ggccagaaag aagcaggcac    1080
atccccttct ctgtgacaca ccctgtccac gcccctggtt cttagttcca gccccactca    1140
taggacactc atagctcagg agggctccgc cttcaatccc acccgctaaa gtacttggag    1200
```

```
cggtctctcc ctccctcatc agcccaccaa accaaaccta gcctccaaga gtgggaagaa    1260
attaaagcaa gataggctat taagtgcaga gggagagaaa atgcctccaa catgtgagga    1320
agtaatgaga gaaatcatag aatttcttcc gcttcctcgc tcactgactc gctgcgctcg    1380
gtcgttcggc tgcggcgagc ggtatcagct cactcaaagg cggtaatacg gttatccaca    1440
gaatcagggg ataacgcagg aaagaacatg tgagcaaaag gccagcaaaa ggccaggaac    1500
cgtaaaaagg ccgcgttgct ggcgtttttc cataggctcc gcccccctga cgagcatcac    1560
aaaaatcgac gctcaagtca gaggtggcga aacccgacag gactataaag ataccaggcg    1620
tttccccctg gaagctccct cgtgcgctct cctgttccga ccctgccgct taccggatac    1680
ctgtccgcct ttctcccttc gggaagcgtg gcgctttctc atagctcacg ctgtaggtat    1740
ctcagttcgg tgtaggtcgt tcgctccaag ctgggctgtg tgcacgaacc cccgttcag    1800 cccgaccgct gcgccttatc cggtaactat cgtcttgagt ccaacccggt aagacacgac    1860
ttatcgccac tggcagcagc cactggtaac aggattagca gagcgaggta tgtaggcggt    1920
gctacagagt tcttgaagtg gtggcctaac tacggctaca ctagaagaac agtatttggt    1980
atctgcgctc tgctgaagcc agttaccttc ggaaaaagag ttggtagctc ttgatccggc    2040
aaacaaacca ccgctggtag cggtggtttt tttgtttgca agcagcagat tacgcgcaga    2100
aaaaaaggat ctcaagaaga tccttttgatc ttttctacgg ggtctgacgc tcagtggaac    2160
gaaaactcac gttaagggat tttggtcatg agattatcaa aaaggatctt cacctagatc    2220
cttttaaatt aaaaatgaag ttttaaatca atctaaagta tatatgagta aacttggtct    2280
gacagttacc aatgcttaat cagtgaggca cctatctcag cgatctgtct atttcgttca    2340
tccatagttg cctgactcgg ggggggggg cgctgaggtc tgcctcgtga agaaggtgtt    2400
gctgactcat accaggcctg aatcgcccca tcatccagcc agaaagtgag ggagccacgg    2460
ttgatgagag ctttgttgta ggtggaccag ttggtgattt tgaacttttg ctttgccacg    2520
gaacggtctg cgttgtcggg aagatgcgtg atctgatcct tcaactcagc aaaagttcga    2580
tttattcaac aaagccgccg tcccgtcaag tcagcgtaat gctctgccag tgttacaacc    2640
aattaaccaa ttctgattag aaaaactcat cgagcatcaa atgaaactgc aatttattca    2700
tatcaggatt atcaatacca tatttttgaa aaagccgttt ctgtaatgaa ggagaaaact    2760
caccgaggca gttccatagg atggcaagat cctggtatcg gtctgcgatt ccgactcgtc    2820
caacatcaat acaacctatt aatttcccct cgtcaaaaat aaggttatca agtgagaaat    2880
caccatgagt gacgactgaa tccggtgaga atggcaaaag cttatgcatt ctttccaga    2940 cttgttcaac aggccagcca ttacgctcgt catcaaaatc actcgcatca accaaaccgt    3000
tattcattcg tgattgcgcc tgagcgagac gaaatacgcg atcgctgtta aaaggacaat    3060
tacaaacagg aatcgaatgc aaccggcgca ggaacactgc cagcgcatca acaatatttt    3120
cacctgaatc aggatattct tctaatacct ggaatgctgt tttcccgggg atcgcagtgg    3180
tgagtaacca tgcatcatca ggagtacgga taaaatgctt gatggtcgga agaggcataa    3240
attccgtcag ccagtttagt ctgaccatct catctgtaac atcattggca acgctacctt    3300
tgccatgttt cagaaacaac tctggcgcat cgggcttccc atacaatcga tagattgtcg    3360
cacctgattg cccgacatta tcgcgagccc atttataccc atataaatca gcatccatgt    3420
tggaatttaa tcgcggcctc gagcaagacg tttcccgttg aatatggctc ataacacccc    3480
ttgtattact gtttatgtaa gcagacagtt ttattgttca tgatgatata tttttatctt    3540
```

```
gtgcaatgta acatcagaga ttttgagaca caacgtggct ttccccccc ccccattatt     3600 gaagcattta tcagggttat tgtctcatga gcggatacat atttgaatgt atttagaaaa     3660
ataaacaaat aggggttccg cgcacatttc cccgaaaagt gccacctgac gtctaagaaa     3720
ccattattat catgacatta acctataaaa ataggcgtat cacgaggccc tttcgtctcg     3780
cgcgtttcgg tgatgacggt gaaaacctct gacacatgca gctcccggag acggtcacag     3840
cttgtctgta agcggatgcc gggagcagac aagcccgtca gggcgcgtca gcgggtgttg     3900
gcgggtgtcg gggctggctt aactatgcgg catcagagca gattgtactg agagtgcacc     3960
atatgcggtg tgaaataccg cacagatgcg taaggagaaa ataccgcatc agattggcta     4020
ttgg                                                                 4024
```

<210> SEQ ID NO 32
<211> LENGTH: 4622
<212> TYPE: DNA
<213> ORGANISM: Artificial Sequence
<220> FEATURE:
<223> OTHER INFORMATION: synthetic dual promoter expression vector DP
      vector backbone

<400> SEQUENCE: 32

```
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg gaggtctat ataagcagag      660 ctcgtttagt gaaccgtcag atcgcctgga cgccatcc acgctgtttt gacctccata       720
gaagacaccg ggaccgatcc agcctccgcg ggcgcgtc gaggaattcg ctagcggcgc       780
gccagatctg atatcggatc tgctgtgcct tctagttgcc agccatctgt tgtttgcccc     840
tcccccgtgc cttccttgac cctggaaggt gccactccca ctgtcctttc ctaataaaat     900
gaggaaattg catcgcattg tctgagtagg tgtcattcta ttctgggggg tggggtgggg    960
caggacagca agggggagga ttgggaagac aatagcaggc atgctgggga tgcggtgggc    1020
tctatgggta cccaggtgct gaagaattga cccggttcct cctgggccag aaagaagcag    1080
gcacatcccc ttctctgtga cacaccctgt ccacgcccct ggttcttagt tccagcccca    1140
ctcataggac actcatagct caggagggct ccgccttcaa tcccacccgc taaagtactt    1200
ggagcggtct ctccctcccct catcagccca ccaaaccaaa cctagcctcc aagagtggga    1260
agaaattaaa gcaagatagg ctattaagtg cagagggaga gaaaatgcct ccaacatgtg    1320
aggaagtaat gagagaaatc atagaatttc ttccgcttcc tcgctcactg actcgctgcg    1380
ctcggtcgtt cggctgcggc gagcggtatc agctcactca aaggcggtaa tacggttatc    1440
cacagaatca ggggataacg caggaaagaa catgtgagca aaaggccagc aaaaggccag    1500
```

```
gaaccgtaaa aaggccgcgt tgctggcgtt tttccatagg ctccgccccc ctgacgagca    1560
tcacaaaaat cgacgctcaa gtcagaggtg gcgaaacccg acaggactat aaagatacca    1620
ggcgtttccc cctggaagct ccctcgtgcg ctctcctgtt ccgaccctgc cgcttaccgg    1680
atacctgtcc gcctttctcc cttcgggaag cgtggcgctt tctcatagct cacgctgtag    1740
gtatctcagt tcggtgtagg tcgttcgctc caagctgggc tgtgtgcacg aaccccccgt    1800
tcagcccgac cgctgcgcct tatccggtaa ctatcgtctt gagtccaacc cggtaagaca    1860
cgacttatcg ccactggcag cagccactgg taacaggatt agcagagcga ggtatgtagg    1920
cggtgctaca gagttcttga agtggtggcc taactacggc tacactagaa gaacagtatt    1980
tggtatctgc gctctgctga agccagttac cttcggaaaa agagttggta gctcttgatc    2040
cggcaaacaa accaccgctg gtagcggtgg ttttttttgtt tgcaagcagc agattacgcg    2100
cagaaaaaaa ggatctcaag aagatccttt gatcttttct acggggtctg acgctcagtg    2160
gaacgaaaac tcacgttaag ggattttggt catgagatta tcaaaaagga tcttcaccta    2220 gatccttttta aattaaaaat gaagttttaa atcaatctaa agtatatatg agtaaacttg    2280
gtctgacagt taccaatgct taatcagtga ggcacctatc tcagcgatct gtctatttcg    2340
ttcatccata gttgcctgac tcgggggggg gggcgctga gtctgcctc gtgaagaagg     2400 tgttgctgac tcataccagg cctgaatcgc cccatcatcc agccagaaag tgagggagcc    2460
acggttgatg agagctttgt tgtaggtgga ccagttggtg attttgaact tttgctttgc    2520
cacggaacgg tctgcgttgt cgggaagatg cgtgatctga tccttcaact cagcaaaagt    2580
tcgatttatt caacaaagcc gccgtcccgt caagtcagcg taatgctctg ccagtgttac    2640
aaccaattaa ccaattctga ttagaaaaac tcatcgagca tcaaatgaaa ctgcaattta    2700
ttcatatcag gattatcaat accatatttt tgaaaaagcc gtttctgtaa tgaaggagaa    2760
aactcaccga ggcagttcca taggatggca agatcctggt atcggtctgc gattccgact    2820
cgtccaacat caatacaacc tattaatttc ccctcgtcaa aaataaggtt atcaagtgag    2880
aaatcaccat gagtgacgac tgaatccggt gagaatggca aaagcttatg catttctttc    2940
cagacttgtt caacaggcca gccattacgc tcgtcatcaa aatcactcgc atcaaccaaa    3000
ccgttattca ttcgtgattg cgcctgagcg agacgaaata cgcgatcgct gttaaaagga    3060
caattacaaa caggaatcga atgcaaccgg cgcaggaaca ctgccagcgc atcaacaata    3120
ttttcacctg aatcaggata ttcttctaat acctggaatg ctgttttccc ggggatcgca    3180
gtggtgagta accatgcatc atcaggagta cggataaaat gcttgatggt cggaagaggc    3240
ataaattccg tcagccagtt tagtctgacc atctcatctg taacatcatt ggcaacgcta    3300
cctttgccat gtttcagaaa caactctggc gcatcgggct tcccatacaa tcgatagatt    3360
gtcgcacctg attgcccgac attatcgcga gcccatttat acccatataa atcagcatcc    3420
atgttggaat ttaatcgcgg cctcgagcaa gacgtttccc gttgaatatg gctcataaca    3480
ccccttgtat tactgtttat gtaagcagac agttttattg ttcatgatga tatattttta    3540
tcttgtgcaa tgtaacatca gagattttga gacacaacgt ggatcatcca gacatgataa    3600
gatacattga tgagtttgga caaaccacaa ctagaatgca gtgaaaaaaa tgctttattt    3660
gtgaaatttg tgatgctatt gctttatttg taaccattat aagctgcaat aaacaagtta    3720
acaacaacaa ttgcattcat tttatgtttc aggttcaggg ggaggtgtgg gaggtttttt    3780
aaagcaagta aaacctctac aaatgtggta tggctgatta tgatcgtcga ggatccggcg    3840
ccgtttaaac gtcgacagat ccaaacgctc ctccgacgtc cccaggcaga atggcggttc    3900
```

-continued

```
cctaaacgag cattgcttat atagacctcc cattaggcac gcctaccgcc catttacgtc    3960
aatggaacgc ccatttgcgt cattgcccct ccccattgac gtcaatgggg atgtacttgg    4020
cagccatcgc gggccattta ccgccattga cgtcaatggg agtactgcca atgtaccctg    4080
gcgtacttcc aatagtaatg tacttgccaa gttactatta atagatattg atgtactgcc    4140
aagtgggcca tttaccgtca ttgacgtcaa taggggcgt gagaacggat atgaatgggc     4200
aatgagccat cccattgacg tcaatggtgg gtggtcctat tgacgtcaat gggcattgag    4260
ccaggcgggc catttaccgt aattgacgtc aatggggag gcgccatata cgtcaatagg     4320
accgcccata tgacgtcaat aggtaagacc atgaggccct ttcgtctcgc gcgtttcggt    4380
gatgacggtg aaaacctctg acacatgcag ctcccggaga cggtcacagc ttgtctgtaa    4440
gcggatgccg ggagcagaca gcccgtcag ggcgcgtcag cgggtgttgg cgggtgtcgg     4500
ggctggctta actatgcggc atcagagcag attgtactga gagtgcacca tatgcggtgt    4560
gaaataccgc acagatgcgt aaggagaaaa taccgcatca gattggctat tggcattatg    4620
cc                                                                   4622
```

<210> SEQ ID NO 33
<211> LENGTH: 987
<212> TYPE: DNA
<213> ORGANISM: Artificial Sequence
<220> FEATURE:
<223> OTHER INFORMATION: synthetic human IL-12 p40 beta subunit improved
    RNA with minimized inhibitory/instability
    sequences

<400> SEQUENCE: 33

```
atgtgccacc agcagctggt catcagctgg ttcagcctcg ttttcctcgc ctcgccgctg      60
gtcgccatat gggagctcaa gaaggacgta tacgtggtgg agctggactg gtaccccgac     120
gcgccgggcg agatggtcgt cctgacgtgc gacacgccgg aggaggacgg catcacgtgg     180
acgctggacc agtccagcga ggtcctcggc tccggcaaga cgctgacgat ccaggtcaag     240
gagttcggcg acgcgggcca gtacacgtgc cacaagggcg gcgaggtcct gagccactcc     300
ctcctcctgc tacacaagaa ggaggacggg atctggagca cggacatcct caaggaccag     360
aaggagccga agaacaagac cttcctgcgc tgcgaggcga agaattactc gggccggttc     420
acgtgctggt ggctcaccac gatcagcacg gacctgacgt tctcggtcaa gtcgtcgcgg     480
ggctcgtcgg accccagg ggtgacctgc ggcgcggcga cgctgtcggc ggagcgggtg        540
cggggcgaca caaggagta cgagtactcg gtcgagtgcc aggaggactc ggcgtgcccg       600
gcggcggagg agtcgctgcc gatcgaggtg atggtcgacg cggtccacaa gctgaagtac     660
gagaactaca cgtcgtcgtt cttcatccgg gacatcatca gccggaccc gccgaagaac      720 ctgcagctga gccgctgaa gaactcgcgc aggtcgagg tctcgtggga gtacccggac       780
acgtggtcga cgccgcactc gtacttctcg ctgacgttct cgtccaagt gcagggcaag      840 tcgaagcggg agaagaagga ccgggtgttc accgacaaga cgagcgcgac ggtgatctgc     900
cggaagaacg cgtcgatctc ggtgcgggcg caggaccggt actactcgtc gtcgtggtcg     960
gagtgggcgt cggtgccgtg cagctag                                        987
```

<210> SEQ ID NO 34
<211> LENGTH: 660
<212> TYPE: DNA
<213> ORGANISM: Artificial Sequence

```
<220> FEATURE:
<223> OTHER INFORMATION: synthetic human IL-12 p35 alpha subunit
      improved RNA with minimized inhibitory/instability
      sequences

<400> SEQUENCE: 34
atgtgcccgg cgcgctccct gctgctcgtg gcgacgctgg tcctgctcga ccacctgagc      60
ctggcgcgga acctgccggt ggcgacgccg gacccgggga tgttcccgtg cctgcaccac     120
agccagaacc tgctgcgggc ggtgtcgaac atgctgcaga aggcgcggca gacgctggag     180
ttctacccgt gcacgagcga ggagatcgac cacgaggaca tcacgaagga caagaccagc     240
acggtggagg cgtgcctgcc gctggagctg acgaagaacg agtcgtgcct gaactcgagg     300
gagacgtcgt tcatcacgaa cgggtcgtgc ctggcgtcgc ggaagacgtc gttcatgatg     360
gcgctgtgcc tgtcgtcgat ctacgaggac ctgaagatgt accaggtgga gttcaagacg     420
atgaacgcga agctgctgat ggacccgaag cggcagatct tcctcgacca gaacatgctg     480
gcggtgatcg acgagctcat gcaggcgctc aacttcaaca gcgagacggt gccgcagaag     540
tcgtcgctcg aggagccgga cttctacaag acgaagatca agctctgcat cctgctgcac     600
gctttccgga tccgggcggt gacgatcgac cgggtgatgt cgtacctgaa cgcttcgtaa     660
```